(12) United States Patent
Fairhurst et al.

(10) Patent No.: US 12,060,428 B2
(45) Date of Patent: Aug. 13, 2024

(54) ANTI-IL36R ANTIBODIES

(71) Applicant: Regeneron Pharmaceuticals, Inc., Tarrytown, NY (US)

(72) Inventors: Jeanette Fairhurst, Thornwood, NY (US); Elena Garnova, White Plains, NY (US); William Olson, Yorktown Heights, NY (US); Sokol Haxhinasto, Brookfield, CT (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 185 days.

(21) Appl. No.: 17/590,319

(22) Filed: Feb. 1, 2022

(65) Prior Publication Data

US 2022/0162326 A1     May 26, 2022

Related U.S. Application Data

(62) Division of application No. 16/512,886, filed on Jul. 16, 2019, now Pat. No. 11,267,893.

(60) Provisional application No. 62/866,028, filed on Jun. 25, 2019, provisional application No. 62/846,989, filed on May 13, 2019, provisional application No. 62/698,482, filed on Jul. 16, 2018.

(51) Int. Cl.
| | | |
|---|---|---|
| *C07K 16/28* | (2006.01) | |
| *A61K 9/00* | (2006.01) | |
| *A61K 45/06* | (2006.01) | |
| *A61P 1/00* | (2006.01) | |
| *A61P 17/00* | (2006.01) | |

(52) U.S. Cl.
CPC ........ *C07K 16/2866* (2013.01); *A61K 9/0019* (2013.01); *A61P 1/00* (2018.01); *A61P 17/00* (2018.01); *A61K 45/06* (2013.01)

(58) Field of Classification Search
None
See application file for complete search history.

(56) References Cited

U.S. PATENT DOCUMENTS

| | | | |
|---|---|---|---|
| 6,239,268 B1 | 5/2001 | Lovenberg et al. | |
| 6,326,472 B1 | 12/2001 | Timans et al. | |
| 6,900,016 B1 | 5/2005 | Venter et al. | |
| 9,023,995 B2 | 5/2015 | Brown et al. | |
| 2006/0003323 A1 | 1/2006 | Alsobrook et al. | |
| 2018/0094065 A1 | 4/2018 | Bowers et al. | |
| 2020/0017592 A1 | 1/2020 | Fairhurst et al. | |

FOREIGN PATENT DOCUMENTS

| | | | |
|---|---|---|---|
| WO | 96/07739 A2 | 3/1996 | |
| WO | 99/19480 A2 | 4/1999 | |
| WO | 02/50277 A2 | 6/2002 | |
| WO | 2005/097421 A2 | 10/2005 | |
| WO | 2005/100604 A2 | 10/2005 | |
| WO | 2005/108415 A2 | 11/2005 | |
| WO | 2007/047796 A2 | 4/2007 | |
| WO | 2010/019570 A2 | 2/2010 | |
| WO | 2013/074569 A1 | 5/2013 | |
| WO | WO-2013074569 A1 * | 5/2013 | ............. A61P 17/06 |
| WO | 2014/144666 A2 | 9/2014 | |
| WO | WO-2014144666 A2 * | 9/2014 | ........... A61K 31/713 |
| WO | 2016/168542 A1 | 10/2016 | |
| WO | WO-2016168542 A1 * | 10/2016 | ....... A61K 39/39533 |
| WO | 2018/183173 A1 | 10/2018 | |
| WO | 2019/177883 A2 | 9/2019 | |
| WO | 2019/177888 A1 | 9/2019 | |
| WO | 2020/018511 A1 | 1/2020 | |

OTHER PUBLICATIONS

Ganesan et al (MAbs. Oct. 2017;9(7):1143-1154. Epub Jul. 20, 2017) (Year: 2017).*
Irina Khanskaya et al ( May 1, 2018, European Academy of Allergy and Clinical Immunology (EAACI) Congress. Retrieved from the Internet from https ://www .anaptysbio.com/wp-content/uploads/ANB019-Phase-1-Study-Poster-EAACI-2018.pdf [retrieved on Mar. 22, 2024]) (Year: 2018).*
Ahlberg J. et al., "Retrospective Analysis of Model-Based Predictivity of Human Pharmacodkinetics for Anti-IL-36r Monoclonal Antibody MAB92 Using a Rat Anti-Mouse IL-36R Monoclonal Antibody and RNA Expression Data (FANTOM5)", MABS 11(5):956-964 (2019).
Amin B. et al., "AnaptysBio (ANAB) First Data in GPP from Competitor Anti-IL36 Provides Proof of Concept of ANB019", Equity Analyst (6 pages) (Sep. 16, 2018).
Brown M. et al., "Tolerance to Single, But Not Multiple, Amino Acid Replacements in Antibody VH CDR2", The Journal of Immunology 156:3285-3291 (1996).
Born T.L. et al., "Identification and Characterization of Two Members of a Novel Class of the Interleukin-1 Receptor (IL-1R) Family", The Journal of Biological Chemistry 275(39):29946-29954 (Sep. 29, 2000).
Ding L. et al., "IL-36 Cytokines in Autoimmunity and Inflammatory Disease", Oncotarget 9(2):2895-2901 (2018).
Ganesan R. et al., "Generation and Functional Characterization of Anti-Human and Anti-Mouse IL-36R Antagonist Monoclonal Antibodies", MABS 9(7):1143-1154 (Oct. 3, 2017).

(Continued)

*Primary Examiner* — Brian Gangle
*Assistant Examiner* — Anread K McCollum
(74) *Attorney, Agent, or Firm* — Scully, Scott, Murphy & Presser, P.C.; Lisa Dornback Flanagan

(57) ABSTRACT

The present invention provides antibodies and antigen-binding fragments (e.g., human antibodies) that bind specifically to human Interleukin-36 receptor (IL36R). Methods for treating or preventing diseases mediated by IL36R (e.g., skin or colon inflammatory conditions such as palmo-plantar pustular psoriasis, palmoplantar pustulosis, generalized pustular psoriasis, ulcerative colitis or IBD) using the antibodies and fragments are also provided along with methods of making the antibodies and fragments.

23 Claims, 4 Drawing Sheets
Specification includes a Sequence Listing.

(56) References Cited

OTHER PUBLICATIONS

Gershoni J.M. et al., "Epitope Mapping—The First Step in Developing Epitope-Based Vaccines", Biodrugs 21(3):145-156 (Jan. 1, 2007).

Khanskaya I. et al., "A Phase 1 Study of ANB019, an Anti-IL-36 Receptor Monoclonal Antibody, in Healthy Volunteers", European Academy of Allergy and Clinical Immunology (EAACI) (May 1, 2018).

Lovenberg T.W. et al., "Cloning of a cDNA Encoding a Novel Interleukin-1 Receptor Related Protein (IL1R-rp2)", Journal of Neuroimmunology 70:113-122 (1996).

Marrakchi S. et al., "Interleukin-36-Receptor Antagonist Deficiency and Generalized Pustular Psoriasis", The New England Journal of Medicine 365(7):620-628 (Aug. 18, 2011).

Rudikoff S. et al., "Single Amino Acid Substitution Altering Antigen-Binding Specificity", Proc. Natl. Acad. Sci. USA 79(6):1979-1983 (Mar. 1982).

Scheibe K. et al., "Inhibiting Interleukin 36 Receptor Signaling Reduces Fibrosis in Mice With Chronic Intestinal Inflammation", Gastroenterology 156(4):1082-1097 (2019).

Torigoe K. et al., "Purification and Characterization of the Human Interleukin-18 Receptor", The Journal of Biological Chemistry 272(41):25737-25742 (Oct. 10, 1997).

Vajdos F.F. et al., "Comprehensive Functional Maps of the Antigen-Binding Site of an Anti-ErbB2 Antibody Obtained With Shotgun Scanning Mutagenesis", J. Mol. Biol. 320:415-428 (Jul. 2002).

Yi G. et al., "Structural and Functional Attributes of the Interleukin-36 Receptor", The Journal of Biological Chemistry 291(32):16597-16609 (Aug. 5, 2016).

Zhao J. et al., "In Silico Methods in Antibody Design", Antibodies 7(3):22 (Jun. 2018).

"Boehringer Ingelheim R&D Pushes to Transcend Disease Boundaries" (https:www.boehringer-ingelheim.com/press-release/transcending-disease-boundaries), (4 pages) (Apr. 25, 2018).

WHO Drug Information 34(3) (203 pages) (2020), together with an English-language translation.

WHO Drug Information 32(2) (116 pages) (2018), together with an English-language translation.

WHO Drug Information, vol. 32, No. 2, pp. 360-361 (2018).

Invitation to Pay Additional Fees and Partial International Search Report dated Oct. 23, 2019 received in International Application No. PCT/US2019/041952.

* cited by examiner

H4H14706P2

| REGN | VDJ | AMINO ACID CHANGES FROM GERMLINE | | |
|---|---|---|---|---|
| | | FW | CDR | +/- 2 AMINO ACID FROM CDR'S |
| H4H14706P2 | VH:IGHV3-9*01,D1-7*01,J4*02 | 2 | 5 | 2 |

```
                    10         20         30         40         50         60
IGHV3-9*01|D1-7*01|J4*02   EVQLVESGGGLVQPGRSLRLSCAAS GFTEDDYA MHWVRQ APGKGLEWVS GISWNS GS  GY
H4H14706P2VH              EVQLVESGGGLVQPGRSLRLSCTAS GFTEDDYA IHWVRQ SPGKGLEWVS VISWNS DV  GY 70         80         90        100        110
IGHV3-9*01|D1-7*01|J4*02   ADSVKGRFTISRDNAKNSLYLQMNSLRAEDTALYYC AK DYNWN YYFDY WGQGTLVTVSS
H4H14706P2VH              ADSVKGRFTISRDNAKNSLYLQMNSLRAEDTALYYC AK GYNWN -FFDY WGQGTLVTVSS
```

| REGN | VDJ | AMINO ACID CHANGES FROM GERMLINE | | |
|---|---|---|---|---|
| | | FW | CDR | +/- 2 AMINO ACID FROM CDR'S |
| H4H14706P2 | VL:IGKV3-11*01,IGKJ4*01 | 1 | 2 | 0 |

```
                    10         20         30         40         50         60
IGKV3-11*01|IGKJ4*01   EIVLTQSPATLSLSPGERATLSCRAS QSVSSY LAWYQQKPGQAPRLLIY DA S NRAT GIPA
H4H14706P2VK          EIVLTQSPATLSLSPGERATLSCRAS QSVSSY LAWYQQKPGQAPRLLIY NA A NRAT DIPA 70         80         90        100
IGKV3-11*01|IGKJ4*01   RFSGSGSGTDFTLTISSLEPEDFAVYYC QQRSNWPLT FGGGTKVEIK
H4H14706P2VK          RFSGSGSGTDFTLTISSLEPEDFAVYYC QQRSNWPLT FGGGTKVEIK
```

| REGN | VDJ | AMINO ACID CHANGES FROM GERMLINE | | |
|---|---|---|---|---|
| | | FW | CDR | +/- 2 AMINO ACID FROM CDR'S |
| H4H14708P2 | VH: IGHV3-9*01,D1-26*01,J4*02 | 3 | 11 | 2 |

```
                   10         20         30         40         50         60
IGHV3-9*01|D1-26*01|J4*02  EVQLVESGG GLVQPGRSLRLSCAAS GFTFDDYAMHWVRQAPGKGLEWVS GISWNS GSIGY
H4H14708P2VH              EVQLVESGG DLVQPGRSLRLSCAAS GFTFDDYAMHWVRQAPGKGLEWVS VISWNS DVIAY 70         80         90        100        110        120
IGHV3-9*01|D1-26*01|J4*02  ADSVKGRFTISRDNAKNSLYLQMNSLRAEDTALYYCAK DYSGSYYY FDY WGQGTLVTVSS
H4H14708P2VH              SDSVKGRFTISRDNAKNSLYLQMNSLRTEDTALYYCTK GHK--WSF FDY WGQGTLVTVSS
```

| REGN | VDJ | AMINO ACID CHANGES FROM GERMLINE | | |
|---|---|---|---|---|
| | | FW | CDR | +/- 2 AMINO ACID FROM CDR'S |
| H4H14708P2 | VL: IGKV3-11*01, IGKJ4*01 | 1 | 4 | 1 |

```
                   10         20         30         40         50         60
IGKV3-11*01|IGKJ4*01  EIVLTQSPATLSLSPGERATLSCRAS QSVSSY LAWYQQKPGQAPRLLIY DAS NRATGIPA
H4H14708P2VK         EIVLTQSPATLSLSPGERATLSCRAS QSISSY LAWYQQKPGQAPRLLIF NVA NRATDIPA 70         80         90        100
IGKV3-11*01|IGKJ4*01  RFSGSGSGTDFTLTISSLEPEDFAVYYC QQRSNWPLT FGGGTKVEIK
H4H14708P2VK         RFSGSGSGTDFTLTISSLEPEDFAVYYC QQRSNWPLT FGGGTKVEIK
```

FIG. 2

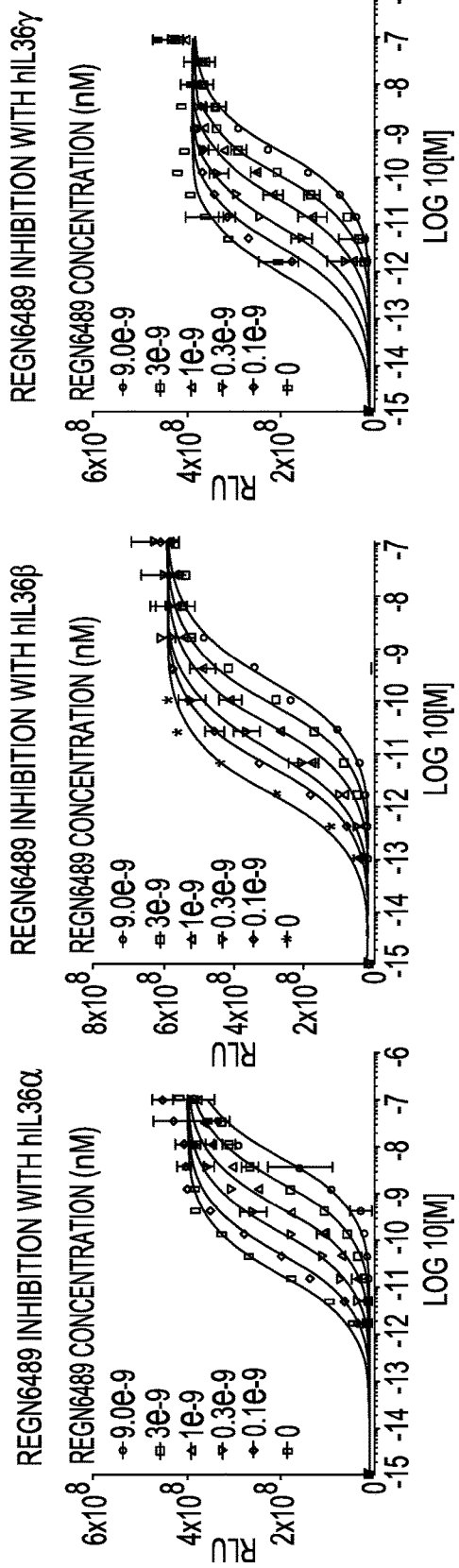
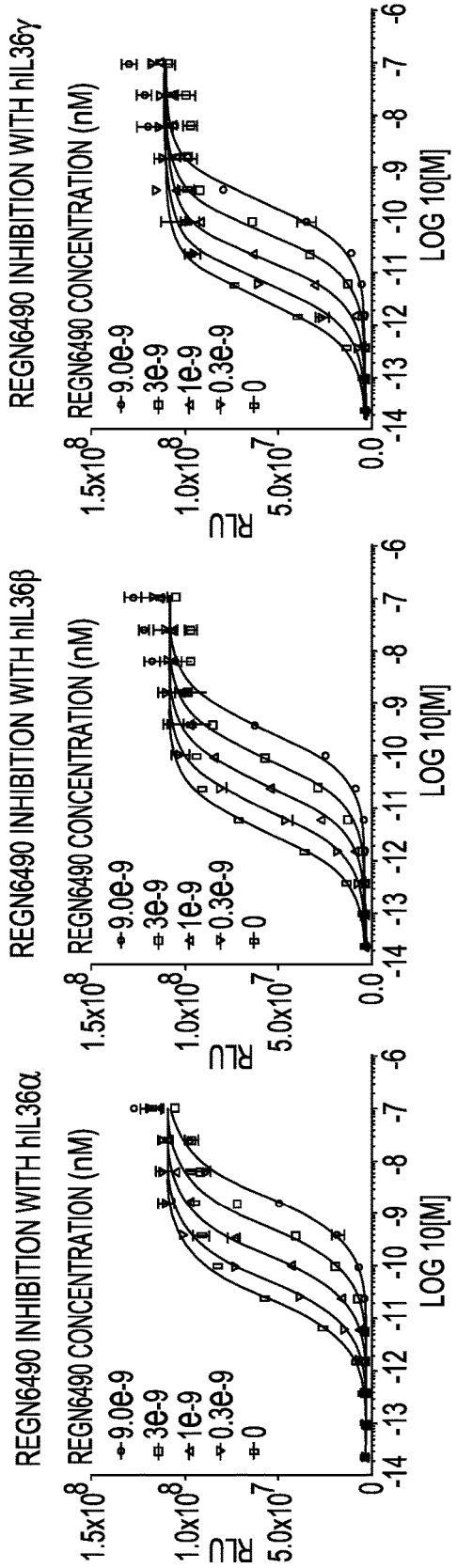

SEQUENCE LISTING

```
<160> NUMBER OF SEQ ID NOS: 243

<210> SEQ ID NO 1
<211> LENGTH: 354
<212> TYPE: DNA
<213> ORGANISM: Homo sapiens

<400> SEQUENCE: 1
gaagtgcagc tggtggagtc tgggggaggc ttggtgcagc ctggcaggtc cctgagactc      60
tcctgtgcgg cctctggatt caccttttgat gattatgcca tacactgggt ccggcaagct     120
ccagggaagg gcctggagtg ggtctcagtt atcagttgga atagtgatat cataggctat     180
gcggactctg tgaagggccg attcaccgtc tccagagaca cgccaagaa ctccctgtat      240 ctgcaaatga atagtctgag aactgaggac acggccttgt attactgtgc aaaaggatat     300
aactggaact tctttgacta ttggggccag ggaaccctgg tcaccgtctc ctca           354

<210> SEQ ID NO 2
<211> LENGTH: 118
<212> TYPE: PRT
<213> ORGANISM: Homo sapiens

<400> SEQUENCE: 2

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Ile His Trp Val Arg Gln Ala Pro Gly Lys Gly Leu Glu Trp Val
        35                  40                  45

Ser Val Ile Ser Trp Asn Ser Asp Ile Ile Gly Tyr Ala Asp Ser Val
    50                  55                  60

Lys Gly Arg Phe Thr Val Ser Arg Asp Asn Ala Lys Asn Ser Leu Tyr
65                  70                  75                  80

Leu Gln Met Asn Ser Leu Arg Thr Glu Asp Thr Ala Leu Tyr Tyr Cys
                85                  90                  95

Ala Lys Gly Tyr Asn Trp Asn Phe Phe Asp Tyr Trp Gly Gln Gly Thr
            100                 105                 110

Leu Val Thr Val Ser Ser
        115

<210> SEQ ID NO 3
<211> LENGTH: 24
<212> TYPE: DNA
<213> ORGANISM: Homo sapiens

<400> SEQUENCE: 3
ggattcacct ttgatgatta tgcc                                             24

<210> SEQ ID NO 4
<211> LENGTH: 8
```

-continued

```
<212> TYPE: PRT
<213> ORGANISM: Homo sapiens

<400> SEQUENCE: 4

Gly Phe Thr Phe Asp Asp Tyr Ala
1               5

<210> SEQ ID NO 5
<211> LENGTH: 24
<212> TYPE: DNA
<213> ORGANISM: Homo sapiens

<400> SEQUENCE: 5
atcagttgga atagtgatat cata                                          24

<210> SEQ ID NO 6
<211> LENGTH: 8
<212> TYPE: PRT
<213> ORGANISM: Homo sapiens

<400> SEQUENCE: 6

Ile Ser Trp Asn Ser Asp Ile Ile
1               5

<210> SEQ ID NO 7
<211> LENGTH: 33
<212> TYPE: DNA
<213> ORGANISM: Homo sapiens

<400> SEQUENCE: 7
gcaaaaggat ataactggaa cttctttgac tat                                33

<210> SEQ ID NO 8
<211> LENGTH: 11
<212> TYPE: PRT
<213> ORGANISM: Homo sapiens

<400> SEQUENCE: 8

Ala Lys Gly Tyr Asn Trp Asn Phe Phe Asp Tyr
1               5                   10

<210> SEQ ID NO 9
<211> LENGTH: 321
<212> TYPE: DNA
<213> ORGANISM: Homo sapiens

<400> SEQUENCE: 9
gaaattgtgt tgacgcagtc tccagccacc ctgtctttat ctccagggga aagagccacc    60
ctctcctgca gggccagtca gagtgttagc agctacttag cctggtacca acagaaacct   120
ggccaggctc ccaggctcct catctataat gcagcaaaca gggccactga catcccagcc   180
aggttcagtg gcagtgggtc tgggacagac ttcactctca ccatcagcag cctagagcct   240
gaagattttg cagtttatta ctgtcagcag cgtagcaact ggcctctcac tttcggcgga   300
gggaccaagg tggagatcaa a                                            321

<210> SEQ ID NO 10
<211> LENGTH: 107
<212> TYPE: PRT
<213> ORGANISM: Homo sapiens

<400> SEQUENCE: 10

Glu Ile Val Leu Thr Gln Ser Pro Ala Thr Leu Ser Leu Ser Pro Gly
```

```
1               5                  10                 15
Glu Arg Ala Thr Leu Ser Cys Arg Ala Ser Gln Ser Val Ser Ser Tyr
              20                 25                 30

Leu Ala Trp Tyr Gln Gln Lys Pro Gly Gln Ala Pro Arg Leu Leu Ile
         35                  40                 45

Tyr Asn Ala Ala Asn Arg Ala Thr Asp Ile Pro Ala Arg Phe Ser Gly
     50                  55                 60

Ser Gly Ser Gly Thr Asp Phe Thr Leu Thr Ile Ser Ser Leu Glu Pro
65                  70                 75                 80

Glu Asp Phe Ala Val Tyr Tyr Cys Gln Gln Arg Ser Asn Trp Pro Leu
                85                 90                 95

Thr Phe Gly Gly Gly Thr Lys Val Glu Ile Lys
            100                105
```

<210> SEQ ID NO 11
<211> LENGTH: 18
<212> TYPE: DNA
<213> ORGANISM: Homo sapiens

<400> SEQUENCE: 11
cagagtgtta gcagctac                                                  18

<210> SEQ ID NO 12
<211> LENGTH: 6
<212> TYPE: PRT
<213> ORGANISM: Homo sapiens

<400> SEQUENCE: 12

Gln Ser Val Ser Ser Tyr
1               5

<210> SEQ ID NO 13
<211> LENGTH: 9
<212> TYPE: DNA
<213> ORGANISM: Homo sapiens

<400> SEQUENCE: 13 aatgcagca                                                            9

<210> SEQ ID NO 14
<211> LENGTH: 3
<212> TYPE: PRT
<213> ORGANISM: Homo sapiens

<400> SEQUENCE: 14

Asn Ala Ala
1

<210> SEQ ID NO 15
<211> LENGTH: 27
<212> TYPE: DNA
<213> ORGANISM: Homo sapiens

<400> SEQUENCE: 15
cagcagcgta gcaactggcc tctcact                                        27

<210> SEQ ID NO 16
<211> LENGTH: 9
<212> TYPE: PRT
<213> ORGANISM: Homo sapiens

<400> SEQUENCE: 16

Gln Gln Arg Ser Asn Trp Pro Leu Thr
1               5

<210> SEQ ID NO 17
<211> LENGTH: 354
<212> TYPE: DNA
<213> ORGANISM: Homo sapiens

<400> SEQUENCE: 17
gaagtgcagc tggtggagtc tgggggaggc ttggtacagc ctggcaggtc cctgagactc      60
tcctgtgcag cctctggatt cacctttgat gattatgcca tgcactgggt ccggcaaact     120
ccagggaagg gcctggagtg gtctcagtt attagttgga atagtgatgt catagcctat     180
tcggactctg tgaagggccg cttcaccatt tccagagaca acgccaagaa ctccctgtat     240
ctgcaaatga acagtctggg aactgaggac acggccttat attactgtgc aaaaggccat     300
aactggaact ctttgactat tggggccag ggaaccctgg tcaccgtctc ctca            354

<210> SEQ ID NO 18
<211> LENGTH: 118
<212> TYPE: PRT
<213> ORGANISM: Homo sapiens

<400> SEQUENCE: 18

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Thr Pro Gly Lys Gly Leu Glu Trp Val
        35                  40                  45

Ser Val Ile Ser Trp Asn Ser Asp Val Ile Ala Tyr Ser Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Gly Thr Glu Asp Thr Ala Leu Tyr Tyr Cys
                85                  90                  95

Ala Lys Gly His Asn Trp Asn Phe Phe Asp Tyr Trp Gly Gln Gly Thr
            100                 105                 110

Leu Val Thr Val Ser Ser
        115

<210> SEQ ID NO 19
<211> LENGTH: 24
<212> TYPE: DNA
<213> ORGANISM: Homo sapiens

<400> SEQUENCE: 19
ggattcacct ttgatgatta tgcc                                              24

<210> SEQ ID NO 20
<211> LENGTH: 8
<212> TYPE: PRT
<213> ORGANISM: Homo sapiens

<400> SEQUENCE: 20

Gly Phe Thr Phe Asp Asp Tyr Ala
1               5

<210> SEQ ID NO 21

```
<211> LENGTH: 24
<212> TYPE: DNA
<213> ORGANISM: Homo sapiens

<400> SEQUENCE: 21
attagttgga atagtgatgt cata                                              24

<210> SEQ ID NO 22
<211> LENGTH: 8
<212> TYPE: PRT
<213> ORGANISM: Homo sapiens

<400> SEQUENCE: 22

Ile Ser Trp Asn Ser Asp Val Ile
1               5

<210> SEQ ID NO 23
<211> LENGTH: 33
<212> TYPE: DNA
<213> ORGANISM: Homo sapiens

<400> SEQUENCE: 23
gcaaaaggcc ataactggaa cttctttgac tat                                    33

<210> SEQ ID NO 24
<211> LENGTH: 11
<212> TYPE: PRT
<213> ORGANISM: Homo sapiens

<400> SEQUENCE: 24

Ala Lys Gly His Asn Trp Asn Phe Phe Asp Tyr
1               5                   10

<210> SEQ ID NO 25
<211> LENGTH: 321
<212> TYPE: DNA
<213> ORGANISM: Homo sapiens

<400> SEQUENCE: 25
gaaattgtgt tgacacagtc tccagccacc ctgtctttgt ctccaggaga aagagccacc       60
ctctcctgca gggccagtca gagtgttagc agctacttag cctggtacca acagaaacct      120
ggccaggctc ccaggctcct catctataat gtagccaaca gggccacaga catcccagcc      180
aggttcagtg gcagtgggtc tgggacagac ttcactctca ccatcagcgg cctagagcct      240
gaagattttg cagtttattt ctgtcagcag cgtagcaact ggcctctcac tttcggcgga      300
gggaccaagg tggagatcaa a                                                321

<210> SEQ ID NO 26
<211> LENGTH: 107
<212> TYPE: PRT
<213> ORGANISM: Homo sapiens

<400> SEQUENCE: 26

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asn Val Ala Asn Arg Ala Thr Asp Ile Pro Ala Arg Phe Ser Gly
    50                  55                  60
```

Ser Gly Ser Gly Thr Asp Phe Thr Leu Thr Ile Ser Gly Leu Glu Pro
65                  70                  75                  80

Glu Asp Phe Ala Val Tyr Phe Cys Gln Gln Arg Ser Asn Trp Pro Leu
                85                  90                  95

Thr Phe Gly Gly Gly Thr Lys Val Glu Ile Lys
            100                 105

<210> SEQ ID NO 27
<211> LENGTH: 18
<212> TYPE: DNA
<213> ORGANISM: Homo sapiens

<400> SEQUENCE: 27
cagagtgtta gcagctac                                                 18

<210> SEQ ID NO 28
<211> LENGTH: 6
<212> TYPE: PRT
<213> ORGANISM: Homo sapiens

<400> SEQUENCE: 28

Gln Ser Val Ser Ser Tyr
1               5

<210> SEQ ID NO 29
<211> LENGTH: 9
<212> TYPE: DNA
<213> ORGANISM: Homo sapiens

<400> SEQUENCE: 29 aatgtagcc                                                            9

<210> SEQ ID NO 30
<211> LENGTH: 3
<212> TYPE: PRT
<213> ORGANISM: Homo sapiens

<400> SEQUENCE: 30

Asn Val Ala
1

<210> SEQ ID NO 31
<211> LENGTH: 27
<212> TYPE: DNA
<213> ORGANISM: Homo sapiens

<400> SEQUENCE: 31
cagcagcgta gcaactggcc tctcact                                       27

<210> SEQ ID NO 32
<211> LENGTH: 9
<212> TYPE: PRT
<213> ORGANISM: Homo sapiens

<400> SEQUENCE: 32

Gln Gln Arg Ser Asn Trp Pro Leu Thr
1               5

<210> SEQ ID NO 33
<211> LENGTH: 354
<212> TYPE: DNA
<213> ORGANISM: Homo sapiens

<400> SEQUENCE: 33

```
gaagtgcagc tggtggagtc tgggggaggc ttggtacagc ctggcaggtc cctgagactc      60
tcctgtacag cctctggatt cacctttgat gattatgcca tacactgggt ccggcaatct     120
ccagggaagg gcctggagtg ggtctcagtt atcagttgga atagtgatgt cataggctat     180
gcggactctg tgaagggccg attcaccatc tccagagaca acgccaagaa ctccctgtat     240
ctgcagatga atagtctgag agctgaggac acggccttgt attactgtgc aaaaggatat     300
aactggaact tctttgacta ttggggccag ggaaccctgg tcaccgtctc ctca           354
```

<210> SEQ ID NO 34
<211> LENGTH: 118
<212> TYPE: PRT
<213> ORGANISM: Homo sapiens

<400> SEQUENCE: 34

```
Glu Val Gln Leu Val Glu Ser Gly Gly Gly Leu Val Gln Pro Gly Arg
1               5                   10                  15

Ser Leu Arg Leu Ser Cys Thr Ala Ser Gly Phe Thr Phe Asp Asp Tyr
            20                  25                  30

Ala Ile His Trp Val Arg Gln Ser Pro Gly Lys Gly Leu Glu Trp Val
        35                  40                  45

Ser Val Ile Ser Trp Asn Ser Asp Val Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Gly Tyr Asn Trp Asn Phe Phe Asp Tyr Trp Gly Gln Gly Thr
            100                 105                 110

Leu Val Thr Val Ser Ser
        115
```

<210> SEQ ID NO 35
<211> LENGTH: 24
<212> TYPE: DNA
<213> ORGANISM: Homo sapiens

<400> SEQUENCE: 35

```
ggattcacct ttgatgatta tgcc                                             24
```

<210> SEQ ID NO 36
<211> LENGTH: 8
<212> TYPE: PRT
<213> ORGANISM: Homo sapiens

<400> SEQUENCE: 36

```
Gly Phe Thr Phe Asp Asp Tyr Ala
1               5
```

<210> SEQ ID NO 37
<211> LENGTH: 24
<212> TYPE: DNA
<213> ORGANISM: Homo sapiens

<400> SEQUENCE: 37

```
atcagttgga atagtgatgt cata                                             24
```

<210> SEQ ID NO 38

```
<211> LENGTH: 8
<212> TYPE: PRT
<213> ORGANISM: Homo sapiens

<400> SEQUENCE: 38

Ile Ser Trp Asn Ser Asp Val Ile
1               5

<210> SEQ ID NO 39
<211> LENGTH: 33
<212> TYPE: DNA
<213> ORGANISM: Homo sapiens

<400> SEQUENCE: 39
gcaaaaggat ataactggaa cttctttgac tat                                 33

<210> SEQ ID NO 40
<211> LENGTH: 11
<212> TYPE: PRT
<213> ORGANISM: Homo sapiens

<400> SEQUENCE: 40

Ala Lys Gly Tyr Asn Trp Asn Phe Phe Asp Tyr
1               5                   10

<210> SEQ ID NO 41
<211> LENGTH: 321
<212> TYPE: DNA
<213> ORGANISM: Homo sapiens

<400> SEQUENCE: 41
gaaattgtgt tgacgcagtc tccagccacc ctgtctttat ctccagggga aagagccacc    60
ctctcctgca gggccagtca gagtgttagc agctacttag cctggtacca acagaaacct   120
ggccaggctc ccaggctcct catctataat gcagcaaaca gggccactga catcccagcc   180
aggttcagtg gcagtgggtc tgggacagac ttcactctca ccatcagcag cctagagcct   240
gaagattttg cagtttatta ctgtcagcag cgtagcaact ggcctctcac tttcggcgga   300
gggaccaagg tggagatcaa a                                             321

<210> SEQ ID NO 42
<211> LENGTH: 107
<212> TYPE: PRT
<213> ORGANISM: Homo sapiens

<400> SEQUENCE: 42

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asn Ala Ala Asn Arg Ala Thr Asp Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Thr Phe Gly Gly Gly Thr Lys Val Glu Ile Lys
            100                 105
```

<210> SEQ ID NO 43
<211> LENGTH: 18
<212> TYPE: DNA
<213> ORGANISM: Homo sapiens

<400> SEQUENCE: 43
cagagtgtta gcagctac                                                   18

<210> SEQ ID NO 44
<211> LENGTH: 6
<212> TYPE: PRT
<213> ORGANISM: Homo sapiens

<400> SEQUENCE: 44

Gln Ser Val Ser Ser Tyr
1               5

<210> SEQ ID NO 45
<211> LENGTH: 9
<212> TYPE: DNA
<213> ORGANISM: Homo sapiens

<400> SEQUENCE: 45 aatgcagca                                                              9

<210> SEQ ID NO 46
<211> LENGTH: 3
<212> TYPE: PRT
<213> ORGANISM: Homo sapiens

<400> SEQUENCE: 46

Asn Ala Ala
1

<210> SEQ ID NO 47
<211> LENGTH: 27
<212> TYPE: DNA
<213> ORGANISM: Homo sapiens

<400> SEQUENCE: 47
cagcagcgta gcaactggcc tctcact                                         27

<210> SEQ ID NO 48
<211> LENGTH: 9
<212> TYPE: PRT
<213> ORGANISM: Homo sapiens

<400> SEQUENCE: 48

Gln Gln Arg Ser Asn Trp Pro Leu Thr
1               5

<210> SEQ ID NO 49
<211> LENGTH: 354
<212> TYPE: DNA
<213> ORGANISM: Homo sapiens

<400> SEQUENCE: 49
gaagtgcagc tggtggagtc tgggggagac ttggtacagc ctggcaggtc cctgagactc     60
tcctgtgcag cctctggatt cacctttgat gattatgcca tgcactgggt ccggcaagct    120
ccagggaagg gcctggaatg ggtctcagtt attagttgga atagtgatgt catagcctat    180
tcggactctg tgaagggccg attcaccatc tccagagaca acgccaagaa ctccctgtat    240

```
ctgcaaatga acagtctgag aactgaggac acggccttat attactgtac aaaaggccat    300
aagtggagct tctttgacta ttggggccag ggaaccctgg tcaccgtctc ctca          354
```

<210> SEQ ID NO 50
<211> LENGTH: 118
<212> TYPE: PRT
<213> ORGANISM: Homo sapiens

<400> SEQUENCE: 50

```
Glu Val Gln Leu Val Glu Ser Gly Gly Asp Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Val Ile Ser Trp Asn Ser Asp Val Ile Ala Tyr Ser Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Thr Glu Asp Thr Ala Leu Tyr Tyr Cys
                85                  90                  95

Thr Lys Gly His Lys Trp Ser Phe Phe Asp Tyr Trp Gly Gln Gly Thr
            100                 105                 110

Leu Val Thr Val Ser Ser
        115
```

<210> SEQ ID NO 51
<211> LENGTH: 24
<212> TYPE: DNA
<213> ORGANISM: Homo sapiens

<400> SEQUENCE: 51

```
ggattcacct ttgatgatta tgcc                                           24
```

<210> SEQ ID NO 52
<211> LENGTH: 8
<212> TYPE: PRT
<213> ORGANISM: Homo sapiens

<400> SEQUENCE: 52

```
Gly Phe Thr Phe Asp Asp Tyr Ala
1               5
```

<210> SEQ ID NO 53
<211> LENGTH: 24
<212> TYPE: DNA
<213> ORGANISM: Homo sapiens

<400> SEQUENCE: 53

```
attagttgga atagtgatgt cata                                           24
```

<210> SEQ ID NO 54
<211> LENGTH: 8
<212> TYPE: PRT
<213> ORGANISM: Homo sapiens

<400> SEQUENCE: 54

```
Ile Ser Trp Asn Ser Asp Val Ile
1               5
```

```
<210> SEQ ID NO 55
<211> LENGTH: 33
<212> TYPE: DNA
<213> ORGANISM: Homo sapiens

<400> SEQUENCE: 55
acaaaaggcc ataagtggag cttctttgac tat                                    33

<210> SEQ ID NO 56
<211> LENGTH: 11
<212> TYPE: PRT
<213> ORGANISM: Homo sapiens

<400> SEQUENCE: 56
```

Thr Lys Gly His Lys Trp Ser Phe Phe Asp Tyr
1               5                   10

```
<210> SEQ ID NO 57
<211> LENGTH: 321
<212> TYPE: DNA
<213> ORGANISM: Homo sapiens

<400> SEQUENCE: 57
gaaattgtgt tgacacagtc tccagccacc ctgtctttgt ctccagggga aagagccacc       60
ctctcctgca gggccagtca gagtattagc agctacttag cctggtacca acagaaacct     120
ggccaggctc ccagactcct catctttaat gtagccaaca gggccactga catcccagcc     180
aggttcagtg gcagtgggtc tgggacagac ttcactctca ccatcagcag cctagagcct     240
gaagattttg cagtttatta ctgtcagcag cgtagcaact ggcctctcac tttcggcgga     300
gggaccaagg tggagatcaa a                                                321

<210> SEQ ID NO 58
<211> LENGTH: 107
<212> TYPE: PRT
<213> ORGANISM: Homo sapiens

<400> SEQUENCE: 58
```

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Ile Ser Ser Tyr
                20                  25                  30

Leu Ala Trp Tyr Gln Gln Lys Pro Gly Gln Ala Pro Arg Leu Leu Ile
            35                  40                  45

Phe Asn Val Ala Asn Arg Ala Thr Asp Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Thr Phe Gly Gly Gly Thr Lys Val Glu Ile Lys
            100                 105

```
<210> SEQ ID NO 59
<211> LENGTH: 18
<212> TYPE: DNA
<213> ORGANISM: Homo sapiens

<400> SEQUENCE: 59
cagagtatta gcagctac                                                     18
```

```
<210> SEQ ID NO 60
<211> LENGTH: 6
<212> TYPE: PRT
<213> ORGANISM: Homo sapiens

<400> SEQUENCE: 60

Gln Ser Ile Ser Ser Tyr
1               5

<210> SEQ ID NO 61
<211> LENGTH: 9
<212> TYPE: DNA
<213> ORGANISM: Homo sapiens

<400> SEQUENCE: 61 aatgtagcc                                                                  9

<210> SEQ ID NO 62
<211> LENGTH: 3
<212> TYPE: PRT
<213> ORGANISM: Homo sapiens

<400> SEQUENCE: 62

Asn Val Ala
1

<210> SEQ ID NO 63
<211> LENGTH: 27
<212> TYPE: DNA
<213> ORGANISM: Homo sapiens

<400> SEQUENCE: 63
cagcagcgta gcaactggcc tctcact                                             27

<210> SEQ ID NO 64
<211> LENGTH: 9
<212> TYPE: PRT
<213> ORGANISM: Homo sapiens

<400> SEQUENCE: 64

Gln Gln Arg Ser Asn Trp Pro Leu Thr
1               5

<210> SEQ ID NO 65
<211> LENGTH: 339
<212> TYPE: DNA
<213> ORGANISM: Homo sapiens

<400> SEQUENCE: 65
gaggtgcagc tggtggagtc tgggggaggc ttggttcagc ctgggggtc cctgagactc          60 tcctgcgcag cctctggatt cacctttagc gactatgcca tgagctgggt ccgccaggct        120
ccggggaagg ggctggagtg ggtctcaggt attagtggaa atggtggtga cacatactac        180
ggagacttcg tgaagggccg gttcaccatc tccagagaca attccaagaa cacgctgtat        240
ctgcaaatga acagcctgag aggcgaggac acggccgcat atttctgtgt gatagatctt        300
gactattggg gtcagggaac cctggtcacc gtctcctca                               339

<210> SEQ ID NO 66
<211> LENGTH: 113
<212> TYPE: PRT
<213> ORGANISM: Homo sapiens
```

<400> SEQUENCE: 66

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Ala Met Ser Trp Val Arg Gln Ala Pro Gly Lys Gly Leu Glu Trp Val
        35                  40                  45

Ser Gly Ile Ser Gly Asn Gly Asp Thr Tyr Tyr Gly Asp Phe Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Gly Glu Asp Thr Ala Ala Tyr Phe Cys
            85                  90                  95

Val Ile Asp Leu Asp Tyr Trp Gly Gln Gly Thr Leu Val Thr Val Ser
            100                 105                 110

Ser

<210> SEQ ID NO 67
<211> LENGTH: 24
<212> TYPE: DNA
<213> ORGANISM: Homo sapiens

<400> SEQUENCE: 67
ggattcacct ttagcgacta tgcc                                              24

<210> SEQ ID NO 68
<211> LENGTH: 8
<212> TYPE: PRT
<213> ORGANISM: Homo sapiens

<400> SEQUENCE: 68

Gly Phe Thr Phe Ser Asp Tyr Ala
1               5

<210> SEQ ID NO 69
<211> LENGTH: 24
<212> TYPE: DNA
<213> ORGANISM: Homo sapiens

<400> SEQUENCE: 69
attagtggaa atggtggtga caca                                              24

<210> SEQ ID NO 70
<211> LENGTH: 8
<212> TYPE: PRT
<213> ORGANISM: Homo sapiens

<400> SEQUENCE: 70

Ile Ser Gly Asn Gly Gly Asp Thr
1               5

<210> SEQ ID NO 71
<211> LENGTH: 18
<212> TYPE: DNA
<213> ORGANISM: Homo sapiens

<400> SEQUENCE: 71
gtgatagatc ttgactat                                                     18

<210> SEQ ID NO 72

```
<211> LENGTH: 6
<212> TYPE: PRT
<213> ORGANISM: Homo sapiens

<400> SEQUENCE: 72

Val Ile Asp Leu Asp Tyr
1               5

<210> SEQ ID NO 73
<211> LENGTH: 321
<212> TYPE: DNA
<213> ORGANISM: Homo sapiens

<400> SEQUENCE: 73
gacatccaga tgacccagtc tccttccacc ctgtctgcat ctgaaggaga cagagtcacc      60
atcacttgcc gggccagtca gagtattagt agctggttgg cctggtatca acagaaacca     120
ggaaaagccc ctaggctcct gatctataag gcgtctattt taggagatgg ggtcccatca     180
aggttcagcg gcagtggatc tgggacagaa ttcactctca ccatcagcag cctgcagcct     240
gatgattttg ctacttatta ctgccaccag tataatagtt atttgtggac gttcggccaa     300
gggaccaagg tggaaatcaa a                                                321

<210> SEQ ID NO 74
<211> LENGTH: 107
<212> TYPE: PRT
<213> ORGANISM: Homo sapiens

<400> SEQUENCE: 74

Asp Ile Gln Met Thr Gln Ser Pro Ser Thr Leu Ser Ala Ser Glu Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Arg Leu Leu Ile
        35                  40                  45

Tyr Lys Ala Ser Ile Leu Gly Asp Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys His Gln Tyr Asn Ser Tyr Leu Trp
                85                  90                  95

Thr Phe Gly Gln Gly Thr Lys Val Glu Ile Lys
            100                 105

<210> SEQ ID NO 75
<211> LENGTH: 18
<212> TYPE: DNA
<213> ORGANISM: Homo sapiens

<400> SEQUENCE: 75
cagagtatta gtagctgg                                                     18

<210> SEQ ID NO 76
<211> LENGTH: 6
<212> TYPE: PRT
<213> ORGANISM: Homo sapiens

<400> SEQUENCE: 76

Gln Ser Ile Ser Ser Trp
1               5
```

<210> SEQ ID NO 77
<211> LENGTH: 9
<212> TYPE: DNA
<213> ORGANISM: Homo sapiens

<400> SEQUENCE: 77 aaggcgtct                                                                              9

<210> SEQ ID NO 78
<211> LENGTH: 3
<212> TYPE: PRT
<213> ORGANISM: Homo sapiens

<400> SEQUENCE: 78

Lys Ala Ser
1

<210> SEQ ID NO 79
<211> LENGTH: 27
<212> TYPE: DNA
<213> ORGANISM: Homo sapiens

<400> SEQUENCE: 79
caccagtata atagttattt gtggacg                                                         27

<210> SEQ ID NO 80
<211> LENGTH: 9
<212> TYPE: PRT
<213> ORGANISM: Homo sapiens

<400> SEQUENCE: 80

His Gln Tyr Asn Ser Tyr Leu Trp Thr
1               5

<210> SEQ ID NO 81
<211> LENGTH: 363
<212> TYPE: DNA
<213> ORGANISM: Homo sapiens

<400> SEQUENCE: 81
caggtgcagc tgcaggagtc gggcccagga ctggtgaagc cttcacagac cctgtccctc        60
acctgcactg tctctggtgg ctccatcagc agtgctgatt actattggag ctggatccgc       120
cagcacccag ggaagggcct ggagtggatt ggatccatct attatactgg gagtacttac       180
tacaacccgt ccctcaagag tcgacttacc atatcaatag acacgtctga gaaccagttc       240
tctttgaaac tgacctctct gactgccgcg gacacggccg tgtattactg tgcgagcgag       300
gaggctaact ggggatccca ctttgactcc tggggccagg gaaccctggt caccgtctcc       360
tca                                                                    363

<210> SEQ ID NO 82
<211> LENGTH: 121
<212> TYPE: PRT
<213> ORGANISM: Homo sapiens

<400> SEQUENCE: 82

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Ala
            20                  25                  30

Asp Tyr Tyr Trp Ser Trp Ile Arg Gln His Pro Gly Lys Gly Leu Glu

```
              35                  40                  45
Trp Ile Gly Ser Ile Tyr Tyr Thr Gly Ser Thr Tyr Tyr Asn Pro Ser
         50                  55                  60

Leu Lys Ser Arg Leu Thr Ile Ser Ile Asp Thr Ser Glu Asn Gln Phe
 65                  70                  75                  80

Ser Leu Lys Leu Thr Ser Leu Thr Ala Ala Asp Thr Ala Val Tyr Tyr
                 85                  90                  95

Cys Ala Ser Glu Glu Ala Asn Trp Gly Ser His Phe Asp Ser Trp Gly
            100                 105                 110

Gln Gly Thr Leu Val Thr Val Ser Ser
        115                 120
```

<210> SEQ ID NO 83
<211> LENGTH: 30
<212> TYPE: DNA
<213> ORGANISM: Homo sapiens

<400> SEQUENCE: 83
ggtggctcca tcagcagtgc tgattactat                                    30

<210> SEQ ID NO 84
<211> LENGTH: 10
<212> TYPE: PRT
<213> ORGANISM: Homo sapiens

<400> SEQUENCE: 84

```
Gly Gly Ser Ile Ser Ser Ala Asp Tyr Tyr
1               5                   10
```

<210> SEQ ID NO 85
<211> LENGTH: 21
<212> TYPE: DNA
<213> ORGANISM: Homo sapiens

<400> SEQUENCE: 85
atctattata ctgggagtac t                                             21

<210> SEQ ID NO 86
<211> LENGTH: 7
<212> TYPE: PRT
<213> ORGANISM: Homo sapiens

<400> SEQUENCE: 86

```
Ile Tyr Tyr Thr Gly Ser Thr
1               5
```

<210> SEQ ID NO 87
<211> LENGTH: 39
<212> TYPE: DNA
<213> ORGANISM: Homo sapiens

<400> SEQUENCE: 87
gcgagcgagg aggctaactg gggatcccac tttgactcc                          39

<210> SEQ ID NO 88
<211> LENGTH: 13
<212> TYPE: PRT
<213> ORGANISM: Homo sapiens

<400> SEQUENCE: 88

```
Ala Ser Glu Glu Ala Asn Trp Gly Ser His Phe Asp Ser
1               5                   10
```

<210> SEQ ID NO 89
<211> LENGTH: 324
<212> TYPE: DNA
<213> ORGANISM: Homo sapiens

<400> SEQUENCE: 89

```
gacatccaga tgacccagtc tccatcctcc ctgtctgcat ctgtaggaga cagagtcacc      60
atcacttgcc gggcaagtca gagcattgac aactttttaa attggtatca gcagaaacca     120
gggaaagccc ctaagctcct gatctatgct gcatccagtt tgcaaagtgg ggtcccatca     180
aggttcagtg gcagtggatc tgggacagat ttcactctca ccatcagcag tctgcaacct     240
gaagattttg catcttacta ctgtcaacat agtcacagtg cccatccgat caccttcggc     300
caagggacac gactggagat taaa                                            324
```

<210> SEQ ID NO 90
<211> LENGTH: 108
<212> TYPE: PRT
<213> ORGANISM: Homo sapiens

<400> SEQUENCE: 90

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Asp Asn Phe
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Ser Tyr Tyr Cys Gln His Ser His Ser Ala His Pro
                85                  90                  95

Ile Thr Phe Gly Gln Gly Thr Arg Leu Glu Ile Lys
            100                 105

<210> SEQ ID NO 91
<211> LENGTH: 18
<212> TYPE: DNA
<213> ORGANISM: Homo sapiens

<400> SEQUENCE: 91

```
cagagcattg acaacttt                                                    18
```

<210> SEQ ID NO 92
<211> LENGTH: 6
<212> TYPE: PRT
<213> ORGANISM: Homo sapiens

<400> SEQUENCE: 92

Gln Ser Ile Asp Asn Phe
1               5

<210> SEQ ID NO 93
<211> LENGTH: 9
<212> TYPE: DNA
<213> ORGANISM: Homo sapiens

<400> SEQUENCE: 93 gctgcatcc 9

<210> SEQ ID NO 94
<211> LENGTH: 3
<212> TYPE: PRT
<213> ORGANISM: Homo sapiens

<400> SEQUENCE: 94

Ala Ala Ser
1

<210> SEQ ID NO 95
<211> LENGTH: 30
<212> TYPE: DNA
<213> ORGANISM: Homo sapiens

<400> SEQUENCE: 95
caacatagtc acagtgccca tccgatcacc 30

<210> SEQ ID NO 96
<211> LENGTH: 10
<212> TYPE: PRT
<213> ORGANISM: Homo sapiens

<400> SEQUENCE: 96

Gln His Ser His Ser Ala His Pro Ile Thr
1               5                   10

<210> SEQ ID NO 97
<211> LENGTH: 363
<212> TYPE: DNA
<213> ORGANISM: Homo sapiens

<400> SEQUENCE: 97
cagctgcagc tgcaggagtc gggcccagga ctggtgaagc cttcggagac cctgtccctc    60
acctgcactg tctctggtgg ctccatcagc agtagtaatt actactgggg ctggatccgc   120
cagcccccag ggaagagact ggagtggatt gggagtatct attatagtgg gagcacctac   180
tacaacccgt ccctcaagac tcgagtcacc atatccgtag acacgtccaa gaatcagttc   240
tccctgaagc tgacctctgt gaccgccgca gacacggctg tgtattactg tgcgagagag   300
gaagcagcag ctttgacgca ctttgacttc tggggccagg gaaccctggt caccgtctcc   360
tca                                                                 363

<210> SEQ ID NO 98
<211> LENGTH: 121
<212> TYPE: PRT
<213> ORGANISM: Homo sapiens

<400> SEQUENCE: 98

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Asn Tyr Tyr Trp Gly Trp Ile Arg Gln Pro Pro Gly Lys Arg Leu Glu
        35                  40                  45

Trp Ile Gly Ser Ile Tyr Tyr Ser Gly Ser Thr Tyr Tyr Asn Pro Ser
    50                  55                  60

Leu Lys Thr Arg Val Thr Ile Ser Val Asp Thr Ser Lys Asn Gln Phe
65                  70                  75                  80

```
Ser Leu Lys Leu Thr Ser Val Thr Ala Ala Asp Thr Ala Val Tyr Tyr
                85                  90                  95

Cys Ala Arg Glu Glu Ala Ala Ala Leu Thr His Phe Asp Phe Trp Gly
            100                 105                 110

Gln Gly Thr Leu Val Thr Val Ser Ser
        115                 120
```

<210> SEQ ID NO 99
<211> LENGTH: 30
<212> TYPE: DNA
<213> ORGANISM: Homo sapiens

<400> SEQUENCE: 99
ggtggctcca tcagcagtag taattactac                                    30

<210> SEQ ID NO 100
<211> LENGTH: 10
<212> TYPE: PRT
<213> ORGANISM: Homo sapiens

<400> SEQUENCE: 100

```
Gly Gly Ser Ile Ser Ser Ser Asn Tyr Tyr
1               5                   10
```

<210> SEQ ID NO 101
<211> LENGTH: 21
<212> TYPE: DNA
<213> ORGANISM: Homo sapiens

<400> SEQUENCE: 101
atctattata gtgggagcac c                                             21

<210> SEQ ID NO 102
<211> LENGTH: 7
<212> TYPE: PRT
<213> ORGANISM: Homo sapiens

<400> SEQUENCE: 102

```
Ile Tyr Tyr Ser Gly Ser Thr
1               5
```

<210> SEQ ID NO 103
<211> LENGTH: 39
<212> TYPE: DNA
<213> ORGANISM: Homo sapiens

<400> SEQUENCE: 103
gcgagagagg aagcagcagc tttgacgcac tttgacttc                          39

<210> SEQ ID NO 104
<211> LENGTH: 13
<212> TYPE: PRT
<213> ORGANISM: Homo sapiens

<400> SEQUENCE: 104

```
Ala Arg Glu Glu Ala Ala Ala Leu Thr His Phe Asp Phe
1               5                   10
```

<210> SEQ ID NO 105
<211> LENGTH: 324
<212> TYPE: DNA
<213> ORGANISM: Homo sapiens

<400> SEQUENCE: 105

```
gacatccaga tgacccagtc tccatcctcc ctgtctgcat ctgtaggaga cagagtcacc      60
atcacttgcc gggcaagtca gagcattagc aactatttaa attggtatca gcagaaacca    120
gggaaagccc ctaagctcct gatctttgct gcatccagtt tacaaagtgg ggtcccatca    180
aggttcagtg gcagtggatc tgggacagat ttcactctca ccatcagcag tctgcaacct    240
gaagattttg caacttacta ctgtcaacat agtcacagtt cccatccgat caccttcggc    300
caagggacac gactggagat taaa                                            324
```

<210> SEQ ID NO 106
<211> LENGTH: 108
<212> TYPE: PRT
<213> ORGANISM: Homo sapiens

<400> SEQUENCE: 106

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asn Tyr
            20                  25                  30

Leu Asn Trp Tyr Gln Gln Lys Pro Gly Lys Ala Pro Lys Leu Leu Ile
        35                  40                  45

Phe Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His Ser His Ser Ser His Pro
                85                  90                  95

Ile Thr Phe Gly Gln Gly Thr Arg Leu Glu Ile Lys
            100                 105

<210> SEQ ID NO 107
<211> LENGTH: 18
<212> TYPE: DNA
<213> ORGANISM: Homo sapiens

<400> SEQUENCE: 107
cagagcatta gcaactat                                                    18

<210> SEQ ID NO 108
<211> LENGTH: 6
<212> TYPE: PRT
<213> ORGANISM: Homo sapiens

<400> SEQUENCE: 108

Gln Ser Ile Ser Asn Tyr
1               5

<210> SEQ ID NO 109
<211> LENGTH: 9
<212> TYPE: DNA
<213> ORGANISM: Homo sapiens

<400> SEQUENCE: 109 gctgcatcc                                                               9

<210> SEQ ID NO 110
<211> LENGTH: 3
<212> TYPE: PRT
<213> ORGANISM: Homo sapiens

<400> SEQUENCE: 110

Ala Ala Ser
1

<210> SEQ ID NO 111
<211> LENGTH: 30
<212> TYPE: DNA
<213> ORGANISM: Homo sapiens

<400> SEQUENCE: 111
caacatagtc acagttccca tccgatcacc                                      30

<210> SEQ ID NO 112
<211> LENGTH: 10
<212> TYPE: PRT
<213> ORGANISM: Homo sapiens

<400> SEQUENCE: 112

Gln His Ser His Ser Ser His Pro Ile Thr
1               5                   10

<210> SEQ ID NO 113
<211> LENGTH: 366
<212> TYPE: DNA
<213> ORGANISM: Homo sapiens

<400> SEQUENCE: 113
gaagtgcagc tggtggagtc tgggggaggc ttggtacagc ctggcaggtc cctgagactc      60
tcctgtgcag cctctggatt cacctttgat gattatgcca tgcactgggt ccggcaagct     120
ccagggaagg gcctggagtg ggtctcaggt attaattggg ctggttataa catagactat     180
gcggactctg tgaagggccg attcaccatc tccagagaca cgccaagaa ctccctgtat      240
ctgcaaatga acagtctgag agctgaggac acggccttgt attactgtgc aaaagatatg     300
cgtggattca gttatggttt ccccttttgac tactggggcc agggaaccct ggtcaccgtc     360
tcctca                                                              366

<210> SEQ ID NO 114
<211> LENGTH: 122
<212> TYPE: PRT
<213> ORGANISM: Homo sapiens

<400> SEQUENCE: 114

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Asn Trp Ala Gly Tyr Asn Ile Asp Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Met Arg Gly Phe Ser Tyr Gly Phe Pro Phe Asp Tyr Trp
            100                 105                 110

Gly Gln Gly Thr Leu Val Thr Val Ser Ser
        115                 120

<210> SEQ ID NO 115
<211> LENGTH: 24
<212> TYPE: DNA
<213> ORGANISM: Homo sapiens

<400> SEQUENCE: 115
ggattcacct ttgatgatta tgcc                                              24

<210> SEQ ID NO 116
<211> LENGTH: 8
<212> TYPE: PRT
<213> ORGANISM: Homo sapiens

<400> SEQUENCE: 116

Gly Phe Thr Phe Asp Asp Tyr Ala
1               5

<210> SEQ ID NO 117
<211> LENGTH: 24
<212> TYPE: DNA
<213> ORGANISM: Homo sapiens

<400> SEQUENCE: 117
attaattggg ctggttataa cata                                              24

<210> SEQ ID NO 118
<211> LENGTH: 8
<212> TYPE: PRT
<213> ORGANISM: Homo sapiens

<400> SEQUENCE: 118

Ile Asn Trp Ala Gly Tyr Asn Ile
1               5

<210> SEQ ID NO 119
<211> LENGTH: 45
<212> TYPE: DNA
<213> ORGANISM: Homo sapiens

<400> SEQUENCE: 119
gcaaaagata tgcgtggatt cagttatggt ttcccctttg actac                       45

<210> SEQ ID NO 120
<211> LENGTH: 15
<212> TYPE: PRT
<213> ORGANISM: Homo sapiens

<400> SEQUENCE: 120

Ala Lys Asp Met Arg Gly Phe Ser Tyr Gly Phe Pro Phe Asp Tyr
1               5                   10                  15

<210> SEQ ID NO 121
<211> LENGTH: 324
<212> TYPE: DNA
<213> ORGANISM: Homo sapiens

<400> SEQUENCE: 121
gacatccaga tgacccagtc tccatcctcc ctgtctgcat ctgtaggaga cagagtcacc        60
atcacttgcc gggcaagtca gagcattagc agctatttaa attggtatca gcagaaacca      120
gggaaagccc ctaagctcct gatctatgct gcatccagtt tgcaaagtgg ggtcccgtca      180
aggttcagtg gcagtggatc tgggacagat ttcactctca ccatcagcag tctgcaacct      240

```
gaagattttg caacttacta ctgtcaacag agttacagta ccccatccgat caccttcggc    300 caagggacac gactggagat taaa                                            324
```

```
<210> SEQ ID NO 122
<211> LENGTH: 108
<212> TYPE: PRT
<213> ORGANISM: Homo sapiens

<400> SEQUENCE: 122
```

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Ile Thr Phe Gly Gln Gly Thr Arg Leu Glu Ile Lys
            100                 105

```
<210> SEQ ID NO 123
<211> LENGTH: 18
<212> TYPE: DNA
<213> ORGANISM: Homo sapiens

<400> SEQUENCE: 123
cagagcatta gcagctat                                                    18

<210> SEQ ID NO 124
<211> LENGTH: 6
<212> TYPE: PRT
<213> ORGANISM: Homo sapiens

<400> SEQUENCE: 124
```

Gln Ser Ile Ser Ser Tyr
1               5

```
<210> SEQ ID NO 125
<211> LENGTH: 9
<212> TYPE: DNA
<213> ORGANISM: Homo sapiens

<400> SEQUENCE: 125 gctgcatcc                                                               9

<210> SEQ ID NO 126
<211> LENGTH: 3
<212> TYPE: PRT
<213> ORGANISM: Homo sapiens

<400> SEQUENCE: 126
```

Ala Ala Ser
1

```
<210> SEQ ID NO 127
<211> LENGTH: 30
```

```
<212> TYPE: DNA
<213> ORGANISM: Homo sapiens

<400> SEQUENCE: 127
caacagagtt acagtacccc tccgatcacc                                           30

<210> SEQ ID NO 128
<211> LENGTH: 10
<212> TYPE: PRT
<213> ORGANISM: Homo sapiens

<400> SEQUENCE: 128

Gln Gln Ser Tyr Ser Thr Pro Pro Ile Thr
1               5                   10

<210> SEQ ID NO 129
<211> LENGTH: 399
<212> TYPE: DNA
<213> ORGANISM: Homo sapiens

<400> SEQUENCE: 129
gaggtgcagc tggtggagtc tgggggaggc ttggtaaagc cggggggggtc ccttagactc        60 tcctgtgcag cctctggatt tatttttcagt aacgcctgga tgaactgggt ccgccaggct       120
ccagggaagg gactggcgtg ggttggccgt attaaaaccg aaactgatgg tgggacaaca        180
gactacgctg caccccgtaaa aggcagattc accatctcaa gagatgactc aaaaaacacg      240
ctgtatctgc aaatgaacag cgtgaaaacc gaggacacag ccgtgtatta ctgtacaggg        300
ggatacagct atggtgacga tagcagcagc tggaacgagg gctactacta ctacggtatg       360
gacgtctggg gccaagggac cacggtcacc gtctcctca                               399

<210> SEQ ID NO 130
<211> LENGTH: 133
<212> TYPE: PRT
<213> ORGANISM: Homo sapiens

<400> SEQUENCE: 130

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Ile Phe Ser Asn Ala
            20                  25                  30

Trp Met Asn Trp Val Arg Gln Ala Pro Gly Lys Gly Leu Ala Trp Val
        35                  40                  45

Gly Arg Ile Lys Thr Glu Thr Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Val Lys Thr Glu Asp Thr Ala Val Tyr
                85                  90                  95

Tyr Cys Thr Gly Gly Tyr Ser Tyr Gly Asp Asp Ser Ser Ser Trp Asn
            100                 105                 110

Glu Gly Tyr Tyr Tyr Tyr Gly Met Asp Val Trp Gly Gln Gly Thr Thr
        115                 120                 125

Val Thr Val Ser Ser
    130

<210> SEQ ID NO 131
<211> LENGTH: 24
<212> TYPE: DNA
```

```
<213> ORGANISM: Homo sapiens

<400> SEQUENCE: 131
ggatttattt tcagtaacgc ctgg                                          24

<210> SEQ ID NO 132
<211> LENGTH: 8
<212> TYPE: PRT
<213> ORGANISM: Homo sapiens

<400> SEQUENCE: 132

Gly Phe Ile Phe Ser Asn Ala Trp
1               5

<210> SEQ ID NO 133
<211> LENGTH: 30
<212> TYPE: DNA
<213> ORGANISM: Homo sapiens

<400> SEQUENCE: 133
attaaaaccg aaactgatgg tgggacaaca                                    30

<210> SEQ ID NO 134
<211> LENGTH: 10
<212> TYPE: PRT
<213> ORGANISM: Homo sapiens

<400> SEQUENCE: 134

Ile Lys Thr Glu Thr Asp Gly Gly Thr Thr
1               5                   10

<210> SEQ ID NO 135
<211> LENGTH: 72
<212> TYPE: DNA
<213> ORGANISM: Homo sapiens

<400> SEQUENCE: 135 acaggggat acagctatgg tgacgatagc agcagctgga acgagggcta ctactactac    60
ggtatggacg tc                                                       72

<210> SEQ ID NO 136
<211> LENGTH: 24
<212> TYPE: PRT
<213> ORGANISM: Homo sapiens

<400> SEQUENCE: 136

Thr Gly Gly Tyr Ser Tyr Gly Asp Asp Ser Ser Ser Trp Asn Glu Gly
1               5                   10                  15
Tyr Tyr Tyr Tyr Gly Met Asp Val
            20

<210> SEQ ID NO 137
<211> LENGTH: 378
<212> TYPE: DNA
<213> ORGANISM: Homo sapiens

<400> SEQUENCE: 137
gaagtgcagc tggtggagtc tgggggaggc ttggtacagc ctggcaggtc cctgagactc    60
tcctgtacag cctctggatt cacctttgat gattatgcca tgcactgggt ccggcaagct   120
ccagggaagg gcctgagtg gtctcaggt attcgttgga atggtggtag tataggctat    180
gtggactctg tgaagggccg attcaccatc tccagagaca cgccaagaa gtccctgcat    240
```

```
ctgcaaatga acagtctaaa aactgaggac acggccttgt attactgtgc aaaagatata    300
ggcgatattt tgactggttt ttatggagaa tacggaatgg acgtctgggg ccaagggacc    360
acggtcaccg tctcctca                                                   378
```

<210> SEQ ID NO 138
<211> LENGTH: 126
<212> TYPE: PRT
<213> ORGANISM: Homo sapiens

<400> SEQUENCE: 138

```
Glu Val Gln Leu Val Glu Ser Gly Gly Gly Leu Val Gln Pro Gly Arg
1               5                   10                  15

Ser Leu Arg Leu Ser Cys Thr Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Arg Trp Asn Gly Gly Ser Ile Gly Tyr Val Asp Ser Val
    50                  55                  60

Lys Gly Arg Phe Thr Ile Ser Arg Asp Asn Ala Lys Lys Ser Leu His
65                  70                  75                  80

Leu Gln Met Asn Ser Leu Lys Thr Glu Asp Thr Ala Leu Tyr Tyr Cys
                85                  90                  95

Ala Lys Asp Ile Gly Asp Ile Leu Thr Gly Phe Tyr Gly Glu Tyr Gly
            100                 105                 110

Met Asp Val Trp Gly Gln Gly Thr Thr Val Thr Val Ser Ser
        115                 120                 125
```

<210> SEQ ID NO 139
<211> LENGTH: 24
<212> TYPE: DNA
<213> ORGANISM: Homo sapiens

<400> SEQUENCE: 139

```
ggattcacct ttgatgatta tgcc                                            24
```

<210> SEQ ID NO 140
<211> LENGTH: 8
<212> TYPE: PRT
<213> ORGANISM: Homo sapiens

<400> SEQUENCE: 140

```
Gly Phe Thr Phe Asp Asp Tyr Ala
1               5
```

<210> SEQ ID NO 141
<211> LENGTH: 24
<212> TYPE: DNA
<213> ORGANISM: Homo sapiens

<400> SEQUENCE: 141

```
attcgttgga atggtggtag tata                                            24
```

<210> SEQ ID NO 142
<211> LENGTH: 8
<212> TYPE: PRT
<213> ORGANISM: Homo sapiens

<400> SEQUENCE: 142

Ile Arg Trp Asn Gly Gly Ser Ile

<210> SEQ ID NO 143
<211> LENGTH: 57
<212> TYPE: DNA
<213> ORGANISM: Homo sapiens

<400> SEQUENCE: 143
gcaaaagata taggcgatat tttgactggt ttttatggag aatacggaat ggacgtc        57

<210> SEQ ID NO 144
<211> LENGTH: 19
<212> TYPE: PRT
<213> ORGANISM: Homo sapiens

<400> SEQUENCE: 144

Ala Lys Asp Ile Gly Asp Ile Leu Thr Gly Phe Tyr Gly Glu Tyr Gly
1               5                   10                  15

Met Asp Val

<210> SEQ ID NO 145
<211> LENGTH: 321
<212> TYPE: DNA
<213> ORGANISM: Homo sapiens

<400> SEQUENCE: 145
gacatccaga tgacccagtc tccatcctcc ctgtctgcat ctgaaggaga cagagtcacc       60
atcacttgcc gggcaagtca gagcattagc agctatttaa attggtatca gcagaaagca      120
gggaaagccc ctaacctcct gatctatgct gcatccagtt tgcaaagtgg ggtcccatca      180
aggttcagtg gcagtggatc tgggacagag tacactctca ccatcagcag tctgcaacct      240
gaagattttg caacttacta ctgtcaacag agttacatta tcccgtacac ttttggccag      300
gggaccaagc tggagatcaa a                                                321

<210> SEQ ID NO 146
<211> LENGTH: 107
<212> TYPE: PRT
<213> ORGANISM: Homo sapiens

<400> SEQUENCE: 146

Asp Ile Gln Met Thr Gln Ser Pro Ser Ser Leu Ser Ala Ser Glu Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Ala Gly Lys Ala Pro Asn Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Tyr Thr Leu Thr Ile Ser Ser Leu Gln Pro
65                  70                  75                  80

Glu Asp Phe Ala Thr Tyr Tyr Cys Gln Gln Ser Tyr Ile Ile Pro Tyr
                85                  90                  95

Thr Phe Gly Gln Gly Thr Lys Leu Glu Ile Lys
            100                 105

<210> SEQ ID NO 147
<211> LENGTH: 18
<212> TYPE: DNA
<213> ORGANISM: Homo sapiens

```
<400> SEQUENCE: 147
cagagcatta gcagctat                                                 18

<210> SEQ ID NO 148
<211> LENGTH: 6
<212> TYPE: PRT
<213> ORGANISM: Homo sapiens

<400> SEQUENCE: 148

Gln Ser Ile Ser Ser Tyr
1               5

<210> SEQ ID NO 149
<211> LENGTH: 9
<212> TYPE: DNA
<213> ORGANISM: Homo sapiens

<400> SEQUENCE: 149 gctgcatcc                                                            9

<210> SEQ ID NO 150
<211> LENGTH: 3
<212> TYPE: PRT
<213> ORGANISM: Homo sapiens

<400> SEQUENCE: 150

Ala Ala Ser
1

<210> SEQ ID NO 151
<211> LENGTH: 27
<212> TYPE: DNA
<213> ORGANISM: Homo sapiens

<400> SEQUENCE: 151
caacagagtt acattatccc gtacact                                       27

<210> SEQ ID NO 152
<211> LENGTH: 9
<212> TYPE: PRT
<213> ORGANISM: Homo sapiens

<400> SEQUENCE: 152

Gln Gln Ser Tyr Ile Ile Pro Tyr Thr
1               5

<210> SEQ ID NO 153
<211> LENGTH: 378
<212> TYPE: DNA
<213> ORGANISM: Homo sapiens

<400> SEQUENCE: 153
gaagtgcagc tggtggagtc tgggggaggg ttggtacagc ctggcaggtc cctgagactc    60
tcctgtgcag cctctggatt caccttttgat gattatgcca tgcactgggt ccggcaagct   120
ccagggaagg gcctggagtg ggtctcaagt gttaggtgga atggtggtat tataggctat   180
gcggactctg tgaagggccg attcaccatc tccagagaca cgccaagaa ctccctgtat    240 ctgcaaatga acagtctgag acctgaggac acggccctct attactgtgc aaaagatata   300
ggcgatgttt tgactggtta ttatggagaa tacggtatgg acgtctgggg ccaagggacc   360
acggtcaccg tctcctca                                                378
```

<210> SEQ ID NO 154
<211> LENGTH: 126
<212> TYPE: PRT
<213> ORGANISM: Homo sapiens

<400> SEQUENCE: 154

```
Glu Val Gln Leu Val Glu Ser Gly Gly Gly Leu Val Gln Pro Gly Arg
1               5                  10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Ser Val Arg Trp Asn Gly Gly Ile Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Pro Glu Asp Thr Ala Leu Tyr Tyr Cys
                85                  90                  95

Ala Lys Asp Ile Gly Asp Val Leu Thr Gly Tyr Tyr Gly Glu Tyr Gly
            100                 105                 110

Met Asp Val Trp Gly Gln Gly Thr Thr Val Thr Val Ser Ser
        115                 120                 125
```

<210> SEQ ID NO 155
<211> LENGTH: 24
<212> TYPE: DNA
<213> ORGANISM: Homo sapiens

<400> SEQUENCE: 155
ggattcacct ttgatgatta tgcc                                          24

<210> SEQ ID NO 156
<211> LENGTH: 8
<212> TYPE: PRT
<213> ORGANISM: Homo sapiens

<400> SEQUENCE: 156

```
Gly Phe Thr Phe Asp Asp Tyr Ala
1               5
```

<210> SEQ ID NO 157
<211> LENGTH: 24
<212> TYPE: DNA
<213> ORGANISM: Homo sapiens

<400> SEQUENCE: 157
gttaggtgga atggtggtat tata                                          24

<210> SEQ ID NO 158
<211> LENGTH: 8
<212> TYPE: PRT
<213> ORGANISM: Homo sapiens

<400> SEQUENCE: 158

```
Val Arg Trp Asn Gly Gly Ile Ile
1               5
```

<210> SEQ ID NO 159
<211> LENGTH: 57
<212> TYPE: DNA

```
<213> ORGANISM: Homo sapiens

<400> SEQUENCE: 159
gcaaaagata taggcgatgt tttgactggt tattatggag aatacggtat ggacgtc        57

<210> SEQ ID NO 160
<211> LENGTH: 19
<212> TYPE: PRT
<213> ORGANISM: Homo sapiens

<400> SEQUENCE: 160
```

Ala Lys Asp Ile Gly Asp Val Leu Thr Gly Tyr Tyr Gly Glu Tyr Gly
1               5                   10                  15

Met Asp Val

```
<210> SEQ ID NO 161
<211> LENGTH: 321
<212> TYPE: DNA
<213> ORGANISM: Homo sapiens

<400> SEQUENCE: 161
gacatccaga tgacccagtc tccatcctcc ctgtctgcat ctgtgggaga cagagtcacc      60
atcgcttgcc gggcaagtca gagcattacc acctatttaa attggtatca gcagaaacca    120
gggaaagccc ctaaactcct gatctatgct gcatccagtt tgcaaagtgg ggtcccatca    180
aggttcagtg gcagtggatc tgggacagat ttcactctca ccatcagtag tctgcaacct    240
gaagattttg caacttacta ctgtcaacag agttacattt ccccgtacac ttttggccag    300
gggaccaagc tggagatcaa a                                              321

<210> SEQ ID NO 162
<211> LENGTH: 107
<212> TYPE: PRT
<213> ORGANISM: Homo sapiens

<400> SEQUENCE: 162
```

Asp Ile Gln Met Thr Gln Ser Pro Ser Ser Leu Ser Ala Ser Val Gly
1               5                   10                  15

Asp Arg Val Thr Ile Ala Cys Arg Ala Ser Gln Ser Ile Thr Thr Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ile Ser Pro Tyr
                85                  90                  95

Thr Phe Gly Gln Gly Thr Lys Leu Glu Ile Lys
            100                 105

```
<210> SEQ ID NO 163
<211> LENGTH: 18
<212> TYPE: DNA
<213> ORGANISM: Homo sapiens

<400> SEQUENCE: 163
cagagcatta ccacctat                                                   18
```

```
<210> SEQ ID NO 164
<211> LENGTH: 6
<212> TYPE: PRT
<213> ORGANISM: Homo sapiens

<400> SEQUENCE: 164

Gln Ser Ile Thr Thr Tyr
1               5

<210> SEQ ID NO 165
<211> LENGTH: 9
<212> TYPE: DNA
<213> ORGANISM: Homo sapiens

<400> SEQUENCE: 165 gctgcatcc                                                                    9

<210> SEQ ID NO 166
<211> LENGTH: 3
<212> TYPE: PRT
<213> ORGANISM: Homo sapiens

<400> SEQUENCE: 166

Ala Ala Ser
1

<210> SEQ ID NO 167
<211> LENGTH: 27
<212> TYPE: DNA
<213> ORGANISM: Homo sapiens

<400> SEQUENCE: 167
caacagagtt acatttcccc gtacact                                               27

<210> SEQ ID NO 168
<211> LENGTH: 9
<212> TYPE: PRT
<213> ORGANISM: Homo sapiens

<400> SEQUENCE: 168

Gln Gln Ser Tyr Ile Ser Pro Tyr Thr
1               5

<210> SEQ ID NO 169
<211> LENGTH: 378
<212> TYPE: DNA
<213> ORGANISM: Homo sapiens

<400> SEQUENCE: 169
caggtgcagc tggtggagtc tgggggaggc gtggtccagc ctgggaagtc cctgagactc          60
tcctgtgcag cctctggatt caccttcagt aattatggca tacactgggt ccgccaggct         120
ccaggcaagg ggctggagtg ggtggcgatt atattatatg atggaagtaa tcaaacatat         180
gcagattccg tgaagggccg attcaccatt tccagagaca attccaaaaa cacgctgtat         240
cttcaaatga acaacctgag agctgaggac acggccgttt attactgtgc gagagatctt         300
gatctttgga gtggttatta tacaaacggg gacggtatgg acgtctgggg ccaagggacc         360
acggtcaccg tctcctca                                                       378

<210> SEQ ID NO 170
<211> LENGTH: 126
<212> TYPE: PRT
<213> ORGANISM: Homo sapiens
```

<400> SEQUENCE: 170

Gln Val Gln Leu Val Glu Ser Gly Gly Val Val Gln Pro Gly Lys
1               5                   10                  15

Ser Leu Arg Leu Ser Cys Ala Ala Ser Gly Phe Thr Phe Ser Asn Tyr
            20                  25                  30

Gly Ile His Trp Val Arg Gln Ala Pro Gly Lys Gly Leu Glu Trp Val
        35                  40                  45

Ala Ile Ile Leu Tyr Asp Gly Ser Asn Gln His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Asn Leu Arg Ala Glu Asp Thr Ala Val Tyr Tyr Cys
                85                  90                  95

Ala Arg Asp Leu Asp Leu Trp Ser Gly Tyr Tyr Thr Asn Gly Asp Gly
            100                 105                 110

Met Asp Val Trp Gly Gln Gly Thr Thr Val Thr Val Ser Ser
        115                 120                 125

<210> SEQ ID NO 171
<211> LENGTH: 24
<212> TYPE: DNA
<213> ORGANISM: Homo sapiens

<400> SEQUENCE: 171
ggattcacct tcagtaatta tggc                                          24

<210> SEQ ID NO 172
<211> LENGTH: 8
<212> TYPE: PRT
<213> ORGANISM: Homo sapiens

<400> SEQUENCE: 172

Gly Phe Thr Phe Ser Asn Tyr Gly
1               5

<210> SEQ ID NO 173
<211> LENGTH: 24
<212> TYPE: DNA
<213> ORGANISM: Homo sapiens

<400> SEQUENCE: 173
atattatatg atggaagtaa tcaa                                          24

<210> SEQ ID NO 174
<211> LENGTH: 8
<212> TYPE: PRT
<213> ORGANISM: Homo sapiens

<400> SEQUENCE: 174

Ile Leu Tyr Asp Gly Ser Asn Gln
1               5

<210> SEQ ID NO 175
<211> LENGTH: 57
<212> TYPE: DNA
<213> ORGANISM: Homo sapiens

<400> SEQUENCE: 175
gcgagagatc ttgatctttg gagtggttat tatacaaacg gggacggtat ggacgtc      57

<210> SEQ ID NO 176
<211> LENGTH: 19
<212> TYPE: PRT
<213> ORGANISM: Homo sapiens

<400> SEQUENCE: 176

```
Ala Arg Asp Leu Asp Leu Trp Ser Gly Tyr Tyr Thr Asn Gly Asp Gly
1               5                   10                  15

Met Asp Val
```

<210> SEQ ID NO 177
<211> LENGTH: 575
<212> TYPE: PRT
<213> ORGANISM: Homo sapiens

<400> SEQUENCE: 177

```
Met Trp Ser Leu Leu Leu Cys Gly Leu Ser Ile Ala Leu Pro Leu Ser
1               5                   10                  15

Val Thr Ala Asp Gly Cys Lys Asp Ile Phe Met Lys Asn Glu Ile Leu
            20                  25                  30

Ser Ala Ser Gln Pro Phe Ala Phe Asn Cys Thr Phe Pro Pro Ile Thr
        35                  40                  45

Ser Gly Glu Val Ser Val Thr Trp Tyr Lys Asn Ser Ser Lys Ile Pro
    50                  55                  60

Val Ser Lys Ile Ile Gln Ser Arg Ile His Gln Asp Glu Thr Trp Ile
65                  70                  75                  80

Leu Phe Leu Pro Met Glu Trp Gly Asp Ser Gly Val Tyr Gln Cys Val
                85                  90                  95

Ile Lys Gly Arg Asp Ser Cys His Arg Ile His Val Asn Leu Thr Val
            100                 105                 110

Phe Glu Lys His Trp Cys Asp Thr Ser Ile Gly Gly Leu Pro Asn Leu
        115                 120                 125

Ser Asp Glu Tyr Lys Gln Ile Leu His Leu Gly Lys Asp Asp Ser Leu
    130                 135                 140

Thr Cys His Leu His Phe Pro Lys Ser Cys Val Leu Gly Pro Ile Lys
145                 150                 155                 160

Trp Tyr Lys Asp Cys Asn Glu Ile Lys Gly Glu Arg Phe Thr Val Leu
                165                 170                 175

Glu Thr Arg Leu Leu Val Ser Asn Val Ser Ala Glu Asp Arg Gly Asn
            180                 185                 190

Tyr Ala Cys Gln Ala Ile Leu Thr His Ser Gly Lys Gln Tyr Glu Val
        195                 200                 205

Leu Asn Gly Ile Thr Val Ser Ile Thr Glu Arg Ala Gly Tyr Gly Gly
    210                 215                 220

Ser Val Pro Lys Ile Ile Tyr Pro Lys Asn His Ser Ile Glu Val Gln
225                 230                 235                 240

Leu Gly Thr Thr Leu Ile Val Asp Cys Asn Val Thr Asp Thr Lys Asp
                245                 250                 255

Asn Thr Asn Leu Arg Cys Trp Arg Val Asn Asn Thr Leu Val Asp Asp
            260                 265                 270

Tyr Tyr Asp Glu Ser Lys Arg Ile Arg Glu Gly Val Glu Thr His Val
        275                 280                 285

Ser Phe Arg Glu His Asn Leu Tyr Thr Val Asn Ile Thr Phe Leu Glu
    290                 295                 300

Val Lys Met Glu Asp Tyr Gly Leu Pro Phe Met Cys His Ala Gly Val
```

```
            305                 310                 315                 320
Ser Thr Ala Tyr Ile Ile Leu Gln Leu Pro Ala Pro Asp Phe Arg Ala
                325                 330                 335

Tyr Leu Ile Gly Gly Leu Ile Ala Leu Val Ala Val Ala Val Ser Val
                340                 345                 350

Val Tyr Ile Tyr Asn Ile Phe Lys Ile Asp Ile Val Leu Trp Tyr Arg
                355                 360                 365

Ser Ala Phe His Ser Thr Glu Thr Ile Val Asp Gly Lys Leu Tyr Asp
                370                 375                 380

Ala Tyr Val Leu Tyr Pro Lys Pro His Lys Glu Ser Gln Arg His Ala
385                 390                 395                 400

Val Asp Ala Leu Val Leu Asn Ile Leu Pro Glu Val Leu Glu Arg Gln
                405                 410                 415

Cys Gly Tyr Lys Leu Phe Ile Phe Gly Arg Asp Glu Phe Pro Gly Gln
                420                 425                 430

Ala Val Ala Asn Val Ile Asp Glu Asn Val Lys Leu Cys Arg Arg Leu
                435                 440                 445

Ile Val Ile Val Val Pro Glu Ser Leu Gly Phe Gly Leu Leu Lys Asn
                450                 455                 460

Leu Ser Glu Glu Gln Ile Ala Val Tyr Ser Ala Leu Ile Gln Asp Gly
465                 470                 475                 480

Met Lys Val Ile Leu Ile Glu Leu Glu Lys Ile Glu Asp Tyr Thr Val
                485                 490                 495

Met Pro Glu Ser Ile Gln Tyr Ile Lys Gln Lys His Gly Ala Ile Arg
                500                 505                 510

Trp His Gly Asp Phe Thr Glu Gln Ser Gln Cys Met Lys Thr Lys Phe
                515                 520                 525

Trp Lys Thr Val Arg Tyr His Met Pro Pro Arg Arg Cys Arg Pro Phe
                530                 535                 540

Pro Pro Val Gln Leu Leu Gln His Thr Pro Cys Tyr Arg Thr Ala Gly
545                 550                 555                 560

Pro Glu Leu Gly Ser Arg Arg Lys Lys Cys Thr Leu Thr Thr Gly
                565                 570                 575

<210> SEQ ID NO 178
<211> LENGTH: 570
<212> TYPE: PRT
<213> ORGANISM: Homo sapiens

<400> SEQUENCE: 178

Met Thr Leu Leu Trp Cys Val Val Ser Leu Tyr Phe Tyr Gly Ile Leu
1               5                   10                  15

Gln Ser Asp Ala Ser Glu Arg Cys Asp Asp Trp Gly Leu Asp Thr Met
                20                  25                  30

Arg Gln Ile Gln Val Phe Glu Asp Glu Pro Ala Arg Ile Lys Cys Pro
                35                  40                  45

Leu Phe Glu His Phe Leu Lys Phe Asn Tyr Ser Thr Ala His Ser Ala
                50                  55                  60

Gly Leu Thr Leu Ile Trp Tyr Trp Thr Arg Gln Asp Arg Asp Leu Glu
65              70                  75                  80

Glu Pro Ile Asn Phe Arg Leu Pro Glu Asn Arg Ile Ser Lys Glu Lys
                85                  90                  95

Asp Val Leu Trp Phe Arg Pro Thr Leu Leu Asn Asp Thr Gly Asn Tyr
                100                 105                 110
```

```
Thr Cys Met Leu Arg Asn Thr Thr Tyr Cys Ser Lys Val Ala Phe Pro
            115                 120                 125

Leu Glu Val Val Gln Lys Asp Ser Cys Phe Asn Ser Pro Met Lys Leu
        130                 135                 140

Pro Val His Lys Leu Tyr Ile Glu Tyr Gly Ile Gln Arg Ile Thr Cys
145                 150                 155                 160

Pro Asn Val Asp Gly Tyr Phe Pro Ser Ser Val Lys Pro Thr Ile Thr
                165                 170                 175

Trp Tyr Met Gly Cys Tyr Lys Ile Gln Asn Phe Asn Asn Val Ile Pro
            180                 185                 190

Glu Gly Met Asn Leu Ser Phe Leu Ile Ala Leu Ile Ser Asn Asn Gly
        195                 200                 205

Asn Tyr Thr Cys Val Val Thr Tyr Pro Glu Asn Gly Arg Thr Phe His
        210                 215                 220

Leu Thr Arg Thr Leu Thr Val Lys Val Val Gly Ser Pro Lys Asn Ala
225                 230                 235                 240

Val Pro Pro Val Ile His Ser Pro Asn Asp His Val Val Tyr Glu Lys
                245                 250                 255

Glu Pro Gly Glu Glu Leu Leu Ile Pro Cys Thr Val Tyr Phe Ser Phe
            260                 265                 270

Leu Met Asp Ser Arg Asn Glu Val Trp Trp Thr Ile Asp Gly Lys Lys
        275                 280                 285

Pro Asp Asp Ile Thr Ile Asp Val Thr Ile Asn Glu Ser Ile Ser His
        290                 295                 300

Ser Arg Thr Glu Asp Glu Thr Arg Thr Gln Ile Leu Ser Ile Lys Lys
305                 310                 315                 320

Val Thr Ser Glu Asp Leu Lys Arg Ser Tyr Val Cys His Ala Arg Ser
                325                 330                 335

Ala Lys Gly Glu Val Ala Lys Ala Ala Lys Val Lys Gln Lys Val Pro
            340                 345                 350

Ala Pro Arg Tyr Thr Val Glu Leu Ala Cys Gly Phe Gly Ala Thr Val
        355                 360                 365

Leu Leu Val Val Ile Leu Ile Val Val Tyr His Val Tyr Trp Leu Glu
        370                 375                 380

Met Val Leu Phe Tyr Arg Ala His Phe Gly Thr Asp Glu Thr Ile Leu
385                 390                 395                 400

Asp Gly Lys Glu Tyr Asp Ile Tyr Val Ser Tyr Ala Arg Asn Ala Glu
                405                 410                 415

Glu Glu Glu Phe Val Leu Leu Thr Leu Arg Gly Val Leu Glu Asn Glu
            420                 425                 430

Phe Gly Tyr Lys Leu Cys Ile Phe Asp Arg Asp Ser Leu Pro Gly Gly
        435                 440                 445

Ile Val Thr Asp Glu Thr Leu Ser Phe Ile Gln Lys Ser Arg Arg Leu
        450                 455                 460

Leu Val Val Leu Ser Pro Asn Tyr Val Leu Gln Gly Thr Gln Ala Leu
465                 470                 475                 480

Leu Glu Leu Lys Ala Gly Leu Glu Asn Met Ala Ser Arg Gly Asn Ile
                485                 490                 495

Asn Val Ile Leu Val Gln Tyr Lys Ala Val Lys Glu Thr Lys Val Lys
            500                 505                 510

Glu Leu Lys Arg Ala Lys Thr Val Leu Thr Val Ile Lys Trp Lys Gly
        515                 520                 525

Glu Lys Ser Lys Tyr Pro Gln Gly Arg Phe Trp Lys Gln Leu Gln Val
```

Ala Met Pro Val Lys Lys Ser Pro Arg Arg Ser Ser Asp Glu Gln
545                 550                 555                 560

Gly Leu Ser Tyr Ser Ser Leu Lys Asn Val
                565                 570

<210> SEQ ID NO 179
<211> LENGTH: 1338
<212> TYPE: DNA
<213> ORGANISM: Homo sapiens

<400> SEQUENCE: 179

```
gaagtgcagc tggtggagtc tgggggaggc ttggtgcagc ctggcaggtc cctgagactc      60
tcctgtgcgg cctctggatt cacctttgat gattatgcca tacactgggt ccggcaagct     120
ccagggaagg gcctggagtg ggtctcagtt atcagttgga atagtgatat cataggctat     180
gcggactctg tgaagggccg attcaccgtc tccagagaca acgccaagaa ctccctgtat     240
ctgcaaatga atagtctgag aactgaggac acggccttgt attactgtgc aaaaggatat     300
aactggaact tctttgacta ttggggccag ggaaccctgg tcaccgtctc ctcagcctcc     360
accaagggcc catcggtctt ccccctggcg ccctgctcca ggagcacctc cgagagcaca     420
gccgccctgg gctgcctggt caaggactac ttccccgaac cggtgacggt gtcgtggaac     480
tcaggcgccc tgaccagcgg cgtgcacacc ttcccggctg tcctacagtc ctcaggactc     540
tactccctca gcagcgtggt gaccgtgccc tccagcagct gggcacgaa gacctacacc      600
tgcaacgtag atcacaagcc cagcaacacc aaggtggaca gagagttga gtccaaatat      660
ggtccccat gcccaccctg cccagcacct gagttcctgg ggggaccatc agtcttcctg      720
ttccccccaa aacccaagga cactctcatg atctcccgga cccctgaggt cacgtgcgtg     780
gtggtggacg tgagccagga agaccccgag gtccagttca actggtacgt ggatggcgtg     840
gaggtgcata atgccaagac aaagccgcgg gaggagcagt tcaacagcac gtaccgtgtg     900
gtcagcgtcc tcaccgtcct gcaccaggac tggctgaacg gcaaggagta caagtgcaag     960
gtctccaaca aaggcctccc gtcctccatc gagaaaacca tctccaaagc caaagggcag    1020
ccccgagagc cacaggtgta caccctgccc ccatcccagg aggagatgac caagaaccag    1080
gtcagcctga cctgcctggt caaaggcttc taccccagcg acatcgccgt ggagtgggag    1140
agcaatgggc agccggagaa caactacaag accacgcctc ccgtgctgga ctccgacggc    1200
tccttcttcc tctacagcag gctcaccgtg gacaagagca ggtggcagga ggggaatgtc    1260
ttctcatgct ccgtgatgca tgaggctctg cacaaccact acacacagaa gtccctctcc    1320
ctgtctctgg gtaaatga                                                  1338
```

<210> SEQ ID NO 180
<211> LENGTH: 445
<212> TYPE: PRT
<213> ORGANISM: Homo sapiens

<400> SEQUENCE: 180

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Ile His Trp Val Arg Gln Ala Pro Gly Lys Gly Leu Glu Trp Val
        35                  40                  45

Ser Val Ile Ser Trp Asn Ser Asp Ile Ile Gly Tyr Ala Asp Ser Val
 50                  55                  60

Lys Gly Arg Phe Thr Val Ser Arg Asp Asn Ala Lys Asn Ser Leu Tyr
 65                  70                  75                  80

Leu Gln Met Asn Ser Leu Arg Thr Glu Asp Thr Ala Leu Tyr Tyr Cys
                 85                  90                  95

Ala Lys Gly Tyr Asn Trp Asn Phe Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
210                 215                 220

Pro Pro Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Tyr Arg Val Val Ser Val Leu
290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
            420                 425                 430

His Tyr Thr Gln Lys Ser Leu Ser Leu Ser Leu Gly Lys
        435                 440                 445

<210> SEQ ID NO 181
<211> LENGTH: 642
<212> TYPE: DNA

<213> ORGANISM: Homo sapiens

<400> SEQUENCE: 181

```
gaaattgtgt tgacgcagtc tccagccacc ctgtctttat ctccagggga aagagccacc    60
ctctcctgca gggccagtca gagtgttagc agctacttag cctggtacca acagaaacct   120
ggccaggctc ccaggctcct catctataat gcagcaaaca gggccactga catcccagcc   180
aggttcagtg gcagtgggtc tgggacagac ttcactctca ccatcagcag cctagagcct   240
gaagattttg cagtttatta ctgtcagcag cgtagcaact ggcctctcac tttcggcgga   300
gggaccaagg tggagatcaa acgaactgtg gctgcaccat ctgtcttcat cttcccgcca   360
tctgatgagc agttgaaatc tggaactgcc tctgttgtgt gcctgctgaa taacttctat   420
cccagagagg ccaaagtaca gtggaaggtg gataacgccc tccaatcggg taactcccag   480
gagagtgtca cagagcagga cagcaaggac agcacctaca gcctcagcag caccctgacg   540
ctgagcaaag cagactacga gaaacacaaa gtctacgcct gcgaagtcac ccatcagggc   600
ctgagctcgc ccgtcacaaa gagcttcaac aggggagagt gt                      642
```

<210> SEQ ID NO 182
<211> LENGTH: 214
<212> TYPE: PRT
<213> ORGANISM: Homo sapiens

<400> SEQUENCE: 182

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asn Ala Ala Asn Arg Ala Thr Asp Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 183
<211> LENGTH: 1338

```
<212> TYPE: DNA
<213> ORGANISM: Homo sapiens

<400> SEQUENCE: 183
gaagtgcagc tggtggagtc tgggggaggc ttggtacagc ctggcaggtc cctgagactc      60
tcctgtgcag cctctggatt cacctttgat gattatgcca tgcactgggt ccggcaaact     120
ccagggaagg gcctggagtg ggtctcagtt attagttgga atagtgatgt catagcctat     180
tcggactctg tgaagggccg cttcaccatt tccagagaca cgccaagaa ctccctgtat      240
ctgcaaatga acagtctggg aactgaggac acggccttat attactgtgc aaaaggccat     300
aactggaact tctttgacta ttggggccag ggaaccctgg tcaccgtctc ctcagcctcc     360
accaagggcc catcggtctt ccccctggcg ccctgctcca ggagcacctc cgagagcaca     420
gccgccctgg gctgcctggt caaggactac ttccccgaac cggtgacggt gtcgtggaac     480
tcaggcgccc tgaccagcgg cgtgcacacc ttcccggctg tcctacagtc ctcaggactc     540
tactccctca gcagcgtggt gaccgtgccc tccagcagct gggcacgaa gacctacacc      600
tgcaacgtag atcacaagcc cagcaacacc aaggtggaca agagagttga gtccaaatat     660
ggtccccat gcccaccctg cccagcacct gagttcctgg ggggaccatc agtcttcctg      720
ttcccccca aacccaagga cactctcatg atctcccgga cccctgaggt cacgtgcgtg      780
gtggtggacg tgagccagga agaccccgag gtccagttca actggtacgt ggatggcgtg     840
gaggtgcata atgccaagac aaagccgcgg gaggagcagt tcaacagcac gtaccgtgtg     900
gtcagcgtcc tcaccgtcct gcaccaggac tggctgaacg gcaaggagta caagtgcaag     960
gtctccaaca aaggcctccc gtcctccatc gagaaaacca tctccaaagc caaagggcag    1020
ccccgagagc cacaggtgta caccctgccc ccatcccagg aggagatgac caagaaccag    1080
gtcagcctga cctgcctggt caaaggcttc taccccagcg acatcgccgt ggagtgggag    1140
agcaatgggc agccggagaa caactacaag accacgcctc ccgtgctgga ctccgacggc    1200
tccttcttcc tctacagcag gctcaccgtg gacaagagca ggtggcagga ggggaatgtc    1260
ttctcatgct ccgtgatgca tgaggctctg cacaaccact acacacagaa gtccctctcc    1320
ctgtctctgg gtaaatga                                                  1338

<210> SEQ ID NO 184
<211> LENGTH: 445
<212> TYPE: PRT
<213> ORGANISM: Homo sapiens

<400> SEQUENCE: 184

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Thr Pro Gly Lys Gly Leu Glu Trp Val
        35                  40                  45

Ser Val Ile Ser Trp Asn Ser Asp Val Ile Ala Tyr Ser Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Gly Thr Glu Asp Thr Ala Leu Tyr Tyr Cys
                85                  90                  95

Ala Lys Gly His Asn Trp Asn Phe Phe Asp Tyr Trp Gly Gln Gly Thr
            100                 105                 110
```

Leu Val Thr Val Ser Ser Ala Ser Thr Lys Gly Pro Ser Val Phe Pro
                115                 120                 125

Leu Ala Pro Cys Ser Arg Ser Thr Ser Glu Ser Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
        180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
        210                 215                 220

Pro Pro Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
                260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Tyr Arg Val Val Ser Val Leu
        290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
                340                 345                 350

Gln Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
        370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
                420                 425                 430

His Tyr Thr Gln Lys Ser Leu Ser Leu Ser Leu Gly Lys
        435                 440                 445

<210> SEQ ID NO 185
<211> LENGTH: 642
<212> TYPE: DNA
<213> ORGANISM: Homo sapiens

<400> SEQUENCE: 185
gaaattgtgt tgacacagtc tccagccacc ctgtctttgt ctccaggaga aagagccacc      60
ctctcctgca gggccagtca gagtgttagc agctacttag cctggtacca acagaaacct    120
ggccaggctc ccaggctcct catctataat gtagccaaca gggccacaga catcccagcc    180
aggttcagtg gcagtgggtc tgggacagac ttcactctca ccatcagcgg cctagagcct    240

| | |
|---|---|
| gaagattttg cagtttattt ctgtcagcag cgtagcaact ggcctctcac tttcggcgga | 300 |
| gggaccaagg tggagatcaa acgaactgtg gctgcaccat ctgtcttcat cttcccgcca | 360 |
| tctgatgagc agttgaaatc tggaactgcc tctgttgtgt gcctgctgaa taacttctat | 420 |
| cccagagagc ccaaagtaca gtggaaggtg gataacgccc tccaatcggg taactcccag | 480 |
| gagagtgtca cagagcagga cagcaaggac agcacctaca gcctcagcag caccctgacg | 540 |
| ctgagcaaag cagactacga aaacacaaa gtctacgcct gcgaagtcac ccatcagggc | 600 |
| ctgagctcgc ccgtcacaaa gagcttcaac aggggagagt gt | 642 |

<210> SEQ ID NO 186
<211> LENGTH: 214
<212> TYPE: PRT
<213> ORGANISM: Homo sapiens

<400> SEQUENCE: 186

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asn Val Ala Asn Arg Ala Thr Asp Ile Pro Ala Arg Phe Ser Gly
    50                  55                  60

Ser Gly Ser Gly Thr Asp Phe Thr Leu Thr Ile Ser Gly Leu Glu Pro
65                  70                  75                  80

Glu Asp Phe Ala Val Tyr Phe Cys Gln Gln Arg Ser Asn Trp Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 187
<211> LENGTH: 1338
<212> TYPE: DNA
<213> ORGANISM: Homo sapiens

<400> SEQUENCE: 187

| | |
|---|---|
| gaagtgcagc tggtggagtc tgggggaggc ttggtacagc ctggcaggtc cctgagactc | 60 |
| tcctgtacag cctctggatt caccttggat gattatgcca tacactgggt ccggcaatct | 120 |
| ccagggaagg gcctggagtg ggtctcagtt atcagttgga atagtgatgt cataggctat | 180 |

```
gcggactctg tgaagggccg attcaccatc tccagagaca acgccaagaa ctccctgtat     240
ctgcagatga atagtctgag agctgaggac acggccttgt attactgtgc aaaaggatat     300
aactggaact tctttgacta ttggggccag ggaaccctgg tcaccgtctc ctcagcctcc     360
accaagggcc catcggtctt ccccctggcg ccctgctcca ggagcacctc cgagagcaca     420
gccgccctgg gctgcctggt caaggactac ttccccgaac cggtgacggt gtcgtggaac     480
tcaggcgccc tgaccagcgg cgtgcacacc ttcccggctg tcctacagtc ctcaggactc     540
tactccctca gcagcgtggt gaccgtgccc tccagcagct gggcacgaa gacctacacc      600 tgcaacgtag atcacaagcc cagcaacacc aaggtggaca gagagttga gtccaaatat      660 ggtcccccat gcccaccctg cccagcacct gagttcctgg ggggaccatc agtcttcctg     720
ttccccccaa acccaagga cactctcatg atctcccgga cccctgaggt cacgtgcgtg      780
gtggtggacg tgagccagga agaccccgag gtccagttca actggtacgt ggatggcgtg     840
gaggtgcata atgccaagac aaagccgcgg gaggagcagt tcaacagcac gtaccgtgtg     900
gtcagcgtcc tcaccgtcct gcaccaggac tggctgaacg gcaaggagta caagtgcaag     960
gtctccaaca aaggcctccc gtcctccatc gagaaaacca tctccaaagc caaagggcag    1020
ccccgagagc cacaggtgta caccctgccc ccatcccagg aggagatgac caagaaccag    1080
gtcagcctga cctgcctggt caaaggcttc taccccagcg acatcgccgt ggagtgggag    1140
agcaatgggc agccggagaa caactacaag accacgcctc ccgtgctgga ctccgacggc    1200
tccttcttcc tctacagcag gctcaccgtg gacaagagca ggtggcagga ggggaatgtc    1260
ttctcatgct ccgtgatgca tgaggctctg cacaaccact acacacagaa gtccctctcc    1320
ctgtctctgg gtaaatga                                                  1338
```

<210> SEQ ID NO 188
<211> LENGTH: 445
<212> TYPE: PRT
<213> ORGANISM: Homo sapiens

<400> SEQUENCE: 188

```
Glu Val Gln Leu Val Glu Ser Gly Gly Gly Leu Val Gln Pro Gly Arg
1               5                   10                  15

Ser Leu Arg Leu Ser Cys Thr Ala Ser Gly Phe Thr Phe Asp Asp Tyr
            20                  25                  30

Ala Ile His Trp Val Arg Gln Ser Pro Gly Lys Gly Leu Glu Trp Val
        35                  40                  45

Ser Val Ile Ser Trp Asn Ser Asp Val Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Gly Tyr Asn Trp Asn Phe Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
```

```
                165                 170                 175
Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
            195                 200                 205

Asn Thr Lys Val Asp Lys Arg Val Glu Ser Lys Tyr Gly Pro Pro Cys
        210                 215                 220

Pro Pro Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
            420                 425                 430

His Tyr Thr Gln Lys Ser Leu Ser Leu Ser Leu Gly Lys
        435                 440                 445

<210> SEQ ID NO 189
<211> LENGTH: 642
<212> TYPE: DNA
<213> ORGANISM: Homo sapiens

<400> SEQUENCE: 189
gaaattgtgt tgacgcagtc tccagccacc ctgtctttat ctccagggga aagagccacc     60
ctctcctgca gggccagtca gagtgttagc agctacttag cctggtacca acagaaacct    120
ggccaggctc ccaggctcct catctataat gcagcaaaca gggccactga catcccagcc    180
aggttcagtg gcagtgggtc tgggacagac ttcactctca ccatcagcag cctagagcct    240
gaagattttg cagtttatta ctgtcagcag cgtagcaact ggcctctcac tttcggcgga    300
gggaccaagg tggagatcaa acgaactgtg gctgcaccat ctgtcttcat cttcccgcca    360
tctgatgagc agttgaaatc tggaactgcc tctgttgtgt gcctgctgaa taacttctat    420
cccagagagg ccaaagtaca gtggaaggtg gataacgccc tccaatcggg taactcccag    480
gagagtgtca cagagcagga cagcaaggac agcacctaca gcctcagcag caccctgacg    540
```
ctgagcaaag cagactacga gaaacacaaa gtctacgcct gcgaagtcac ccatcagggc    600
ctgagctcgc ccgtcacaaa gagcttcaac aggggagagt gt    642

<210> SEQ ID NO 190
<211> LENGTH: 214
<212> TYPE: PRT
<213> ORGANISM: Homo sapiens

<400> SEQUENCE: 190

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asn Ala Ala Asn Arg Ala Thr Asp Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 191
<211> LENGTH: 1338
<212> TYPE: DNA
<213> ORGANISM: Homo sapiens

<400> SEQUENCE: 191
gaagtgcagc tggtggagtc tgggggagac ttggtacagc ctggcaggtc cctgagactc    60
tcctgtgcag cctctggatt cacctttgat gattatgcca tgcactgggt ccggcaagct   120
ccagggaagg gcctggaatg ggtctcagtt attagttgga atagtgatgt catagcctat   180
tcggactctg tgaagggccg attcaccatc tccagagaca acgccaagaa ctccctgtat   240
ctgcaaatga acagtctgag aactgaggac acggccttat attactgtac aaaaggccat   300
aagtggagct tctttgacta ttggggccag ggaaccctgg tcaccgtctc ctcagcctcc   360
accaagggcc catcggtctt ccccctggcg ccctgctcca ggagcacctc cgagagcaca   420
gccgccctgg gctgcctggt caaggactac ttccccgaac cggtgacggt gtcgtggaac   480
tcaggcgccc tgaccagcgg cgtgcacacc ttcccggctg tcctacagtc ctcaggactc   540

```
tactccctca gcagcgtggt gaccgtgccc tccagcagct tgggcacgaa gacctacacc    600
tgcaacgtag atcacaagcc cagcaacacc aaggtggaca agagagttga gtccaaatat    660
ggtcccccat gcccaccctg cccagcacct gagttcctgg ggggaccatc agtcttcctg    720
ttccccccaa aacccaagga cactctcatg atctcccgga cccctgaggt cacgtgcgtg    780
gtggtggacg tgagccagga agaccccgag gtccagttca actggtacgt ggatggcgtg    840
gaggtgcata atgccaagac aaagccgcgg gaggagcagt tcaacagcac gtaccgtgtg    900
gtcagcgtcc tcaccgtcct gcaccaggac tggctgaacg gcaaggagta caagtgcaag    960
gtctccaaca aaggcctccc gtcctccatc gagaaaacca tctccaaagc caagggcag   1020 ccccgagagc cacaggtgta caccctgccc ccatcccagg aggagatgac caagaaccag   1080
gtcagcctga cctgcctggt caaaggcttc taccccagcg acatcgccgt ggagtgggag   1140
agcaatgggc agccggagaa caactacaag accacgcctc ccgtgctgga ctccgacggc   1200
tccttcttcc tctacagcag gctcaccgtg gacaagagca ggtggcagga ggggaatgtc   1260
ttctcatgct ccgtgatgca tgaggctctg cacaaccact acacacagaa gtccctctcc   1320
ctgtctctgg gtaaatga                                                 1338
```

<210> SEQ ID NO 192
<211> LENGTH: 445
<212> TYPE: PRT
<213> ORGANISM: Homo sapiens

<400> SEQUENCE: 192

```
Glu Val Gln Leu Val Glu Ser Gly Gly Asp Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Val Ile Ser Trp Asn Ser Asp Val Ile Ala Tyr Ser Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Thr Glu Asp Thr Ala Leu Tyr Tyr Cys
                85                  90                  95

Thr Lys Gly His Lys Trp Ser Phe Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
    210                 215                 220
```

| | | | | | | | | | | | | |
|---|---|---|---|---|---|---|---|---|---|---|---|---|
|Pro|Pro|Cys|Pro|Ala|Pro|Glu|Phe|Leu|Gly|Gly|Pro|Ser|Val|Phe|Leu|
|225| | | |230| | | | |235| | | | |240| |

Pro Pro Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
            275                 280                 285

Pro Arg Glu Glu Gln Phe Asn Ser Thr Tyr Arg Val Val Ser Val Leu
290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
            420                 425                 430

His Tyr Thr Gln Lys Ser Leu Ser Leu Ser Leu Gly Lys
            435                 440                 445

<210> SEQ ID NO 193
<211> LENGTH: 642
<212> TYPE: DNA
<213> ORGANISM: Homo sapiens

<400> SEQUENCE: 193

```
gaaattgtgt tgacacagtc tccagccacc ctgtctttgt ctccagggga aagagccacc    60
ctctcctgca gggccagtca gagtattagc agctacttag cctggtacca acagaaacct   120
ggccaggctc ccagactcct catctttaat gtagccaaca gggccactga catcccagcc   180
aggttcagtg gcagtgggtc tgggacagac ttcactctca ccatcagcag cctagagcct   240
gaagattttg cagtttatta ctgtcagcag cgtagcaact ggcctctcac tttcggcgga   300
gggaccaagg tggagatcaa acgaactgtg gctgcaccat ctgtcttcat cttcccgcca   360
tctgatgagc agttgaaatc tggaactgcc tctgttgtgt gcctgctgaa taacttctat   420
cccagagagg ccaaagtaca gtggaaggtg gataacgccc tccaatcggg taactcccag   480
gagagtgtca cagagcagga cagcaaggac agcacctaca gcctcagcag caccctgacg   540
ctgagcaaag cagactacga gaaacacaaa gtctacgcct gcgaagtcac ccatcagggc   600
ctgagctcgc ccgtcacaaa gagcttcaac aggggagagt gt                     642
```

<210> SEQ ID NO 194
<211> LENGTH: 214
<212> TYPE: PRT
<213> ORGANISM: Homo sapiens

<400> SEQUENCE: 194

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Ile Ser Ser Tyr
            20                  25                  30

Leu Ala Trp Tyr Gln Gln Lys Pro Gly Gln Ala Pro Arg Leu Leu Ile
        35                  40                  45

Phe Asn Val Ala Asn Arg Ala Thr Asp Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 195
<211> LENGTH: 1323
<212> TYPE: DNA
<213> ORGANISM: Homo sapiens

<400> SEQUENCE: 195

```
gaggtgcagc tggtggagtc tgggggaggc ttggttcagc ctggggggtc cctgagactc      60
tcctgcgcag cctctggatt cacctttagc gactatgcca tgagctgggt ccgccaggct     120
ccggggaagg gctggagtg gtctcaggt attagtggaa atggtggtga cacatactac     180
ggagacttcg tgaagggccg gttcaccatc tccagagaca attccaagaa cacgctgtat     240
ctgcaaatga acagcctgag aggcgaggac acggccgcat atttctgtgt gatagatctt     300
gactattggg gtcagggaac cctggtcacc gtctcctcag cctccaccaa gggcccatcg     360
gtcttccccc tggcgccctg ctccaggagc acctccgaga gcacagccgc cctgggctgc     420
ctggtcaagg actacttccc cgaaccggtg acggtgtcgt ggaactcagg cgccctgacc     480
agcggcgtgc acaccttccc ggctgtccta cagtcctcag gactctactc cctcagcagc     540
gtggtgaccg tgccctccag cagcttgggc acgaagacct acacctgcaa cgtagatcac     600
aagcccagca acaccaaggt ggacaagaga gttgagtcca aatatggtcc cccatgccca     660
ccctgcccag cacctgagtt cctggggggga ccatcagtct tcctgttccc cccaaaaccc     720
aaggacactc tcatgatctc ccggacccct gaggtcacgt gcgtggtggt ggacgtgagc     780
caggaagacc ccgaggtcca gttcaactgg tacgtggatg gcgtggaggt gcataatgcc     840
```

```
aagacaaagc cgcgggagga gcagttcaac agcacgtacc gtgtggtcag cgtcctcacc      900
gtcctgcacc aggactggct gaacggcaag gagtacaagt gcaaggtctc caacaaaggc      960
ctcccgtcct ccatcgagaa aaccatctcc aaagccaaag ggcagccccg agagccacag     1020
gtgtacaccc tgcccccatc ccaggaggag atgaccaaga accaggtcag cctgacctgc     1080
ctggtcaaag gcttctaccc cagcgacatc gccgtggagt gggagagcaa tgggcagccg     1140
gagaacaact acaagaccac gcctcccgtg ctggactccg acggctcctt cttcctctac     1200
agcaggctca ccgtggacaa gagcaggtgg caggagggga atgtcttctc atgctccgtg     1260
atgcatgagg ctctgcacaa ccactacaca cagaagtccc tctccctgtc tctgggtaaa     1320
tga                                                                  1323
```

<210> SEQ ID NO 196
<211> LENGTH: 440
<212> TYPE: PRT
<213> ORGANISM: Homo sapiens

<400> SEQUENCE: 196

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Ala Met Ser Trp Val Arg Gln Ala Pro Gly Lys Gly Leu Glu Trp Val
        35                  40                  45

Ser Gly Ile Ser Gly Asn Gly Gly Asp Thr Tyr Tyr Gly Asp Phe Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Gly Glu Asp Thr Ala Ala Tyr Phe Cys
                85                  90                  95

Val Ile Asp Leu Asp Tyr Trp Gly Gln Gly Thr Leu Val Thr Val Ser
            100                 105                 110

Ser Ala Ser Thr Lys Gly Pro Ser Val Phe Pro Leu Ala Pro Cys Ser
        115                 120                 125

Arg Ser Thr Ser Glu Ser Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Lys
            180                 185                 190

Thr Tyr Thr Cys Asn Val Asp His Lys Pro Ser Asn Thr Lys Val Asp
        195                 200                 205

Lys Arg Val Glu Ser Lys Tyr Gly Pro Pro Cys Pro Pro Cys Pro Ala
    210                 215                 220

Pro Glu Phe Leu Gly Gly Pro Ser Val Phe Leu Phe Pro Pro Lys Pro
225                 230                 235                 240

Lys Asp Thr Leu Met Ile Ser Arg Thr Pro Glu Val Thr Cys Val Val
                245                 250                 255

Val Asp Val Ser Gln Glu Asp Pro Glu Val Gln Phe Asn Trp Tyr Val
            260                 265                 270

Asp Gly Val Glu Val His Asn Ala Lys Thr Lys Pro Arg Glu Glu Gln
        275                 280                 285
```

```
Phe Asn Ser Thr Tyr Arg Val Ser Val Leu Thr Val Leu His Gln
            290                 295                 300

Asp Trp Leu Asn Gly Lys Glu Tyr Lys Cys Lys Val Ser Asn Lys Gly
305                 310                 315                 320

Leu Pro Ser Ser Ile Glu Lys Thr Ile Ser Lys Ala Lys Gly Gln Pro
                325                 330                 335

Arg Glu Pro Gln Val Tyr Thr Leu Pro Pro Ser Gln Glu Met Thr
            340                 345                 350

Lys Asn Gln Val Ser Leu Thr Cys Leu Val Lys Gly Phe Tyr Pro Ser
            355                 360                 365

Asp Ile Ala Val Glu Trp Glu Ser Asn Gly Gln Pro Glu Asn Asn Tyr
    370                 375                 380

Lys Thr Thr Pro Pro Val Leu Asp Ser Asp Gly Ser Phe Phe Leu Tyr
385                 390                 395                 400

Ser Arg Leu Thr Val Asp Lys Ser Arg Trp Gln Glu Gly Asn Val Phe
                405                 410                 415

Ser Cys Ser Val Met His Glu Ala Leu His Asn His Tyr Thr Gln Lys
            420                 425                 430

Ser Leu Ser Leu Ser Leu Gly Lys
            435                 440

<210> SEQ ID NO 197
<211> LENGTH: 642
<212> TYPE: DNA
<213> ORGANISM: Homo sapiens

<400> SEQUENCE: 197
gacatccaga tgacccagtc tccttccacc ctgtctgcat ctgaaggaga cagagtcacc      60
atcacttgcc gggccagtca gagtattagt agctggttgg cctggtatca acagaaacca    120
ggaaaagccc ctaggctcct gatctataag gcgtctattt taggagatgg ggtcccatca    180
aggttcagcg gcagtggatc tgggacagaa ttcactctca ccatcagcag cctgcagcct    240
gatgattttg ctacttatta ctgccaccag tataatagtt atttgtggac gttcggccaa    300
gggaccaagg tggaaatcaa acgaactgtg gctgcaccat ctgtcttcat cttcccgcca    360
tctgatgagc agttgaaatc tggaactgcc tctgttgtgt gcctgctgaa taacttctat    420
cccagagagg ccaaagtaca gtggaaggtg gataacgccc tccaatcggg taactcccag    480
gagagtgtca cagagcagga cagcaaggac agcacctaca gcctcagcag caccctgacg    540
ctgagcaaag cagactacga gaaacacaaa gtctacgcct gcgaagtcac ccatcagggc    600
ctgagctcgc ccgtcacaaa gagcttcaac aggggagagt gt                        642

<210> SEQ ID NO 198
<211> LENGTH: 214
<212> TYPE: PRT
<213> ORGANISM: Homo sapiens

<400> SEQUENCE: 198

Asp Ile Gln Met Thr Gln Ser Pro Ser Thr Leu Ser Ala Ser Glu Gly
1                   5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Arg Leu Leu Ile
        35                  40                  45

Tyr Lys Ala Ser Ile Leu Gly Asp Gly Val Pro Ser Arg Phe Ser Gly
```

```
                    50                  55                  60
Ser Gly Ser Gly Thr Glu Phe Thr Leu Thr Ile Ser Ser Leu Gln Pro
 65                  70                  75                  80

Asp Asp Phe Ala Thr Tyr Tyr Cys His Gln Tyr Asn Ser Tyr Leu Trp
                 85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 199
<211> LENGTH: 1347
<212> TYPE: DNA
<213> ORGANISM: Homo sapiens

<400> SEQUENCE: 199

```
caggtgcagc tgcaggagtc gggcccagga ctggtgaagc cttcacagac cctgtccctc    60
acctgcactg tctctggtgg ctccatcagc agtgctgatt actattggag ctggatccgc   120
cagcacccag ggaagggcct ggagtggatt ggatccatct attatactgg gagtacttac   180
tacaacccgt ccctcaagag tcgacttacc atatcaatag acacgtctga gaaccagttc   240
tctttgaaac tgacctctct gactgccgcg gacacggccg tgtattactg tgcgagcgag   300
gaggctaact ggggatccca ctttgactcc tggggccagg gaaccctggt caccgtctcc   360
tcagcctcca ccaagggccc atcggtcttc cccctggcgc cctgctccag gagcacctcc   420
gagagcacag ccgccctggg ctgcctggtc aaggactact ccccgaacc ggtgacggtg   480
tcgtggaact caggcgccct gaccagcggc gtgcacacct tcccggctgt cctacagtcc   540
tcaggactct actccctcag cagcgtggtg accgtgccct ccagcagctt gggcacgaag   600
acctacacct gcaacgtaga tcacaagccc agcaacacca aggtggacaa gagagttgag   660
tccaaatatg gtcccccatg cccaccctgc ccagcacctg agttcctggg gggaccatca   720
gtcttcctgt tccccccaaa acccaaggac actctcatga tctcccggac ccctgaggtc   780
acgtgcgtgg tggtggacgt gagccaggaa gaccccgagg tccagttcaa ctggtacgtg   840
gatggcgtgg aggtgcataa tgccaagaca aagccgcggg aggagcagtt caacagcacg   900
taccgtgtgg tcagcgtcct caccgtcctg caccaggact ggctgaacgg caaggagtac   960
aagtgcaagg tctccaacaa aggcctcccg tcctccatcg agaaaaccat ctccaaagcc  1020
aaagggcagc cccgagagcc acaggtgtac accctgcccc catcccagga ggagatgacc  1080
aagaaccagg tcagcctgac ctgcctggtc aaaggcttct accccagcga catcgccgtg  1140
gagtgggaga gcaatgggca gccggagaac aactacaaga ccacgcctcc cgtgctggac  1200
```

```
tccgacggct ccttcttcct ctacagcagg ctcaccgtgg acaagagcag gtggcaggag    1260
gggaatgtct tctcatgctc cgtgatgcat gaggctctgc acaaccacta cacacagaag    1320
tccctctccc tgtctctggg taaatga                                       1347
```

<210> SEQ ID NO 200
<211> LENGTH: 448
<212> TYPE: PRT
<213> ORGANISM: Homo sapiens

<400> SEQUENCE: 200

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Ala
            20                  25                  30

Asp Tyr Tyr Trp Ser Trp Ile Arg Gln His Pro Gly Lys Gly Leu Glu
        35                  40                  45

Trp Ile Gly Ser Ile Tyr Tyr Thr Gly Ser Thr Tyr Tyr Asn Pro Ser
    50                  55                  60

Leu Lys Ser Arg Leu Thr Ile Ser Ile Asp Thr Ser Glu Asn Gln Phe
65                  70                  75                  80

Ser Leu Lys Leu Thr Ser Leu Thr Ala Ala Asp Thr Ala Val Tyr Tyr
                85                  90                  95

Cys Ala Ser Glu Glu Ala Asn Trp Gly Ser His Phe Asp Ser Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys Tyr Gly
    210                 215                 220

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
```

```
             340                 345                 350
Pro Pro Ser Gln Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly Lys
        435                 440                 445
```

<210> SEQ ID NO 201
<211> LENGTH: 645
<212> TYPE: DNA
<213> ORGANISM: Homo sapiens

<400> SEQUENCE: 201

```
gacatccaga tgacccagtc tccatcctcc ctgtctgcat ctgtaggaga cagagtcacc      60
atcacttgcc gggcaagtca gagcattgac aacttttttaa attggtatca gcagaaacca   120
gggaaagccc ctaagctcct gatctatgct gcatccagtt tgcaaagtgg ggtcccatca   180
aggttcagtg cagtggatc tgggacagat ttcactctca ccatcagcag tctgcaacct   240
gaagattttg catcttacta ctgtcaacat agtcacagtg cccatccgat caccttcggc   300
caagggacac gactggagat taacgaact gtggctgcac catctgtctt catcttcccg   360
ccatctgatg agcagttgaa atctggaact gcctctgttg tgtgcctgct gaataacttc   420
tatcccagag aggccaaagt acagtggaag gtggataacg ccctccaatc gggtaactcc   480
caggagagtg tcacagagca ggacagcaag gacagcacct acagcctcag cagcaccctg   540
acgctgagca aagcagacta cgagaaacac aaagtctacg cctgcgaagt cacccatcag   600
ggcctgagct cgcccgtcac aaagagcttc aacaggggag agtgt                    645
```

<210> SEQ ID NO 202
<211> LENGTH: 215
<212> TYPE: PRT
<213> ORGANISM: Homo sapiens

<400> SEQUENCE: 202

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Asp Asn Phe
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Ser Tyr Tyr Cys Gln His Ser His Ser Ala His Pro
                85                  90                  95

Ile Thr Phe Gly Gln Gly Thr Arg Leu Glu Ile Lys Arg Thr Val Ala
            100                 105                 110
```

```
Ala Pro Ser Val Phe Ile Phe Pro Ser Asp Glu Gln Leu Lys Ser
            115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 203
<211> LENGTH: 1347
<212> TYPE: DNA
<213> ORGANISM: Homo sapiens

<400> SEQUENCE: 203
cagctgcagc tgcaggagtc gggcccagga ctggtgaagc cttcggagac cctgtccctc      60
acctgcactg tctctggtgg ctccatcagc agtagtaatt actactgggg ctggatccgc     120
cagcccccag ggaagagact ggagtggatt gggagtatct attatagtgg gagcacctac     180
tacaacccgt ccctcaagac tcgagtcacc atatccgtag acacgtccaa gaatcagttc     240
tccctgaagc tgacctctgt gaccgccgca gacacggctg tgtattactg tgcgagagag     300
gaagcagcag cttttgacgca ctttgacttc tggggccagg gaaccctggt caccgtctcc     360
tcagcctcca ccaagggccc atcggtcttc ccectggcgc cctgctccag gagcacctcc     420
gagagcacag ccgccctggg ctgcctggtc aaggactact ccccgaacc ggtgacggtg      480 tcgtggaact caggcgccct gaccagcggc gtgcacacct tcccggctgt cctacagtcc     540
tcaggactct actccctcag cagcgtggtg accgtgccct ccagcagctt gggcacgaag     600
acctacacct gcaacgtaga tcacaagccc agcaacacca aggtggacaa gagagttgag     660
tccaaatatg gtcccccatg cccacccctgc ccagcacctg agttcctggg gggaccatca     720
gtcttcctgt tccccccaaa acccaaggac actctcatga tctcccggac ccctgaggtc     780
acgtgcgtgg tggtggacgt gagccaggaa gaccccgagg tccagttcaa ctggtacgtg     840
gatggcgtgg aggtgcataa tgccaagaca aagccgcggg aggagcagtt caacagcacg     900
taccgtgtgg tcagcgtcct caccgtcctg caccaggact ggctgaacgg caaggagtac     960
aagtgcaagg tctccaacaa aggcctcccg tcctccatcg agaaaaccat ctccaaagcc    1020
aaagggcagc cccgagagcc acaggtgtac accctgcccc catcccagga ggagatgacc    1080
aagaaccagg tcagcctgac ctgcctggtc aaaggcttct accccagcga catcgccgtg    1140
gagtgggaga gcaatgggca gccggagaac aactacaaga ccacgcctcc cgtgctggac    1200
tccgacggct ccttcttcct ctacagcagg ctcaccgtgg acaagagcag gtggcaggag    1260
gggaatgtct tctcatgctc cgtgatgcat gaggctctgc acaaccacta cacacagaag    1320
tccctctccc tgtctctggg taaatga                                        1347

<210> SEQ ID NO 204
<211> LENGTH: 448
<212> TYPE: PRT
```

<213> ORGANISM: Homo sapiens

<400> SEQUENCE: 204

Gln Leu Gln Leu Gln Glu Ser Gly Pro Gly Leu Val Lys Pro Ser Glu
1               5                   10                  15
Thr Leu Ser Leu Thr Cys Thr Val Ser Gly Gly Ser Ile Ser Ser Ser
            20                  25                  30
Asn Tyr Tyr Trp Gly Trp Ile Arg Gln Pro Pro Gly Lys Arg Leu Glu
        35                  40                  45
Trp Ile Gly Ser Ile Tyr Tyr Ser Gly Ser Thr Tyr Tyr Asn Pro Ser
    50                  55                  60
Leu Lys Thr Arg Val Thr Ile Ser Val Asp Thr Ser Lys Asn Gln Phe
65                  70                  75                  80
Ser Leu Lys Leu Thr Ser Val Thr Ala Ala Asp Thr Ala Val Tyr Tyr
                85                  90                  95
Cys Ala Arg Glu Glu Ala Ala Leu Thr His Phe Asp Phe Trp Gly
            100                 105                 110
Gln Gly Thr Leu Val Thr Val Ser Ser Ala Ser Thr Lys Gly Pro Ser
        115                 120                 125
Val Phe Pro Leu Ala Pro Cys Ser Arg Ser Thr Ser Glu Ser Thr Ala
    130                 135                 140
Ala Leu Gly Cys Leu Val Lys Asp Tyr Phe Pro Glu Pro Val Thr Val
145                 150                 155                 160
Ser Trp Asn Ser Gly Ala Leu Thr Ser Gly Val His Thr Phe Pro Ala
                165                 170                 175
Val Leu Gln Ser Ser Gly Leu Tyr Ser Leu Ser Ser Val Val Thr Val
            180                 185                 190
Pro Ser Ser Ser Leu Gly Thr Lys Thr Tyr Thr Cys Asn Val Asp His
        195                 200                 205
Lys Pro Ser Asn Thr Lys Val Asp Lys Arg Val Glu Ser Lys Tyr Gly
    210                 215                 220
Pro Pro Cys Pro Pro Cys Pro Ala Pro Glu Phe Leu Gly Gly Pro Ser
225                 230                 235                 240
Val Phe Leu Phe Pro Pro Lys Pro Lys Asp Thr Leu Met Ile Ser Arg
                245                 250                 255
Thr Pro Glu Val Thr Cys Val Val Val Asp Val Ser Gln Glu Asp Pro
            260                 265                 270
Glu Val Gln Phe Asn Trp Tyr Val Asp Gly Val Glu Val His Asn Ala
        275                 280                 285
Lys Thr Lys Pro Arg Glu Glu Gln Phe Asn Ser Thr Tyr Arg Val Val
    290                 295                 300
Ser Val Leu Thr Val Leu His Gln Asp Trp Leu Asn Gly Lys Glu Tyr
305                 310                 315                 320
Lys Cys Lys Val Ser Asn Lys Gly Leu Pro Ser Ser Ile Glu Lys Thr
                325                 330                 335
Ile Ser Lys Ala Lys Gly Gln Pro Arg Glu Pro Gln Val Tyr Thr Leu
            340                 345                 350
Pro Pro Ser Gln Glu Glu Met Thr Lys Asn Gln Val Ser Leu Thr Cys
        355                 360                 365
Leu Val Lys Gly Phe Tyr Pro Ser Asp Ile Ala Val Glu Trp Glu Ser
    370                 375                 380
Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
            405                 410                 415

Arg Trp Gln Glu Gly Asn Val Phe Ser Cys Ser Val Met His Glu Ala
        420                 425                 430

Leu His Asn His Tyr Thr Gln Lys Ser Leu Ser Leu Ser Leu Gly Lys
        435                 440                 445

<210> SEQ ID NO 205
<211> LENGTH: 645
<212> TYPE: DNA
<213> ORGANISM: Homo sapiens

<400> SEQUENCE: 205
gacatccaga tgacccagtc tccatcctcc ctgtctgcat ctgtaggaga cagagtcacc      60
atcacttgcc gggcaagtca gagcattagc aactatttaa attggtatca gcagaaacca     120
gggaaagccc ctaagctcct gatctttgct gcatccagtt tacaaagtgg ggtcccatca     180
aggttcagtg gcagtggatc tgggacagat ttcactctca ccatcagcag tctgcaacct     240
gaagattttg caacttacta ctgtcaacat agtcacagtt cccatccgat caccttcggc     300
caagggacac gactggagat taaacgaact gtggctgcac catctgtctt catcttcccg     360
ccatctgatg agcagttgaa atctggaact gcctctgttg tgtgcctgct gaataacttc     420
tatcccagag aggccaaagt acagtggaag gtggataacg ccctccaatc gggtaactcc     480
caggagagtg tcacagagca ggacagcaag gacagcacct acagcctcag cagcaccctg     540
acgctgagca agcagactac gagaaacac aaagtctacg cctgcgaagt cacccatcag     600
ggcctgagct cgcccgtcac aaagagcttc aacaggggag agtgt               645

<210> SEQ ID NO 206
<211> LENGTH: 215
<212> TYPE: PRT
<213> ORGANISM: Homo sapiens

<400> SEQUENCE: 206

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asn Tyr
            20                  25                  30

Leu Asn Trp Tyr Gln Gln Lys Pro Gly Lys Ala Pro Lys Leu Leu Ile
        35                  40                  45

Phe Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His Ser His Ser Ser His Pro
                85                  90                  95

Ile Thr Phe Gly Gln Gly Thr Arg Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 207
<211> LENGTH: 1350
<212> TYPE: DNA
<213> ORGANISM: Homo sapiens

<400> SEQUENCE: 207

| | | | | | |
|---|---|---|---|---|---|
| gaagtgcagc | tggtggagtc | tgggggaggc | ttggtacagc | ctggcaggtc | cctgagactc | 60 |
| tcctgtgcag | cctctggatt | cacctttgat | gattatgcca | tgcactgggt | ccggcaagct | 120 |
| ccagggaagg | gcctggagtg | ggtctcaggt | attaattggg | ctggttataa | catagactat | 180 |
| gcggactctg | tgaagggccg | attcaccatc | tccagagaca | acgccaagaa | ctccctgtat | 240 |
| ctgcaaatga | acagtctgag | agctgaggac | acggccttgt | attactgtgc | aaaagatatg | 300 |
| cgtggattca | gttatggttt | ccccttttgac | tactggggcc | agggaaccct | ggtcaccgtc | 360 |
| tcctcagcct | ccaccaaggg | cccatcggtc | ttccccctgg | cgccctgctc | caggagcacc | 420 |
| tccgagagca | cagccgccct | gggctgcctg | gtcaaggact | acttccccga | accggtgacg | 480 |
| gtgtcgtgga | actcaggcgc | cctgaccagc | ggcgtgcaca | ccttcccggc | tgtcctacag | 540 |
| tcctcaggac | tctactccct | cagcagcgtg | gtgaccgtgc | cctccagcag | cttgggcacg | 600 |
| aagacctaca | cctgcaacgt | agatcacaag | cccagcaaca | ccaaggtgga | caagagagtt | 660 |
| gagtccaaat | atggtccccc | atgcccaccc | tgcccagcac | ctgagttcct | ggggggacca | 720 |
| tcagtcttcc | tgttcccccc | aaaacccaag | gacactctca | tgatctcccg | gacccctgag | 780 |
| gtcacgtgcg | tggtggtgga | cgtgagccag | gaagaccccg | aggtccagtt | caactggtac | 840 |
| gtggatggcg | tggaggtgca | taatgccaag | acaaagccgc | gggaggagca | gttcaacagc | 900 |
| acgtaccgtg | tggtcagcgt | cctcaccgtc | ctgcaccagg | actggctgaa | cggcaaggag | 960 |
| tacaagtgca | aggtctccaa | caaaggcctc | ccgtcctcca | tcgagaaaac | catctccaaa | 1020 |
| gccaaagggc | agccccgaga | gccacaggtg | tacaccctgc | ccccatccca | ggaggagatg | 1080 |
| accaagaacc | aggtcagcct | gacctgcctg | gtcaaaggct | tctaccccag | cgacatcgcc | 1140 |
| gtggagtggg | agagcaatgg | gcagccggag | aacaactaca | agaccacgcc | tcccgtgctg | 1200 |
| gactccgacg | gctccttctt | cctctacagc | aggctcaccg | tggacaagag | caggtggcag | 1260 |
| gaggggaatg | tcttctcatg | ctccgtgatg | catgaggctc | tgcacaacca | ctacacacag | 1320 |
| aagtccctct | ccctgtctct | gggtaaatga | | | | 1350 |

<210> SEQ ID NO 208
<211> LENGTH: 449
<212> TYPE: PRT
<213> ORGANISM: Homo sapiens

<400> SEQUENCE: 208

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val

```
                35                  40                  45
Ser Gly Ile Asn Trp Ala Gly Tyr Asn Ile Asp Tyr Ala Asp Ser Val
 50                  55                  60
Lys Gly Arg Phe Thr Ile Ser Arg Asp Asn Ala Lys Asn Ser Leu Tyr
 65                  70                  75                  80
Leu Gln Met Asn Ser Leu Arg Ala Glu Asp Thr Ala Leu Tyr Tyr Cys
                 85                  90                  95
Ala Lys Asp Met Arg Gly Phe Ser Tyr Gly Phe Pro Phe Asp Tyr Trp
                100                 105                 110
Gly Gln Gly Thr Leu Val Thr Val Ser Ser Ala Ser Thr Lys Gly Pro
                115                 120                 125
Ser Val Phe Pro Leu Ala Pro Cys Ser Arg Ser Thr Ser Glu Ser Thr
                130                 135                 140
Ala Ala Leu Gly Cys Leu Val Lys Asp Tyr Phe Pro Glu Pro Val Thr
145                 150                 155                 160
Val Ser Trp Asn Ser Gly Ala Leu Thr Ser Gly Val His Thr Phe Pro
                165                 170                 175
Ala Val Leu Gln Ser Ser Gly Leu Tyr Ser Leu Ser Ser Val Val Thr
                180                 185                 190
Val Pro Ser Ser Ser Leu Gly Thr Lys Thr Tyr Thr Cys Asn Val Asp
                195                 200                 205
His Lys Pro Ser Asn Thr Lys Val Asp Lys Arg Val Glu Ser Lys Tyr
                210                 215                 220
Gly Pro Pro Cys Pro Pro Cys Pro Ala Pro Glu Phe Leu Gly Gly Pro
225                 230                 235                 240
Ser Val Phe Leu Phe Pro Pro Lys Pro Lys Asp Thr Leu Met Ile Ser
                245                 250                 255
Arg Thr Pro Glu Val Thr Cys Val Val Val Asp Val Ser Gln Glu Asp
                260                 265                 270
Pro Glu Val Gln Phe Asn Trp Tyr Val Asp Gly Val Glu Val His Asn
                275                 280                 285
Ala Lys Thr Lys Pro Arg Glu Glu Gln Phe Asn Ser Thr Tyr Arg Val
                290                 295                 300
Val Ser Val Leu Thr Val Leu His Gln Asp Trp Leu Asn Gly Lys Glu
305                 310                 315                 320
Tyr Lys Cys Lys Val Ser Asn Lys Gly Leu Pro Ser Ser Ile Glu Lys
                325                 330                 335
Thr Ile Ser Lys Ala Lys Gly Gln Pro Arg Glu Pro Gln Val Tyr Thr
                340                 345                 350
Leu Pro Pro Ser Gln Glu Glu Met Thr Lys Asn Gln Val Ser Leu Thr
                355                 360                 365
Cys Leu Val Lys Gly Phe Tyr Pro Ser Asp Ile Ala Val Glu Trp Glu
                370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Arg Leu Thr Val Asp Lys
                405                 410                 415
Ser Arg Trp Gln Glu Gly Asn Val Phe Ser Cys Ser Val Met His Glu
                420                 425                 430
Ala Leu His Asn His Tyr Thr Gln Lys Ser Leu Ser Leu Ser Leu Gly
                435                 440                 445
Lys
```

<210> SEQ ID NO 209
<211> LENGTH: 645
<212> TYPE: DNA
<213> ORGANISM: Homo sapiens

<400> SEQUENCE: 209

```
gacatccaga tgacccagtc tccatcctcc ctgtctgcat ctgtaggaga cagagtcacc    60
atcacttgcc gggcaagtca gagcattagc agctatttaa attggtatca gcagaaacca   120
gggaaagccc ctaagctcct gatctatgct gcatccagtt tgcaaagtgg ggtcccgtca   180
aggttcagtg gcagtggatc tgggacagat ttcactctca ccatcagcag tctgcaacct   240
gaagattttg caacttacta ctgtcaacag agttacagta cccctccgat caccttcggc   300
caagggacac gactggagat taaaactgtg gctgcaccat ctgtcttcat cttcccgcca   360
tctgatgagc agttgaaatc tggaactgcc tctgttgtgt gcctgctgaa taacttctat   420
cccagagagg ccaaagtaca gtggaaggtg gataacgccc tccaatcggg taactcccag   480
gagagtgtca cagagcagga cagcaaggac agcacctaca gcctcagcag caccctgacg   540
ctgagcaaag cagactacga gaaacacaaa gtctacgcct gcgaagtcac ccatcagggc   600
ctgagctcgc ccgtcacaaa gagcttcaac aggggagagt gttag                   645
```

<210> SEQ ID NO 210
<211> LENGTH: 214
<212> TYPE: PRT
<213> ORGANISM: Homo sapiens

<400> SEQUENCE: 210

```
Asp Ile Gln Met Thr Gln Ser Pro Ser Ser Leu Ser Ala Ser Val Gly
1               5                  10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Ile Thr Phe Gly Gln Gly Thr Arg Leu Glu Ile Lys Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 211
<211> LENGTH: 1383
<212> TYPE: DNA
<213> ORGANISM: Homo sapiens

<400> SEQUENCE: 211

```
gaggtgcagc tggtggagtc tgggggaggc ttggtaaagc cggggggggtc ccttagactc      60
tcctgtgcag cctctggatt tattttcagt aacgcctgga tgaactgggt ccgccaggct     120
ccagggaagg gactggcgtg ggttggccgt attaaaaccg aaactgatgg tgggacaaca     180
gactacgctg cacccgtaaa aggcagattc accatctcaa gagatgactc aaaaaacacg     240
ctgtatctgc aaatgaacag cgtgaaaacc gaggacacag ccgtgtatta ctgtacaggg     300
ggatacagct atggtgacga tagcagcagc tggaacgagg ctactacta ctacggtatg     360
gacgtctggg gccaagggac cacggtcacc gtctcctcag cctccaccaa gggcccatcg     420
gtcttccccc tggcgccctg ctccaggagc acctccgaga gcacagccgc cctgggctgc     480
ctggtcaagg actacttccc cgaaccggtg acggtgtcgt ggaactcagg cgccctgacc     540
agcggcgtgc acaccttccc ggctgtccta cagtcctcag gactctactc cctcagcagc     600
gtggtgaccg tgccctccag cagcttgggc acgaagacct acacctgcaa cgtagatcac     660
aagcccagca acaccaaggt ggacaagaga gttgagtcca aatatggtcc cccatgccca     720
ccctgcccag cacctgagtt cctgggggga ccatcagtct tcctgttccc cccaaaaccc     780
aaggacactc tcatgatctc ccggaccccct gaggtcacgt gcgtggtggt ggacgtgagc     840
caggaagacc ccgaggtcca gttcaactgg tacgtggatg gcgtggaggt gcataatgcc     900
aagacaaagc cgcgggagga gcagttcaac agcacgtacc gtgtggtcag cgtcctcacc     960
gtcctgcacc aggactggct gaacggcaag gagtacaagt gcaaggtctc caacaaaggc    1020
ctcccgtcct ccatcgagaa aaccatctcc aaagccaaag gcagccccg agagccacag     1080
gtgtacaccc tgcccccatc ccaggaggag atgaccaaga accaggtcag cctgacctgc    1140
ctggtcaaag gcttctaccc cagcgacatc gccgtggagt gggagagcaa tgggcagccg    1200
gagaacaact acaagaccac gcctcccgtg ctggactccg acggctcctt cttcctctac    1260
agcaggctca ccgtggacaa gagcaggtgg caggagggga atgtcttctc atgctccgtg    1320
atgcatgagg ctctgcacaa ccactacaca cagaagtccc tctccctgtc tctgggtaaa    1380
tga                                                                 1383
```

<210> SEQ ID NO 212
<211> LENGTH: 460
<212> TYPE: PRT
<213> ORGANISM: Homo sapiens

<400> SEQUENCE: 212

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Ile Phe Ser Asn Ala
            20                  25                  30

Trp Met Asn Trp Val Arg Gln Ala Pro Gly Lys Gly Leu Ala Trp Val
        35                  40                  45

Gly Arg Ile Lys Thr Glu Thr Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80
```

-continued

Leu Tyr Leu Gln Met Asn Ser Val Lys Thr Glu Asp Thr Ala Val Tyr
                 85                  90                  95

Tyr Cys Thr Gly Gly Tyr Ser Tyr Gly Asp Asp Ser Ser Trp Asn
            100                 105                 110

Glu Gly Tyr Tyr Tyr Gly Met Asp Val Trp Gly Gln Gly Thr Thr
            115                 120                 125

Val Thr Val Ser Ser Ala Ser Thr Lys Gly Pro Ser Val Phe Pro Leu
130                 135                 140

Ala Pro Cys Ser Arg Ser Thr Ser Glu Ser Thr Ala Ala Leu Gly Cys
145                 150                 155                 160

Leu Val Lys Asp Tyr Phe Pro Glu Pro Val Thr Val Ser Trp Asn Ser
                165                 170                 175

Gly Ala Leu Thr Ser Gly Val His Thr Phe Pro Ala Val Leu Gln Ser
            180                 185                 190

Ser Gly Leu Tyr Ser Leu Ser Ser Val Val Thr Val Pro Ser Ser Ser
        195                 200                 205

Leu Gly Thr Lys Thr Tyr Thr Cys Asn Val Asp His Lys Pro Ser Asn
    210                 215                 220

Thr Lys Val Asp Lys Arg Val Glu Ser Lys Tyr Gly Pro Pro Cys Pro
225                 230                 235                 240

Pro Cys Pro Ala Pro Glu Phe Leu Gly Gly Pro Ser Val Phe Leu Phe
                245                 250                 255

Pro Pro Lys Pro Lys Asp Thr Leu Met Ile Ser Arg Thr Pro Glu Val
            260                 265                 270

Thr Cys Val Val Val Asp Val Ser Gln Glu Asp Pro Glu Val Gln Phe
        275                 280                 285

Asn Trp Tyr Val Asp Gly Val Glu Val His Asn Ala Lys Thr Lys Pro
    290                 295                 300

Arg Glu Glu Gln Phe Asn Ser Thr Tyr Arg Val Val Ser Val Leu Thr
305                 310                 315                 320

Val Leu His Gln Asp Trp Leu Asn Gly Lys Glu Tyr Lys Cys Lys Val
                325                 330                 335

Ser Asn Lys Gly Leu Pro Ser Ser Ile Glu Lys Thr Ile Ser Lys Ala
            340                 345                 350

Lys Gly Gln Pro Arg Glu Pro Gln Val Tyr Thr Leu Pro Pro Ser Gln
        355                 360                 365

Glu Glu Met Thr Lys Asn Gln Val Ser Leu Thr Cys Leu Val Lys Gly
    370                 375                 380

Phe Tyr Pro Ser Asp Ile Ala Val Glu Trp Glu Ser Asn Gly Gln Pro
385                 390                 395                 400

Glu Asn Asn Tyr Lys Thr Thr Pro Pro Val Leu Asp Ser Asp Gly Ser
                405                 410                 415

Phe Phe Leu Tyr Ser Arg Leu Thr Val Asp Lys Ser Arg Trp Gln Glu
            420                 425                 430

Gly Asn Val Phe Ser Cys Ser Val Met His Glu Ala Leu His Asn His
        435                 440                 445

Tyr Thr Gln Lys Ser Leu Ser Leu Ser Leu Gly Lys
    450                 455                 460

<210> SEQ ID NO 213
<211> LENGTH: 645
<212> TYPE: DNA
<213> ORGANISM: Homo sapiens

<400> SEQUENCE: 213

```
gacatccaga tgacccagtc tccatcctcc ctgtctgcat ctgtaggaga cagagtcacc    60
atcacttgcc gggcaagtca gagcattagc agctatttaa attggtatca gcagaaacca   120
gggaaagccc ctaagctcct gatctatgct gcatccagtt tgcaaagtgg ggtcccgtca   180
aggttcagtg gcagtggatc tgggacagat ttcactctca ccatcagcag tctgcaacct   240
gaagattttg caacttacta ctgtcaacag agttacagta cccctccgat caccttcggc   300
caagggacac gactggagat taaaactgtg gctgcaccat ctgtcttcat cttcccgcca   360
tctgatgagc agttgaaatc tggaactgcc tctgttgtgt gcctgctgaa taacttctat   420
cccagagagg ccaaagtaca gtggaaggtg gataacgccc tccaatcggg taactcccag   480
gagagtgtca cagagcagga cagcaaggac agcacctaca gcctcagcag caccctgacg   540
ctgagcaaag cagactacga gaaacacaaa gtctacgcct gcgaagtcac ccatcagggc   600
ctgagctcgc ccgtcacaaa gagcttcaac aggggagagt gttag                   645
```

<210> SEQ ID NO 214
<211> LENGTH: 214
<212> TYPE: PRT
<213> ORGANISM: Homo sapiens

<400> SEQUENCE: 214

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Ile Thr Phe Gly Gln Gly Thr Arg Leu Glu Ile Lys Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 215
<211> LENGTH: 1362
<212> TYPE: DNA
<213> ORGANISM: Homo sapiens

<400> SEQUENCE: 215

```
gaagtgcagc tggtggagtc tgggggaggc ttggtacagc ctggcaggtc cctgagactc      60
tcctgtacag cctctggatt cacctttgat gattatgcca tgcactgggt ccggcaagct     120
ccagggaagg gcctggagtg ggtctcaggt attcgttgga atggtggtag tataggctat     180
gtggactctg tgaagggccg attcaccatc tccagagaca acgccaagaa gtccctgcat     240
ctgcaaatga acagtctaaa aactgaggac acggccttgt attactgtgc aaaagatata     300
ggcgatattt tgactggttt ttatggagaa tacggaatgg acgtctgggg ccaagggacc     360
acggtcaccg tctcctcagc ctccaccaag ggcccatcgg tcttccccct ggcgccctgc     420
tccaggagca cctccgagag cacagccgcc ctgggctgcc tggtcaagga ctacttcccc     480
gaaccggtga cggtgtcgtg gaactcaggc gccctgacca gcggcgtgca caccttcccg     540
gctgtcctac agtcctcagg actctactcc ctcagcagcg tggtgaccgt gcctccagc      600
agcttgggca cgaagaccta cacctgcaac gtagatcaca agcccagcaa caccaaggtg     660
gacaagagag ttgagtccaa atatggtccc ccatgcccac cctgcccagc acctgagttc     720
ctgggggac catcagtctt cctgttcccc ccaaaaccca aggacactct catgatctcc      780
cggacccctg aggtcacgtg cgtggtggtg gacgtgagcc aggaagaccc cgaggtccag     840
ttcaactggt acgtggatgg cgtggaggtg cataatgcca agacaaagcc gcgggaggag     900
cagttcaaca gcacgtaccg tgtggtcagc gtcctcaccg tcctgcacca ggactggctg     960
aacggcaagg agtacaagtg caaggtctcc aacaaaggcc tcccgtcctc catcgagaaa    1020
accatctcca aagccaaagg gcagccccga gagccacagg tgtacaccct gcccccatcc    1080
caggaggaga tgaccaagaa ccaggtcagc ctgacctgcc tggtcaaagg cttctacccc    1140
agcgacatcg ccgtggagtg ggagagcaat gggcagccgg agaacaacta caagaccacg    1200
cctcccgtgc tggactccga cggctccttc ttcctctaca gcaggctcac cgtggacaag    1260
agcaggtggc aggaggggaa tgtcttctca tgctccgtga tgcatgaggc tctgcacaac    1320
cactacacac agaagtccct ctccctgtct ctgggtaaat ga                       1362
```

<210> SEQ ID NO 216
<211> LENGTH: 453
<212> TYPE: PRT
<213> ORGANISM: Homo sapiens

<400> SEQUENCE: 216

```
Glu Val Gln Leu Val Glu Ser Gly Gly Gly Leu Val Gln Pro Gly Arg
1               5                   10                  15

Ser Leu Arg Leu Ser Cys Thr Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Arg Trp Asn Gly Gly Ser Ile Gly Tyr Val Asp Ser Val
    50                  55                  60

Lys Gly Arg Phe Thr Ile Ser Arg Asp Asn Ala Lys Lys Ser Leu His
65                  70                  75                  80

Leu Gln Met Asn Ser Leu Lys Thr Glu Asp Thr Ala Leu Tyr Tyr Cys
                85                  90                  95

Ala Lys Asp Ile Gly Asp Ile Leu Thr Gly Phe Tyr Gly Glu Tyr Gly
            100                 105                 110

Met Asp Val Trp Gly Gln Gly Thr Thr Val Thr Val Ser Ser Ala Ser
```

115                 120                 125
Thr Lys Gly Pro Ser Val Phe Pro Leu Ala Pro Cys Ser Arg Ser Thr
    130                 135                 140

Ser Glu Ser Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Lys Thr Tyr Thr
        195                 200                 205

Cys Asn Val Asp His Lys Pro Ser Asn Thr Lys Val Asp Lys Arg Val
    210                 215                 220

Glu Ser Lys Tyr Gly Pro Pro Cys Pro Pro Cys Pro Ala Pro Glu Phe
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser Gln Glu Asp Pro Glu Val Gln Phe Asn Trp Tyr Val Asp Gly Val
        275                 280                 285

Glu Val His Asn Ala Lys Thr Lys Pro Arg Glu Glu Gln Phe Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Gly Leu Pro Ser
                325                 330                 335

Ser Ile Glu Lys Thr Ile Ser Lys Ala Lys Gly Gln Pro Arg Glu Pro
            340                 345                 350

Gln Val Tyr Thr Leu Pro Pro Ser Gln Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Arg Leu
                405                 410                 415

Thr Val Asp Lys Ser Arg Trp Gln Glu Gly Asn Val Phe Ser Cys Ser
            420                 425                 430

Val Met His Glu Ala Leu His Asn His Tyr Thr Gln Lys Ser Leu Ser
        435                 440                 445

Leu Ser Leu Gly Lys
    450

<210> SEQ ID NO 217
<211> LENGTH: 642
<212> TYPE: DNA
<213> ORGANISM: Homo sapiens

<400> SEQUENCE: 217
gacatccaga tgacccagtc tccatcctcc ctgtctgcat ctgaaggaga cagagtcacc      60
atcacttgcc gggcaagtca gagcattagc agctatttaa attggtatca gcagaaagca     120
gggaaagccc ctaacctcct gatctatgct gcatccagtt tgcaaagtgg ggtcccatca     180

```
aggttcagtg gcagtggatc tgggacagag tacactctca ccatcagcag tctgcaacct    240
gaagattttg caacttacta ctgtcaacag agttacatta tcccgtacac ttttggccag    300
gggaccaagc tggagatcaa acgaactgtg gctgcaccat ctgtcttcat cttcccgcca    360
tctgatgagc agttgaaatc tggaactgcc tctgttgtgt gcctgctgaa taacttctat    420
cccagagagg ccaaagtaca gtggaaggtg gataacgccc tccaatcggg taactcccag    480
gagagtgtca cagagcagga cagcaaggac agcacctaca gcctcagcag caccctgacg    540
ctgagcaaag cagactacga gaaacacaaa gtctacgcct gcgaagtcac ccatcagggc    600
ctgagctcgc ccgtcacaaa gagcttcaac aggggagagt gt                     642

<210> SEQ ID NO 218
<211> LENGTH: 214
<212> TYPE: PRT
<213> ORGANISM: Homo sapiens

<400> SEQUENCE: 218

Asp Ile Gln Met Thr Gln Ser Pro Ser Ser Leu Ser Ala Ser Glu Gly
 1               5                  10                  15

Asp Arg Val Thr Ile Thr Cys Arg Ala Ser Gln Ser Ile Ser Ser Tyr
            20                  25                  30

Leu Asn Trp Tyr Gln Gln Lys Ala Gly Lys Ala Pro Asn Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Tyr Thr Leu Thr Ile Ser Ser Leu Gln Pro
65                  70                  75                  80

Glu Asp Phe Ala Thr Tyr Tyr Cys Gln Gln Ser Tyr Ile Ile Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 219
<211> LENGTH: 1362
<212> TYPE: DNA
<213> ORGANISM: Homo sapiens

<400> SEQUENCE: 219
gaagtgcagc tggtggagtc tgggggaggg ttggtacagc ctggcaggtc cctgagactc     60
tcctgtgcag cctctggatt cacctttgat gattatgcca tgcactgggt ccggcaagct    120
ccagggaagg gcctggagtg ggtctcaagt gttaggtgga tggtggtat tataggctat    180
```

-continued

```
gcggactctg tgaagggccg attcaccatc tccagagaca acgccaagaa ctccctgtat    240
ctgcaaatga acagtctgag acctgaggac acggccctct attactgtgc aaaagatata    300
ggcgatgttt tgactggtta ttatggagaa tacggtatgg acgtctgggg ccaagggacc    360
acggtcaccg tctcctcagc ctccaccaag ggcccatcgg tcttccccct ggcgccctgc    420
tccaggagca cctccgagag cacagccgcc ctgggctgcc tggtcaagga ctacttcccc    480
gaaccggtga cggtgtcgtg aactcaggc gccctgacca cggcgtgca caccttcccg     540 gctgtcctac agtcctcagg actctactcc ctcagcagcg tggtgaccgt gccctccagc    600
agcttgggca cgaagaccta cacctgcaac gtagatcaca agcccagcaa caccaaggtg    660
gacaagagag ttgagtccaa atatggtccc ccatgcccac cctgcccagc acctgagttc    720 ctgggggac catcagtctt cctgttcccc ccaaaaccca aggacactct catgatctcc     780
cggacccctg aggtcacgtg cgtggtggtg gacgtgagcc aggaagaccc cgaggtccag    840
ttcaactggt acgtggatgg cgtggaggtg cataatgcca agacaaagcc gcgggaggag    900
cagttcaaca gcacgtaccg tgtggtcagc gtcctcaccg tcctgcacca ggactggctg    960
aacggcaagg agtacaagtg caaggtctcc aacaaaggcc tcccgtcctc catcgagaaa    1020
accatctcca aagccaaagg gcagccccga gagccacagg tgtacaccct gcccccatcc    1080
caggaggaga tgaccaagaa ccaggtcagc ctgacctgcc tggtcaaagg cttctacccc    1140
agcgacatcg ccgtggagtg ggagagcaat gggcagccgg agaacaacta caagaccacg    1200
cctcccgtgc tggactccga cggctccttc ttcctctaca gcaggctcac cgtggacaag    1260
agcaggtggc aggaggggaa tgtcttctca tgctccgtga tgcatgaggc tctgcacaac    1320
cactacacac agaagtccct ctccctgtct ctgggtaaat ga                        1362
```

<210> SEQ ID NO 220
<211> LENGTH: 453
<212> TYPE: PRT
<213> ORGANISM: Homo sapiens

<400> SEQUENCE: 220

```
Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Ser Val Arg Trp Asn Gly Ile Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Pro Glu Asp Thr Ala Leu Tyr Tyr Cys
                85                  90                  95

Ala Lys Asp Ile Gly Asp Val Leu Thr Gly Tyr Tyr Gly Glu Tyr Gly
            100                 105                 110

Met Asp Val Trp Gly Gln Gly Thr Thr Val Thr Val Ser Ser Ala Ser
        115                 120                 125

Thr Lys Gly Pro Ser Val Phe Pro Leu Ala Pro Cys Ser Arg Ser Thr
    130                 135                 140

Ser Glu Ser Thr Ala Ala Leu Gly Cys Leu Val Lys Asp Tyr Phe Pro
145                 150                 155                 160
```

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Lys Thr Tyr Thr
        195                 200                 205

Cys Asn Val Asp His Lys Pro Ser Asn Thr Lys Val Asp Lys Arg Val
    210                 215                 220

Glu Ser Lys Tyr Gly Pro Pro Cys Pro Pro Cys Pro Ala Pro Glu Phe
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser Gln Glu Asp Pro Glu Val Gln Phe Asn Trp Tyr Val Asp Gly Val
        275                 280                 285

Glu Val His Asn Ala Lys Thr Lys Pro Arg Glu Glu Gln Phe Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Gly Leu Pro Ser
                325                 330                 335

Ser Ile Glu Lys Thr Ile Ser Lys Ala Lys Gly Gln Pro Arg Glu Pro
            340                 345                 350

Gln Val Tyr Thr Leu Pro Pro Ser Gln Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Arg Leu
                405                 410                 415

Thr Val Asp Lys Ser Arg Trp Gln Glu Gly Asn Val Phe Ser Cys Ser
            420                 425                 430

Val Met His Glu Ala Leu His Asn His Tyr Thr Gln Lys Ser Leu Ser
        435                 440                 445

Leu Ser Leu Gly Lys
    450

<210> SEQ ID NO 221
<211> LENGTH: 642
<212> TYPE: DNA
<213> ORGANISM: Homo sapiens

<400> SEQUENCE: 221
gacatccaga tgacccagtc tccatcctcc ctgtctgcat ctgtgggaga cagagtcacc    60
atcgcttgcc gggcaagtca gagcattacc acctatttaa attggtatca gcagaaacca   120
gggaaagccc ctaaactcct gatctatgct gcatccagtt tgcaaagtgg ggtcccatca   180
aggttcagtg gcagtggatc tgggacagat tcactctcac catcagtag tctgcaacct   240 gaagattttg caacttacta ctgtcaacag agttacattt ccccgtacac ttttggccag   300
gggaccaagc tggagatcaa acgaactgtg gctgcaccat ctgtcttcat cttcccgcca   360
tctgatgagc agttgaaatc tggaactgcc tctgttgtgt gcctgctgaa taacttctat   420

```
cccagagagg ccaaagtaca gtggaaggtg ataacgccc tccaatcggg taactcccag      480
gagagtgtca cagagcagga cagcaaggac agcacctaca gcctcagcag caccctgacg      540
ctgagcaaag cagactacga gaaacacaaa gtctacgcct gcgaagtcac ccatcagggc      600
ctgagctcgc ccgtcacaaa gagcttcaac aggggagagt gt                        642
```

<210> SEQ ID NO 222
<211> LENGTH: 214
<212> TYPE: PRT
<213> ORGANISM: Homo sapiens

<400> SEQUENCE: 222

```
Asp Ile Gln Met Thr Gln Ser Pro Ser Ser Leu Ser Ala Ser Val Gly
1               5                   10                  15

Asp Arg Val Thr Ile Ala Cys Arg Ala Ser Gln Ser Ile Thr Thr Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ile Ser Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 223
<211> LENGTH: 1362
<212> TYPE: DNA
<213> ORGANISM: Homo sapiens

<400> SEQUENCE: 223

```
caggtgcagc tggtggagtc tgggggaggc gtggtccagc ctgggaagtc cctgagactc      60
tcctgtgcag cctctggatt caccttcagt aattatggca tacactgggt ccgccaggct     120
ccaggcaagg ggctggagtg gtggcgatt atattatatg atggaagtaa tcaacactat      180
gcagattccg tgaagggccg attcaccatt tccagagaca attccaaaaa cacgctgtat     240
cttcaaatga caacctgag agctgaggac acggccgttt attactgtgc gagagatctt     300 gatcttttgga gtggttatta taacaaacggg acggtatgg acgtctgggg ccaagggacc     360
acggtcaccg tctcctcagc ctccaccaag ggcccatcgg tcttccccct ggcgccctgc     420
```

-continued

```
tccaggagca cctccgagag cacagccgcc ctgggctgcc tggtcaagga ctacttcccc    480
gaaccggtga cggtgtcgtg gaactcaggc gccctgacca gcggcgtgca caccttcccg    540
gctgtcctac agtcctcagg actctactcc ctcagcagcg tggtgaccgt gccctccagc    600
agcttgggca cgaagaccta cacctgcaac gtagatcaca agcccagcaa caccaaggtg    660
gacaagagag ttgagtccaa atatggtccc ccatgcccac cctgcccagc acctgagttc    720
ctgggggac catcagtctt cctgttcccc ccaaaaccca aggacactct catgatctcc     780
cggaccctg aggtcacgtg cgtggtggtg gacgtgagcc aggaagaccc cgaggtccag     840
ttcaactggt acgtggatgg cgtggaggtg cataatgcca agacaaagcc gcggaggag     900
cagttcaaca gcacgtaccg tgtggtcagc gtcctcaccg tcctgcacca ggactggctg    960
aacggcaagg agtacaagtg caaggtctcc aacaaaggcc tcccgtcctc catcgagaaa   1020
accatctcca aagccaaagg gcagccccga gagccacagg tgtacaccct gcccccatcc   1080
caggaggaga tgaccaagaa ccaggtcagc ctgacctgcc tggtcaaagg cttctacccc   1140
agcgacatcg ccgtggagtg ggagagcaat gggcagccgg agaacaacta caagaccacg   1200
cctcccgtgc tggactccga cggctccttc ttcctctaca gcaggctcac cgtggacaag   1260
agcaggtggc aggagggaa tgtcttctca tgctccgtga tgcatgaggc tctgcacaac   1320
cactacacac agaagtccct ctccctgtct ctgggtaaat ga                       1362
```

<210> SEQ ID NO 224
<211> LENGTH: 453
<212> TYPE: PRT
<213> ORGANISM: Homo sapiens

<400> SEQUENCE: 224

```
Gln Val Gln Leu Val Glu Ser Gly Gly Gly Val Val Gln Pro Gly Lys
1               5                   10                  15

Ser Leu Arg Leu Ser Cys Ala Ala Ser Gly Phe Thr Phe Ser Asn Tyr
            20                  25                  30

Gly Ile His Trp Val Arg Gln Ala Pro Gly Lys Gly Leu Glu Trp Val
        35                  40                  45

Ala Ile Ile Leu Tyr Asp Gly Ser Asn Gln His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Asn Leu Arg Ala Glu Asp Thr Ala Val Tyr Tyr Cys
                85                  90                  95

Ala Arg Asp Leu Asp Leu Trp Ser Gly Tyr Tyr Thr Asn Gly Asp Gly
            100                 105                 110

Met Asp Val Trp Gly Gln Gly Thr Thr Val Thr Val Ser Ser Ala Ser
        115                 120                 125

Thr Lys Gly Pro Ser Val Phe Pro Leu Ala Pro Cys Ser Arg Ser Thr
    130                 135                 140

Ser Glu Ser Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Lys Thr Tyr Thr
        195                 200                 205
```

Cys Asn Val Asp His Lys Pro Ser Asn Thr Lys Val Asp Lys Arg Val
            210                 215                 220

Glu Ser Lys Tyr Gly Pro Cys Pro Pro Cys Pro Ala Pro Glu Phe
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser Gln Glu Asp Pro Glu Val Gln Phe Asn Trp Tyr Val Asp Gly Val
            275                 280                 285

Glu Val His Asn Ala Lys Thr Lys Pro Arg Glu Gln Phe Asn Ser
            290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Gly Leu Pro Ser
                325                 330                 335

Ser Ile Glu Lys Thr Ile Ser Lys Ala Lys Gly Gln Pro Arg Glu Pro
            340                 345                 350

Gln Val Tyr Thr Leu Pro Pro Ser Gln Glu Glu Met Thr Lys Asn Gln
            355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Arg Leu
                405                 410                 415

Thr Val Asp Lys Ser Arg Trp Gln Glu Gly Asn Val Phe Ser Cys Ser
            420                 425                 430

Val Met His Glu Ala Leu His Asn His Tyr Thr Gln Lys Ser Leu Ser
            435                 440                 445

Leu Ser Leu Gly Lys
    450

<210> SEQ ID NO 225
<211> LENGTH: 645
<212> TYPE: DNA
<213> ORGANISM: Homo sapiens

<400> SEQUENCE: 225
gacatccaga tgacccagtc tccatcctcc ctgtctgcat ctgtaggaga cagagtcacc        60
atcacttgcc gggcaagtca gagcattagc agctatttaa attggtatca gcagaaacca       120
gggaaagccc ctaagctcct gatctatgct gcatccagtt tgcaaagtgg ggtcccgtca       180
aggttcagtg gcagtggatc tgggacagat ttcactctca ccatcagcag tctgcaacct       240
gaagattttg caacttacta ctgtcaacag agttacagta cccctccgat caccttcggc       300
caagggacac gactggagat taaaactgtg gctgcaccat ctgtcttcat cttcccgcca       360
tctgatgagc agttgaaatc tggaactgcc tctgttgtgt gcctgctgaa taacttctat       420
cccagagagg ccaaagtaca gtggaaggtg gataacgccc tccaatcggg taactcccag       480
gagagtgtca cagagcagga cagcaaggac agcacctaca gcctcagcag caccctgacg       540
ctgagcaaag cagactacga gaaacacaaa gtctacgcct gcgaagtcac ccatcagggc       600
ctgagctcgc ccgtcacaaa gagcttcaac aggggagagt gttag                      645

<210> SEQ ID NO 226
<211> LENGTH: 214
<212> TYPE: PRT
<213> ORGANISM: Homo sapiens

<400> SEQUENCE: 226

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Ile Thr Phe Gly Gln Gly Thr Arg Leu Glu Ile Lys Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 227
<211> LENGTH: 346
<212> TYPE: PRT
<213> ORGANISM: Artificial Sequence
<220> FEATURE:
<223> OTHER INFORMATION: Recombinant Human IL-36R polypeptide (hIL-36R.mmH)

<400> SEQUENCE: 227

```
Asp Gly Cys Lys Asp Ile Phe Met Lys Asn Glu Ile Leu Ser Ala Ser
1               5                   10                  15

Gln Pro Phe Ala Phe Asn Cys Thr Phe Pro Pro Ile Thr Ser Gly Glu
            20                  25                  30

Val Ser Val Thr Trp Tyr Lys Asn Ser Ser Lys Ile Pro Val Ser Lys
        35                  40                  45

Ile Ile Gln Ser Arg Ile His Gln Asp Glu Thr Trp Ile Leu Phe Leu
50                  55                  60

Pro Met Glu Trp Gly Asp Ser Gly Val Tyr Gln Cys Val Ile Lys Gly
65                  70                  75                  80

Arg Asp Ser Cys His Arg Ile His Val Asn Leu Thr Val Phe Glu Lys
                85                  90                  95
```

His Trp Cys Asp Thr Ser Ile Gly Gly Leu Pro Asn Leu Ser Asp Glu
            100                 105                 110

Tyr Lys Gln Ile Leu His Leu Gly Lys Asp Asp Ser Leu Thr Cys His
        115                 120                 125

Leu His Phe Pro Lys Ser Cys Val Leu Gly Pro Ile Lys Trp Tyr Lys
    130                 135                 140

Asp Cys Asn Glu Ile Lys Gly Glu Arg Phe Thr Val Leu Glu Thr Arg
145                 150                 155                 160

Leu Leu Val Ser Asn Val Ser Ala Glu Asp Arg Gly Asn Tyr Ala Cys
                165                 170                 175

Gln Ala Ile Leu Thr His Ser Gly Lys Gln Tyr Glu Val Leu Asn Gly
            180                 185                 190

Ile Thr Val Ser Ile Thr Glu Arg Ala Gly Tyr Gly Gly Ser Val Pro
        195                 200                 205

Lys Ile Ile Tyr Pro Lys Asn His Ser Ile Glu Val Gln Leu Gly Thr
    210                 215                 220

Thr Leu Ile Val Asp Cys Asn Val Thr Asp Thr Lys Asp Asn Thr Asn
225                 230                 235                 240

Leu Arg Cys Trp Arg Val Asn Asn Thr Leu Val Asp Asp Tyr Tyr Asp
                245                 250                 255

Glu Ser Lys Arg Ile Arg Glu Gly Val Glu Thr His Val Ser Phe Arg
            260                 265                 270

Glu His Asn Leu Tyr Thr Val Asn Ile Thr Phe Leu Glu Val Lys Met
        275                 280                 285

Glu Asp Tyr Gly Leu Pro Phe Met Cys His Ala Gly Val Ser Thr Ala
    290                 295                 300

Tyr Ile Ile Leu Gln Leu Pro Ala Pro Asp Phe Arg Ala Tyr Glu Gln
305                 310                 315                 320

Lys Leu Ile Ser Glu Glu Asp Leu Gly Gly Glu Gln Lys Leu Ile Ser
                325                 330                 335

Glu Glu Asp Leu His His His His His
            340                 345

<210> SEQ ID NO 228
<211> LENGTH: 7
<212> TYPE: PRT
<213> ORGANISM: Artificial Sequence
<220> FEATURE:
<223> OTHER INFORMATION: Synthetic peptide

<400> SEQUENCE: 228

Tyr Lys Gln Ile Leu His Leu
1               5

<210> SEQ ID NO 229
<211> LENGTH: 10
<212> TYPE: PRT
<213> ORGANISM: Artificial Sequence
<220> FEATURE:
<223> OTHER INFORMATION: Synthetic peptide

<400> SEQUENCE: 229

Tyr Lys Gln Ile Leu His Leu Gly Lys Asp
1               5                   10

<210> SEQ ID NO 230
<211> LENGTH: 14
<212> TYPE: PRT
<213> ORGANISM: Artificial Sequence
<220> FEATURE:
<223> OTHER INFORMATION: Synthetic peptide

<400> SEQUENCE: 230

Gly Val Glu Thr His Val Ser Phe Arg Glu His Asn Tyr Leu
1               5                   10

<210> SEQ ID NO 231
<211> LENGTH: 4
<212> TYPE: PRT
<213> ORGANISM: Artificial Sequence
<220> FEATURE:
<223> OTHER INFORMATION: Synthetic peptide

<400> SEQUENCE: 231

Ile Leu His Leu
1

<210> SEQ ID NO 232
<211> LENGTH: 7
<212> TYPE: PRT
<213> ORGANISM: Artificial Sequence
<220> FEATURE:
<223> OTHER INFORMATION: Synthetic peptide

<400> SEQUENCE: 232

Ile Leu His Leu Gly Lys Asp
1               5

<210> SEQ ID NO 233
<211> LENGTH: 8
<212> TYPE: PRT
<213> ORGANISM: Artificial Sequence
<220> FEATURE:
<223> OTHER INFORMATION: Synthetic peptide

<400> SEQUENCE: 233

Gly Val Glu Thr His Val Ser Phe
1               5

<210> SEQ ID NO 234
<211> LENGTH: 5
<212> TYPE: PRT
<213> ORGANISM: Artificial Sequence
<220> FEATURE:
<223> OTHER INFORMATION: Synthetic peptide

<400> SEQUENCE: 234

Thr His Val Ser Phe
1               5

<210> SEQ ID NO 235
<211> LENGTH: 4
<212> TYPE: PRT
<213> ORGANISM: Artificial Sequence
<220> FEATURE:
<223> OTHER INFORMATION: Synthetic peptide

<400> SEQUENCE: 235

His Val Ser Phe
1

<210> SEQ ID NO 236
<211> LENGTH: 9
<212> TYPE: PRT
<213> ORGANISM: Artificial Sequence
<220> FEATURE:

<223> OTHER INFORMATION: Synthetic peptide

<400> SEQUENCE: 236

His Val Ser Phe Arg Glu His Asn Leu
1               5

<210> SEQ ID NO 237
<211> LENGTH: 10
<212> TYPE: PRT
<213> ORGANISM: Artificial Sequence
<220> FEATURE:
<223> OTHER INFORMATION: Synthetic peptide

<400> SEQUENCE: 237

His Val Ser Phe Arg Glu His Asn Leu Tyr
1               5                   10

<210> SEQ ID NO 238
<211> LENGTH: 6
<212> TYPE: PRT
<213> ORGANISM: Artificial Sequence
<220> FEATURE:
<223> OTHER INFORMATION: Synthetic peptide

<400> SEQUENCE: 238

Phe Arg Glu His Asn Leu
1               5

<210> SEQ ID NO 239
<211> LENGTH: 446
<212> TYPE: PRT
<213> ORGANISM: Artificial Sequence
<220> FEATURE:
<223> OTHER INFORMATION: Polypeptide: APE6155 heavy chain (comprising an
      IgG4 constant domain)

<400> SEQUENCE: 239

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
                20                  25                  30

Trp Met Asn Trp Val Arg Gln Ala Pro Arg Gln Gly Leu Glu Trp Met
            35                  40                  45

Gly Met Phe His Pro Thr Gly Asp Val Thr Arg Leu Asn Gln Lys Phe
        50                  55                  60

Lys Asp Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Thr Thr Ser Met Ile Ile Gly Gly Phe Ala Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
            195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Val Ala Gly Pro Ser Val Phe
225             230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
                260                 265                 270

Gln Phe Asn Trp Tyr Val Asp Gly Val Glu Val His Asn Ala Lys Thr
            275                 280                 285

Lys Pro Arg Glu Glu Gln Phe Asn Ser Thr Tyr Arg Val Val Ser Val
            290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
            370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Leu Gly Lys
            435                 440                 445

<210> SEQ ID NO 240
<211> LENGTH: 219
<212> TYPE: PRT
<213> ORGANISM: Artificial Sequence
<220> FEATURE:
<223> OTHER INFORMATION: Polypeptide: APE6155 light chain (comprising a
      Kappa constant domain)

<400> SEQUENCE: 240

Asp Ile Val Met Thr Gln Thr Pro Leu Ser Leu Ser Val Thr Pro Gly
1               5                   10                  15

Gln Pro Ala Ser Ile Ser Cys Arg Ser Ser Lys Ser Leu Leu His Arg
            20                  25                  30

Asn Ala Ile Thr Tyr Phe Tyr Trp Tyr Leu His Lys Pro Gly Gln Pro
            35                  40                  45

Pro Gln Leu Leu Ile Tyr Gln Met Ser Asn Leu Ala Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95

Leu Glu Leu Pro Leu Thr Phe Gly Gly Gly Thr Lys Val Glu Ile Lys

```
                100             105             110
Arg Thr Val Ala Ala Pro Ser Val Phe Ile Phe Pro Pro Ser Asp Glu
            115                 120             125

Gln Leu Lys Ser Gly Thr Ala Ser Val Val Cys Leu Leu Asn Asn Phe
            130                 135             140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
            195                 200                 205

Pro Val Thr Lys Ser Phe Asn Arg Gly Glu Cys
            210                 215
```

<210> SEQ ID NO 241
<211> LENGTH: 119
<212> TYPE: PRT
<213> ORGANISM: Homo sapiens

<400> SEQUENCE: 241

```
Glu Val Gln Leu Val Glu Ser Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Tyr Asn Trp Asn Tyr Tyr Phe Asp Tyr Trp Gly Gln Gly
                100                 105                 110

Thr Leu Val Thr Val Ser Ser
            115
```

<210> SEQ ID NO 242
<211> LENGTH: 107
<212> TYPE: PRT
<213> ORGANISM: Homo sapiens

<400> SEQUENCE: 242

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
        50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
```

```
                          85                  90                  95
Thr Phe Gly Gly Gly Thr Lys Val Glu Ile Lys
                 100                 105

<210> SEQ ID NO 243
<211> LENGTH: 120
<212> TYPE: PRT
<213> ORGANISM: Homo sapiens

<400> SEQUENCE: 243

Glu Val Gln Leu Val Glu Ser Gly Gly Leu Val Gln Pro Gly Arg
1               5                   10                  15

Ser Leu Arg Leu Ser Cys Ala Ala Ser Gly Phe Thr Phe Asp Asp Tyr
                20                  25                  30

Ala Met His Trp Val Arg Gln Ala Pro Gly Lys Gly Leu Glu Trp Val
            35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Tyr Ser Gly Ser Tyr Tyr Tyr Phe Asp Tyr Trp Gly Gln
                100                 105                 110

Gly Thr Leu Val Thr Val Ser Ser
                115                 120
```

ANTI-IL36R ANTIBODIES

CROSS REFERENCE TO RELATED APPLICATIONS

This application is a divisional of U.S. patent application Ser. No. 16/512,886, filed Jul. 16, 2019, which claims the benefit of U.S. Provisional Patent Application No. 62/698,482, filed Jul. 16, 2018; U.S. Provisional Patent Application No. 62/846,989, filed May 13, 2019; and U.S. Provisional Patent Application No. 62/866,028, filed Jun. 25, 2019; each of which is herein incorporated by reference in its entirety.

FIELD OF THE INVENTION

The field of the invention relates, in part, to antibodies that bind to IL-36 receptor and the use of such antibodies to treat inflammatory disorders including psoriasis or inflammatory bowel disease.

INCORPORATION BY REFERENCE OF SEQUENCE LISTING

The Sequence Listing in the ASCII text file, named as 36432A_10484US02_SequenceListing of 179 KB, created on Jan. 24, 2022 and submitted to the United States Patent and Trademark Office via EFS-Web, is incorporated herein by reference.

BACKGROUND OF THE INVENTION

The interleukin (IL)-36 cytokines include 3 agonists, IL-36α, IL-36β, and IL-36γ that bind to a common receptor composed of IL-36R and IL-1RAcP to stimulate inflammatory responses. IL-36 receptor (IL-36R) is a single-pass membrane receptor for a subset of the IL-1 family of cytokines, IL-36α, IL-36β, and IL-36γ, and upon binding to any of these ligands, there is recruitment of its co-receptor, the IL-1R accessory protein (IL-1RAcP), which induces a signaling cascade that involves NFκB and mitogen-activated kinase pathways (Sims et al, 2010.

A mediator of some inflammatory skin conditions, such as psoriasis, is IL-36. Psoriasis is a common, immune-mediated, inflammatory skin disease which includes the variants plaque psoriasis and generalized pustular psoriasis. Standard therapeutic guidelines include the use of topical steroids, topical vitamin D, systemic immunosuppressants and various biologics, such as anti-tumor necrosis factor (TNF) α, anti-interleukin (IL)-23 and anti-IL-17 antibodies. IL-36 members are overexpressed in the lesional skin of plaque psoriasis and activation of IL-36R might contribute to the persistence and perpetuation of psoriatic inflammation together with the TNF-α/IL-23/IL-17/IL-22 axis. (Di Cesare et al., The IL-23/Th17 axis in the immunopathogenesis of psoriasis, Journal of Investigative Dermatology 129: 1339-1350 (2009) and Blumberg et al., IL-1RL2 and its ligands contribute to the cytokine network in psoriasis. J Immunol 185: 4354-4362 (2010)).

Currently available treatments for palmoplantar pustulosis (PPP) and palmoplantar pustular psoriasis (PPPP), however, are limited. Spesolimab and ANB019 are anti-IL36R antibodies in clinical development which suffer from drawbacks related to immunogenicity and potency.

SUMMARY OF THE INVENTION

The present invention provides anti-IL36R antibodies and antigen-binding fragments thereof that exhibit superior properties. For example, we observed in pharmacokinetic studies in three cynomolgous monkeys per group (0.5 and 5 mg/kg subcutaneous dose groups; n=3/group), that the anti-IL36R antibodies set forth herein (e.g., H4H14708P2) exhibited about 1.2-fold greater exposure than anti-IL36R antibody, APE6155. Moreover, we also observed that APE6155 exhibited less potency than anti-IL36R antibodies set forth herein, e.g., in reducing skin thickness and pathology scores in IMQ-induced skin inflammation and in reducing pro-inflammatory cytokines in skin. Spesolimab, a humanized anti-IL36R antibody, exhibited high levels of anti-drug antibody in human subjects with GPP. In a Phase 1 clinical trial, 3 of 7 patients had anti-drug antibodies at week 2 and these sustained to week 20 after a single dose. This property of spesolimab would not be ideal for chronic long-term treatment. Amin, First Data in GPP from Competitor Anti-IL36 Provides Proof of Concept of ANB019, Flash Note, Company Update, AnaptysBio, Jefferies (Sep. 16, 2018). The human anti-IL36R antibodies of the present invention are not expected to be highly immunogenic in humans.

The present invention provides an antigen-binding protein (e.g., an antibody or antigen-binding fragment thereof, e.g., a human antibody or antigen-binding fragment thereof or a multispecific antibody) that (i) specifically binds to the same epitope on IL36R as a reference antigen-binding protein; or (ii) competes for binding to IL36R polypeptide with a reference antigen-binding protein, wherein the reference antigen-binding protein comprises: (a) a heavy chain immunoglobulin that comprises CDR-H1, CDR-H2 and CDR-H3 of a heavy chain immunoglobulin that comprises the amino acid sequence set forth in SEQ ID NO: 2, 18, 34, 50, 66, 82, 98, 114, 130, 138, 154, 170, 180, 184, 188, 192, 196, 200, 204, 208, 212, 216, 220 or 224; and/or (b) a light chain immunoglobulin that comprises CDR-L1, CDR-L2 and CDR-L3 of a light chain immunoglobulin that comprises the amino acid sequence set forth in SEQ ID NO: 10, 26, 42, 58, 74, 90, 106, 122, 146, 162, 182, 186, 190, 194, 198, 202, 206, 210, 214, 218, 222 or 226. For example, in an embodiment of the invention, the antigen-binding protein comprises: (i) a heavy chain immunoglobulin that comprises CDR-H1, CDR-H2 and CDR-H3 of a heavy chain immunoglobulin that comprises the amino acid sequence set forth in SEQ ID NO: 2, 18, 34, 50, 66, 82, 98, 114, 130, 138, 154, 170, 180, 184, 188, 192, 196, 200, 204, 208, 212, 216, 220 or 224; and/or (ii) a light chain immunoglobulin that comprises CDR-L1, CDR-L2 and CDR-L3 of a light chain immunoglobulin that comprises the amino acid sequence set forth in SEQ ID NO: 10, 26, 42, 58, 74, 90, 106, 122, 146, 162, 182, 186, 190, 194, 198, 202, 206, 210, 214, 218, 222 or 226. In an embodiment of the invention, the antigen-binding protein comprises (a) a heavy chain immunoglobulin variable region comprising an amino acid sequence having at least 90% amino acid sequence identity to the amino acid sequence set forth in SEQ ID NO: 2, 18, 34, 50, 66, 82, 98, 114, 130, 138, 154, 170, 180, 184, 188, 192, 196, 200, 204, 208, 212, 216, 220 or 224; and/or (b) a light chain immunoglobulin variable region comprising an amino acid sequence having at least 90% amino acid sequence identity to the amino acid sequence set forth in SEQ ID NO: 10, 26, 42, 58, 74, 90, 106, 122, 146, 162, 182, 186, 190, 194, 198, 202, 206, 210, 214, 218, 222 or 226. For example, in an embodiment of the invention, the antigen-binding protein comprises: (a) a heavy chain immunoglobulin comprising the CDR-H1, CDR-H2 and CDR-H3 of a heavy chain immunoglobulin comprising an amino acid sequence set forth in SEQ ID NO: 2, 18, 34, 50, 66, 82, 98, 114, 130, 138, 154, 170, 180, 184, 188, 192, 196, 200, 204, 208, 212, 216, 220 or 224 and at least 90% amino acid sequence identity to the amino acid sequence set forth in SEQ ID NO: 2, 18, 34, 50, 66, 82, 98, 114, 130, 138, 154, 170, 180, 184, 188, 192, 196, 200, 204, 208, 212, 216, 220 or 224; and/or (b) an light chain immunoglobulin comprising the CDR-L1, CDR-L2 and CDR-L3 of a light chain immunoglobulin comprising an amino acid sequence set forth in SEQ ID NO: 10, 26, 42, 58, 74, 90, 106, 122, 146, 162, 182, 186, 190, 194, 198, 202, 206, 210, 214, 218, 222 or 226 and at least 90% amino acid sequence identity to the amino acid sequence set forth in SEQ ID NO: 10, 26, 42, 58, 74, 90, 106, 122, 146, 162, 182, 186, 190, 194, 198, 202, 206, 210, 214, 218, 222 or 226. In an embodiment of the invention, the antigen-binding protein comprises: a heavy chain immunoglobulin that comprises: CDR-H1 comprising the amino acid sequence set forth in SEQ ID NO: 4; CDR-H2 comprising the amino acid sequence set forth in SEQ ID NO: 6; and CDR-H3 comprising the amino acid sequence set forth in SEQ ID NO: 8 and/or CDR-H1 comprising the amino acid sequence set forth in SEQ ID NO: 20; CDR-H2 comprising the amino acid sequence set forth in SEQ ID NO: 22; and CDR-H3 comprising the amino acid sequence set forth in SEQ ID NO: 24 and/or CDR-H1 comprising the amino acid sequence set forth in SEQ ID NO: 36; CDR-H2 comprising the amino acid sequence set forth in SEQ ID NO: 38; and CDR-H3 comprising the amino acid sequence set forth in SEQ ID NO: 40 and/or CDR-H1 comprising the amino acid sequence set forth in SEQ ID NO: 52; CDR-H2 comprising the amino acid sequence set forth in SEQ ID NO: 54; and CDR-H3 comprising the amino acid sequence set forth in SEQ ID NO: 56 and/or CDR-H1 comprising the amino acid sequence set forth in SEQ ID NO: 68; CDR-H2 comprising the amino acid sequence set forth in SEQ ID NO: 70; and CDR-H3 comprising the amino acid sequence set forth in SEQ ID NO: 72 and/or CDR-H1 comprising the amino acid sequence set forth in SEQ ID NO: 84; CDR-H2 comprising the amino acid sequence set forth in SEQ ID NO: 86; and CDR-H3 comprising the amino acid sequence set forth in SEQ ID NO: 88 and/or CDR-H1 comprising the amino acid sequence set forth in SEQ ID NO: 100; CDR-H2 comprising the amino acid sequence set forth in SEQ ID NO: 102; and CDR-H3 comprising the amino acid sequence set forth in SEQ ID NO: 104 and/or CDR-H1 comprising the amino acid sequence set forth in SEQ ID NO: 116; CDR-H2 comprising the amino acid sequence set forth in SEQ ID NO: 118; and CDR-H3 comprising the amino acid sequence set forth in SEQ ID NO: 120 and/or CDR-H1 comprising the amino acid sequence set forth in SEQ ID NO: 132; CDR-H2 comprising the amino acid sequence set forth in SEQ ID NO: 134; and CDR-H3 comprising the amino acid sequence set forth in SEQ ID NO: 136 and/or CDR-H1 comprising the amino acid sequence set forth in SEQ ID NO: 140; CDR-H2 comprising the amino acid sequence set forth in SEQ ID NO: 142; and CDR-H3 comprising the amino acid sequence set forth in SEQ ID NO: 144 and/or CDR-H1 comprising the amino acid sequence set forth in SEQ ID NO: 156; CDR-H2 comprising the amino acid sequence set forth in SEQ ID NO: 158; and CDR-H3 comprising the amino acid sequence set forth in SEQ ID NO: 160 and/or CDR-H1 comprising the amino acid sequence set forth in SEQ ID NO: 172; CDR-H2 comprising the amino acid sequence set forth in SEQ ID NO: 174; and CDR-H3 comprising the amino acid sequence set forth in SEQ ID NO: 176 and/or CDR-L1 comprising the amino acid sequence set forth in SEQ ID NO: 12; CDR-L2 comprising the amino acid sequence set forth in SEQ ID NO: 14; and CDR-L3 comprising the amino acid sequence set forth in SEQ ID NO: 16 and/or CDR-L1 comprising the amino acid sequence set forth in SEQ ID NO: 28; CDR-L2 comprising the amino acid sequence set forth in SEQ ID NO: 30; and CDR-L3 comprising the amino acid sequence set forth in SEQ ID NO: 32 and/or CDR-L1 comprising the amino acid sequence set forth in SEQ ID NO: 44; CDR-L2 comprising the amino acid sequence set forth in SEQ ID NO: 46; and CDR-L3 comprising the amino acid sequence set forth in SEQ ID NO: 48 and/or CDR-L1 comprising the amino acid sequence set forth in SEQ ID NO: 60; CDR-L2 comprising the amino acid sequence set forth in SEQ ID NO: 62; and CDR-L3 comprising the amino acid sequence set forth in SEQ ID NO: 64 and/or CDR-L1 comprising the amino acid sequence set forth in SEQ ID NO: 76; CDR-L2 comprising the amino acid sequence set forth in SEQ ID NO: 78; and CDR-L3 comprising the amino acid sequence set forth in SEQ ID NO: 80 and/or CDR-L1 comprising the amino acid sequence set forth in SEQ ID NO: 92; CDR-L2 comprising the amino acid sequence set forth in SEQ ID NO: 94; and CDR-L3 comprising the amino acid sequence set forth in SEQ ID NO: 96 and/or CDR-L1 comprising the amino acid sequence set forth in SEQ ID NO: 108; CDR-L2 comprising the amino acid sequence set forth in SEQ ID NO: 110; and CDR-L3 comprising the amino acid sequence set forth in SEQ ID NO: 112 and/or CDR-L1 comprising the amino acid sequence set forth in SEQ ID NO: 124; CDR-L2 comprising the amino acid sequence set forth in SEQ ID NO: 126; and CDR-L3 comprising the amino acid sequence set forth in SEQ ID NO: 128 and/or CDR-L1 comprising the amino acid sequence set forth in SEQ ID NO: 124; CDR-L2 comprising the amino acid sequence set forth in SEQ ID NO: 126; and CDR-L3 comprising the amino acid sequence set forth in SEQ ID NO: 128 and/or CDR-L1 comprising the amino acid sequence set forth in SEQ ID NO: 148; CDR-L2 comprising the amino acid sequence set forth in SEQ ID NO: 150; and CDR-L3 comprising the amino acid sequence set forth in SEQ ID NO: 152 and/or CDR-L1 comprising the amino acid sequence set forth in SEQ ID NO: 164; CDR-L2 comprising the amino acid sequence set forth in SEQ ID NO: 166; and CDR-L3 comprising the amino acid sequence set forth in SEQ ID NO: 168 and/or CDR-L1 comprising the amino acid sequence set forth in SEQ ID NO: 124; CDR-L2 comprising the amino acid sequence set forth in SEQ ID NO: 126; and CDR-L3 comprising the amino acid sequence set forth in SEQ ID NO: 128. In an embodiment of the invention, the antigen-binding protein comprises: (1) a heavy chain immunoglobulin variable region comprising a CDR-H1 comprising the amino acid sequence set forth in SEQ ID NO: 4; a CDR-H2 comprising the amino acid sequence set forth in SEQ ID NO: 6; and a CDR-H3 comprising the amino acid sequence set forth in SEQ ID NO: 8; and a light chain immunoglobulin variable region comprising a CDR-L1 comprising the amino acid sequence set forth in SEQ ID NO: 12; a CDR-L2 comprising the amino acid sequence set forth in SEQ ID NO: 14; and a CDR-L3 comprising the amino acid sequence set forth in SEQ ID NO: 16; (2) a heavy chain immunoglobulin variable region comprising a CDR-H1 comprising the amino acid sequence set forth in SEQ ID NO: 20; a CDR-H2 comprising the amino acid sequence set forth in SEQ ID NO: 22; and a CDR-H3 comprising the amino acid sequence set forth in SEQ ID NO: 24; and a light chain immunoglobulin variable region comprising a CDR-L1 comprising the amino acid sequence set forth in SEQ ID NO: 28; a CDR-L2 comprising the amino acid sequence set forth in SEQ ID NO: 30; and a CDR-L3 comprising the amino acid sequence set forth in SEQ ID NO: 32; (3) a heavy chain immunoglobulin variable region comprising a CDR-H1 comprising the amino acid sequence set forth in SEQ ID NO: 36; a CDR-H2 comprising the amino acid sequence set forth in SEQ ID NO: 38; and a CDR-H3 comprising the amino acid sequence set forth in SEQ ID NO: 40; and a light chain immunoglobulin variable region comprising a CDR-L1 comprising the amino acid sequence set forth in SEQ ID NO: 44; a CDR-L2 comprising the amino acid sequence set forth in SEQ ID NO: 46; and a CDR-L3 comprising the amino acid sequence set forth in SEQ ID NO: 48; (4) a heavy chain immunoglobulin variable region comprising a CDR-H1 comprising the amino acid sequence set forth in SEQ ID NO: 52; a CDR-H2 comprising the amino acid sequence set forth in SEQ ID NO: 54; and a CDR-H3 comprising the amino acid sequence set forth in SEQ ID NO: 56; and a light chain immunoglobulin variable region comprising a CDR-L1 comprising the amino acid sequence set forth in SEQ ID NO: 60; a CDR-L2 comprising the amino acid sequence set forth in SEQ ID NO: 62; and a CDR-L3 comprising the amino acid sequence set forth in SEQ ID NO: 64; (5) a heavy chain immunoglobulin variable region comprising a CDR-H1 comprising the amino acid sequence set forth in SEQ ID NO: 68; a CDR-H2 comprising the amino acid sequence set forth in SEQ ID NO: 70; and a CDR-H3 comprising the amino acid sequence set forth in SEQ ID NO: 72; and a light chain immunoglobulin variable region comprising a CDR-L1 comprising the amino acid sequence set forth in SEQ ID NO: 76; a CDR-L2 comprising the amino acid sequence set forth in SEQ ID NO: 78; and a CDR-L3 comprising the amino acid sequence set forth in SEQ ID NO: 80; (6) a heavy chain immunoglobulin variable region comprising a CDR-H1 comprising the amino acid sequence set forth in SEQ ID NO: 84; a CDR-H2 comprising the amino acid sequence set forth in SEQ ID NO: 86; and a CDR-H3 comprising the amino acid sequence set forth in SEQ ID NO: 88; and a light chain immunoglobulin variable region comprising a CDR-L1 comprising the amino acid sequence set forth in SEQ ID NO: 92; a CDR-L2 comprising the amino acid sequence set forth in SEQ ID NO: 94; and a CDR-L3 comprising the amino acid sequence set forth in SEQ ID NO: 96; (7) a heavy chain immunoglobulin variable region comprising a CDR-H1 comprising the amino acid sequence set forth in SEQ ID NO: 100; a CDR-H2 comprising the amino acid sequence set forth in SEQ ID NO: 102; and a CDR-H3 comprising the amino acid sequence set forth in SEQ ID NO: 104; and a light chain immunoglobulin variable region comprising a CDR-L1 comprising the amino acid sequence set forth in SEQ ID NO: 108; a CDR-L2 comprising the amino acid sequence set forth in SEQ ID NO: 110; and a CDR-L3 comprising the amino acid sequence set forth in SEQ ID NO: 112; (8) a heavy chain immunoglobulin variable region comprising a CDR-H1 comprising the amino acid sequence set forth in SEQ ID NO: 116; a CDR-H2 comprising the amino acid sequence set forth in SEQ ID NO: 118; and a CDR-H3 comprising the amino acid sequence set forth in SEQ ID NO: 120; and a light chain immunoglobulin variable region comprising a CDR-L1 comprising the amino acid sequence set forth in SEQ ID NO: 124; a CDR-L2 comprising the amino acid sequence set forth in SEQ ID NO: 126; and a CDR-L3 comprising the amino acid sequence set forth in SEQ ID NO: 128; (9) a heavy chain immunoglobulin variable region comprising a CDR-H1 comprising the amino acid sequence set forth in SEQ ID NO: 132; a CDR-H2 comprising the amino acid sequence set forth in SEQ ID NO: 134; and a CDR-H3 comprising the amino acid sequence set forth in SEQ ID NO: 136; and a light chain immunoglobulin variable region comprising a CDR-L1 comprising the amino acid sequence set forth in SEQ ID NO: 124; a CDR-L2 comprising the amino acid sequence set forth in SEQ ID NO: 126; and a CDR-L3 comprising the amino acid sequence set forth in SEQ ID NO: 128; (10) a heavy chain immunoglobulin variable region comprising a CDR-H1 comprising the amino acid sequence set forth in SEQ ID NO: 140; a CDR-H2 comprising the amino acid sequence set forth in SEQ ID NO: 142; and a CDR-H3 comprising the amino acid sequence set forth in SEQ ID NO: 144; and a light chain immunoglobulin variable region comprising a CDR-L1 comprising the amino acid sequence set forth in SEQ ID NO: 148; a CDR-L2 comprising the amino acid sequence set forth in SEQ ID NO: 150; and a CDR-L3 comprising the amino acid sequence set forth in SEQ ID NO: 152; (11) a heavy chain immunoglobulin variable region comprising a CDR-H1 comprising the amino acid sequence set forth in SEQ ID NO: 156; a CDR-H2 comprising the amino acid sequence set forth in SEQ ID NO: 158; and a CDR-H3 comprising the amino acid sequence set forth in SEQ ID NO: 160; and a light chain immunoglobulin variable region comprising a CDR-L1 comprising the amino acid sequence set forth in SEQ ID NO: 164; a CDR-L2 comprising the amino acid sequence set forth in SEQ ID NO: 166; and a CDR-L3 comprising the amino acid sequence set forth in SEQ ID NO: 168; or (12) a heavy chain immunoglobulin variable region comprising a CDR-H1 comprising the amino acid sequence set forth in SEQ ID NO: 172; a CDR-H2 comprising the amino acid sequence set forth in SEQ ID NO: 174; and a CDR-H3 comprising the amino acid sequence set forth in SEQ ID NO: 176; and a light chain immunoglobulin variable region comprising a CDR-L1 comprising the amino acid sequence set forth in SEQ ID NO: 124; a CDR-L2 comprising the amino acid sequence set forth in SEQ ID NO: 126; and a CDR-L3 comprising the amino acid sequence set forth in SEQ ID NO: 128. In an embodiment of the invention, the antigen-binding protein comprises (a) a heavy chain immunoglobulin that comprises the amino acid sequence set forth in SEQ ID NO: 2, 18, 34, 50, 66, 82, 98, 114, 130, 138, 154, 170, 180, 184, 188, 192, 196, 200, 204, 208, 212, 216, 220 or 224; and/or (b) a light chain immunoglobulin that comprises the amino acid sequence set forth in SEQ ID NO: 10, 26, 42, 58, 74, 90, 106, 122, 146, 162, 182, 186, 190, 194, 198, 202, 206, 210, 214, 218, 222 or 226. The present invention includes an antigen-binding protein (e.g., antibody or antigen-binding fragment thereof) comprising: (a) a heavy chain immunoglobulin variable region that comprises the amino acid sequence set forth in SEQ ID NO: 2, and a light chain immunoglobulin variable region that comprises the amino acid sequence set forth in SEQ ID NO: 10; (b) a heavy chain immunoglobulin variable region that comprises the amino acid sequence set forth in SEQ ID NO: 18, and a light chain immunoglobulin variable region that comprises the amino acid sequence set forth in SEQ ID NO: 26; (c) a heavy chain immunoglobulin variable region that comprises the amino acid sequence set forth in SEQ ID NO: 34, and a light chain immunoglobulin variable region that comprises the amino acid sequence set forth in SEQ ID NO: 42; (d) a heavy chain immunoglobulin variable region that comprises the amino acid sequence set forth in SEQ ID NO: 50, and a light chain immunoglobulin variable region that comprises the amino acid sequence set forth in SEQ ID NO: 58; (e) a heavy chain immunoglobulin variable region that comprises the amino acid sequence set forth in SEQ ID NO: 66, and a light chain immunoglobulin variable region that comprises the amino acid sequence set forth in SEQ ID NO: 74; (f) a heavy chain immunoglobulin variable region that comprises the amino acid sequence set forth in SEQ ID NO: 82, and a light chain immunoglobulin variable region that comprises the amino acid sequence set forth in SEQ ID NO: 90; (g) a heavy chain immunoglobulin variable region that comprises the amino acid sequence set forth in SEQ ID NO: 98, and a light chain immunoglobulin variable region that comprises the amino acid sequence set forth in SEQ ID NO: 106; (h) a heavy chain immunoglobulin variable region that comprises the amino acid sequence set forth in SEQ ID NO: 114, and a light chain immunoglobulin variable region that comprises the amino acid sequence set forth in SEQ ID NO: 122; (i) a heavy chain immunoglobulin variable region that comprises the amino acid sequence set forth in SEQ ID NO: 130, and a light chain immunoglobulin variable region that comprises the amino acid sequence set forth in SEQ ID NO: 122; (j) a heavy chain immunoglobulin variable region that comprises the amino acid sequence set forth in SEQ ID NO: 138, and a light chain immunoglobulin variable region that comprises the amino acid sequence set forth in SEQ ID NO: 146; (k) a heavy chain immunoglobulin variable region that comprises the amino acid sequence set forth in SEQ ID NO: 154, and a light chain immunoglobulin variable region that comprises the amino acid sequence set forth in SEQ ID NO: 162; and/or (l) a heavy chain immunoglobulin variable region that comprises the amino acid sequence set forth in SEQ ID NO: 170, and a light chain immunoglobulin variable region that comprises the amino acid sequence set forth in SEQ ID NO: 122—for example wherein the heavy chain immunoglobulin variable region is linked to an heavy chain constant region (e.g., IgG (e.g., IgG1 or IgG4)) and the light chain immunoglobulin variable region is linked to a light chain constant region (e.g., lambda or kappa). For example, the light and heavy chain constant regions are human constant regions. In an embodiment of the invention, the antigen-binding protein (e.g., antibody or antigen-binding fragment thereof) of the present invention comprises: (a) a heavy chain immunoglobulin that comprises the amino acid sequence set forth in SEQ ID NO: 180, and a light chain immunoglobulin that comprises the amino acid sequence set forth in SEQ ID NO: 182; (b) a heavy chain immunoglobulin that comprises the amino acid sequence set forth in SEQ ID NO: 184, and a light chain immunoglobulin that comprises the amino acid sequence set forth in SEQ ID NO: 186; (c) a heavy chain immunoglobulin that comprises the amino acid sequence set forth in SEQ ID NO: 188, and a light chain immunoglobulin that comprises the amino acid sequence set forth in SEQ ID NO: 190; (d) a heavy chain immunoglobulin that comprises the amino acid sequence set forth in SEQ ID NO: 192, and a light chain immunoglobulin that comprises the amino acid sequence set forth in SEQ ID NO: 194; (e) a heavy chain immunoglobulin that comprises the amino acid sequence set forth in SEQ ID NO: 196, and a light chain immunoglobulin that comprises the amino acid sequence set forth in SEQ ID NO: 198; (f) a heavy chain immunoglobulin that comprises the amino acid sequence set forth in SEQ ID NO: 200, and a light chain immunoglobulin that comprises the amino acid sequence set forth in SEQ ID NO: 202; (g) a heavy chain immunoglobulin that comprises the amino acid sequence set forth in SEQ ID NO: 204, and a light chain immunoglobulin that comprises the amino acid sequence set forth in SEQ ID NO: 206; (h) a heavy chain immunoglobulin that comprises the amino acid sequence set forth in SEQ ID NO: 208, and a light chain immunoglobulin that comprises the amino acid sequence set forth in SEQ ID NO: 210; (i) a heavy chain immunoglobulin that comprises the amino acid sequence set forth in SEQ ID NO: 212, and a light chain immunoglobulin that comprises the amino acid sequence set forth in SEQ ID NO: 214; (j) a heavy chain immunoglobulin that comprises the amino acid sequence set forth in SEQ ID NO: 216, and a light chain immunoglobulin that comprises the amino acid sequence set forth in SEQ ID NO: 218; (k) a heavy chain immunoglobulin that comprises the amino acid sequence set forth in SEQ ID NO: 220, and a light chain immunoglobulin that comprises the amino acid sequence set forth in SEQ ID NO: 222; and/or (l) a heavy chain immunoglobulin that comprises the amino acid sequence set forth in SEQ ID NO: 224, and a light chain immunoglobulin that comprises the amino acid sequence set forth in SEQ ID NO: 226.

Antigen-binding proteins of the present invention, may, in an embodiment of the invention, be characterized by one or more of the following properties:

Binds to human IL36R with a $K_D$ of about 2.18 nM to about 13.9 nM at 25° C. or with a $K_D$ of about 4.25 nM to about 29.5 nM at 37° C.;

Binds to *Macaca fascicularis* IL36R with a $K_D$ of about 7.87 nM to about 34.4 nM at 25° C. or with a $K_D$ of about 14.4 nM to about 58.2 nM at 37° C.;

Binds to human IL36R fused to a mouse IgG2a with a $K_D$ of about 173 pM to about 5.79 nM at 25° C. or with a $K_D$ of about 205 pM to about 28.7 nM at 37° C.;

Binds to human IL36R fused to IL1RAcP extracellular domain expressed with mouse IgG2a Fc tag with a $K_D$ of about 212 pM to about 14 nM at 25° C. or with a $K_D$ of about 264 pM to about 40.9 nM at 37° C.;

Competes with H4H14699P2; H4H14700P2; H4H14706P2; H4H14708P2; H4H14709P; H4H14728P; H4H14731P; H4H14732P2; H4H14734P2; H4H14757P; H4H14758P or H4H14760P2 for binding to IL36R;

Blocks activation of one or more NFκB elements, which is/are fused to a reporter gene, in a host cell, by IL-36R (e.g., human or *Macaca fascicularis*) in the presence of IL-1RAcP and IL36R ligand;

Prevents or ameliorates skin inflammation or reduces skin thickness or total pathology score or reduces pro-inflammatory cytokine levels in a subject suffering from skin inflammation;

Prevents or ameliorates colitis or colon inflammation or reduces fecal levels of LCN2 polypeptide in a subject with such colitis or inflammation;

Protects residues (a) 113-119, 113-122, 116-119 and/or 116-122; and/or (b) 264-271, 267-271, 268-271, 268-276, 268-277 and/or 271-276, of human IL36R (IL-1RL2) set forth herein in SEQ ID NO: 227 (or the corresponding residues in wild-type IL-1RL2), when bound, from digestion with pepsin and/or Protease XIII and/or deuteration in the presence of deuterium;

Binds to IL36R (IL-1RL2) (e.g., human IL36R) at residues 113-119, 113-122, 116-119, 116-122, 264-271, 267-271, 268-271, 268-276, 268-277 and/or 271-276 of human IL36R comprising the amino acid sequence set forth herein in SEQ ID NO: 227 (or the corresponding residues in wild-type IL-1RL2);

Binds Domain II of IL36R (IL-1RL2) (e.g., human IL36R), e.g., with a coverage of about 80.0, 80.1, 81.0 or 81.5% or about 80-81 or 80-82% coverage; and/or Binds a polypeptide comprising the amino acid sequence YKQILHLGKD (SEQ ID: 229) (amino acids 113-122 of SEQ ID NO: 227);

Inhibits IL36α, IL36β and/or IL36γ (e.g., at a concentration of about 10 nM), e.g., in in vitro epidermal keratinocytes, intestinal myofibroblasts and/or CD14+ monocytes, with an $IC_{50}$ of about 1, 2, 3, 4, 5 or 6 nM or 1-6 nM; and/or Competitively inhibits IL36α, IL36β and/or IL36γ-mediated activation of NFκB (e.g., an NFκB response element (5×)-luciferase-IRES-GFP reporter in a cell such as HEK293) by IL36R: for example, as measured in a Schild Assay format.

Complexes comprising an IL36R polypeptide or antigenic fragment thereof complexed with an antigen-binding protein of the present invention (e.g., an antibody or antigen-binding fragment thereof, e.g., a human antibody or antigen-binding fragment thereof or a multispecific antibody) are also within the scope of the present invention.

Also provided by the present invention are methods for making an antigen-binding protein of the present invention (e.g., an antibody or antigen-binding fragment thereof, e.g., a human antibody or antigen-binding fragment thereof or a multispecific antibody) or an immunoglobulin chain thereof comprising: (a) introducing one or more polynucleotides encoding an immunoglobulin chain of said antigen-binding protein into a host cell (e.g., a Chinese hamster ovary (CHO) cell); (b) culturing the host cell under conditions favorable to expression of the polynucleotide; and (c) optionally, isolating the antigen-binding protein or immunoglobulin chain from the host cell and/or medium in which the host cell is grown. Antigen-binding proteins and immunoglobulin chains which are products of such a method are also part of the present invention.

The present invention also provides a polypeptide comprising: (a) CDR-H1, CDR-H2, and CDR-H3 of an immunoglobulin heavy chain variable region of an immunoglobulin chain that comprises the amino acid sequence set forth in SEQ ID NO: 2, 18, 34, 50, 66, 82, 98, 114, 130, 138, 154, 170, 180, 184, 188, 192, 196, 200, 204, 208, 212, 216, 220 or 224; and/or (b) CDR-L1, CDR-L2, and CDR-L3 of immunoglobulin light chain variable region of an immunoglobulin chain that comprises the amino acid sequence set forth in SEQ ID NO: 10, 26, 42, 58, 74, 90, 106, 122, 146, 162, 182, 186, 190, 194, 198, 202, 206, 210, 214, 218, 222 or 226; or, any amino acid sequence set forth herein, e.g., (c) the amino acid sequence set forth in a member selected from the group consisting of SEQ ID NO: 1-226. A polynucleotide encoding one or more (e.g., 2, e.g., a heavy and a light chain immunoglobulin set forth herein) of such polypeptides are also part of the present invention. Vectors, e.g., plasmids, comprising such a polynucleotide are also part of present invention. A host cell (e.g., a CHO cell) comprising any antigen-binding protein or immunoglobulin chain or polypeptide or polynucleotide or vector set forth herein is part of the present invention, e.g., wherein the polynucleotide and/or vector is integrated into a chromosome of the host cell or is ectopic.

A composition or kit comprising one or more of the antigen-binding proteins set forth herein (e.g., an antibody or antigen-binding fragment thereof, e.g., a human antibody or antigen-binding fragment thereof or a multispecific antibody), optionally in association with a further therapeutic agent (e.g., an anti-inflammatory agent, an anti-TNFalpha antibody or antigen-binding fragment thereof, an IL17 inhibitor, an IL23p19 inhibitor, an IL12p40 inhibitor, guselkumab, ustekinumab, brodalumab, ixekizumab, secukinumab, one or more human TNF receptors or fragments thereof linked to an immunoglobulin, infliximab, adalimumab, etanercept, dupilumab, sarilumab, tocilizumab, golimumab, abatacept, tofacitinib, abatacept, a nonsteroidal anti-inflammatory drug (NSAID), ibuprofen, naproxen, acetaminophen, aspirin, celecoxib, cyclophosphamide, methotrexate, a corticosteroid, cortisone and prednisone, form part of the present invention.

Pharmaceutical compositions comprising an antigen-binding protein set forth herein (e.g., an antibody or antigen-binding fragment thereof, e.g., a human antibody or antigen-binding fragment thereof or a multispecific antibody) and a pharmaceutically acceptable carrier and, optionally, a further therapeutic agent, are also part of the present invention.

The present invention also provides a vessel or injection device (e.g., a pre-filled syringe) comprising an antigen-binding protein (e.g., an antibody or antigen-binding fragment thereof, e.g., a human antibody or antigen-binding fragment thereof or a multispecific antibody) or composition set forth herein.

The present invention further provides a method for treating or preventing an IL36R mediated disorder (e.g., an inflammatory or autoimmune disease or inflammatory bowel disease) in a subject in need thereof (e.g., a human), comprising administering (e.g., parenterally), to the subject, a therapeutically effective amount of antigen-binding protein as set forth herein (e.g., an antibody or antigen-binding fragment thereof, e.g., a human antibody or antigen-binding fragment thereof or a multispecific antibody), optionally in association with a further therapeutic agent (e.g., an anti-inflammatory agent).

The present invention also provides a method for administering an antigen-binding protein as set forth herein (e.g., an antibody or antigen-binding fragment thereof, e.g., a human antibody or antigen-binding fragment thereof or a multispecific antibody) into the body of a subject (e.g., a human) comprising injecting (e.g., subcutaneously, intravenously or intramuscularly) the antigen-binding protein into the body of the subject, optionally in association with a further therapeutic agent (e.g., an anti-inflammatory agent).

The present invention encompasses any polypeptide comprising an amino acid sequence which is set forth in SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 180, 184, 188, 192, 196, 200, 204, 208, 212, 216, 220, 224, 182, 186, 190, 194, 198, 202, 206, 210, 214, 218, 222 and/or 226 or a variant thereof.

The present invention includes any polynucleotide comprising a nucleotide sequence which is set forth in SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 179, 183, 187, 191, 195, 199, 203, 207, 211, 215, 219, 223, 181, 185, 189, 193, 197, 201, 205, 209, 213, 217, 221 and/or 225 or a variant thereof.

BRIEF DESCRIPTION OF THE FIGURES

FIG. 1. Sequence comparison between germline $V_H$ (IGHV3-9*01/D1-7*01/J4*02, SEQ ID NO: 241) and $V_H$ (SEQ ID NO: 34) of H4H14706P2, and between germline $V_L$ (IGKV3-11*01/IGKJ4*01, SEQ ID NO: 242) and $V_L$ (SEQ ID NO: 42) of H4H14706P2.

FIG. 2. Sequence comparison between germline $V_H$ (IGHV3-9*01/D1-26*01/J4*02, SEQ ID NO: 243) and $V_H$ (SEQ ID NO: 50) of H4H14708P2, and between germline V$_L$(IGKV3-11*01/IGKJ4*01, SEQ ID NO: 242) and V$_L$ (SEQ ID NO: 58) of H4H14708P2.

FIGS. 3A-3F. Increasing concentration of H4H14706P2 and H4H14708P2 generated rightward shift of IL-36α (3A and 3D), IL-36β (3B and 3E), or IL-36γ (3C and 3F) dose response curves revealing competitive nature of inhibition by H4H14706P2 and H4H14708P2 (RLU, relative light units)

DETAILED DESCRIPTION OF THE INVENTION

Figure 4:
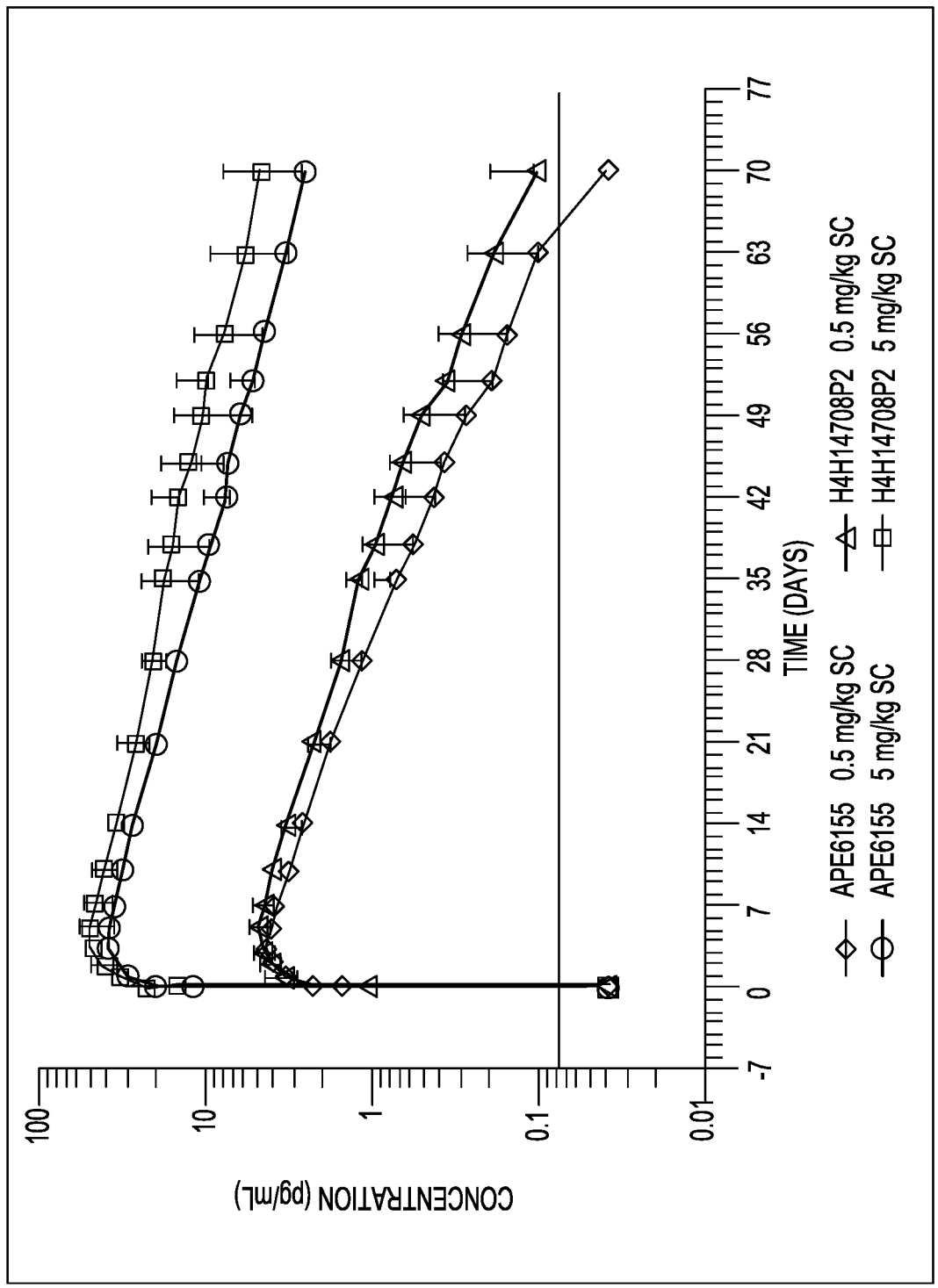
FIG. 4. H4H141708P2 and APE6155 pharmacokinetic analysis (concentration of antibody in serum over time) in cynomolgus monkeys dosed subcutaneously with 0.5 mg/kg or 5.0 mg/kg of antibody.

In accordance with the present invention there may be employed conventional molecular biology, microbiology, and recombinant DNA techniques within the skill of the art. Such techniques are explained fully in the literature. See, e.g., Sambrook, Fritsch & Maniatis, Molecular Cloning: A Laboratory Manual, Second Edition (1989) Cold Spring Harbor Laboratory Press, Cold Spring Harbor, N.Y. (herein "Sambrook, et al., 1989"); DNA Cloning: A Practical Approach, Volumes I and 11 (D. N. Glover ed. 1985); Oligonucleotide Synthesis (M. J. Gait ed. 1984); Nucleic Acid Hybridization (B. D. Hames & S. J. Higgins eds. (1985)); Transcription And Translation (B. D. Hames & S. J. Higgins, eds. (1984)); Animal Cell Culture (R. I. Freshney, ed. (1986)); Immobilized Cells And Enzymes (IRL Press, (1986)); B. Perbal, A Practical Guide To Molecular Cloning (1984); F. M. Ausubel, et al. (eds.), Current Protocols in Molecular Biology, John Wiley & Sons, Inc. (1994).

An anti-IL36R "antigen-binding protein" is a single polypeptide (e.g., an ScFv (single chain variable fragment)) or complex of more than one polypeptide (e.g., a tetrameric IgG antibody) that binds specifically to the IL36 receptor at the IL1RL2 subunit (IL-1Rrp2). IL-36R, in the context of binding of an antigen-binding protein thereto, refers to IL-RL2. In an embodiment of the invention, the antigen-binding protein is an antibody or antigen-binding fragment whether monospecific or multispecific (e.g., bispecific) or monovalent or multivalent (e.g., bivalent). A monovalent antigen-binding protein has a single antigen-binding domain whereas a bivalent antigen-binding protein has two antigen-binding domains.

A polynucleotide includes DNA and RNA. The present invention includes any polynucleotide of the present invention which is operably linked to a promoter or other expression control sequence.

In general, a "promoter" or "promoter sequence" is a DNA regulatory region capable of binding an RNA polymerase in a cell (e.g., directly or through other promoter-bound proteins or substances) and initiating transcription of a coding sequence. A promoter sequence is, in general, bounded at its 3' terminus by the transcription initiation site and extends upstream (5' direction) to include the minimum number of bases or elements necessary to initiate transcription at any level. Within the promoter sequence may be found a transcription initiation site (conveniently defined, for example, by mapping with nuclease S1), as well as protein binding domains (consensus sequences) responsible for the binding of RNA polymerase. The promoter may be operably associated with other expression control sequences, including enhancer and repressor sequences or with a nucleic acid of the invention. Promoters which may be used to control gene expression include, but are not limited to, cytomegalovirus (CMV) promoter (U.S. Pat. Nos. 5,385,839 and 5,168,062), the SV40 early promoter region (Benoist, et al., (1981) Nature 290:304-310), the promoter contained in the 3' long terminal repeat of Rous sarcoma virus (Yamamoto, et al., (1980) Cell 22:787-797), the herpes thymidine kinase promoter (Wagner, et al., (1981) Proc. Natl. Acad. Sci. USA 78:1441-1445), the regulatory sequences of the metallothionein gene (Brinster, et al., (1982) Nature 296:39-42); prokaryotic expression vectors such as the beta-lactamase promoter (VIIIa-Komaroff, et al., (1978) Proc. Natl. Acad. Sci. USA 75:3727-3731), or the tac promoter (DeBoer, et al., (1983) Proc. Natl. Acad. Sci. USA 80:21-25); see also "Useful proteins from recombinant bacteria" in Scientific American (1980) 242:74-94; and promoter elements from yeast or other fungi such as the Gal 4 promoter, the ADC (alcohol dehydrogenase) promoter, PGK (phosphoglycerol kinase) promoter or the alkaline phosphatase promoter.

A polynucleotide encoding a polypeptide is "operably linked" to a promoter or other expression control sequence when, in a cell, the sequence directs RNA polymerase mediated transcription of the coding sequence into RNA, preferably mRNA, which then may be RNA spliced (if it contains introns) and, optionally, translated into a protein encoded by the coding sequence.

Interleukin-36 Receptor (IL36R)

IL-36R is a member of the IL-1 receptor family that contains six receptor proteins that form four signaling complexes: IL-1RI, IL-18R, IL-33R, and IL-36R, and two decoy receptors and two negative regulators. IL-36R is a heterodimer that consists of a receptor subunit named IL-1Rrp2 (also known as IL-1RL2, Interleukin 1 receptor-like 2 or Interleukin 1 receptor-related protein 2) and a co-receptor subunit Interleukin-1 receptor accessory protein, IL-1RAcP. The receptor can recognize three different agonists, IL-36α, IL-36β, and IL-36γ (also known as IL-1F6, IL-1F8, and IL-1F9), to induce the expression of inflammatory cytokines. There are also two receptor antagonists, IL-36Ra and IL-38, which bind to IL-36 receptor and decrease the expression of inflammatory cytokines. IL-36α, IL-36β, and IL-36γ signal through the IL-36R/IL-1RAcP receptor to activate NF-κB and MAPKs, such as p38 and JNK, and promote inflammatory responses.

In an embodiment of the invention, the *Homo sapiens* IL1RL2 sequence is available under Genbank accession number NP_003845.2. In an embodiment of the invention, the amino acid sequence of *Homo sapiens* IL1RL2 is set forth in SEQ ID NO: 177.

In an embodiment of the invention, *Homo sapiens* IL-1RAcP sequence is available under Genbank accession no. NP_002173.1. In an embodiment of the invention, the amino acid sequence of *Homo sapiens* IL-1RAcP is set forth in SEQ ID NO: 178.

Anti-IL36 Antibodies and Antigen-Binding Fragments Thereof

The present invention provides antigen-binding proteins, such as antibodies (e.g., human antibodies) and antigen-binding fragments thereof, that specifically bind to IL36R protein or an antigenic fragment thereof. Antigen-binding proteins that bind to the same epitope on IL36R as, or compete for binding to IL36R with any of the antigen-binding proteins set forth herein are also part of the present invention.

The term "antibody", as used herein, refers to immunoglobulin molecules comprising four polypeptide chains, two heavy chains (HCs) and two light chains (LCs) inter-connected by disulfide bonds (i.e., "full antibody molecules"), as well as multimers thereof—for example H4H14699P2; H4H14700P2; H4H14706P2; H4H14708P2; H4H14709P; H4H14728P; H4H14731P; H4H14732P2; H4H14734P2; H4H14757P; H4H14758P or H4H14760P2. In an embodiment of the invention, each heavy chain (HC) comprises a heavy chain variable region ("HCVR" or "$V_H$") (e.g., SEQ ID NO: 2, 18, 34, 50, 66, 82, 98, 114, 130, 138, 154 or 170 or a variant thereof) and a heavy chain constant region (including domains CH1, CH2 and CH3); and each light chain (LC) comprises a light chain variable region ("LCVR or "$V_L$") (e.g., SEQ ID NO: 10, 26, 42, 58, 74, 90, 106, 122, 146 or 162 or a variant thereof) and a light chain constant region ($C_L$). The $V_H$ and $V_L$ regions can be further subdivided into regions of hypervariability, termed complementarity determining regions (CDR), interspersed with regions that are more conserved, termed framework regions (FR). Each $V_H$ and $V_L$ comprises three CDRs and four FRs, arranged from amino-terminus to carboxy-terminus in the following order: FR1, CDR1, FR2, CDR2, FR3, CDR3, FR4. In certain embodiments of the invention, the FRs of the antibody (or antigen binding fragment thereof) are identical to the human germline sequences, or are naturally or artificially modified.

Typically, the variable domains of both the heavy and light immunoglobulin chains comprise three hypervariable regions, also called complementarity determining regions (CDRs), located within relatively conserved framework regions (FR). In general, from N-terminal to C-terminal, both light and heavy chains variable domains comprise FR1, CDR1, FR2, CDR2, FR3, CDR3 and FR4. In an embodiment of the invention, the assignment of amino acids to each domain is in accordance with the definitions of Sequences of Proteins of Immunological Interest, Kabat, et al.; National Institutes of Health, Bethesda, Md.; 5th ed.; NIH Publ. No. 91-3242 (1991); Kabat (1978) Adv. Prot. Chem. 32:1-75; Kabat, et al., (1977) J. Biol. Chem. 252:6609-6616; Chothia, et al., (1987) J Mol. Biol. 196:901-917 or Chothia, et al., (1989) Nature 342:878-883.

For example, the present invention provides an antigen-binding protein that includes (a) a heavy chain immunoglobulin comprising the CDR-H1, CDR-H2 and CDR-H3 of a heavy chain immunoglobulin comprising an amino acid sequence set forth in SEQ ID NO: 2, 18, 34, 50, 66, 82, 98, 114, 130, 138, 154, 170, 180, 184, 188, 192, 196, 200, 204, 208, 212, 216, 220 or 224 and at least 70, 80 or 90% amino acid sequence identity to the amino acid sequence set forth in SEQ ID NO: 2, 18, 34, 50, 66, 82, 98, 114, 130, 138, 154, 170, 180, 184, 188, 192, 196, 200, 204, 208, 212, 216, 220 or 224; and (b) an light chain immunoglobulin comprising the CDR-L1, CDR-L2 and CDR-L3 of a light chain immunoglobulin comprising an amino acid sequence set forth in SEQ ID NO: 10, 26, 42, 58, 74, 90, 106, 122, 146, 162, 182, 186, 190, 194, 198, 202, 206, 210, 214, 218, 222 or 226 and at least 70, 80 or 90% amino acid sequence identity to the amino acid sequence set forth in SEQ ID NO: 10, 26, 42, 58, 74, 90, 106, 122, 146, 162, 182, 186, 190, 194, 198, 202, 206, 210, 214, 218, 222 or 226. In an embodiment of the invention, the antigen-binding protein includes (i) a heavy chain immunoglobulin that comprises CDR-H1, CDR-H2 and CDR-H3 of a heavy chain immunoglobulin that comprises the amino acid sequence set forth in SEQ ID NO: 2, 18, 34, 50, 66, 82, 98, 114, 130, 138, 154, 170, 180, 184, 188, 192, 196, 200, 204, 208, 212, 216, 220 or 224; or a variant thereof: and (ii) a light chain immunoglobulin that comprises CDR-L1, CDR-L2 and CDR-L3 of a light chain immunoglobulin that comprises the amino acid sequence set forth in SEQ ID NO: 10, 26, 42, 58, 74, 90, 106, 122, 146, 162, 182, 186, 190, 194, 198, 202, 206, 210, 214, 218, 222 or 226; or a variant thereof.

In an embodiment of the invention, an antigen-binding protein of the present invention includes a heavy chain immunoglobulin that comprises a $V_H$ including CDR-H1, CDR-H2 and CDR-H3, wherein the:
   CDR-H1 comprises the amino acid sequence set forth in SEQ ID NO: 4, 20, 36, 52, 68, 84, 100, 116, 132, 140, 156 or 172, or a variant thereof;
   CDR-H2 comprises the amino acid sequence set forth in SEQ ID NO: 6, 22, 38, 54, 70, 86, 102, 118, 134, 142, 158 or 174, or a variant thereof; and
   CDR-H3 comprises the amino acid sequence set forth in SEQ ID NO: 8, 24, 40, 56, 72, 88, 104, 120, 136, 144, 160 or 176, or a variant thereof; and
   a light chain immunoglobulin that comprises a $V_L$ including CDR-L1, CDR-L2 and CDR-L3, wherein the:
   CDR-L1 comprises the amino acid sequence set forth in SEQ ID NO: 12, 28, 44, 60, 76, 92, 108, 124, 124, 148 or 164, or a variant thereof;
   CDR-L2 comprises the amino acid sequence set forth in SEQ ID NO: 14, 30, 46, 62, 78, 94, 110, 126, 126, 150 or 166, or a variant thereof; and
   CDR-L3 comprises the amino acid sequence set forth in SEQ ID NO: 16, 32, 48, 64, 80, 96, 112, 128, 128, 152 or 168, or a variant thereof.

The present invention includes monoclonal anti-IL36R antigen-binding proteins, e.g., antibodies and antigen-binding fragments thereof, as well as monoclonal compositions comprising a plurality of isolated monoclonal antigen-binding proteins. The term "monoclonal antibody" or "mAb", as used herein, refers to a member of a population of substantially homogeneous antibodies, i.e., the antibody molecules comprising the population are identical in amino acid sequence except for possible naturally occurring mutations that may be present in minor amounts. A "plurality" of such monoclonal antibodies and fragments in a composition refers to a concentration of identical (i.e., as discussed above, in amino acid sequence except for possible naturally occurring mutations that may be present in minor amounts) antibodies and fragments which is above that which would normally occur in nature, e.g., in the blood of a host organism such as a mouse or a human.

In an embodiment of the invention, an anti-IL36R antigen-binding protein, e.g., antibody or antigen-binding fragment comprises a heavy chain constant domain, e.g., of the type IgA (e.g., IgA1 or IgA2), IgD, IgE, IgG (e.g., IgG1, IgG2, IgG3 and IgG4) or IgM. In an embodiment of the invention, an antigen-binding protein, e.g., antibody or antigen-binding fragment, comprises a light chain constant domain, e.g., of the type kappa or lambda.

The present invention includes human antigen-binding proteins. The term "human" antigen-binding protein, such as an antibody or antigen-binding fragment, as used herein, includes antibodies and fragments having variable and constant regions derived from human germline immunoglobulin sequences whether in a human cell or grafted into a non-human cell, e.g., a mouse cell. See e.g., U.S. Pat. Nos. 8,502,018, 6,596,541 or 5,789,215. The human mAbs of the invention may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include mAbs in which CDR sequences derived from the germline of another mammalian species (e.g., mouse) have been grafted onto human FR sequences. The term includes antibodies recombinantly produced in a non-human mammal or in cells of a non-human mammal. The term is not intended to include natural antibodies directly isolated from a human subject.

The present invention includes anti-IL36R chimeric antigen-binding proteins, e.g., antibodies and antigen-binding fragments thereof, and methods of use thereof. As used herein, a "chimeric antibody" is an antibody having the variable domain from a first antibody and the constant domain from a second antibody, where the first and second antibodies are from different species. (see e.g., U.S. Pat. No. 4,816,567; and Morrison et al., (1984) Proc. Natl. Acad. Sci. USA 81: 6851-6855).

The term "recombinant" antigen-binding proteins, such as antibodies or antigen-binding fragments thereof, refers to such molecules created, expressed, isolated or obtained by technologies or methods known in the art as recombinant DNA technology which include, e.g., DNA splicing and transgenic expression. The term includes antibodies expressed in a non-human mammal (including transgenic non-human mammals, e.g., transgenic mice), or a cell (e.g., CHO cells) such as a cellular expression system or isolated from a recombinant combinatorial human antibody library.

Recombinant anti-IL36R antigen-binding proteins, e.g., antibodies and antigen-binding fragments, disclosed herein may also be produced in an *E. coli*/T7 expression system. In this embodiment, nucleic acids encoding the anti-IL36R antibody immunoglobulin molecules of the invention (e.g., H4H14699P2; H4H14700P2; H4H14706P2; H4H14708P2; H4H14709P; H4H14728P; H4H14731P; H4H14732P2; H4H14734P2; H4H14757P; H4H14758P or H4H14760P2) may be inserted into a pET-based plasmid and expressed in the *E. coli*/T7 system. For example, the present invention includes methods for expressing an antibody or antigen-binding fragment thereof or immunoglobulin chain thereof in a host cell (e.g., bacterial host cell such as *E. coli* such as BL21 or BL21DE3) comprising expressing T7 RNA polymerase in the cell which also includes a polynucleotide encoding an immunoglobulin chain that is operably linked to a T7 promoter. For example, in an embodiment of the invention, a bacterial host cell, such as an *E. coli*, includes a polynucleotide encoding the T7 RNA polymerase gene operably linked to a lac promoter and expression of the polymerase and the chain is induced by incubation of the host cell with IPTG (isopropyl-beta-D-thiogalactopyranoside). See U.S. Pat. Nos. 4,952,496 and 5,693,489 or Studier & Moffatt, Use of bacteriophage T7 RNA polymerase to direct selective high-level expression of cloned genes, J. Mol. Biol. 1986 May 5; 189(1): 113-30.

There are several methods by which to produce recombinant antibodies which are known in the art. One example of a method for recombinant production of antibodies is disclosed in U.S. Pat. No. 4,816,567.

Transformation can be by any known method for introducing polynucleotides into a host cell. Methods for introduction of heterologous polynucleotides into mammalian cells are well known in the art and include dextran-mediated transfection, calcium phosphate precipitation, polybrene-mediated transfection, protoplast fusion, electroporation, encapsulation of the polynucleotide(s) in liposomes, biolistic injection and direct microinjection of the DNA into nuclei. In addition, nucleic acid molecules may be introduced into mammalian cells by viral vectors. Methods of transforming cells are well known in the art. See, for example, U.S. Pat. Nos. 4,399,216; 4,912,040; 4,740,461 and 4,959,455. Thus, the present invention includes recombinant methods for making an anti-IL36R antigen-binding protein, such as an antibody or antigen-binding fragment thereof of the present invention, or an immunoglobulin chain thereof, comprising (i) introducing one or more polynucleotides (e.g., including the nucleotide sequence in any one or more of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 179, 181, 183, 185, 187, 189, 191, 193, 195, 197, 199, 201, 203, 205, 207, 209, 211, 213, 215, 217, 219, 221, 223 and/or 225; or a variant thereof) encoding light and/or heavy immunoglobulin chains of the antigen-binding protein, e.g., H4H14699P2; H4H14700P2; H4H14706P2; H4H14708P2; H4H14709P; H4H14728P; H4H14731P; H4H14732P2; H4H14734P2; H4H14757P; H4H14758P or H4H14760P2, for example, wherein the polynucleotide is in a vector; and/or integrated into a host cell chromosome and/or is operably linked to a promoter; (ii) culturing the host cell (e.g., CHO or *Pichia* or *Pichia pastoris*) under conditions favorable to expression of the polynucleotide and, (iii) optionally, isolating the antigen-binding protein (e.g., antibody or fragment) or chain from the host cell and/or medium in which the host cell is grown. When making an antigen-binding protein (e.g., antibody or antigen-binding fragment) comprising more than one immunoglobulin chain, e.g., an antibody that comprises two heavy immunoglobulin chains and two light immunoglobulin chains, co-expression of the chains in a single host cell leads to association of the chains, e.g., in the cell or on the cell surface or outside the cell if such chains are secreted, so as to form the antigen-binding protein (e.g., antibody or antigen-binding fragment). The methods of the present invention include those wherein only a heavy immunoglobulin chain or only a light immunoglobulin chain or both (e.g., any of those discussed herein including mature fragments and/or variable domains thereof) are expressed in a cell. Such single chains are useful, for example, as intermediates in the expression of an antibody or antigen-binding fragment that includes such a chain. For example, the present invention also includes anti-IL36R antigen-binding proteins, such as antibodies and antigen-binding fragments thereof, comprising a heavy chain immunoglobulin (or variable domain thereof or comprising the CDRs thereof) encoded by a polynucleotide comprising the nucleotide sequences set forth in SEQ ID NO: 1, 17, 33, 49, 65, 81, 97, 113, 129, 137, 153, 169, 179, 183, 187, 191, 195, 199, 203, 207, 211, 215, 219 or 223; and a light chain immunoglobulin (or variable domain thereof or comprising the CDRs thereof) encoded by the nucleotide sequence set forth in SEQ ID NO: 9, 25, 41, 57, 73, 89, 105, 121, 145, 161, 181, 185, 189, 193, 197, 201, 205, 209, 213, 217, 221 or 225 which are the product of such production methods, and, optionally, the purification methods set forth herein. For example, in an embodiment of the invention, the product of the method is an anti-IL36R antigen-binding protein which is an antibody or fragment comprising a heavy chain immunoglobulin or $V_H$ comprising the amino acid sequence set forth in SEQ ID NO: 2, 18, 34, 50, 66, 82, 98, 114, 130, 138, 154, 170, 180, 184, 188, 192, 196, 200, 204, 208, 212, 216, 220 or 224 and a light chain immunoglobulin or $V_L$ comprising the amino acid sequence set forth in SEQ ID NO: 10, 26, 42, 58, 74, 90, 106, 122, 146, 162, 182, 186, 190, 194, 198, 202, 206, 210, 214, 218, 222 or 226.

In an embodiment of the invention, a method for making an anti-IL36R antigen-binding protein, e.g., antibody or antigen-binding fragment thereof, includes a method of purifying the antigen-binding protein, e.g., by column chromatography, precipitation and/or filtration. The product of such a method also forms part of the present invention.

Eukaryotic and prokaryotic host cells, including mammalian cells, may be used as hosts for expression of an anti-IL36R antigen-binding protein (e.g., antibody or antigen-binding fragment thereof). Such host cells are well known in the art and many are available from the American Type Culture Collection (ATCC). These host cells include, inter alia, Chinese hamster ovary (CHO) cells, NSO, SP2 cells, HeLa cells, baby hamster kidney (BHK) cells, monkey kidney cells (COS), human hepatocellular carcinoma cells (e.g., Hep G2), A549 cells, 3T3 cells, HEK-293 cells and a number of other cell lines. Mammalian host cells include human, mouse, rat, dog, monkey, pig, goat, bovine, horse and hamster cells. Other cell lines that may be used are insect cell lines (e.g., *Spodoptera frugiperda* or *Trichoplusia ni*), amphibian cells, bacterial cells, plant cells and fungal cells. Fungal cells include yeast and filamentous fungus cells including, for example, *Pichia, Pichia pastoris, Pichia finlandica, Pichia trehalophila, Pichia koclamae, Pichia membranaefaciens, Pichia minuta (Ogataea minuta, Pichia lindneri), Pichia opuntiae, Pichia thermotolerans, Pichia salictaria, Pichia guercuum, Pichia pijperi, Pichia stiptis, Pichia methanolica, Pichia* sp., *Saccharomyces cerevisiae, Saccharomyces* sp., *Hansenula polymorpha, Kluyveromyces* sp., *Kluyveromyces lactis, Candida albicans, Aspergillus nidulans, Aspergillus niger, Aspergillus oryzae, Trichoderma reesei, Chrysosporium lucknowense, Fusarium* sp., *Fusarium gramineum, Fusarium venenatum, Physcomitrella patens* and *Neurospora crassa*. The present invention includes an isolated host cell (e.g., a CHO cell or any type of host cell set forth above) comprising an antigen-binding protein, such as H4H14699P2; H4H14700P2; H4H14706P2; H4H14708P2; H4H14709P; H4H14728P; H4H14731P; H4H14732P2; H4H14734P2; H4H14757P; H4H14758P or H4H14760P2; and/or a polynucleotide encoding one or more immunoglobulin chains thereof.

The present invention also includes a cell which is expressing IL36R or an antigenic fragment or fusion thereof (e.g., $His_6$, Fc and/or myc) which is bound by an antigen-binding protein of the present invention e.g., H4H14699P2; H4H14700P2; H4H14706P2; H4H14708P2; H4H14709P; H4H14728P; H4H14731P; H4H14732P2; H4H14734P2; H4H14757P; H4H14758P or H4H14760P2, e.g., wherein the cell is in the body of a subject or is in vitro.

In addition, the present invention also provides a complex comprising an anti-IL36R antigen-binding protein, e.g., antibody or antigen-binding fragment, discussed herein complexed with IL36R polypeptide or an antigenic fragment thereof or fusion thereof and/or with a secondary antibody or antigen-binding fragment thereof (e.g., detectably labeled secondary antibody) that binds specifically to the anti-IL36R antibody or fragment. In an embodiment of the invention, the complex is in vitro (e.g., is immobilized to a solid substrate) or is in the body of a subject.

The term "specifically binds" refers to those antigen-binding proteins (e.g., mAbs) having a binding affinity to an antigen, such as IL36R protein, expressed as $K_D$, of at least about 58 nM (e.g., $10^{-9}$ M; $10^{-10}$ M, $10^{-11}$ M, or $10^{-12}$ M), as measured by real-time, label free bio-layer interferometry assay, for example, at 25° C. or 37° C., e.g., an Octet® HTX biosensor, or by surface plasmon resonance, e.g., BIA-CORE™, or by solution-affinity ELISA. The present invention includes antigen-binding proteins that specifically bind to IL36R protein. In an embodiment of the invention, an anti-IL36R antigen-binding protein comprises a $K_D$ value, for binding to human and/or *Macaca fascicularis* IL36R, which value is set forth in any of Tables 4-1 to 4-8.

The terms "antigen-binding portion" or "antigen-binding fragment" of an antibody or antigen-binding protein, and the like, as used herein, include any naturally occurring, enzymatically obtainable, synthetic, or genetically engineered polypeptide or glycoprotein that specifically binds an antigen to form a complex. Non-limiting examples of antigen-binding fragments include: (i) Fab fragments; (ii) F(ab')$_2$ fragments; (iii) Fd fragments; (iv) Fv fragments; (v) single-chain Fv (scFv) molecules; and (vi) dAb fragments; consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies and small modular immunopharmaceuticals (SMIPs), are also encompassed within the expression "antigen-binding fragment," as used herein. In an embodiment of the invention, the antigen-binding fragment comprises three or more CDRs of H4H14699P2; H4H14700P2; H4H14706P2; H4H14708P2; H4H14709P; H4H14728P; H4H14731P; H4H14732P2; H4H14734P2; H4H14757P; H4H14758P or H4H14760P2 (e.g., CDR-H1, CDR-H2 and CDR-H3; or CDR-L1, CDR-L2 and CDR-L3).

An antigen-binding fragment of an antibody will, in an embodiment of the invention, comprise at least one variable domain. The variable domain may be of any size or amino acid composition and will generally comprise at least one CDR, which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present invention include: (i) $V_H$-$C_H1$; (ii) $V_H$-$C_H2$; (iii) $V_H$-$C_H3$; (iv) $V_H$-$C_H1$-$C_H2$; (v) $V_H$-$C_H1$-$C_H2$-$C_H3$; (vi) $V_H$-$C_H2$-$C_H3$; (vii) $V_H$-$C_L$; (viii) $V_L$-$C_H1$; (ix) $V_L$-$C_H2$; (X) $V_L$-$C_H3$; (Xi) $V_L$-$C_H1$-$C_H2$; (xii) $V_L$-$C_H1$-$C_H2$-$C_H3$; (Xiii) $V_L$-$C_H2$-$C_H3$; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids, which result in a flexible or semi-flexible linkage between adjacent variable and/or constant domains in a single polypeptide molecule. Moreover, an antigen-binding fragment of an antibody of the present invention may comprise a homo-dimer or heterodimer (or other multimer) of any of the variable and constant domain configurations listed above in non-covalent association with one another and/or with one or more monomeric $V_H$ or $V_L$ domain (e.g., by disulfide bond(s)).

Antigen-binding proteins (e.g., antibodies and antigen-binding fragments) may be monospecific or multi-specific (e.g., bispecific). Multispecific antigen-binding proteins are discussed further herein.

In specific embodiments, antigen-binding proteins of the present invention (e.g., an antibody or antibody fragment) may be conjugated to a moiety such a ligand, a detectable label or a therapeutic moiety ("immunoconjugate"), a second anti-IL36R antibody, or any other therapeutic moiety.

"Isolated" antigen-binding proteins (e.g., antibodies or antigen-binding fragments thereof), polypeptides, polynucleotides and vectors, are at least partially free of other biological molecules from the cells or cell culture from which they are produced. Such biological molecules include nucleic acids, proteins, other antibodies or antigen-binding fragments, lipids, carbohydrates, or other material such as cellular debris and growth medium. An isolated antigen-binding protein may further be at least partially free of expression system components such as biological molecules from a host cell or of the growth medium thereof. Generally, the term "isolated" is not intended to refer to a complete absence of such biological molecules or to an absence of water, buffers, or salts or to components of a pharmaceutical formulation that includes the antigen-binding proteins (e.g., antibodies or antigen-binding fragments).

The present invention includes antigen-binding proteins, e.g., antibodies or antigen-binding fragments, that bind to the same epitope as an antigen-binding protein of the present invention (e.g., H4H14699P2; H4H14700P2; H4H14706P2; H4H14708P2; H4H14709P; H4H14728P; H4H14731P; H4H14732P2; H4H14734P2; H4H14757P; H4H14758P or H4H14760P2).

The term "epitope" refers to an antigenic determinant (e.g., on IL1RL2) that interacts with a specific antigen-binding site of an antigen-binding protein, e.g., a variable region of an antibody molecule, known as a paratope. A single antigen may have more than one epitope.

Thus, different antibodies may bind to different areas on an antigen and may have different biological effects. The term "epitope" may also refer to a site on an antigen to which B and/or T cells respond and/or to a region of an antigen that is bound by an antibody. Epitopes may be defined as structural or functional. Functional epitopes are generally a subset of the structural epitopes and have those residues that directly contribute to the affinity of the interaction. Epitopes may be linear or conformational, that is, composed of non-linear amino acids. In certain embodiments, epitopes may include determinants that are chemically active surface groupings of molecules such as amino acids, sugar side chains, phosphoryl groups, or sulfonyl groups, and, in certain embodiments, may have specific three-dimensional structural characteristics, and/or specific charge characteristics.

Methods for determining the epitope of an antigen-binding protein, e.g., antibody or fragment or polypeptide, include alanine scanning mutational analysis, peptide blot analysis (Reineke (2004) Methods Mol. Biol. 248: 443-63), peptide cleavage analysis, crystallographic studies and NMR analysis. In addition, methods such as epitope excision, epitope extraction and chemical modification of antigens can be employed (Tomer (2000) Prot. Sci. 9: 487-496). Another method that can be used to identify the amino acids within a polypeptide with which an antigen-binding protein (e.g., antibody or fragment or polypeptide) interacts is hydrogen/deuterium exchange detected by mass spectrometry. See, e.g., Ehring (1999) Analytical Biochemistry 267: 252-259; Engen and Smith (2001) Anal. Chem. 73: 256A-265A.

The present invention includes antigen-binding proteins that compete for binding to IL36R, e.g., a variant IL36R epitope as discussed herein, with an antigen-binding protein of the present invention, e.g., H4H14699P2; H4H14700P2; H4H14706P2; H4H14708P2; H4H14709P; H4H14728P; H4H14731P; H4H14732P2; H4H14734P2; H4H14757P; H4H14758P or H4H14760P2. The term "competes" as used herein, refers to an antigen-binding protein (e.g., antibody or antigen-binding fragment thereof) that binds to an antigen (e.g., IL1RL2) and inhibits or blocks the binding of another antigen-binding protein (e.g., antibody or antigen-binding fragment thereof) to the antigen. The term also includes competition between two antigen-binding proteins e.g., antibodies, in both orientations, i.e., a first antibody that binds and blocks binding of second antibody and vice versa. In certain embodiments, the first antigen-binding protein (e.g., antibody) and second antigen-binding protein (e.g., antibody) may bind to the same epitope. Alternatively, the first and second antigen-binding proteins (e.g., antibodies) may bind to different, but, for example, overlapping epitopes, wherein binding of one inhibits or blocks the binding of the second antibody, e.g., via steric hindrance. Competition between antigen-binding proteins (e.g., antibodies) may be measured by methods known in the art, for example, by a real-time, label-free bio-layer interferometry assay. Also, binding competition between anti-IL36R antigen-binding proteins (e.g., monoclonal antibodies (mAbs)) can be determined using a real time, label-free bio-layer interferometry assay on an Octet RED384 biosensor (Pall ForteBio Corp.).

Typically, an antibody or antigen-binding fragment of the invention which is modified in some way retains the ability to specifically bind to IL36R, e.g., retains at least 10% of its IL36R binding activity (when compared to the parental antibody) when that activity is expressed on a molar basis. Preferably, an antibody or antigen-binding fragment of the invention retains at least 20%, 50%, 70%, 80%, 90%, 95% or 100% or more of the IL36R binding affinity as the parental antibody. It is also intended that an antibody or antigen-binding fragment of the invention may include conservative or non-conservative amino acid substitutions (referred to as "conservative variants" or "function conserved variants" of the antibody) that do not substantially alter its biologic activity.

A "variant" of a polypeptide, such as an immunoglobulin chain (e.g., H4H14699P2; H4H14700P2; H4H14706P2; H4H14708P2; H4H14709P; H4H14728P; H4H14731P; H4H14732P2; H4H14734P2; H4H14757P; H4H14758P or H4H14760P2 $V_H$, $V_L$, HC or LC), refers to a polypeptide comprising an amino acid sequence that is at least about 70-99.9% (e.g., 70, 72, 74, 75, 76, 79, 80, 81, 82, 83, 84, 85, 86, 87, 88, 89, 90, 91, 92, 93, 94, 95, 96, 97, 98, 99, 99.5, 99.9%) identical or similar to a referenced amino acid sequence that is set forth herein (e.g., any of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 180, 182, 184, 186, 188, 190, 192, 194, 196, 198, 200, 202, 204, 206, 208, 210, 212, 214, 216, 218, 220, 222, 224 or 226); when the comparison is performed by a BLAST algorithm wherein the parameters of the algorithm are selected to give the largest match between the respective sequences over the entire length of the respective reference sequences (e.g., expect threshold: 10; word size: 3; max matches in a query range: 0; BLOSUM 62 matrix; gap costs: existence 11, extension 1; conditional compositional score matrix adjustment).

A "variant" of a polynucleotide refers to a polynucleotide comprising a nucleotide sequence that is at least about 70-99.9% (e.g., 70, 72, 74, 75, 76, 79, 80, 81, 82, 83, 84, 85, 86, 87, 88, 89, 90, 91, 92, 93, 94, 95, 96, 97, 98, 99, 99.5, 99.9%) identical to a referenced nucleotide sequence that is set forth herein (e.g., any of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 179, 183, 187, 191, 195, 199, 203, 207, 211, 215, 219, 223, 181, 185, 189, 193, 197, 201, 205, 209, 213, 217, 221 and/or 225); when the comparison is performed by a BLAST algorithm wherein the parameters of the algorithm are selected to give the largest match between the respective sequences over the entire length of the respective reference sequences (e.g., expect threshold: 10; word size: 28; max matches in a query range: 0; match/mismatch scores: 1, −2; gap costs: linear).

The following references relate to BLAST algorithms often used for sequence analysis: BLAST ALGORITHMS: Altschul et al. (2005) FEBS J. 272(20): 5101-5109; Altschul, S. F., et al., (1990) J. Mol. Biol. 215:403-410; Gish, W., et al., (1993) Nature Genet. 3:266-272; Madden, T. L., et al., (1996) Meth. Enzymol. 266:131-141; Altschul, S. F., et al., (1997) Nucleic Acids Res. 25:3389-3402; Zhang, J., et al., (1997) Genome Res. 7:649-656; Wootton, J. C., et al., (1993) Comput. Chem. 17:149-163; Hancock, J. M. et al., (1994) Comput. Appl. Biosci. 10:67-70; ALIGNMENT SCORING SYSTEMS: Dayhoff, M. O., et al., "A model of evolutionary change in proteins." in Atlas of Protein Sequence and Structure, (1978) vol. 5, suppl. 3. M. O. Dayhoff (ed.), pp. 345-352, Natl. Biomed. Res. Found., Washington, D.C.; Schwartz, R. M., et al., "Matrices for detecting distant relationships." in Atlas of Protein Sequence and Structure, (1978) vol. 5, suppl. 3." M. O. Dayhoff (ed.), pp. 353-358, Natl. Biomed. Res. Found., Washington, D.C.; Altschul, S. F., (1991) J. Mol. Biol. 219:555-565; States, D. J., et al., (1991) Methods 3:66-70; Henikoff, S., et al., (1992) Proc. Natl. Acad. Sci. USA 89:10915-10919: Altschul, S. F., et al., (1993) J. Mol. Evol. 36:290-300; ALIGNMENT STATISTICS: Karlin, S., et al., (1990) Proc. Natl. Acad. Sci. USA 87:2264-2268; Karlin, S., et al., (1993) Proc. Natl. Acad. Sci. USA 90:5873-5877: Dembo, A., et al., (1994) Ann. Prob. 22:2022-2039; and Altschul, S. F. "Evaluating the statistical significance of multiple distinct local alignments." in Theoretical and Computational Methods in Genome Research (S. Suhai, ed.), (1997) pp. 1-14, Plenum, N.Y.

Anti-IL36R antigen-binding proteins, e.g., antibodies and antigen-binding fragments thereof of the present invention, in an embodiment of the invention, include a heavy chain immunoglobulin or variable region thereof having at least 70% (e.g., 80%, 85%, 90%, 95%, 99%) amino acid sequence identity to the amino acids set forth in SEQ ID NO: 2, 18, 34, 50, 66, 82, 98, 114, 130, 138, 154, 170, 180, 184, 188, 192, 196, 200, 204, 208, 212, 216, 220 or 224; and/or a light chain immunoglobulin or variable region thereof having at least 70% (e.g., 80%, 85%, 90%, 95%, 99%) amino acid sequence identity to the amino acids set forth in SEQ ID NO: 10, 26, 42, 58, 74, 90, 106, 122, 146, 162, 182, 186, 190, 194, 198, 202, 206, 210, 214, 218, 222 or 226.

In addition, an anti-IL36R antigen-binding protein may include a polypeptide comprising an amino acid sequence that is set forth herein except for one or more (e.g., 1, 2, 3, 4, 5, 6, 7, 8, 9 or 10) mutations such as, for example, missense mutations (e.g., conservative substitutions), non-sense mutations, deletions, or insertions. For example, the present invention includes anti-IL36R antigen-binding proteins which include an immunoglobulin light chain (or $V_L$) variant comprising the amino acid sequence set forth in SEQ ID NO: 10, 26, 42, 58, 74, 90, 106, 122, 146, 162, 182, 186, 190, 194, 198, 202, 206, 210, 214, 218, 222 or 226 but having one or more of such mutations and/or an immunoglobulin heavy chain (or $V_H$) variant comprising the amino acid sequence set forth in SEQ ID NO: 2, 18, 34, 50, 66, 82, 98, 114, 130, 138, 154, 170, 180, 184, 188, 192, 196, 200, 204, 208, 212, 216, 220 or 224 but having one or more of such mutations. In an embodiment of the invention, an anti-IL36R antigen-binding protein includes an immunoglobulin light chain variant comprising CDR-L1, CDR-L2 and CDR-L3 wherein one or more (e.g., 1 or 2 or 3) of such CDRs has one or more of such mutations (e.g., conservative substitutions) and/or an immunoglobulin heavy chain variant comprising CDR-H1, CDR-H2 and CDR-H3 wherein one or more (e.g., 1 or 2 or 3) of such CDRs has one or more of such mutations (e.g., conservative substitutions).

Embodiments of the present invention also include antigen-binding proteins, e.g., anti-IL36R antibodies and antigen-binding fragments thereof, that comprise immunoglobulin $V_H$s and $V_L$s; or HCs and LCs, which comprise a variant amino acid sequence having 70% or more (e.g., 80%, 85%, 90%, 95%, 97% or 99%) overall amino acid sequence identity or similarity to the amino acid sequences of the corresponding $V_H$s, $V_L$s, HCs or LCs specifically set forth herein, but wherein the CDR-L1, CDR-L2, CDR-L3, CDR-H1, CDR-H2 and CDR-H3 of such immunoglobulins are not variants and comprise the amino acid sequences specifically set forth herein. Thus, in such embodiments, the CDRs within variant antigen-binding proteins are not, themselves, variants.

A "conservatively modified variant" or a "conservative substitution", e.g., of an immunoglobulin chain set forth herein, refers to a variant wherein there is one or more substitutions of amino acids in a polypeptide with other amino acids having similar characteristics (e.g. charge, side-chain size, hydrophobicity/hydrophilicity, backbone conformation and rigidity, etc.). Such changes can frequently be made without significantly disrupting the biological activity of the antibody or fragment. Those of skill in this art recognize that, in general, single amino acid substitutions in non-essential regions of a polypeptide do not substantially alter biological activity (see, e.g., Watson et al. (1987) Molecular Biology of the Gene, The Benjamin/Cummings Pub. Co., p. 224 (4M Ed.)). In addition, substitutions of structurally or functionally similar amino acids are less likely to significantly disrupt biological activity. The present invention includes anti-IL36R antigen-binding proteins comprising such conservatively modified variant immunoglobulin chains.

Examples of groups of amino acids that have side chains with similar chemical properties include 1) aliphatic side chains: glycine, alanine, valine, leucine and isoleucine; 2) aliphatic-hydroxyl side chains: serine and threonine; 3) amide-containing side chains: asparagine and glutamine; 4)

aromatic side chains: phenylalanine, tyrosine, and tryptophan: 5) basic side chains: lysine, arginine, and histidine; 6) acidic side chains: aspartate and glutamate, and 7) sulfur-containing side chains: cysteine and methionine. Preferred conservative amino acids substitution groups are: valine-leucine-isoleucine, phenylalanine-tyrosine, lysine-arginine, alanine-valine, glutamate-aspartate, and asparagine-glutamine.

Alternatively, a conservative replacement is any change having a positive value in the PAM250 log-likelihood matrix disclosed in Gonnet et al. (1992) Science 256: 1443 45.

Anti-IL36R antigen-binding proteins set forth herein, e.g., comprising variant immunoglobulin chains, may exhibit one or more of the following properties:

Binds to human IL36R (e.g., IL1RL2) (e.g., fused to a myc-myc-Hise tag) with a $K_D$ of about 2.18 nM to about 13.9 nM, e.g., at 25° C. or with a $K_D$ of about 4.25 nM to about 29.5 nM, e.g., at 37° C.;

Binds to *Macaca fascicularis* IL36R (e.g., IL1RL2) (e.g., fused to a myc-myc-Hiss tag) with a $K_D$ of about 7.87 nM to about 34.4 nM, e.g., at 25° C. or with a $K_D$ of about 14.4 nM to about 58.2 nM, e.g., at 37° C.;

Binds to human IL36R (e.g., IL1RL2) (e.g., fused to a mouse IgG2a) with a $K_D$ of about 173 pM to about 5.79 nM, e.g., at 25° C. or with a $K_D$ of about 205 pM to about 28.7 nM, e.g., at 37° C.;

Binds to human IL36R (e.g., IL1RL2) (e.g., fused to IL1RAcP extracellular domain expressed with mouse IgG2a Fc tag) with a $K_D$ of about 212 pM to about 14 nM, e.g., at 25° C. or with a $K_D$ of about 264 pM to about 40.9 nM, e.g., at 37° C.;

Competes with one or more of the following anti-IL36R antibodies: H4H14699P2; H4H14700P2; H4H14706P2; H4H14708P2; H4H14709P; H4H14728P; H4H14731P; H4H14732P2; H4H14734P2; H4H14757P; H4H14758P and/or H4H14760P2 for binding to IL36R (e.g., IL1RL2), optionally with the proviso that such anti-IL36R antibody or fragment which competes with H4H14699P2; H4H14700P2; H4H14706P2; H4H14708P2; H4H14709P; H4H14728P; H4H14731P; H4H14732P2; H4H14734P2; H4H14757P; H4H14758P and/or H4H14760P2 is not antibody APE3798; APE4086; APE5125/APE5100; APE5216; APE5281; APE5214/APE4881; APE5280; APE5257; APE5258/APE5076; APE5212; APE5213/5066; APE5211; APE5217/APE5060; APE3849; APE3850; APE5600; APE5598; APE5627; APE6064; APE6060; APE6157; APE6155/APE6917; APE6194; APE3847; APE5713; APE6083; APE6903/APE7247; APE6904; and/or APE6907 (e.g., APE6155) or an antigen-binding fragment thereof or antigen-binding protein comprising the CDRs or variable regions thereof (see WO2016/168542);

Blocks activation of NFκB by IL-36R (e.g., human or *Macaca fascicularis*) in the presence of IL-1RAcP and ligand such as hIL-36α, hIL-36β, and/or hIL-36γ, e.g., wherein the NFκB is in a host cell, such as HEK293, e.g., containing NFκB response element (5×)-luciferase-IRES-GFP, e.g., with an IC$_{50}$ of about $1×10^{-10}$ M-$7×10^{-9}$ M;

Prevents or ameliorates skin inflammation (e.g., chronic or acute) or reduces skin thickness or total pathology score or reduces pro-inflammatory cytokine levels (e.g., KC-GRO, IL6, IL1b and/or TNFalpha) in a subject suffering from skin inflammation (e.g., chronic or acute), e.g., chemically-induced skin inflammation (e.g., imiquimod-induced), e.g., in a mouse such as a mouse displaying symptoms of human DITRA (Deficiency of Interleukin Thirty-six Receptor Antagonist) disease, which disease is described in e.g., Marrakchi et al., Interleukin-36-receptor antagonist deficiency and generalized pustular psoriasis, N Engl J Med 365:620-628 (2011)—e.g., relative to a subject not treated with such an antigen-binding protein; and/or Prevents or ameliorates colitis or colon inflammation, e.g., chemically-induced colitis or colon inflammation, e.g., induced by dextran sulfate sodium (DSS) or oxazolone, or reduces fecal levels of LCN2 polypeptide in a subject with such colitis or inflammation e.g., in a mouse such as a DITRA mouse—e.g., relative to a subject not treated with such an antigen-binding protein.

Protects residues (a) 113-119, 113-122, 116-119 and/or 116-122; and/or (b) 264-271, 267-271, 268-271, 268-276, 268-277 and/or 271-276, of an IL36R polypeptide comprising the amino acid sequence set forth in SEQ ID NO: 227, when bound, from digestion with pepsin and/or Protease XIII (e.g., from *Aspergillus saitoi*) and/or deuteration in the presence of deuterium (e.g., $D_2O$);*

Binds to IL36R, for example, the IL1RL2 subunit thereof, at residues 113-119, 113-122, 116-119, 116-122, 264-271, 267-271, 268-271, 268-276, 268-277 and/or 271-276 of an IL36R polypeptide comprising the amino acid sequence set forth in SEQ ID NO: 227;*

Binds Domain II of IL36R, e.g., with a coverage of about 80.0, 80.1, 81.0 or 81.5%;

Binds a polypeptide comprising the amino acid sequence YKQILHLGKD (SEQ ID NO: 229) (amino acids 113-122 of SEQ ID NO: 227) and/or GVETHVSFREH-NYL (SEQ ID NO: 230) (amino acids 264-277 of SEQ ID NO: 227)

Inhibits IL36α, IL36β and/or IL36γ (e.g., at a concentration of about 10 nM), e.g., in in vitro epidermal keratinocytes, intestinal myofibroblasts and/or CD14+ monocytes, with an IC$_{50}$ of about 1, 2, 3, 4, 5 or 6 nM or 1-6 nM; and/or Competitively inhibits IL36α, IL36β and/or IL36γ-mediated activation of NFκB (e.g., an NFκB response element (5×)-luciferase-IRES-GFP reporter in a cell such as HEK293) by IL36R; for example, as measured in a Schild Assay format.

* Includes antigen-binding proteins that bind to a native IL36R (IL1-RL2), e.g., as set forth under UniProt Accession No. Q9HB29, at residues corresponding to those set forth in the tagged IL36R polypeptide comprising the amino acid sequence set forth in SEQ ID NO: 227. See below:

113-119:
(SEQ ID NO: 228)
YKQILHL (amino acids 113-119 of SEQ ID NO: 227);

113-122:
(SEQ ID NO: 229)
YKQIHLGKD (amino acids 113-122 of SEQ ID NO: 227);

116-119:
(SEQ ID NO: 231)
ILHL (amino acids 116-119 of SEQ ID NO: 227);

116-122:
(SEQ ID NO: 232)
ILHLGKD (amino acids 116-122 of SEQ ID NO: 227);

```
264-271:
                                          (SEQ ID NO: 233)
GVETHVSF (amino acids 264-271 of SEQ ID NO: 227);

267-271:
                                          (SEQ ID NO: 234)
THVSF (amino acids 267-271 of SEQ ID NO: 227);

268-271:
                                          (SEQ ID NO: 235)
HVSF (amino acids 268-271 of SEQ ID NO: 227);

268-276:
                                          (SEQ ID NO: 236)
HVSFREHNL (amino acids 268-276 of SEQ ID NO: 227);

268-277:
                                          (SEQ ID NO: 237)
HVSFREHNLY (amino acids 268-277 of SEQ ID NO: 227);

271-276:
                                          (SEQ ID NO: 238)
FREHNL (amino acids 271-276 of SEQ ID NO: 227),
```

See residues highlighted below in human IL36R (IL1RL2):

```
                                          (SEQ ID NO: 117)
MTGLVSLSYF  PLSTRSCALQ  SCRQPGLGMW

SLLLCGLSIA  LPLSVTADGC  KDIFMKNEIL

SASQPFAFNC  TFPPITSGEV  SVTWYKNSSK

IPVSKIIQSR  IHQDETWILF  LPMEWGDSGV

YQCVIKGRDS  CHRIHVNLTV  FEKHWCDTSI

GGLPNLSDEY  KQILHLGKDD  SLTCHLHFPK

SCVLGPIKWY  KDCNEIKGER  FTVLETRLLV

SNVSAEDRGN  YACQAILTHS  GKQYEVLNGI

TVSITERAGY  GGSVPKIIYP  KNHSIEVQLG

TTLIVDCNVT  DTKDNTNLRC  WRVNNTLVDD

YYDESKRIRE  GVETHVSFRE  HNLYTVNITF

LEVKMEDYGL  PFMCHAGVST  AYIILQLPAP

DFRAYLIGGL  IALVAVAVSV  VYIYNIFKID

IVLWYRSAFH  STETIVDGKL  YDAYVLYPKP

HKESQRHAVD  ALVINILPEV  LERQCGYKLF

IFGRDEFPGQ  AVANVIDENV  KLCRRLIVIV

VPESLGFGLL  KNLSEEQIAV  YSALIQDGMK

VILIELEKIE  DYTVMPESIQ  YIKQKHGAIR

WHGDFTEQSQ  CMKTKFWKTV  RYHMPPRRCR

PFPPVQLLQH  TPCYRTAGPE  LGSPRKKCTLTTG
```

The present invention includes "neutralizing" or "antagonist" anti-IL36R antigen-binding proteins, e.g., antibody or antigen-binding fragment, which includes molecules that inhibit an activity of IL36R to any detectable degree (e.g., IL36 ligand binding).

"H4H14699P2", "H4H14700P2", "H4H14706P2", "H4H14708P2", "H4H14709P", "H4H14728P", "H4H14731P", "H4H14732P2", "H4H14734P2", "H4H14757P", "H4H14758P" and "H4H14760P2" refer to antigen-binding proteins, e.g., antibodies and antigen-binding fragments thereof (including multispecific antigen-binding proteins), comprising the immunoglobulin heavy chain or variable region thereof ($V_H$) of SEQ ID NO: 2, 18, 34, 50, 66, 82, 98, 114, 130, 138, 154, 170, 180, 184, 188, 192, 196, 200, 204, 208, 212, 216, 220 or 224 (or a variant thereof), respectively; and the immunoglobulin light chain or variable region thereof ($V_L$) of 10, 26, 42, 58, 74, 90, 106, 122, 146, 162, 182, 186, 190, 194, 198, 202, 206, 210, 214, 218, 222 or 226 (or a variant thereof), respectively; or that comprise a heavy chain or $V_H$ that comprises the CDRs thereof (CDR-H1 (or a variant thereof), CDR-H2 (or a variant thereof) and CDR-H3 (or a variant thereof)) and/or a light chain or $V_L$ that comprises the CDRs thereof (CDR-L1 (or a variant thereof), CDR-L2 (or a variant thereof) and CDR-L3 (or a variant thereof)), e.g., wherein the immunoglobulin chains, variable regions and/or CDRs comprise the specific amino acid sequences described below. In an embodiment of the invention, the $V_H$ is linked to an IgG constant heavy chain domain (e.g., IgG1 or IgG4) and/or the $V_L$ is linked to a lambda or kappa constant light chain domain.

Antibodies and antigen-binding fragments of the present invention comprise immunoglobulin chains including the amino acid sequences set forth herein as well as cellular and in vitro post-translational modifications to the antibody or fragment. For example, the present invention includes antibodies and antigen-binding fragments thereof that specifically bind to IL36R comprising heavy and/or light chain amino acid sequences set forth herein (e.g., CDR-H1, CDR-H2, CDR-H3, CDR-L1, CDR-L2 and/or CDR-L3) as well as antibodies and fragments wherein one or more asparagine, serine and/or threonine residues is glycosylated, one or more asparagine residues is deamidated, one or more residues (e.g., Met, Trp and/or His) is oxidized, the N-terminal glutamine is pyroglutamate (pyroE) and/or the C-terminal lysine is missing.

The present invention provides a vessel (e.g., a plastic or glass vial, e.g., with a cap or a chromatography column, hollow bore needle or a syringe cylinder) comprising an anti-IL36R antigen-binding protein of the present invention, e.g., H4H14699P2; H4H14700P2; H4H14706P2; H4H14708P2; H4H14709P; H4H14728P; H4H14731P; H4H14732P2; H4H14734P2; H4H14757P; H4H14758P or H4H14760P2.

The present invention also provides an injection device comprising one or more antigen-binding proteins (e.g., antibody or antigen-binding fragment) that bind specifically to IL36R, e.g., H4H14699P2; H4H14700P2; H4H14706P2; H4H14708P2; H4H14709P; H4H14728P; H4H14731P; H4H14732P2; H4H14734P2; H4H14757P; H4H14758P or H4H14760P2, or a pharmaceutical composition thereof. The injection device may be packaged into a kit. An injection device is a device that introduces a substance into the body of a subject via a parenteral route, e.g., intramuscular, subcutaneous or intravenous. For example, an injection device may be a syringe (e.g., pre-filled with the pharmaceutical composition, such as an auto-injector) which, for example, includes a cylinder or barrel for holding fluid to be injected (e.g., comprising the antibody or fragment or a pharmaceutical composition thereof), a needle for piecing skin and/or blood vessels for injection of the fluid; and a plunger for pushing the fluid out of the cylinder and through the needle bore.

The present invention further provides methods for administering an anti-IL36R antigen-binding protein of the present invention, e.g., H4H14699P2; H4H14700P2; H4H14706P2; H4H14708P2; H4H14709P; H4H14728P; H4H14731P; H4H14732P2; H4H14734P2; H4H14757P;

H4H14758P or H4H14760P2, to a subject, comprising introducing the antigen-binding protein into the body of the subject (e.g., a human), for example, parenterally. For example, the method comprises piercing the body of the subject with a needle of a syringe and injecting the antigen-binding protein into the body of the subject, e.g., into the vein, artery, tumor, muscular tissue or subcutis of the subject.

Preparation of Human Antibodies

Methods for generating human antibodies in transgenic mice are known in the art. Any such known methods can be used in the context of the present invention to make human antibodies that specifically bind to IL36R (e.g., IL1RL2). In certain embodiments of the invention, the antibodies of the invention are obtained from mice immunized with IL36R (e.g., IL1RL2 polypeptide or an immunogenic fragment thereof), or with a live attenuated or inactivated virus, or with DNA encoding the protein or fragment thereof. Alternatively, IL36R may be produced using standard biochemical techniques and modified and used as immunogen. In certain embodiments of the invention, the immunogen may be an IL36R (e.g., IL1RL2) polypeptide vaccine. In certain embodiments, one or more booster injections may be administered. In certain embodiments, the immunogen may be a recombinant IL36R polypeptide (e.g., IL1RL2) expressed in E. coli or in any other eukaryotic or mammalian cells such as Chinese hamster ovary (CHO) cells.

Using VELOCIMMUNE® technology (see, for example, U.S. Pat. No. 6,596,541, Regeneron Pharmaceuticals, VELOCIMMUNE®) or any other known method for generating monoclonal antibodies, high affinity chimeric antibodies to IL36R can be initially isolated having a human variable region and a mouse constant region. The VELOCIMMUNE® technology involves generation of a transgenic mouse having a genome comprising human heavy and light chain variable regions operably linked to endogenous mouse constant region loci such that the mouse produces an antibody comprising a human variable region and a mouse constant region in response to antigenic stimulation. The DNA encoding the variable regions of the heavy and light chains of the antibody are isolated and operably linked to DNA encoding the human heavy and light chain constant regions. The DNA is then expressed in a cell capable of expressing the fully human antibody.

Generally, a VELOCIMMUNE® mouse is challenged with the antigen of interest, and lymphatic cells (such as B-cells) are recovered from the mice that express antibodies. The lymphatic cells may be fused with a myeloma cell line to prepare immortal hybridoma cell lines, and such hybridoma cell lines are screened and selected to identify hybridoma cell lines that produce antibodies specific to the antigen of interest. DNA encoding the variable regions of the heavy chain and light chain may be isolated and linked to desirable isotypic constant regions of the heavy chain and light chain. Such an antibody protein may be produced in a cell, such as a CHO cell. Alternatively, DNA encoding the antigen-specific chimeric antibodies or the variable domains of the light and heavy chains may be isolated directly from antigen-specific lymphocytes.

Initially, high affinity chimeric antibodies are isolated having a human variable region and a mouse constant region. The antibodies are characterized and selected for desirable characteristics, including affinity, selectivity, epitope, etc. The mouse constant regions are replaced with a desired human constant region to generate the fully human antibody of the invention, for example wild-type or modified IgG1 or IgG4. While the constant region selected may vary according to specific use, high affinity antigen-binding and target specificity characteristics reside in the variable region.

Anti-IL36R Antibodies Comprising Fc Variants

According to certain embodiments of the present invention, anti-IL36R antigen-binding proteins, e.g., antibodies or antigen-binding fragments, are provided comprising an Fc domain comprising one or more mutations, which, for example, enhance or diminish antibody binding to the FcRn receptor, e.g., at acidic pH as compared to neutral pH. For example, the present invention includes anti-IL36R antibodies comprising a mutation in the $C_H2$ or a $C_H3$ region of the Fc domain, wherein the mutation(s) increases the affinity of the Fc domain to FcRn in an acidic environment (e.g., in an endosome where pH ranges from about 5.5 to about 6.0). Such mutations may result in an increase in serum half-life of the antibody when administered to an animal. Non-limiting examples of such Fc modifications include, e.g., a modification at position 250 (e.g., E or Q); 250 and 428 (e.g., L or F); 252 (e.g., L/Y/F/W or T), 254 (e.g., S or T), and 256 (e.g., S/R/Q/E/D or T); or a modification at position 428 and/or 433 (e.g., H/L/R/S/P/Q or K) and/or 434 (e.g., A, W, H, F or Y [N434A, N434W, N434H, N434F or N434Y]); or a modification at position 250 and/or 428; or a modification at position 307 or 308 (e.g., 308F, V308F), and 434. In one embodiment, the modification comprises a 428L (e.g., M428L) and 434S (e.g., N434S) modification; a 428L, 259I (e.g., V259I), and 308F (e.g., V308F) modification; a 433K (e.g., H433K) and a 434 (e.g., 434Y) modification; a 252, 254, and 256 (e.g., 252Y, 254T, and 256E) modification; a 250Q and 428L modification (e.g., T250Q and M428L); and a 307 and/or 308 modification (e.g., 308F or 308P). In yet another embodiment, the modification comprises a 265A (e.g., D265A) and/or a 297A (e.g., N297A) modification.

For example, the present invention includes anti-IL36R antigen-binding proteins, e.g., antibodies or antigen-binding fragments, comprising an Fc domain comprising one or more pairs or groups of mutations selected from the group consisting of: 250Q and 248L (e.g., T250Q and M248L); 252Y, 254T and 256E (e.g., M252Y, S254T and T256E); 428L and 434S (e.g., M428L and N434S); 257I and 311I (e.g., P257I and Q311I); 257I and 434H (e.g., P257I and N434H); 376V and 434H (e.g., D376V and N434H); 307A, 380A and 434A (e.g., T307A, E380A and N434A); and 433K and 434F (e.g., H433K and N434F).

Anti-IL36R antigen-binding proteins, e.g., antibodies and antigen-binding fragments thereof, that comprise a $V_H$ and/or $V_L$ as set forth herein comprising any possible combinations of the foregoing Fc domain mutations, are contemplated within the scope of the present invention.

The present invention also includes anti-IL36R antigen-binding proteins, antibodies or antigen-binding fragments, comprising a $V_H$ set forth herein and a chimeric heavy chain constant ($C_H$) region, wherein the chimeric $C_H$ region comprises segments derived from the $C_H$ regions of more than one immunoglobulin isotype. For example, the antibodies of the invention may comprise a chimeric $C_H$ region comprising part or all of a $C_H2$ domain derived from a human IgG1, human IgG2 or human IgG4 molecule, combined with part or all of a $C_H3$ domain derived from a human IgG1, human IgG2 or human IgG4 molecule. According to certain embodiments, the antibodies of the invention comprise a chimeric $C_H$ region having a chimeric hinge region. For example, a chimeric hinge may comprise an "upper hinge"

amino acid sequence (amino acid residues from positions 216 to 227 according to EU numbering) derived from a human IgG1, a human IgG2 or a human IgG4 hinge region, combined with a "lower hinge" sequence (amino acid residues from positions 228 to 236 according to EU numbering) derived from a human IgG1, a human IgG2 or a human IgG4 hinge region.

According to certain embodiments, the chimeric hinge region comprises amino acid residues derived from a human IgG1 or a human IgG4 upper hinge and amino acid residues derived from a human IgG2 lower hinge. An antibody comprising a chimeric $C_H$ region as described herein may, in certain embodiments, exhibit modified Fc effector functions without adversely affecting the therapeutic or pharmacokinetic properties of the antibody. (See, e.g., WO2014/022540).

Multispecific Antigen-Binding Proteins

The present invention includes anti-IL36R antigen-binding proteins, e.g., antibodies and antigen-binding fragments thereof, as well as methods of use thereof and methods of making such antigen-binding proteins. The term "anti-IL36R" antigen-binding protein, e.g., antibodies or antigen-binding fragments, includes multispecific (e.g., bispecific or biparatopic) molecules that include at least one first antigen-binding domain that specifically binds to IL36R (e.g., IL1RL2) (e.g., an antigen-binding domain from H4H14699P2; H4H14700P2; H4H14706P2; H4H14708P2; H4H14709P; H4H14728P; H4H14731P; H4H14732P2; H4H14734P2; H4H14757P; H4H14758P or H4H14760P2) and at least one second antigen-binding domain that binds to a different antigen or to an epitope in IL36R which is different from that of the first antigen-binding domain (e.g., IL23-p19, IL12/IL23-p40, TNFalpha, IL-22, MADCAM, a4b7, CCR9, and/or CCR6). In an embodiment of the invention, the first and second epitopes overlap. In another embodiment of the invention, the first and second epitopes do not overlap.

"H4H14699P2"; "H4H14700P2"; "H4H14706P2"; "H4H14708P2"; "H4H14709P"; "H4H14728P"; "H4H14731P"; "H4H14732P2"; "H4H14734P2"; "H4H14757P"; "H4H14758P" or "H4H14760P2" includes a multispecific molecules, e.g., antibodies or antigen-binding fragments, that include the HCDRs and LCDRs, $V_H$ and $V_L$, or HC and LC of H4H14699P2; H4H14700P2; H4H14706P2; H4H14708P2; H4H14709P; H4H14728P; H4H14731P; H4H14732P2; H4H14734P2; H4H14757P; H4H14758P or H4H14760P2, respectively and one or more antigen-binding domains that bind to a different epitope.

In an embodiment of the invention, an antigen-binding domain that binds specifically to IL36R (e.g., IL1RL2), which may be included in a multispecific molecule, comprises:

(1)
(i) a heavy chain variable domain ($V_H$) sequence that comprises CDR-H1, CDR-H2 and CDR-H3 from an immunoglobulin heavy chain selected from: H4H14699P2; H4H14700P2; H4H14706P2; H4H14708P2; H4H14709P; H4H14728P; H4H14731P; H4H14732P2; H4H14734P2; H4H14757P; H4H14758P and H4H14760P2, and (ii) a light chain variable domain ($V_L$) sequence that comprises CDR-L1, CDR-L2 and CDR-L3 from an immunoglobulin heavy chain selected from: H4H14699P2; H4H14700P2; H4H14706P2; H4H14708P2; H4H14709P; H4H14728P; H4H14731P; H4H14732P2; H4H14734P2; H4H14757P; H4H14758P and H4H14760P2, respectively;

or, (2)
(i) a heavy chain variable domain ($V_H$) sequence selected from: H4H14699P2; H4H14700P2; H4H14706P2; H4H14708P2; H4H14709P; H4H14728P; H4H14731P; H4H14732P2; H4H14734P2; H4H14757P; H4H14758P and H4H14760P2; and (ii) a light chain variable domain ($V_L$) sequence selected from: H4H14699P2; H4H14700P2; H4H14706P2; H4H14708P2; H4H14709P; H4H14728P; H4H14731P; H4H14732P2; H4H14734P2; H4H14757P; H4H14758P and H4H14760P2, respectively;

and
one or more antigen-binding domains that bind to a different epitope.

In an embodiment of the invention, the multispecific antibody or fragment includes more than two different binding specificities (e.g., a trispecific molecule), for example, one or more additional antigen-binding domains which are the same or different from the first and/or second antigen-binding domain.

In one embodiment of the invention, a bispecific antigen-binding fragment comprises a first scFv (e.g., comprising $V_H$ and $V_L$ of H4H14699P2; H4H14700P2; H4H14706P2; H4H14708P2; H4H14709P; H4H14728P; H4H14731P; H4H14732P2; H4H14734P2; H4H14757P; H4H14758P and H4H14760P2) having binding specificity for a first epitope (e.g., IL36R) and a second scFv having binding specificity for a second, different epitope. For example, in an embodiment of the invention, the first and second scFv are tethered with a linker, e.g., a peptide linker (e.g., a GS linker such as (GGGGS)$_n$ (SEQ ID NO: 177) wherein n is, for example, 1, 2, 3, 4, 5, 6, 7, 8, 9 or 10).

Other bispecific antigen-binding fragments include an F(ab)$_2$ of a bispecific IgG antibody which comprises the heavy and light chain CDRs of H4H14699P2; H4H14700P2; H4H14706P2; H4H14708P2; H4H14709P; H4H14728P; H4H14731P; H4H14732P2; H4H14734P2; H4H14757P; H4H14758P and H4H14760P2 and of another antibody that binds to a different epitope.

Immunoconjugates

The invention encompasses anti-IL36R antigen-binding proteins, e.g., antibodies or antigen-binding fragments, conjugated to another moiety, e.g., a therapeutic moiety (an "immunoconjugate"). In an embodiment of the invention, an anti-IL36R antigen-binding protein, e.g., antibody or antigen-binding fragment, is conjugated to any of the further therapeutic agents set forth herein. As used herein, the term "immunoconjugate" refers to an antigen-binding protein, e.g., an antibody or antigen-binding fragment, which is chemically or biologically linked to another antigen-binding protein, a radioactive agent, a reporter moiety, an enzyme, a peptide, a protein or a therapeutic agent.

Therapeutic and Prophylactic Methods

The present invention provides methods for treating or preventing an IL-36R-mediated disease by administering a therapeutically effective amount of anti-IL36R antigen-binding protein, e.g., antibody or antigen-binding fragment, (e.g., H4H14699P2; H4H14700P2; H4H14706P2;

H4H14708P2; H4H14709P; H4H14728P; H4H14731P; H4H14732P2; H4H14734P2; H4H14757P; H4H14758P or H4H14760P2) to a subject (e.g., a human) in need of such treatment or prevention.

"Treat" or "treating" means to administer an anti-IL36R antigen-binding protein, e.g., antibody or antigen-binding fragment of the present invention (e.g., H4H14699P2; H4H14700P2; H4H14706P2; H4H14708P2; H4H14709P; H4H14728P; H4H14731P; H4H14732P2; H4H14734P2; H4H14757P; H4H14758P or H4H14760P2), to a subject, having an IL36R-mediated disease, such that one or more signs and/or symptoms and/or clinical indicia of the IL36R-mediated disease regresses or is eliminated and/or the progression thereof is inhibited (e.g., the disease in the subject is stabilized, reduced or eliminated).

"Preventing" an IL36R-mediated disease means to administer anti-IL36R antigen-binding protein, e.g., antibody or antigen-binding fragment of the present invention (e.g., H4H14699P2; H4H14700P2; H4H14706P2; H4H14708P2; H4H14709P; H4H14728P; H4H14731P; H4H14732P2; H4H14734P2; H4H14757P; H4H14758P or H4H14760P2), to a subject, prior to manifestation of the disease in the body of the subject.

Interleukin IL-36RN is an IL-1 cytokine family member that antagonizes the proinflammatory signals of IL-36alpha, IL-36beta and IL-36gamma at the IL-36R.

An IL-36R-mediated disease is any disease which is caused or exacerbated by an activity of IL-36R (e.g., activation of downstream inflammatory signaling via NFκB and MAP kinases due to receptor binding of ligand such as IL36γ, IL36γ and/or IL36γ), for example, due to a deficiency in an IL36R antagonist (e.g., IL-36RN). In an embodiment of the invention, a mutation in IL36RN underlies the IL-36R-mediated disease. An example of such a disease is an autoimmune and/or inflammatory disorder. In embodiment of the invention, the IL-36R-mediated disease treated with an anti-IL36R antigen-binding protein is an inflammatory disorder, an autoimmune disorder, deficiency of interleukin IL-36 receptor antagonist (DITRA) syndrome, impetigo herpetiformis, acrodermatitis, a skin neutrophilic pustular disease, psoriasis, a pustular disease, generalized pustular psoriasis (GPP; e.g., familial or sporadic), psoriasis vulgaris/plaque psoriasis, palmoplantar pustular psoriasis (PPPP), palmoplantar pustulosis (PPP), colitis, inflammatory bowel disease, ulcerative colitis, Crohn's disease, chemically-induced colitis, inflammation, airway inflammation (e.g., neutrophilic airway inflammation, COPD (chronic obstructive pulmonary disease) or asthma), joint inflammation (e.g., ankylosing spondylitis, rheumatoid arthritis or psoriatic arthritis), kidney inflammation, alopecia areata, skin inflammation (e.g., chemically-induced skin inflammation, psoriasis, pustular psoriasis, generalized pustular psoriasis, palmoplantar pustulosis, palmo-plantar pustular psoriasis, psoriasis vulgaris or psoriatic skin lesions), acanthosis, hyperkeratosis, kindler syndrome, systemic lupus erythematosus (SLE), nephrotic syndrome, ANCA (anti-neutrophil cytoplasmic antibody)-associated vasculopathies, tubulointerstitial lesions and glomerulonephritis.

An inflammatory disorder is a disorder characterized by uncontrolled or unwanted inflammation which may cause destruction of healthy tissue.

An autoimmune disorder is a condition in which one's immune system mistakenly attacks one's own body.

Impetigo herpetiformis (IH) is among rare dermatosis of pregnancy, which is currently considered as a form of generalized pustular psoriasis. In an embodiment of the invention, a mutation in IL36RN underlies the IH.

Acrodermatitis is a skin condition that may affect children, e.g., between the ages of 3 months and 15 years, which is characterized by itchy red or purple blisters on the body, bloated abdomen, fever, and swollen, sore lymph nodes. The cause of acrodermatitis may be viral. Mutations of IL-36 receptor antagonists (e.g., IL-36Ra) are present in a high proportion of patients with GPP and acrodermatitis continua. In an embodiment of the invention, a mutation in IL36RN underlies the acrodermatitis.

Psoriasis is an autoimmune disease that causes skin plaques, which are itchy or sore patches of thick, red, dry skin. The most common form of psoriasis is psoriasis vulgaris (plaque psoriasis) which is characterized by well-defined plaques of red raised skin that can appear on any area of skin, including the knees, elbows, scalp and trunk. A flaky silvery white buildup on top of the plaques is called scale; it is composed of dead skin cells. This scale comes loose and sheds constantly from the plaques. Skin symptoms include pain, itching and cracking.

Generalized pustular psoriasis (GPP) is a severe form of psoriasis. Individuals with GPP typically have repeated episodes in which large areas of skin become red and inflamed and develop small pus-filled blisters (pustules). A portion of subjects with GPP suffer from plaques. The skin problems can be accompanied by fever, extreme tiredness (fatigue), muscle weakness, an increased number of white blood cells, and other signs of inflammation throughout the body (systemic inflammation). IL-36 cytokine appears to play a role in the development of GPP. In an embodiment of the invention, a mutation in IL36RN underlies the GPP.

Palmoplantar pustular psoriasis (PPPP; 4P) is a form of localized pustular psoriasis characterized by plaques and pustules occurring on palmar and plantar surfaces of the skin.

PPPP may be associated with homozygous or compound heterozygous IL36RN gene mutations leading to aberrations in IL-36R antagonist function. In an embodiment of the invention, a mutation in IL36RN underlies the PPPP.

Palmoplantar pustulosis (PPP; 3P) is an immune-mediated disorder that causes blister-like pustules to show up on the palms of your hands and the soles of your feet.

Generally, subjects with PPP do not suffer from plaques. In an embodiment of the invention, a mutation in IL36RN underlies the PPP.

Deficiency of interleukin IL-36 receptor antagonist (DITRA) syndrome is a rare autosomal recessive disease caused by mutations in IL36RN. DITRA is a rare, genetic, auto-inflammatory syndrome with immune deficiency disease characterized by recurrent and severe flares of generalized pustular psoriasis associated with high fever, asthenia, and systemic inflammation, due to IL36R antagonist deficiency. Psoriatic nail changes (e.g., pitting and onychomadesis) and ichthyosis may occasionally be associated. See Marrakchi et al., New Engl J. Med. 365(7): 620-628 (2011). In an embodiment of the invention, a mutation in IL36RN underlies the DITRA.

An inflammatory disease is a condition characterized by abnormal inflammation at one or more sites within the body of a subject. An autoimmune disease is a condition characterized by the abnormal attack of the subject's body tissue by the subject's own immune system.

ANCA-associated vasculopathies (AAV) are inflammatory disorders that include Granulomatosis with polyangiitis (formerly Wegener's), microscopic polyangiitis, and EGPA/Churg Strauss. These conditions are characterized by chronic inflammation leading to blockages of blood vessels and diminished blood flow to vital organs like the kidney.

Inflammatory bowel disease (IBD) is a term that includes two conditions (Crohn's disease and ulcerative colitis) that are characterized by chronic inflammation of the gastrointestinal (GI) tract.

Neutrophilic airway inflammation is inflammation of the airway which is mediated by the influx of neutrophils into the lungs. Signs and symptoms of neutrophilic airway inflammation include asthma and wheezing.

Chronic obstructive pulmonary disease (COPD) is a chronic inflammatory lung disease that causes obstructed airflow from the lungs. Signs and symptoms include breathing difficulty, cough, mucus (sputum) production and wheezing.

Ankylosing spondylitis (AS) is a disease characterized by long term inflammation of the spine (e.g., the sacroiliac (SI) joints and the axial skeleton). Over time, AS can cause some of the vertebrae in your spine to fuse. Symptoms include pain and stiffness in your lower back and hips.

Rheumatoid arthritis is an autoimmune condition characterized by joint inflammation. Symptoms include tender, warm, swollen joints; joint stiffness, fatigue, fever and weight loss.

Psoriatic arthritis is a form of arthritis that affects some people who have psoriasis. Symptoms can include swollen fingers and toes, foot pain and lower back pain.

Alopecia areata is spot baldness characterized by small bald patches on the body.

Acanthosis is diffuse epidermal thickening (hyperplasia) of the stratum *spinosum* (prickle cell layer) of the skin which may appear to be darker than other skin. Hyperkeratosis is a thickening of the outer layer of the skin.

Hyperkeratosis is the thickening of skin often due to irritation from the sun, chemicals or frequent friction or pressure. The skin thickening typically occurs in the outer layer of the skin, which contains a tough, protective protein called keratin.

Kindler syndrome is an autosomal recessive genodermatosis characterized by congenital acral skin blistering, photosensitivity, progressive poikiloderma, and diffuse cutaneous atrophy. Mucosal manifestations are common, with frequent involvement of the oral mucosa, gingiva, and gastrointestinal tract.

Systemic lupus erythematosus (SLE) is an autoimmune disease. In this disease, the body's immune system mistakenly attacks healthy tissue. SLE can affect the skin, joints, kidneys, brain, and other organs.

Nephrotic syndrome is a kidney disorder that causes your body to excrete too much protein in your urine. Nephrotic syndrome is typically caused by damage to the clusters of small blood vessels in the kidneys that filter waste and excess water from your blood. Nephrotic syndrome symptoms may include swelling (edema), particularly in the feet and ankles, foamy urine, weight gain (from fluid retention), fatigue and loss of appetite.

Glomerulonephritis is inflammation of kidney glomeruli. Symptoms include ink or cola-colored urine from red blood cells in your urine (hematuria), foamy urine (due to proteinuria), high blood pressure (hypertension), fluid retention (edema).

An effective or therapeutically effective dose of anti-IL36R antigen-binding protein, e.g., antibody or antigen-binding fragment (e.g., H4H14699P2; H4H14700P2; H4H14706P2; H4H14708P2; H4H14709P; H4H14728P; H4H14731P; H4H14732P2; H4H14734P2; H4H14757P; H4H14758P or H4H14760P2), for treating or preventing an IL-36R-mediated disease refers to the amount of the antibody or fragment sufficient to alleviate one or more of the clinical indicia, signs and/or symptoms of the disease in the treated subject, whether by inducing the regression or elimination of such indicia, signs and/or symptoms or by inhibiting the progression of such indicia, signs and/or symptoms. The dose amount may vary depending upon the age and the size of a subject to be administered, target disease, conditions, route of administration, and the like. In an embodiment of the invention, an effective or therapeutically effective dose of antibody or antigen-binding fragment thereof of the present invention, for treating or preventing IL36R mediated disease, e.g., in an adult human subject, is about 1 mg/kg or more, e.g., about 1 mg/kg to about 25 mg/kg. Depending on the severity of the infection, the frequency and the duration of the treatment can be adjusted. In certain embodiments, the antigen-binding protein of the present invention can be administered at an initial dose, followed by one or more secondary doses. In certain embodiments, the initial dose may be followed by administration of a second or a plurality of subsequent doses of antigen-binding protein in an amount that can be approximately the same or less than that of the initial dose, wherein the subsequent doses are separated by at least 1 day to 3 days; at least one week, at least 2 weeks; at least 3 weeks; at least 4 weeks; at least 5 weeks; at least 6 weeks; at least 7 weeks; at least 8 weeks; at least 9 weeks; at least 10 weeks; at least 12 weeks; or at least 14 weeks.

As used herein, the term "subject" refers to a mammal (e.g., rat, mouse, cat, dog, cow, sheep, horse, goat, rabbit), preferably a human, for example, in need of prevention and/or treatment of an IL-36R-mediated disease. The subject may have an IL-36R-mediated disease or be predisposed to developing such a disease. In an embodiment of the invention, the subject has a homozygous or heterozygous IL36RN mutation genotype.

The present invention encompasses methods for administering an anti-IL36R antigen-binding protein to a subject at risk of developing an IL36R-mediated disease. For example, in an embodiment of the invention, the disease is a skin inflammatory disease or colon inflammatory disease. Example 5 herein demonstrated that skin inflammation diseases could be prevented in a DITRA-like mouse model prior to exposure to imiquimod and the development of skin inflammation symptoms. In an embodiment of the invention, an IL36R-mediated disease (e.g., skin inflammation) is prevented by administration of a prophylactic dose of anti-gen-binding protein to a subject prior to any clinically significant inflammation, e.g., skin inflammation or any increase in inflammation-induced skin thickness, in total pathology score (as discussed herein) or in the presence of pro-inflammatory cytokines, such as KC-GRO, IL-6, IL-1beta or TNFalpha, in the skin. In an embodiment of the invention, a dose of anti-IL36R antigen-binding protein of the invention for preventing an IL36R-mediated disease is from about 1 mg/kg to about 10 mg/kg.

Combinations and Pharmaceutical Compositions

The present invention provides compositions that include anti-IL36R antigen-binding proteins and one or more ingredients; as well as methods of use thereof and methods of making such compositions.

To prepare pharmaceutical compositions of the anti-IL36R antigen-binding proteins, e.g., antibodies and anti-gen-binding fragments thereof (e.g., H4H14699P2; H4H14700P2; H4H14706P2; H4H14708P2; H4H14709P; H4H14728P; H4H14731P; H4H14732P2; H4H14734P2; H4H14757P; H4H14758P or H4H14760P2), antigen-binding protein is admixed with a pharmaceutically acceptable carrier or excipient. See, e.g., Remington's Pharmaceutical Sciences and U.S. Pharmacopeia: National Formulary, Mack Publishing Company, Easton, Pa. (1984); Hardman, et al. (2001) Goodman and Gilman's The Pharmacological Basis of Therapeutics, McGraw-Hill, New York, N.Y.; Gennaro (2000) Remington: The Science and Practice of Pharmacy, Lippincott, Williams, and Wilkins, New York, N.Y.; Avis, et al. (eds.) (1993) Pharmaceutical Dosage Forms: Parenteral Medications, Marcel Dekker, NY; Lieberman, et al. (eds.) (1990) Pharmaceutical Dosage Forms: Tablets, Marcel Dekker, NY; Lieberman, et al. (eds.) (1990) Pharmaceutical Dosage Forms: Disperse Systems, Marcel Dekker, NY; Weiner and Kotkoskie (2000) Excipient Toxicity and Safety, Marcel Dekker, Inc., New York, N.Y. In an embodiment of the invention, the pharmaceutical composition is sterile. Such compositions are part of the present invention.

Pharmaceutical compositions of the present invention include pharmaceutically acceptable carriers, diluents, excipients and/or stabilizers, such as, for example, water, buffering agents, stabilizing agents, preservatives, isotonifiers, non-ionic detergents, antioxidants and/or other miscellaneous additives.

The scope of the present invention includes desiccated, e.g., freeze-dried, compositions comprising an anti-IL36R antigen-binding protein, e.g., antibody or antigen-binding fragment thereof (e.g., H4H14699P2; H4H14700P2; H4H14706P2; H4H14708P2; H4H14709P; H4H14728P; H4H14731P; H4H14732P2; H4H14734P2; H4H14757P; H4H14758P or H4H14760P2), or a pharmaceutical composition thereof that includes a pharmaceutically acceptable carrier but substantially lacks water.

In a further embodiment of the invention, a further therapeutic agent that is administered to a subject in association with an anti-IL36R antigen-binding protein, e.g., antibody or antigen-binding fragment thereof (e.g., H4H14699P2; H4H14700P2; H4H14706P2; H4H14708P2; H4H14709P; H4H14728P; H4H14731P; H4H14732P2; H4H14734P2; H4H14757P; H4H14758P or H4H14760P2), disclosed herein is administered to the subject in accordance with the Physicians' Desk Reference 2003 (Thomson Healthcare; 57$^{th}$ edition (Nov. 1, 2002)).

The mode of administration of an antigen-binding protein or composition thereof can vary. Routes of administration include oral, rectal, transmucosal, intestinal, parenteral; intramuscular, subcutaneous, intradermal, intramedullary, intrathecal, direct intraventricular, intravenous, intraperitoneal, intranasal, intraocular, inhalation, insufflation, topical, cutaneous, transdermal or intra-arterial.

The present invention provides methods for administering an anti-IL36R antigen-binding protein, e.g., antibody or antigen-binding fragment thereof (e.g., H4H14699P2; H4H14700P2; H4H14706P2; H4H14708P2; H4H14709P; H4H14728P; H4H14731P; H4H14732P2; H4H14734P2; H4H14757P; H4H14758P or H4H14760P2) to a subject, comprising introducing the protein or a pharmaceutical composition or combination thereof into the body of the subject. For example, in an embodiment of the invention, the method comprises piercing the body of the subject, e.g., with a needle of a syringe, and injecting the antigen-binding protein or a pharmaceutical composition or combination thereof into the body of the subject, e.g., into the vein, artery, tumor, muscular tissue or subcutis of the subject.

The present invention provides a vessel (e.g., a plastic or glass vial, e.g., with a cap or a chromatography column, hollow bore needle or a syringe cylinder) comprising any of the anti-IL36R antigen-binding proteins, e.g., antibodies or antigen-binding fragments thereof (e.g., H4H14699P2; H4H14700P2; H4H14706P2; H4H14708P2; H4H14709P; H4H14728P; H4H14731P; H4H14732P2; H4H14734P2; H4H14757P; H4H14758P or H4H14760P2), or a pharmaceutical composition comprising a pharmaceutically acceptable carrier or combination thereof.

The present invention includes combinations including an anti-IL36R antigen-binding protein, e.g., antibody or antigen-binding fragment thereof of the present invention (e.g., H4H14699P2; H4H14700P2; H4H14706P2; H4H14708P2; H4H14709P; H4H14728P; H4H14731P; H4H14732P2; H4H14734P2; H4H14757P; H4H14758P or H4H14760P2), in association with one or more further therapeutic agents. The anti-IL36R antigen-binding protein and the further therapeutic agent can be in a single composition or in separate compositions. For example, in an embodiment of the invention, the further therapeutic agent is an anti-inflammatory drug. In an embodiment of the invention, the further therapeutic agent is another anti-IL35R antigen-binding protein, an IL17 inhibitor, an IL23p19 inhibitor, an IL12p40 inhibitor, guselkumab, ustekinumab, brodalumab, ixekizumab, secukinumab, an anti-TNFalpha antibody or antigen-binding fragment thereof, one or more human TNF receptors or fragments thereof linked to an immunoglobulin such as an Fc portion of a human IgG1, infliximab, adalimumab, etanercept, dupilumab, sarilumab, tocilizumab, golimumab, abatacept, tofacitinib, abatacept, a non-steroidal anti-inflammatory drug (NSAID), ibuprofen, naproxen, acetaminophen, aspirin, celecoxib, cyclophosphamide, methotrexate, a corticosteroid, cortisone or prednisone.

Methods for treating or preventing an IL-36-mediated disease in a subject in need of said treatment or prevention by administering an anti-IL36R antigen-binding protein, e.g., H4H14699P2; H4H14700P2; H4H14706P2; H4H14708P2; H4H14709P; H4H14728P; H4H14731P; H4H14732P2; H4H14734P2; H4H14757P; H4H14758P or H4H14760P2, in association with a further therapeutic agent are part of the present invention.

The term "in association with" indicates that components, an anti-IL36R antigen-binding protein, e.g., antibody or antigen-binding fragment thereof of the present invention, along with another agent such as methotrexate, can be formulated into a single composition, e.g., for simultaneous delivery, or formulated separately into two or more compositions (e.g., a kit including each component). Each component can be administered to a subject at a different time than when the other component is administered; for example, each administration may be given non-simultaneously (e.g., separately or sequentially) at intervals over a given period of time. Moreover, the separate components may be administered to a subject by the same or by a different route.

EXAMPLES

The following examples are put forth so as to provide those of ordinary skill in the art with a complete disclosure and description of how to make and use the methods and compositions of the invention, and are not intended to limit the scope of what the inventors regard as their invention.

Example 1: Generation of Human Antibodies that Specifically Bind to IL-36R

Anti-IL36R antibodies were obtained by immunizing a VELOCIMMUNE mouse (i.e., an engineered mouse comprising DNA encoding human immunoglobulin heavy and kappa light chain variable regions) with a DNA immunogen comprising the full length IL36R (IL-1RL2) sequence. The antibody immune response was monitored by an IL36R-specific immunoassay and fully human anti-IL36R antibodies were isolated and purified. Two exemplary comparisons between the $V_H$ and $V_L$ of antibodies generated as set forth herein and their respective germlines are set forth in FIG. 1 and FIG. 2.

TABLE 1

Immunoglobulin chain sequences of the present invention*

| Antibody # | Name | VH DNA | PEP | CDR1 DNA | PEP | CDR2 DNA | PEP | CDR3 DNA | PEP | VK DNA | PEP | CDR1 DNA | PEP | CDR2 DNA | PEP | CDR3 DNA | PEP |
|---|---|---|---|---|---|---|---|---|---|---|---|---|---|---|---|---|---|
| 1 | H4H14699P2 | 1 | 2 | 3 | 4 | 5 | 6 | 7 | 8 | 9 | 10 | 11 | 12 | 13 | 14 | 15 | 16 |
| 2 | H4H14700P2 | 17 | 18 | 19 | 20 | 21 | 22 | 23 | 24 | 25 | 26 | 27 | 28 | 29 | 30 | 31 | 32 |
| 3 | H4H14706P2 | 33 | 34 | 35 | 36 | 37 | 38 | 39 | 40 | 41 | 42 | 43 | 44 | 45 | 46 | 47 | 48 |
| 4 | H4H14708P2 | 49 | 50 | 51 | 52 | 53 | 54 | 55 | 56 | 57 | 58 | 59 | 60 | 61 | 62 | 63 | 64 |
| 5 | H4H14709P | 65 | 66 | 67 | 68 | 69 | 70 | 71 | 72 | 73 | 74 | 75 | 76 | 77 | 78 | 79 | 80 |
| 6 | H4H14728P | 81 | 82 | 83 | 84 | 85 | 86 | 87 | 88 | 89 | 90 | 91 | 92 | 93 | 94 | 95 | 96 |
| 7 | H4H14731P | 97 | 98 | 99 | 100 | 101 | 102 | 103 | 104 | 105 | 106 | 107 | 108 | 109 | 110 | 111 | 112 |
| 8 | H4H14732P2 | 113 | 114 | 115 | 116 | 117 | 118 | 119 | 120 | 121 | 122 | 123 | 124 | 125 | 126 | 127 | 128 |
| 9 | H4H14734P2 | 129 | 130 | 131 | 132 | 133 | 134 | 135 | 136 | 121 | 122 | 123 | 124 | 125 | 126 | 127 | 128 |
| 10 | H4H14757P | 137 | 138 | 139 | 140 | 141 | 142 | 143 | 144 | 145 | 146 | 147 | 148 | 149 | 150 | 151 | 152 |
| 11 | H4H14758P | 153 | 154 | 155 | 156 | 157 | 158 | 159 | 160 | 161 | 162 | 163 | 164 | 165 | 166 | 167 | 168 |
| 12 | H4H14760P2 | 169 | 170 | 171 | 172 | 173 | 174 | 175 | 176 | 121 | 122 | 123 | 124 | 125 | 126 | 127 | 128 |

*Numbers corresponding to $V_H$, CDR-H1, CDR-H2, CDR-H3, $V_L$, CDR-L1, CDR-L2 and CDR-L3 refer to SEQ ID NOs set forth herein.
"PEP" refers to an amino acid sequence;
"DNA" refers to a nucleotide sequence.

```
SEQ ID NO: 1
GAAGTGCAGCTGGTGGAGTCTGGGGGAGGCTTGGTGCAGCCTGGCAGGTCCCTGAGACTCTCCTGTGCGGCCTCTGGATT
CACCTTTGATGATTATGCCATACACTGGGTCCGGCAAGCTCCAGGGAAGGGCCTGGAGTGGGTCTCAGTTATCAGTTGGA
ATAGTGATATCATAGGCTATGCGGACTCTGTGAAGGGCCGATTCACCGTCTCCAGAGACAACGCCAAGAACTCCCTGTAT
CTGCAAATGAATAGTCTGAGAACTGAGGACACGGCCTTGTATTACTGTGCAAAAGGATATAACTGGAACTTCTTTGACTA
TTGGGGCCAGGGAACCCTGGTCACCGTCTCCTCA;

SEQ ID NO: 2
EVQLVESGGGLVQPGRSLRLSCAASGFTFDDYAIHWVRQAPGKGLEWVSVISWNSDIIGYADSVKGRFTVSRDKAKNSLY
LQMNSLRTEDTALYYCAKGYNWNFFDYWGQGTLVTVSS;

SEQ ID NO: 3
GGA TTC ACC TTT GAT GAT TAT GCC;

SEQ ID NO: 4
G F T F D D Y A;

SEQ ID NO: 5
ATC AGT TGG AAT AGT GAT ATC ATA;

SEQ ID NO: 6
I S W N S D I I;

SEQ ID NO: 7
GCA AAA GGA TAT AAC TGG AAC TTC TTT GAC TAT;

SEQ ID NO: 8
A K G Y N W N F F D Y;

SEQ ID NO: 9
GAAATTGTGTTGACGCAGTCTCCAGCCACCCTGTCTTTATCTCCAGGGGAAAGAGCCACCCTCTCCTGCAGGGCCAGTCA
GAGTGTTAGCAGCTACTTAGCCTGGTACCAACAGAAACCTGGCCAGGCTCCCAGGCTCCTCATCTATAATGCAGCAAACA
GGGCCACTGACATCCCAGCCAGGTTCAGTGGCAGTGGGTCTGGGACAGACTTCACTCTCACCATCAGCAGCCTAGAGCCT
GAAGATTTTGCAGTTTATTACTGTCAGCAGCGTAGCAACTGGCCTCTCACTTTCGGCGGAGGGACCAAGGTGGAGATCAA
A;

SEQ ID NO: 10
EIVLTQSPATLSLSPGERATLSCRASQSVSSYLAWYQQKPGQAPRLLIYNAANRATDIPARFSGSGSGTDFTLTISSLEP
EDFAVYYCQQRSNWPLTFGGGTKVEIK;

SEQ ID NO: 11
CAG AGT GTT AGC AGC TAC;

SEQ ID NO: 12
Q S V S S Y;

SEQ ID NO: 13
AAT GCA GCA;
```

SEQ ID NO: 14
N A A;

SEQ ID NO: 15
CAG CAG CGT AGC AAC TGG CCT CTC ACT;

SEQ ID NO: 16
Q Q R S N W P L T;

SEQ ID NO: 17
GAAGTGCAGCTGGTGGAGTCTGGGGGAGGCTTGGTACAGCCTGGCAGGTCCCTGAGACTCTCCTGTGCAGCCTCTGGATT
CACCTTTGATGATTATGCCATGCACTGGGTCCGGCAAACTCCAGGGAAGGGCCTGGAGTGGGTCTCAGTTATTAGTTGGA
ATAGTGATGTCATAGCCTATTCGGACTCTGTGAAGGGCCGCTTCACCATTTCCAGAGACAACGCCAAGAACTCCCTGTAT
CTGCAAATGAACAGTCTGGGAACTGAGGACACGGCCTTATATTACTGTGCAAAAGGCCATAACTGGAACTTCTTTGACTA
TTGGGGCCAGGGAACCCTGGTCACCGTCTCCTCA;

SEQ ID NO: 18
EVQLVESGGGLVQPGRSLRLSCAASGFTFDDYAMHWVRQTPGKGLEWVSVISWNSDVIAYSDSVKGRFTISRDNAKNSLY
LQMNSLGTEDTALYYCAKGHNWNFFDYWGQGTLVTVSS;

SEQ ID NO: 19
GGA TTC ACC TTT GAT GAT TAT GCC;

SEQ ID NO: 20
G F T F D D Y A;

SEQ ID NO: 21
ATT AGT TGG AAT AGT GAT GTC ATA;

SEQ ID NO: 22
I S W N S D V I;

SEQ ID NO: 23
GCA AAA GGC CAT AAC TGG AAC TTC TTT GAC TAT;

SEQ ID NO: 24
A K G H N W N F F D Y;

SEQ ID NO: 25
GAAATTGTGTTGACACAGTCTCCAGCCACCCTGTCTTTGTCTCCAGGAGAAAGAGCCACCCTCTCCTGCAGGGCCAGTCA
GAGTGTTAGCAGCTACTTAGCCTGGTACCAACAGAAACCTGGCCAGGCTCCCAGGCTCCTCATCTATAATGTAGCCAACA
GGGCCACAGACATCCCAGCCAGGTTCAGTGGCAGTGGGTCTGGGACAGACTTCACTCTCACCATCAGCGGCCTAGAGCCT
GAAGATTTTGCAGTTTATTTCTGTCAGCAGCGTAGCAACTGGCCTCTCACTTTCGGCGGAGGGACCAAGGTGGAGATCAA
A;

SEQ ID NO: 26
EIVLTQSPATLSLSPGEPRATLSCRASQSVSSYLAWYQQKPGQAPRLLIYKVANRATDIPARFSGSGSGTDFTLTISGLEP
EDFAVYFCQQRSNWPLTFGGGTKVEIK;

SEQ ID NO: 27
CAG AGT GTT AGC AGC TAG;

SEQ ID NO: 28
Q S V S S Y;

SEQ ID NO: 29
AAT GTA GCC;

SEQ ID NO: 30
N V A;

SEQ ID NO: 31
CAG CAG CGT AGC AAC TGG CCT CTC ACT;

SEQ ID NO: 32
Q Q R S N W P L T;

SEQ ID NO: 33
GAAGTGCAGCTGGTGGAGTCTGGGGGAGGCTTGGTACAGCCTGGCAGGTCCCTGAGACTCTCCTGTACAGCCTCTGGATT
CACCTTTGATGATTATGCCATAGACTGGGTCCGGCAATCTCCAGGGAAGGGCCTGGAGTGGGTCTCAGTTATCAGTTGGA
ATAGTGATGTCATAGGCTATGCGGACTCTGTGAAGGGCCGATTCACCATCTCCAGAGACAACGCCAAGAACTCCCTGTAT
CTGCAGATGAATAGTCTGAGAGCTGAGGACACGGCCTTGTATTACTGTGCAAAAGGATATAACTGGAACTTCTTTGACTA
TTGGGGCCAGGGAACCCTGGTCACCGTCTCCTCA;

SEQ ID NO: 34
EVQLVESGGGLVQPGRSLRLSCTASGFTFDDYAIHWVRQSPGKGLEWVSVISWNSDVIGYADSVKGRFTISRDNAKNSLY
LQMNSLRAEDTALYYCAKGYNWNFFDYWGQGTLVTVSS;

SEQ ID NO: 35
GGA TTC ACC TTT GAT GAT TAT GCC;

SEQ ID NO: 36
G F T F D D Y A;

SEQ ID NO: 37
ATC AGT TGG AAT AGT GAT GTC ATA;

SEQ ID NO: 38
I S W N S D V I;

SEQ ID NO: 39
GCA AAA GGA TAT AAC TGG AAC TTC TTT GAC TAT;

SEQ ID NO: 40
A K G Y N W N F F D Y;

SEQ ID NO: 41
GAAATTGTGTTGACGCAGTCTCCAGCCACCCTGTCTTTATCTCCAGGGGAAAGAGCCACCCTCTCCTGCAGGGCCAGTCA
GAGTGTTAGCAGCTACTTAGCCTGGTACCAACAGAAACCTGGCCAGGCTCCCAGGCTCCTCATCTATAATGCAGCAAACA
GGGCCACTGACATCCCAGCCAGGTTCAGTGGCAGTGGGTCTGGGACAGACTTCACTCTCACCATCAGCAGCCTAGAGCCT
GAAGATTTTGCAGTTTATTACTGTCAGCAGCGTAGCAACTGGCCTCTCACTTTCGGCGGAGGGACCAAGGTGGAGATCAA
A;

SEQ ID NO: 42
EIVLTQSPATLSLSPGERATLSCRASQSVSSYLAWYQQKPGQAPRLLIYNAANRATDIPARFSGSGSGTDFTLTISSLEP
EDFAVYYCQQRSNWPLTFGGGTKVEIK;

SEQ ID NO: 43
CAG AGT GTT AGC AGC TAC;

SEQ ID NO: 44
Q S V S S Y;

SEQ ID NO: 45
AAT GCA GCA;

SEQ ID NO: 46
K A A;

SEQ ID NO: 47
CAG CAG CGT AGC AAC TGG CCT CTC ACT;

SEQ ID NO: 48
Q Q R S N W P L T;

SEQ ID NO: 49
GAAGTGCAGCTGGTGGAGTCTGGGGGAGACTTGGTACAGCCTGGCAGGTCCCTGAGACTCTCCTGTGCAGCCTCTGGATT
CACCTTTGATGATTATGCCATGCACTGGGTGCGGCAAGCTCCAGGGAAGGGCCTGGAATGGGTCTCAGTTATTAGTTGGA
ATAGTGATGTCATAGCCTATTCGGACTCTGTGAAGGGCCGATTCACCATCTCCAGAGACAACGCCAAGAACTCCCTGTAT
CTGCAAATGAACAGTCTGAGAACTGAGGACACGGCCTTATATTACTGTACAAAAGGCCATAAGTGGAGCTTCTTTGACTA
TTGGGGCCAGGGAACCCTGGTCACCGTCTCCTCA;

SEQ ID NO: 50
EVQLVESGGDLVQPGRSLRLSCAASGFTFDDYAMHWVRQAPGKGLEWVSVISWNSDVIAYSDSVKGRFTISRDNAKMSLY
LQMNSLRTEDTALYYCTKGHKWSFFDYWGQGTLVTVSS;

SEQ ID NO: 51
GGA TTC ACC TTT GAT GAT TAT GCC;

SEQ ID NO: 52
G F T F D D Y A;

SEQ ID NO: 53
ATT AGT TGG AAT AGT GAT GTC ATA;

SEQ ID NO: 54
I S W N S D V I;

SEQ ID NO: 55
AGA AAA GGC CAT AAG TGG AGC TTC TTT GAC TAT;

SEQ ID NO: 56
T K G H K W S F F D Y;

SEQ ID NO: 57
GAAATTGTGTTGACACAGTCTCCAGCCACCCTGTCTTTGTCTCCAGGGGAAAGAGCCACCCTCTCCTGCAGGGCCAGTCA
GAGTATTAGCAGCTACTTAGCCTGGTACCAACAGAAACCTGGCCAGGCTCCCAGACTCCTCATCTTTAATGTAGCCAACA

```
GGGCCACTGACATCCCAGCCAGGTTCAGTGGCAGTGGGTCTGGGACAGACTTCACTCTCACCATCAGCAGCCTAGAGCCT
GAAGATTTTGCAGTTTATTACTGTCAGCAGCGTAGCAACTGGCCTCTCACTTTCGGCGGAGGGACCAAGGTGGAGATCAA
A;

SEQ ID NO: 58
EIVLTQSPATLSLSPGERATLSCRASQSISSYLAWYQQKPGQAPRLLIFNVANRATDIPARFSGSGSGTDFTLTISSLEP
EDFAVYYCQQRSNWPLTFGGGTKVEIK;

SEQ ID NO: 59
CAG AGT ATT AGC AGC TAC;

SEQ ID NO: 60
Q S I S S Y;

SEQ ID NO: 61
AAT GTA GCC;

SEQ ID NO: 62
N V A;

SEQ ID NO: 63
CAG CAG CGT AGC AAC TGG CCT CTC ACT;

SEQ ID NO: 64
Q Q R S N W P L T;

SEQ ID NO: 65
GAGGTGCAGCTGGTGGAGTCTGGGGGAGGCTTGGTTCAGCCTGGGGGGTCCCTGAGACTCTCCTGCGCAGCCTCTGGATT
CACCTTTAGCGACTATGCCATGAGCTGGGTCCGCCAGGCTCCGGGGAAGGGGCTGGAGTGGGTCTCAGGTATTAGTGGAA
ATGGTGGTGACACATACTACGGAGACTTCGTGAAGGGCCGGTTCACCATCTCCAGAGACAATTCCAAGAACACGCTGTAT
CTGCAAATGAACAGCCTGAGAGGCGAGGACACGGCCGCATATTTCTGTGTGATAGATCTTGACTATTGGGGTCAGGGAAC
CCTGGTCACCGTCTCCTCA;

SEQ ID NO: 66
EVQLVESGGGLVQPGGSLRLSCAASGFTFSDYAMSWVRQAPGKGLEWVSGISGNGGDTYYGDFVKGRFTISRDNSKNTLY
LQMNSLRGEDTAAYFCVIDLDYWGQGTLVTVSS;

SEQ ID NO: 67
GGA TTC ACC TTT AGC GAC TAT GCC;

SEQ ID NO: 68
G F T F S D A;

SEQ ID NO: 69
ATT AGT GGA AAT GGT GGT GAC ACA;

SEQ ID NO: 70
I S G N G G D T;

SEQ ID NO: 71
GTG ATA GAT CTT GAC TAT;

SEQ ID NO: 72
V I D L D Y;

SEQ ID NO: 73
GACATCCAGATGACCCAGTCTCCTTCCACCCTGTCTGCATCTGAAGGAGACAGAGTCACCATCACTTGCCGGGCCAGTCA
GAGTATTAGTAGCTGGTTGGCCTGGTATCAACAGAAACCAGGAAAAGCCCCTAGGCTCCTGATCTATAAGGCGTCTATTT
TAGGAGATGGGGTCCCATCAAGGTTCAGCGGCAGTGGATCTGGGACAGAATTCACTCTCACCATCAGCAGCCTGCAGCCT
GATGATTTTGCTACTTATTACTGCCACCAGTATAATAGTTATTTGTGGACGTTCGGCCAAGGGACCAAGGTGGAAATCAA
A;

SEQ ID NO: 74
DIQMTQSPSTLSASEGDRVTITCRASQSISSWLAWYQQKPGKAPRLLIYKASILGDVPSRFSGSGSGTEFTLTISSLQP
DDFATYYCHQYNSYLWTFGQGTKVEIK;

SEQ ID NO: 75
CAG AGT ATT AGT AGC TGG;

SEQ ID NO: 76
Q S I S S W;

SEQ ID NO: 77
AAG GCG TCT;

SEQ ID NO: 78
K A S;
```

SEQ ID NO: 79
CAC CAG TAT AAT AGT TAT TTG TGG ACG;

SEQ ID NO: 80
H Q Y N S Y L W T;

SEQ ID NO: 81
CAGGTGCAGCTGCAGGAGTCGGGCCCAGGACTGGTGAAGCCTTCACAGACCCTGTCCCTCACCTGCACTGTCTCTGGTGG
CTCCATCAGCAGTGCTGATTACTATTGGAGCTGGATCCGCCAGCACCCAGGGAAGGGCCTGGAGTGGATTGGATCCATCT
ATTATACTGGGAGTACTTACTACAACCCGTCCCTCAAGAGTCGACTTACCATATCAATAGACACGTCTGAGAACCAGTTC
TCTTTGAAACTGACCTCTCTGACTGCCGCGGACACGGCCGTGTATTACTGTGCGAGCGAGGAGGCTAACTGGGGATCCGA
CTTTGACTCCTGGGGCCAGGGAACCCTGGTCACCGTCTCCTCA;

SEQ ID NO: 82
QVQLQESGPGLVKPSQTLSLTCTVSGGSISSADYYWSWIRQKPGKGLEWIGSIYYTGSTYYNPSLKSRLTISIDTSENQF
SLKLTSLTAADTAVYYCAEEANWGSHFDSWGQGTLVTVSS;

SEQ ID NO: 83
GGT GGC TCC ATC AGC AGT GCT GAT TAC TAT;

SEQ ID NO: 84
G G S I S S A D Y Y;

SEQ ID NO: 85
ATC TAT TAT ACT GGG AGT ACT;

SEQ ID NO: 86
I Y Y T G S T;

SEQ ID NO: 87
GCG AGC GAG GAG GCT AAC TGG GGA TCC CAC TTT GAC TCC;

SEQ ID NO: 88
A S E E A N W G S H F D S;

SEQ ID NO: 89
GACATCCAGATGACCCAGTCTCCATCCTCCCTGTCTGCATCTGTAGGAGACAGAGTCACCATCACTTGCCGGGCAAGTCA
GAGCATTGACAACTTTTTAAATTGGTATCAGCAGAAACCAGGGAAAGCCCCTAAGCTCCTGATCTATGCTGCATCCAGTT
TGCAAAGTGGGGTCCCATCAAGGTTCAGTGGCAGTGGATCTGGGACAGATTTCACTCTCACCATCAGCAGTCTGCAACCT
GAAGATTTTGCATCTTACTACTGTCAAGATAGTCACAGTGCCCATCCGATCACCTTCGGCCAAGGGACACGACTGGAGAT
TAAA;

SEQ ID NO: 90
DIQMTQSPSSLSASVGDRVTITCRASQSIDNFLNWYQQKPGKAPKLLIYAASSLQSGVPSRFSGSGSGTDFTLTISSLQP
EDFASYYCQHSHSAHPITFGQGTRLEIK;

SEQ ID NO: 91
CAG AGC ATT GAC AAC TTT;

SEQ ID NO: 92
Q S I D N F;

SEQ ID NO: 93
GCT GCA TCC;

SEQ ID NO: 94
A A S;

SEQ ID NO: 95
CAA CAT AGT CAC AGT GCC CAT CCG ATC ACC;

SEQ ID NO: 96
Q H S K S A H P I T;

SEQ ID NO: 97
CAGCTGCAGCTGCAGGAGTCGGGCCCAGGACTGGTGAAGCCTTCGGAGACCCTGTCCCTCACCTGCACTGTCTCTGGTGG
CTCCATCAGCAGTAGTAATTACTACTGGGGCTGGATCCGCCAGCCCCCAGGGAAGAGACTGGAGTGGATTGGGAGTATCT
ATTATAGTGGGAGCACCTACTACAACCCGTCCCTCAAGACTCGAGTCACCATATCCGTAGACACGTCCAAGAATCAGTTC
TCCCTGAAGCTGACCTCTGTGACCGCCGCAGACACGGCTGTGTATTACTGTGCGAGAGAGGAAGCAGCAGCTTTGACGCA
CTTTGACTTCTGGGGCCAGGGAACCCTGGTCACCGTCTCCTCA;

SEQ ID NO: 98
QLQLQESGPGLVKPSETLSLTCTVSGGSISSSNYYWGWIRQPPGKRLEWIGSIYYSGSTYYNPSLKTRVTISVDTSKNQF
SLKLTSVTAADTAVYYCAREEAAALTHFDFWGQGTLVTVSS;

SEQ ID NO: 99
GGT GGC TCC ATC AGC AGT AGT AAT TAC TAG;

SEQ ID NO: 100
G G S I S S S N Y Y;

SEQ ID NO: 101
ATC TAT TAT AGT GGG AGC ACC;

SEQ ID NO: 102
I Y Y S G S T;

SEQ ID NO: 103
GCG AGA GAG GAA GCA GCA GCT TTG ACG CAC TTT GAC TTC;

SEQ ID NO: 104
A R E E A A A L T H F D F;

SEQ ID NO: 105
GACATCCAGATGACCCAGTCTCCATCCTCCCTGTCTGCATCTGTAGGAGACAGAGTCACCATCACTTGCCGGGCAAGTCA
GAGCATTAGCAACTATTTAAATTGGTATCAGCAGAAACCAGGGAAAGCCCCTAAGCTCCTGATCTTTGCTGCATCCAGTT
TACAAAGTGGGGTCCCATCAAGGTTCAGTGGCAGTGGATCTGGGACAGATTTCACTCTCACCATCAGCAGTCTGCAACCT
GAAGATTTTGCAACTTACTACTGTCAACATAGTCACAGTTCCCATCCGATCACCTTCGGCCAAGGGACACGACTGGAGAT
TAAA;

SEQ ID NO: 106
DIQMTQSPSSLSASVGDRVTITCRASQSISNYLNWYQQKPGKAPKLLIFAASSLQSGVPSRFSGSGSGTDFTLTISSLQP
EDFATYYCQHSHSSHPITFGQGTRLEIK;

SEQ ID NO: 107
CAG AGC ATT AGC AAC TAT;

SEQ ID NO: 108
Q S I S N Y;

SEQ ID NO: 109
GCT GCA TCC;

SEQ ID NO: 110
A A S;

SEQ ID NO: 111
CAA CAT AGT CAC AGT TCC CAT CCG ATC ACC;

SEQ ID NO: 112
Q H S H S S H P I T;

SEQ ID NO: 113
GAAGTGCAGCTGGTGGAGTCTGGGGGAGGCTTGGTACAGCCTGGCAGGTCCCTGAGACTCTCCTGTGCAGCCTCTGGATT
CACCTTTGATGATTATGCCATGCACTGGGTCCGGCAAGCTCCAGGGAAGGGCCTGGAGTGGGTCTCAGGTATTAATTGGG
CTGGTTATAACATAGACTATGCGGACTCTGTGAAGGGCCGATTCACCATCTCCAGAGACAACGCCAAGAACTCCCTGTAT
CTGCAAATGAACAGTCTGAGAGCTGAGGACACGGCCTTGTATTACTGTGCAAAAGATATGCGTGGATTCAGTTATGGTTT
CCCCTTTGACTACTGGGGCCAGGGAACCCTGGTCACCGTCTCCTCA;

SEQ ID NO: 114
EVQLVESGGGLVQPGRSLRLSCAASGFTFDDYAMHWVRQAPGKGLEWVSGINWAGYNIDYADSVKGRFTISRDNAKNSLY
LQMNSLRAEDTALYYCAKDMRGFSYGFPFDYWGQGTLVTVSS;

SEQ ID NO: 115
GGA TTC ACC TTT GAT GAT TAT GCC;

SEQ ID NO: 116
G F T F D D Y A;

SEQ ID NO: 117
ATT AAT TGG GCT GGT TAT AAC ATA;

SEQ ID NO: 118
I N W A G Y N I;

SEQ ID NO: 119
GCA AAA GAT ATG CGT GGA TTC AGT TAT GGT TTC CCC TTT GAC TAC;

SEQ ID NO: 120
A K D M R G F S Y G F P F D Y;

SEQ ID NO: 121
GACATCCAGATGACCCAGTCTCCATCCTCCCTGTCTGCATCTGTAGGAGACAGAGTCACCATCACTTGCCGGGCAAGTCA
GAGCATTAGCAGCTATTTAAATTGGTATCAGCAGAAACCAGGGAAAGCCCCTAAGCTCCTGATCTATGCTGCATCCAGTT
TGCAAAGTGGGGTCCCGTCAAGGTTCAGTGGCAGTGGATCTGGGACAGATTTCACTCTCACCATCAGCAGTCTGCAACCT
GAAGATTTTGCAACTTACTACTGTCAACAGAGTTACAGTACCCCTCCGATCACCTTCGGCCAAGGGACACGACTGGAGAT
TAAA;

SEQ ID NO: 122
DIQMTQSPSSLSASVGDRVTITCRASQSISSYLNWYQQKPGKAPKLLIYAASSLQSGVPSRFSGSGSGTDFTLTISSLQP
EDFATYYCQQSYSTPPITFGQGTRLEIK;

SEQ ID NO: 123
CAG AGC ATT AGC AGC TAT;

SEQ ID NO: 124
Q S I S S Y;

SEQ ID NO: 125
GCT GCA TCC;

SEQ ID NO: 126
A A S;

SEQ ID NO: 127
CAA CAG AGT TAG AGT ACC CCT CCG ATC ACC;

SEQ ID NO: 128
Q Q S Y S T P P I T;

SEQ ID NO: 129
GAGGTGCAGCTGGTGGAGTCTGGGGGAGGCTTGGTAAAGCCGGGGGGGTCCCTTAGACTCTCCTGTGCAGCCTCTGGATT
TATTTTCAGTAACGCCTGGATGAACTGGGTCCGCCAGGCTCCAGGGAAGGGACTGGCGTGGGTTGGCCGTATTAAAACCG
AAACTGATGGTGGGACAACAGACTACGCTGCACCCGTAAAAGGCAGATTCACCATCTCAAGAGATGACTCAAAAAACACG
CTGTATCTGCAAATGAACAGCGTGAAAACCGAGGACACAGCCGTGTATTACTGTACAGGGGGATACAGCTATGGTGACGA
TAGCAGCAGCTGGAACGAGGGCTACTACTACTACGGTATGGACGTCTGGGGCCAAGGGACCACGGTCACCGTCTCCTCA;

SEQ ID NO: 130
EVQLVESGGGLVKPGGSLRLSCAASGFIFSNAWMNWVRQAPGKGLAWVGRIKTETDGGTTDYAAPVKGRFTISRDDSKNT
LYLQMNSVKTEDTAVYYCTGGYSYGDDSSSWNEGYYYYGMDVWGQGTTVTVSS;

SEQ ID NO: 131
GGA TTT ATT TTC AGT AAC GCC TGG;

SEQ ID NO: 132
G F I F S N A W;

SEQ ID NO: 133
ATT AAA ACC GAA ACT GAT GGT GGG ACA ACA;

SEQ ID NO: 134
I K T E T D G G T T;

SEQ ID NO: 135
ACA GGG GGA TAC AGC TAT GGT GAC GAT AGC AGC AGC TGG AAC GAG GGC TAG TAC TAG TAC
GGT ATG GAC GTC;

SEQ ID NO: 136
T G G Y S Y G D D S S S W N E G Y Y Y Y
G M D V;

SEQ ID NO: 137
GAAGTGGAGCTGGTGGAGTCTGGGGGAGGCTTGGTACAGCCTGGCAGGTCCCTGAGACTCTCCTGTACAGCCTCTGGATT
CACCTTTGATGATTATGCCATGCACTGGGTCCGGCAAGCTCCAGGGAAGGGCCTGGAGTGGGTCTCAGGTATTCGTTGGA
ATGGTGGTAGTATAGGCTATGTGGAGTCTGTGAAGGGCCGATTCACCATCTCCAGAGAGAACGCCAAGAAGTCCGTGCAT
CTGCAAATGAACAGTCTAAAAACTGAGGACACGGCCTTGTATTACTGTGCAAAAGATATAGGCGATATTTTGACTGGTTT
TTATGGAGAATACGGAATGGACGTCTGGGGCCAAGGGACCACGGTCACCGTCTCCTCA;

SEQ ID NO: 138
EVQLVESGGGLVQPGRSLRLSCTASGFTFDDYAMHWVRQAPGKGLEWVSGIRWNGGSIGYVDSVKGRFTISRDNAKKSLH
LQMNSLKTEDTALYYCAKDIGDILTGFYGEYGMDVWGQGTTVTVSS;

SEQ ID NO: 139
GGA TTC ACC TTT GAT GAT TAT GCC;

SEQ ID NO: 140
G F T F D D Y A;

SEQ ID NO: 141
ATT CGT TGG AAT GGT GGT AGT ATA;

SEQ ID NO: 142
I R W N G G S I;

SEQ ID NO: 143
GCA AAA GAT ATA GGC GAT ATT TTG ACT GGT TTT TAT GGA GAA TAC GGA ATG GAC GTC;

SEQ ID NO: 144
A K D I G D I L T G F Y G E Y G M D V;

SEQ ID NO: 145
GACATCCAGATGACCCAGTCTCCATCCTCCCTGTCTGCATCTGAAGGAGACAGAGTCACCATCACTTGCCGGGCAAGTCA
GAGCATTAGCAGCTATTTAAATTGGTATCAGCAGAAAGCAGGGAAAGCCCCTAACCTCCTGATCTATGCTGCATCCAGTT
TGCAAAGTGGGGTCCCATCAAGGTTCAGTGGCAGTGGATCTGGGACAGAGTACACTCTCACCATCAGCAGTCTGCAACCT
GAAGATTTTGCAACTTACTACTGTCAACAGAGTTACATTATCCCGTACACTTTTGGCCAGGGGACCAAGCTGGAGATCAA
A;

SEQ ID NO: 146
DIQMTQSPSSLSASEGDRVTITCRASQSISSYLNWYQQKAGKAPNLLIYAASSLQSGVPSRFSGSGSGTEYTLTISSLQP
EDFATYYCQQSYIIPYTFGQGTKLETK;

SEQ ID NO: 147
CAG AGC ATT AGC AGC TAT;

SEQ ID NO: 148
Q S I S S Y;

SEQ ID NO: 149
GCT GCA TCC;

SEQ ID NO: 150
A A S;

SEQ ID NO: 151
CAA CAG AGT TAG ATT ATG CCG TAG ACT;

SEQ ID NO: 152
Q Q S Y I I P Y T;

SEQ ID NO: 153
GAAGTGCAGCTGGTGGAGTCTGGGGGAGGGTTGGTACAGCCTGGCAGGTCCCTGAGACTCTCCTGTGCAGCCTCTGGATT
CACCTTTGATGATTATGCCATGCACTGGGTCCGGCAAGCTCCAGGGAAGGGCCTGGAGTGGGTCTCAAGTGTTAGGTGGA
ATGGTGGTATTATAGGCTATGCGGACTCTGTGAAGGGCCGATTCACCATCTCCAGAGACAACGCCAAGAACTCCCTGTAT
CTGCAAATGAACAGTCTGAGACCTGAGGACACGGCCCTCTATTACTGTGCAAAAGATATAGGCGATGTTTTGACTGGTTA
TTATGGAGAATACGGTATGGACGTCTGGGGCCAAGGGACCACGGTCACCGTCTCCTCA;

SEQ ID NO: 154
EVQLVESGGGLVQPGRSLRLSCAASGFTFDDYAMHWVRQAPGKGLEWVSSVRWKGGIIGYADSVKGRFTISRDNAKNSLY
LQMNSLRPEDTALYYCAKDIGDVLTGYYGEYGMDVWGQGTTVTSS;

SEQ ID NO: 155
GGA TTC ACC TTT GAT GAT TAT GCC;

SEQ ID NO: 156
G F T F D D Y A;

SEQ ID NO: 157
GTT AGG TGG AAT GGT GGT ATT ATA;

SEQIDNO: 158
V R W N G G I I;

SEQ ID NO: 159
GCA AAA GAT ATA GGC GAT GTT TTG ACT GGT TAT TAT GGA GAA TAG GGT ATG GAC GTC;

SEQ ID NO: 160
A K D I G D V L T G Y Y G E Y G M D V;

SEQ ID NO: 161
GACATCCAGATGACCCAGTCTCCATCCTCCCTGTCTGCATCTGTGGGAGACAGAGTCACCATCGCTTGCCGGGCAAGTCA
GAGCATTACCACCTATTTAAATTGGTATCAGCAGAAACCAGGGAAAGCCCCTAAACTCCTGATCTATGCTGCATCCAGTT
TGCAAAGTGGGGTCCCATCAAGGTTCAGTGGCAGTGGATCTGGGACAGATTTCACTCTCACCATCAGTAGTCTGCAACCT
GAAGATTTTGCAACTTACTACTGTCAACAGAGTTACATTTCCCCGTACACTTTTGGCCAGGGGACCAAGCTGGAGATCAAA;

SEQ ID NO: 162
DIQMTQSPSSLSASVGDRVTIACRASQSITTYLNWYQQKPGKAPKLLIYAASSLQSGVPSRFSGSGSGTDFTLTISSLQP
EDFATYYCQQSYISPYTFGQGTKLEIK;

SEQ ID NO: 163
CAG AGC ATT ACC ACC TAT;

SEQ ID NO: 164
Q S I T T Y;

SEQ ID NO: 165
GCT GCA TCC;

SEQ ID NO: 166
A A S;

SEQ ID NO: 167
CAA CAG AGT TAC ATT TCC CCG TAC ACT;

SEQ ID NO: 168
Q Q S Y I S P Y T;

SEQ ID NO: 169
CAGGTGCAGCTGGTGGAGTCTGGGGGAGGCGTGGTCCAGCCTGGGAAGTCCCTGAGACTCTCCTGTGCAGCCTCTGGATT
CACCCTTCAGTAATTATGGCATACACTGGGTCCGCCAGGCTCCAGGCAAGGGGCTGGAGTGGGTGGCGATTATATTATATG
ATGGAAGTAATCAACACTATGCAGATTCCGTGAAGGGCCGATTCACCATTTCCAGAGACAATTCCAAAAACACGCTGTAT
CTTCAAATGAACAACCTGAGAGCTGAGGACACGGCCGTTTATTACTGTGCGAGAGATCTTGATCTTTGGAGTGGTTATTA
TACAAACGGGGACGGTATGGACGTCTGGGGCCAAGGGACCACGGTCACCGTCTCCTCA;

SEQ ID NO: 170
QVQLVESGGGVVQPGKSLRLSCAASGFTFSNYGIHWVRQAPGKGLEWVAIILYDGSNQHYADSVKGRFTISRDKSKNTLY
LQMNNLRAEDTAVYYCARDLDLWSGYYTNGDGMDVWGQGTTVTVSS;

SEQ ID NO: 171
GGA TTC ACC TTC AGT AAT TAT GGC;

SEQ ID NO: 172
G F T F S N Y G;

SEQ ID NO: 173
ATA TTA TAT GAT GGA AGT AAT CAA;

SEQ ID NO: 174
I L Y D G S N Q;

SEQ ID NO: 175
GCG AGA GAT CTT GAT CTT TGG AGT GGT TAT TAT ACA AAC GGG GAC GGT ATG GAG GTC;

SEQ ID NO: 176
A R D L D L W S G Y Y T N G D G M D V;

The amino acid and nucleotide sequences of heavy and light chain immunoglobulins, including constant domains, of antigen-binding proteins of the present invention are set forth below:

H4H14699P2
Heavy chain DNA
(SEQ ID NO: 179)
GAAGTGCAGCTGGTGGAGTCTGGGGGAGGCTTGGTGCAGCCTGGCAGGTCCCTGAGACTCTCCTGTGCGGCCTCTGGATT

CACCTTTGATGATTATGCCATACACTGGGTCCGGCAAGCTCCAGGGAAGGGCCTGGAGTGGGTCTCAGTTATCAGTTGGA

ATAGTGATATCATAGGCTATGCGGACTCTGTGAAGGGCCGATTCACCGTCTCCAGAGACAACGCCAAGAACTCCCTGTAT

CTGCAAATGAATAGTCTGAGAACTGAGGACACGGCCTTGTATTACTGTGCAAAAGGATATAACTGGAACTTCTTTGACTA

TTGGGGCCAGGGAACCCTGGTCACCGTCTCCTCAGCCTCCACCAAGGGCCCATCGGTCTTCCCCCTGGCGCCCTGCTCCA

GGAGCACCTCCGAGAGCACAGCCGCCCTGGGCTGCCTGGTCAAGGACTACTTCCCCGAACCGGTGACGGTGTCGTGGAAC

TCAGGCGCCCTGACCAGCGGCGTGCACACCTTCCCGGCTGTCCTACAGTCCTCAGGACTCTACTCCCTCAGCAGCGTGGT

GACCGTGCCCTCCAGCAGCTTGGGCACGAAGACCTACACCTGCAACGTAGATCACAAGCCCAGCAACACCAAGGTGGACA

AGAGAGTTGAGTCCAAATATGGTCCCCCATGCCCACCCTGCCCAGCACCTGAGTTCCTGGGGGGACCATCAGTCTTCCTG

TTCCCCCCAAAACCCAAGGACACTCTCATGATCTCCCGGACCCCTGAGGTCACGTGCGTGGTGGTGGACGTGAGCCAGGA

AGACCCCGAGGTCCAGTTCAACTGGTACGTGGATGGCGTGGAGGTGCATAATGCCAAGACAAAGCCGCGGGAGGAGCAGT

TCAACAGCACGTACCGTGTGGTCAGCGTCCTCACCGTCCTGCACCAGGACTGGCTGAACGGCAAGGAGTACAAGTGCAAG

GTCTCCAACAAAGGCCTCCCGTCCTCCATCGAGAAAACCATCTCCAAAGCCAAAGGGCAGCCCCGAGAGCCACAGGTGTA

-continued

```
CACCCTGCCCCCATCCCAGGAGGAGATGACCAAGAACCAGGTCAGCCTGACCTGCCTGGTCAAAGGCTTCTACCCCAGCG

ACATCGCCGTGGAGTGGGAGAGCAATGGGCAGCCGGAGAACAACTACAAGACCACGCCTCCCGTGCTGGACTCCGACGGC

TCCTTCTTCCTCTACAGCAGGCTCACCGTGGACAAGAGCAGGTGGCAGGAGGGGAATGTCTTCTCATGCTCCGTGATGCA

TGAGGCTCTGCACAACCACTACACACAGAAGTCCCTCTCCCTGTCTCTGGGTAAATGA
```

Heavy chain polypeptide
(SEQ ID NO: 180)

```
EVQLVESGGGLVQPGRSLRLSCAASGFTFDDYAIHWVRQAPGKGLEWVSVISWDSDIIGYADSVKGRFTVSRDNAKNSLY

LQMNSLRTEDTALYYCAKGYNWNFFDYWGQGTLVTVSSASTKGPSVFPLAPCSRSTSESTAALGCLVKDYFPEPVTVSWN

SGALTSGVHTFPAVLQSSGLYSLSSVVTVPSSSLGTKTYTCNVDHKPSNTKVDKRVESKYGPPCPPCPAPEFLGGPSVFL

FPPKPKDTLMISRTPEVTCVVVDVSQEDPEVQFNWYVDGVEVHNAKTKPREEQFNSTYRVVSVLTVLHQDWLNGKEYKCK

VSNKGLPSSIEKTISKAKGQPREPQVYTLPPSQEEMTKNQVSLTCLVKGFYPSDIAVEWESNGQPENNYKTTPPVLDSDG

SFFLYSRLTVDKSRWQEGNVFSCSVMHEALHNHYTQKSLSLSLGK
```

Light chain DNA
(SEQ ID NO: 181)

```
GAAATTGTGTTGACGCAGTCTCCAGCCACCCTGTCTTTATCTCCAGGGGAAAGAGCCACCCTCTCCTGCAGGGCCAGTCA

GAGTGTTAGCAGCTACTTAGCCTGGTACCAACAGAAACCTGGCCAGGCTCCCAGGCTCCTCATCTATAATGCAGCAAACA

GGGCCACTGACATCCCAGCCAGGTTCAGTGGCAGTGGGTCTGGGACAGACTTCACTCTCACCATCAGCAGCCTAGAGCCT

GAAGATTTTGCAGTTTATTACTGTCAGCAGCGTAGCAACTGGCCTCTCACTTTCGGCGGAGGGACCAAGGTGGAGATCAA

ACGAACTGTGGCTGCACCATCTGTCTTCATCTTCCCGCCATCTGATGAGCAGTTGAAATCTGGAACTGCCTCTGTTGTGT

GCCTGCTGAATAACTTCTATCCCAGAGAGGCCAAAGTACAGTGGAAGGTGGATAACGCCCTCCAATCGGGTAACTCCCAG

GAGAGTGTCACAGAGCAGGACAGCAAGGACAGCACCTACAGCCTCAGCAGCACCCTGACGCTGAGCAAAGCAGACTACGA

GAAACACAAAGTCTACGCCTGCGAAGTCACCCATCAGGGCCTGAGCTCGCCCGTCACAAAGAGCTTCAACAGGGGAGAGT

GT
```

Light chain polypeptide
(SEQ ID NO: 182)

```
EIVLTQSPATLSLSPGERATLSCRASQSVSSYLAWYQQKPGQAPRLLIYNAANRATDIPARFSGSGSGTDFTLTISSLEP

EDFAVYYCQQRSNWPLTFGGGTKVEIKRTVAAPSVFIFPPSDEQLKSGTASVVCLLNNFYPREAKVQWKVDNALQSGNSQ

ESVTEQDSKDSTYSLSSTLTLSKADYEKHKVYACEVTHQGLSSPVTKSFNRGEC
```

H4H14700P2
Heavy chain DNA
(SEQ ID NO: 183)

```
GAAGTGCAGCTGGTGGAGTCTGGGGGAGGCTTGGTACAGCCTGGCAGGTCCCTGAGACTCTCCTGTGCAGCCTCTGGATT

CACCTTTGATGATTATGCCATGCACTGGGTCCGGCAAACTCCAGGGAAGGGCCTGGAGTGGGTCTCAGTTATTAGTTGGA

ATAGTGATGTCATAGCCTATTCGGACTCTGTGAAGGGCCGCTTCACCATTTCCAGAGACAACGCCAAGAACTCCCTGTAT

CTGCAAATGAACAGTCTGGGAACTGAGGACACGGCCTTATATTACTGTGCAAAAGGCCATAACTGGAACTTCTTTGACTA

TTGGGGCCAGGGAACCCTGGTCACCGTCTCCTCAGCCTCCACCAAGGGCCCATCGGTCTTCCCCCTGGCGCCCTGCTCCA

GGAGCACCTCCGAGAGCACAGCCGCCCTGGGCTGCCTGGTCAAGGACTACTTCCCCGAACCGGTGACGGTGTCGTGGAAC

TCAGGCGCCCTGACCAGCGGCGTGCACACCTTCCCGGCTGTCCTACAGTCCTCAGGACTCTACTCCCTCAGCAGCGTGGT

GACCGTGCCCTCCAGCAGCTTGGGCACGAAGACCTACACCTGCAACGTAGATCACAAGCCCAGCAACACCAAGGTGGACA

AGAGAGTTGAGTCCAAATATGGTCCCCCATGCCCACCCTGCCCAGCACCTGAGTTCCTGGGGGGACCATCAGTCTTCCTG

TTCCCCCCAAAACCCAAGGACACTCTCATGATCTCCCGGACCCCTGAGGTCACGTGCGTGGTGGTGGACGTGAGCCAGGA

AGACCCCGAGGTCCAGTTCAACTGGTACGTGGATGGCGTGGAGGTGCATAATGCCAAGACAAAGCCGCGGGAGGAGCAGT

TCAACAGCACGTACCGTGTGGTCAGCGTCCTCACCGTCCTGCACCAGGACTGGCTGAACGGCAAGGAGTACAAGTGCAAG

GTCTCCAACAAAGGCCTCCCGTCCTCCATCGAGAAAACCATCTCCAAAGCCAAAGGGCAGCCCCGAGAGCCACAGGTGTA

CACCCTGCCCCCATCCCAGGAGGAGATGACCAAGAACCAGGTCAGCCTGACCTGCCTGGTCAAAGGCTTCTACCCCAGCG
```

-continued

ACATCGCCGTGGAGTGGGAGAGCAATGGGCAGCCGGAGAACAACTACAAGACCACGCCTCCCGTGCTGGACTCCGACGGC

TCCTTCTTCCTCTACAGCAGGCTCACCGTGGACAAGAGCAGGTGGCAGGAGGGGAATGTCTTCTCATGCTCCGTGATGCA

TGAGGCTCTGCACAACCACTACACACAGAAGTCCCTCTCCCTGTCTCTGGGTAAATGA

Heavy chain polypeptide
(SEQ ID NO: 184)
EVQLVESGGGLVQPGRSLRLSCAASGFTFDDYAMHWVRQTPGKGLEWVSVISWNSDVIAYSDSVKGRFTISRDNAKNSLY

LQMNSLGTEDTALYYCAKGHNWNFFDYWGQGTLVTVSSASTKGPSVFPLAPCSRSTSESTAALGCLVKDYFPEPVTVSWN

SGALTSGVHTFPAVLQSSGLYSLSSVVTVPSSSLGTKTYTCNVDHKPSNTKVDKRVESKYGPPCPPCPAPEFLGGPSVFL

FPPKPKDTLMISRTPEVTCVVVDVSQEDPEVQFNWYVDGVEVHNAKTKPREEQFNSTYRVVSVLTVLHQDWLNGKEYKCK

VSNKGLPSSIEKTISKAKGQPREPQVYTLPPSQEEMTKNQVSLTCLVKGFYPSDIAVEWESNGQPENNYKTTPPVLDSDG

SFFLYSRLTVDKSRWQEGNVFSCSVMHEALHNHYTQKSLSLSLGK

Light chain DNA
(SEQ ID NO: 185)
GAAATTGTGTTGACACAGTCTCCAGCCACCCTGTCTTTGTCTCCAGGAGAAAGAGCCACCCTCTCCTGCAGGGCCAGTCA

GAGTGTTAGCAGCTACTTAGCCTGGTACCAACAGAAACCTGGCCAGGCTCCCAGGCTCCTCATCTATAATGTAGCCAACA

GGGCCACAGACATCCCAGCCAGGTTCAGTGGCAGTGGGTCTGGGACAGACTTCACTCTCACCATCAGCGGCCTAGAGCCT

GAAGATTTTGCAGTTTATTTCTGTCAGCAGCGTAGCAACTGGCCTCTCACTTTCGGCGGAGGGACCAAGGTGGAGATCAA

ACGAACTGTGGCTGCACCATCTGTCTTCATCTTCCCGCCATCTGATGAGCAGTTGAAATCTGGAACTGCCTCTGTTGTGT

GCCTGCTGAATAACTTCTATCCCAGAGAGGCCAAAGTACAGTGGAAGGTGGATAACGCCCTCCAATCGGGTAACTCCCAG

GAGAGTGTCACAGAGCAGGACAGCAAGGACAGCACCTACAGCCTCAGCAGCACCCTGACGCTGAGCAAAGCAGACTACGA

GAAACACAAAGTCTACGCCTGCGAAGTCACCCATCAGGGCCTGAGCTCGCCCGTCACAAAGAGCTTCAACAGGGGAGAGT

GT

Light chain polypeptide
(SEQ ID NO: 186)
EIVLTQSPATLSLSPGERATLSCRASQSVSSYLAWYQQKPGQAPRLLIYNVANRATDIPARFSGSGSGTDFTLTISGLEP

EDFAVYFCQQRSNWPLTFGGGTKVEIKRTVAAPSVFIFPPSDEQLKSGTASVVCLLNNFYPREAKVQWKVDNALQSGNSQ

ESVTEQDSKDSTYSLSSTLTLSKADYEKHKVYACEVTHQGLSSPVTKSFNRGEC

H4H14706P2
Heavy chain DNA
(SEQ ID NO: 187)
GAAGTGCAGCTGGTGGAGTCTGGGGGAGGCTTGGTACAGCCTGGCAGGTCCCTGAGACTCTCCTGTACAGCCTCTGGATT

CACCTTTGATGATTATGCCATACACTGGGTCCGGCAATCTCCAGGGAAGGGCCTGGAGTGGGTCTCAGTTATCAGTTGGA

ATAGTGATGTCATAGGCTATGCGGACTCTGTGAAGGGCCGATTCACCATCTCCAGAGACAACGCCAAGAACTCCCTGTAT

CTGCAGATGAATAGTCTGAGAGCTGAGGACACGGCCTTGTATTACTGTGCAAAAGGATATAACTGGAACTTCTTTGACTA

TTGGGGCCAGGGAACCCTGGTCACCGTCTCCTCAGCCTCCACCAAGGGCCCATCGGTCTTCCCCCTGGCGCCCTGCTCCA

GGAGCACCTCCGAGAGCACAGCCGCCCTGGGCTGCCTGGTCAAGGACTACTTCCCCGAACCGGTGACGGTGTCGTGGAAC

TCAGGCGCCCTGACCAGCGGCGTGCACACCTTCCCGGCTGTCCTACAGTCCTCAGGACTCTACTCCCTCAGCAGCGTGGT

GACCGTGCCCTCCAGCAGCTTGGGCACGAAGACCTACACCTGCAACGTAGATCACAAGCCCAGCAACACCAAGGTGGACA

AGAGAGTTGAGTCCAAATATGGTCCCCCATGCCCACCCTGCCCAGCACCTGAGTTCCTGGGGGGACCATCAGTCTTCCTG

TTCCCCCCAAAACCCAAGGACACTCTCATGATCTCCCGGACCCCTGAGGTCACGTGCGTGGTGGTGGACGTGAGCCAGGA

AGACCCCGAGGTCCAGTTCAACTGGTACGTGGATGGCGTGGAGGTGCATAATGCCAAGACAAAGCCGCGGGAGGAGCAGT

TCAACAGCACGTACCGTGTGGTCAGCGTCCTCACCGTCCTGCACCAGGACTGGCTGAACGGCAAGGAGTACAAGTGCAAG

GTCTCCAACAAAGGCCTCCCGTCCTCCATCGAGAAAACCATCTCCAAAGCCAAAGGGCAGCCCCGAGAGCCACAGGTGTA

CACCCTGCCCCCATCCCAGGAGGAGATGACCAAGAACCAGGTCAGCCTGACCTGCCTGGTCAAAGGCTTCTACCCCAGCG

ACATCGCCGTGGAGTGGGAGAGCAATGGGCAGCCGGAGAACAACTACAAGACCACGCCTCCCGTGCTGGACTCCGACGGC

-continued

TCCTTCTTCCTCTACAGCAGGCTCACCGTGGACAAGAGCAGGTGGCAGGAGGGGAATGTCTTCTCATGCTCCGTGATGCA

TGAGGCTCTGCACAACCACTACACACAGAAGTCCCTCTCCCTGTCTCTGGGTAAATGA

Heavy chain polypeptide (SEQ ID NO: 188)
EVQLVESGGGLVQPGRSLRLSCTASGFTFDDYAIHWVRQSPGKGLEWVSVISWNSDVIGYADSVKGRFTISRDNAKNSLY

LQMNSLRAEDTALYYCAKGYNWNFFDYWGQGTLVTVSSASTKGPSVFPLAPCSRSTSESTAALGCLVKDYFPEPVTVSWN

SGALTSGVHTFPAVLQSSGLYSLSSVVTVPSSSLGTKTYTCNVDHKPSNTKVDKRVESKYGPPCPPCPAPEFLGGPSVFL

FPPKPKDTLMISRTPEVTCVVVDVSQEDPEVQFNWYVDGVEVHNAKTKPREEQFNSTYRVVSVLTVLHQDWLNGKEYKCK

VSNKGLPSSIEKTISKAKGQPREPQVYTLPPSQEEMTKNQVSLTCLVKGFYPSDIAVEWESNGQPENNYKTTPPVLDSDG

SFFLYSRLTVDKSRWQEGNVFSCSVMHEALHNHYTQKSLSLSLGK

Light chain DNA (SEQ ID NO: 189)
GAAATTGTGTTGACGCAGTCTCCAGCCACCCTGTCTTTATCTCCAGGGGAAAGAGCCACCCTCTCCTGCAGGGCCAGTCA

GAGTGTTAGCAGCTACTTAGCCTGGTACCAACAGAAACCTGGCCAGGCTCCCAGGCTCCTCATCTATAATGCAGCAAACA

GGGCCACTGACATCCCAGCCAGGTTCAGTGGCAGTGGGTCTGGGACAGACTTCACTCTCACCATCAGCAGCCTAGAGCCT

GAAGATTTTGCAGTTTATTACTGTCAGCAGCGTAGCAACTGGCCTCTCACTTTCGGCGGAGGGACCAAGGTGGAGATCAA

ACGAACTGTGGCTGCACCATCTGTCTTCATCTTCCCGCCATCTGATGAGCAGTTGAAATCTGGAACTGCCTCTGTTGTGT

GCCTGCTGAATAACTTCTATCCCAGAGAGGCCAAAGTACAGTGGAAGGTGGATAACGCCCTCCAATCGGGTAACTCCCAG

GAGAGTGTCACAGAGCAGGACAGCAAGGACAGCACCTACAGCCTCAGCAGCACCCTGACGCTGAGCAAAGCAGACTACGA

GAAACACAAAGTCTACGCCTGCGAAGTCACCCATCAGGGCCTGAGCTCGCCCGTCACAAAGAGCTTCAACAGGGGAGAGT

GT

Light chain polypeptide (SEQ ID NO: 190)
EIVLTQSPATLSLSPGERATLSCRASQSVSSYLAWYQQKPGQAPRLLIYNAANRATDIPARFSGSGSGTDFTLTISSLEP

EDFAVYYCQQRSNWPLTFGGGTKVEIKRTVAAPSVFIFPPSDEQLKSGTASVVCLLNNFYPREAKVQWKVDNALQSGNSQ

ESVTEQDSKDSTYSLSSTLTLSKADYEKHKVYACEVTHQGLSSPVTKSFNRGEC

H4H14708P2
Heavy chain DNA (SEQ ID NO: 191)
GAAGTGCAGCTGGTGGAGTCTGGGGGAGACTTGGTACAGCCTGGCAGGTCCCTGAGACTCTCCTGTGCAGCCTCTGGATT

CACCTTTGATGATTATGCCATGCACTGGGTCCGGCAAGCTCCAGGGAAGGGCCTGGAATGGGTCTCAGTTATTAGTTGGA

ATAGTGATGTCATAGCCTATTCGGACTCTGTGAAGGGCCGATTCACCATCTCCAGAGACAACGCCAAGAACTCCCTGTAT

CTGCAAATGAACAGTCTGAGAACTGAGGACACGGCCTTATATTACTGTACAAAAGGCCATAAGTGGAGCTTCTTTGACTA

TTGGGGCCAGGGAACCCTGGTCACCGTCTCCTCAGCCTCCACCAAGGGCCCATCGGTCTTCCCCCTGGCGCCCTGCTCCA

GGAGCACCTCCGAGAGCACAGCCGCCCTGGGCTGCCTGGTCAAGGACTACTTCCCCGAACCGGTGACGGTGTCGTGGAAC

TCAGGCGCCCTGACCAGCGGCGTGCACACCTTCCCGGCTGTCCTACAGTCCTCAGGACTCTACTCCCTCAGCAGCGTGGT

GACCGTGCCCTCCAGCAGCTTGGGCACGAAGACCTACACCTGCAACGTAGATCACAAGCCCAGCAACACCAAGGTGGACA

AGAGAGTTGAGTCCAAATATGGTCCCCCATGCCCACCCTGCCCAGCACCTGAGTTCCTGGGGGGACCATCAGTCTTCCTG

TTCCCCCCAAAACCCAAGGACACTCTCATGATCTCCCGGACCCCTGAGGTCACGTGCGTGGTGGTGGACGTGAGCCAGGA

AGACCCCGAGGTCCAGTTCAACTGGTACGTGGATGGCGTGGAGGTGCATAATGCCAAGACAAAGCCGCGGGAGGAGCAGT

TCAACAGCACGTACCGTGTGGTCAGCGTCCTCACCGTCCTGCACCAGGACTGGCTGAACGGCAAGGAGTACAAGTGCAAG

GTCTCCAACAAAGGCCTCCCGTCCTCCATCGAGAAAACCATCTCCAAAGCCAAAGGGCAGCCCCGAGAGCCACAGGTGTA

CACCCTGCCCCCATCCCAGGAGGAGATGACCAAGAACCAGGTCAGCCTGACCTGCCTGGTCAAAGGCTTCTACCCCAGCG

ACATCGCCGTGGAGTGGGAGAGCAATGGGCAGCCGGAGAACAACTACAAGACCACGCCTCCCGTGCTGGACTCCGACGGC
TCCTTCTTCCTCTACAGCAGGCTCACCGTGGACAAGAGCAGGTGGCAGGAGGGGAATGTCTTCTCATGCTCCGTGATGCA
TGAGGCTCTGCACAACCACTACACACAGAAGTCCCTCTCCCTGTCTCTGGGTAAATGA

Heavy chain polypeptide
(SEQ ID NO: 192)
EVQLVESGGDLVQPGRSLRLSCAASGFTFDDYAMHWVRQAPGKGLEWVSVISWNSDVIAYSDSVKGRFTISRDNAKNSLY
LQMNSLRTEDTALYYCTKGHKWSFFDYWGQGTLVTVSSASTKGPSVFPLAPCSRSTSESTAALGCLVKDYFPEPVTVSWN
SGALTSGVHTFPAVLQSSGLYSLSSVVTVPSSSLGTKTYTCNVDHKPSNTKVDKRVESKYGPPCPPCPAPEFLGGPSVFL
FPPKPKDTLMISRTPEVTCVVVDVSQEDPEVQFNWYVDGVEVHNAKTKPREEQFNSTYRVVSVLTVLHQDWLNGKEYKCK
VSNKGLPSSIEKTISKAKGQPREPQVYTLPPSQEEMTKNQVSLTCLVKGFYPSDIAVEWESNGQPENNYKTTPPVLDSDG
SFFLYSRLTVDKSRWQEGNVFSCSVMHEALHNHYTQKSLSLSLGK Light chain DNA
(SEQ ID NO: 193)
GAAATTGTGTTGACACAGTCTCCAGCCACCCTGTCTTTGTCTCCAGGGGAAAGAGCCACCCTCTCCTGCAGGGCCAGTCA
GAGTATTAGCAGCTACTTAGCCTGGTACCAACAGAAACCTGGCCAGGCTCCCAGACTCCTCATCTTTAATGTAGCCAACA
GGGCCACTGACATCCCAGCCAGGTTCAGTGGCAGTGGGTCTGGGACAGACTTCACTCTCACCATCAGCAGCCTAGAGCCT
GAAGATTTTGCAGTTTATTACTGTCAGCAGCGTAGCAACTGGCCTCTCACTTTCGGCGGAGGGACCAAGGTGGAGATCAA
ACGAACTGTGGCTGCACCATCTGTCTTCATCTTCCCGCCATCTGATGAGCAGTTGAAATCTGGAACTGCCTCTGTTGTGT
GCCTGCTGAATAACTTCTATCCCAGAGAGGCCAAAGTACAGTGGAAGGTGGATAACGCCCTCCAATCGGGTAACTCCCAG
GAGAGTGTCACAGAGCAGGACAGCAAGGACAGCACCTACAGCCTCAGCAGCACCCTGACGCTGAGCAAAGCAGACTACGA
GAAACACAAAGTCTACGCCTGCGAAGTCACCCATCAGGGCCTGAGCTCGCCCGTCACAAAGAGCTTCAACAGGGGAGAGT
GT Light chain polypeptide
(SEQ ID NO: 194)
EIVLTQSPATLSLSPGERATLSCRASQSISSYLAWYQQKPGQAPRLLIFNVANRATDIPARFSGSGSGTDFTLTISSLEP
EDFAVYYCQQRSNWPLTFGGGTKVEIKRTVAAPSVFIFPPSDEQLKSGTASVVCLLNNFYPREAKVQWKVDNALQSGNSQ
ESVTEQDSKDSTYSLSSTLTLSKADYEKHKVYACEVTHQGLSSPVTKSFNRGEC H4H14709P
Heavy chain DNA
(SEQ ID NO: 195)
GAGGTGCAGCTGGTGGAGTCTGGGGGAGGCTTGGTTCAGCCTGGGGGGTCCCTGAGACTCTCCTGCGCAGCCTCTGGATT
CACCTTTAGCGACTATGCCATGAGCTGGGTCCGCCAGGCTCCGGGGAAGGGGCTGGAGTGGGTCTCAGGTATTAGTGGAA
ATGGTGGTGACACATACTACGGAGACTTCGTGAAGGGCCGGTTCACCATCTCCAGAGACAATTCCAAGAACACGCTGTAT
CTGCAAATGAACAGCCTGAGAGGCGAGGACACGGCCGCATATTTCTGTGTGATAGATCTTGACTATTGGGGTCAGGGAAC
CCTGGTCACCGTCTCCTCAGCCTCCACCAAGGGCCCATCGGTCTTCCCCCTGGCGCCCTGCTCCAGGAGCACCTCCGAGA
GCACAGCCGCCCTGGGCTGCCTGGTCAAGGACTACTTCCCCGAACCGGTGACGGTGTCGTGGAACTCAGGCGCCCTGACC
AGCGGCGTGCACACCTTCCCGGCTGTCCTACAGTCCTCAGGACTCTACTCCCTCAGCAGCGTGGTGACCGTGCCCTCCAG
CAGCTTGGGCACGAAGACCTACACCTGCAACGTAGATCACAAGCCCAGCAACACCAAGGTGGACAAGAGAGTTGAGTCCA
AATATGGTCCCCCATGCCCACCCTGCCCAGCACCTGAGTTCCTGGGGGGACCATCAGTCTTCCTGTTCCCCCCAAAACCC
AAGGACACTCTCATGATCTCCCGGACCCCTGAGGTCACGTGCGTGGTGGTGGACGTGAGCCAGGAAGACCCCGAGGTCCA
GTTCAACTGGTACGTGGATGGCGTGGAGGTGCATAATGCCAAGACAAAGCCGCGGGAGGAGCAGTTCAACAGCACGTACC
GTGTGGTCAGCGTCCTCACCGTCCTGCACCAGGACTGGCTGAACGGCAAGGAGTACAAGTGCAAGGTCTCCAACAAAGGC
CTCCCGTCCTCCATCGAGAAAACCATCTCCAAAGCCAAAGGGCAGCCCCGAGAGCCACAGGTGTACACCCTGCCCCCATC
CCAGGAGGAGATGACCAAGAACCAGGTCAGCCTGACCTGCCTGGTCAAAGGCTTCTACCCCAGCGACATCGCCGTGGAGT
GGGAGAGCAATGGGCAGCCGGAGAACAACTACAAGACCACGCCTCCCGTGCTGGACTCCGACGGCTCCTTCTTCCTCTAC -continued

AGCAGGCTCACCGTGGACAAGAGCAGGTGGCAGGAGGGGAATGTCTTCTCATGCTCCGTGATGCATGAGGCTCTGCACAA

CCACTACACACAGAAGTCCCTCTCCCTGTCTCTGGGTAAATGA

Heavy chain polypeptide
(SEQ ID NO: 196)
EVQLVESGGGLVQPGGSLRLSCAASGFTFSDYAMSWVRQAPGKGLEWVSGISGNGGDTYYGDFVKGRFTISRDNSKNTLY

LQMNSLRGEDTAAYFCVIDLDYWGQGTLVTVSSASTKGPSVFPLAPCSRSTSESTAALGCLVKDYFPEPVTVSWNSGALT

SGVHTFPAVLQSSGLYSLSSVVTVPSSSLGTKTYTCNVDHKPSNTKVDKRVESKYGPPCPPCPAPEFLGGPSVFLFPPKP

KDTLMISRTPEVTCVVVDVSQEDPEVQFNWYVDGVEVHNAKTKPREEQFNSTYRVVSVLTVLHQDWLNGKEYKCKVSNKG

LPSSIEKTISKAKGQPREPQVYTLPPSQEEMTKNQVSLTCLVKGFYPSDIAVEWESNGQPENNYKTTPPVLDSDGSFFLY

SRLTVDKSRWQEGNVFSCSVMHEALHNHYTQKSLSLSLGK

Light chain DNA
(SEQ ID NO: 197)
GACATCCAGATGACCCAGTCTCCTTCCACCCTGTCTGCATCTGAAGGAGACAGAGTCACCATCACTTGCCGGGCCAGTCA

GAGTATTAGTAGCTGGTTGGCCTGGTATCAACAGAAACCAGGAAAAGCCCCTAGGCTCCTGATCTATAAGGCGTCTATTT

TAGGAGATGGGGTCCCATCAAGGTTCAGCGGCAGTGGATCTGGGACAGAATTCACTCTCACCATCAGCAGCCTGCAGCCT

GATGATTTTGCTACTTATTACTGCCACCAGTATAATAGTTATTTGTGGACGTTCGGCCAAGGGACCAAGGTGGAAATCAA

ACGAACTGTGGCTGCACCATCTGTCTTCATCTTCCCGCCATCTGATGAGCAGTTGAAATCTGGAACTGCCTCTGTTGTGT

GCCTGCTGAATAACTTCTATCCCAGAGAGGCCAAAGTACAGTGGAAGGTGGATAACGCCCTCCAATCGGGTAACTCCCAG

GAGAGTGTCACAGAGCAGGACAGCAAGGACAGCACCTACAGCCTCAGCAGCACCCTGACGCTGAGCAAAGCAGACTACGA

GAAACACAAAGTCTACGCCTGCGAAGTCACCCATCAGGGCCTGAGCTCGCCCGTCACAAAGAGCTTCAACAGGGGAGAGT

GT

Light chain polypeptide
(SEQ ID NO: 198)
DIQMTQSPSTLSASEGDRVTITCRASQSISSWLAWYQQKPGKAPRLLIYKASILGDGVPSRFSGSGSGTEFTLTISSLQP

DDFATYYCHQYNSYLWTFGQGTKVEIKRTVAAPSVFIFPPSDEQLKSGTASVVCLLNNFYPREAKVQWKVDNALQSGNSQ

ESVTEQDSKDSTYSLSSTLTLSKADYEKHKVYACEVTHQGLSSPVTKSFNRGEC

H4H14728P
Heavy chain DNA
(SEQ ID NO: 199)
CAGGTGCAGCTGCAGGAGTCGGGCCCAGGACTGGTGAAGCCTTCACAGACCCTGTCCCTCACCTGCACTGTCTCTGGTGG

CTCCATCAGCAGTGCTGATTACTATTGGAGCTGGATCCGCCAGCACCCAGGGAAGGGCCTGGAGTGGATTGGATCCATCT

ATTATACTGGGAGTACTTACTACAACCCGTCCCTCAAGAGTCGACTTACCATATCAATAGACACGTCTGAGAACCAGTTC

TCTTTGAAACTGACCTCTCTGACTGCCGCGGACACGGCCGTGTATTACTGTGCGAGCGAGGAGGCTAACTGGGGATCCCA

CTTTGACTCCTGGGGCCAGGGAACCCTGGTCACCGTCTCCTCAGCCTCCACCAAGGGCCCATCGGTCTTCCCCCTGGCGC

CCTGCTCCAGGAGCACCTCCGAGAGCACAGCCGCCCTGGGCTGCCTGGTCAAGGACTACTTCCCCGAACCGGTGACGGTG

TCGTGGAACTCAGGCGCCCTGACCAGCGGCGTGCACACCTTCCCGGCTGTCCTACAGTCCTCAGGACTCTACTCCCTCAG

CAGCGTGGTGACCGTGCCCTCCAGCAGCTTGGGCACGAAGACCTACACCTGCAACGTAGATCACAAGCCCAGCAACACCA

AGGTGGACAAGAGAGTTGAGTCCAAATATGGTCCCCCATGCCCACCCTGCCCAGCACCTGAGTTCCTGGGGGGACCATCA

GTCTTCCTGTTCCCCCCAAAACCCAAGGACACTCTCATGATCTCCCGGACCCCTGAGGTCACGTGCGTGGTGGTGGACGT

GAGCCAGGAAGACCCCGAGGTCCAGTTCAACTGGTACGTGGATGGCGTGGAGGTGCATAATGCCAAGACAAAGCCGCGGG

AGGAGCAGTTCAACAGCACGTACCGTGTGGTCAGCGTCCTCACCGTCCTGCACCAGGACTGGCTGAACGGCAAGGAGTAC

AAGTGCAAGGTCTCCAACAAAGGCCTCCCGTCCTCCATCGAGAAAACCATCTCCAAAGCCAAAGGGCAGCCCCGAGAGCC

ACAGGTGTACACCCTGCCCCCATCCCAGGAGGAGATGACCAAGAACCAGGTCAGCCTGACCTGCCTGGTCAAAGGCTTCT

ACCCCAGCGACATCGCCGTGGAGTGGGAGAGCAATGGGCAGCCGGAGAACAACTACAAGACCACGCCTCCCGTGCTGGAC

-continued

TCCGACGGCTCCTTCTTCCTCTACAGCAGGCTCACCGTGGACAAGAGCAGGTGGCAGGAGGGGAATGTCTTCTCATGCTC
CGTGATGCATGAGGCTCTGCACAACCACTACACAGAAGTCCCTCTCCCTGTCTCTGGGTAAATGA

Heavy chain polypeptide
(SEQ ID NO: 200)
QVQLQESGPGLVKPSQTLSLTCTVSGGSISSADYYWSWIRQHPGKGLEWIGSIYYTGSTYYNPSLKSRLTISIDTSENQF
SLKLTSLTAADTAVYYCASEAANWGSHFDSWGQGTLVTVSSASTKGPSVFPLAPCSRSTSESTAALGCLVKDYFPEPVTV
WSNSGALTSGVHTFPAVLQSSGLYSLSSVVTVPSSSLGTKTYTCNVDHKPSNTKVDKRVESKYGPPCPPCPAPEFLGGPS
VFLFPPKPKDTLMISRTPEVTCVVVDVSQEDPEVQFNWYVDGVEVHNAKTKPREEQFNSTYRVVSVLTVLHQDWLNGKEY
KCKVSNKGLPSSIEKTISKAKGQPREPQVYTLPPSQEEMTKNQVSLTCLVKGFYPSDIAVEWESNGQPENNYKTTPPVLD
SDGSFFLYSRLTVDKSRWQEGNVFSCSVMHEALHNHYTQKSLSLSLGK Light chain DNA
(SEQ ID NO: 201)
GACATCCAGATGACCCAGTCTCCATCCTCCCTGTCTGCATCTGTAGGAGACAGAGTCACCATCACTTGCCGGGCAAGTCA
GAGCATTGACAACTTTTTAAATTGGTATCAGCAGAAACCAGGGAAAGCCCCTAAGCTCCTGATCTATGCTGCATCCAGTT
TGCAAAGTGGGGTCCCATCAAGGTTCAGTGGCAGTGGATCTGGGACAGATTTCACTCTCACCATCAGCAGTCTGCAACCT
GAAGATTTTGCATCTTACTACTGTCAACATAGTCACAGTGCCCATCCGATCACCTTCGGCCAAGGGACACGACTGGAGAT
TAAACGAACTGTGGCTGCACCATCTGTCTTCATCTTCCCGCCATCTGATGAGCAGTTGAAATCTGGAACTGCCTCTGTTG
TGTGCCTGCTGAATAACTTCTATCCCAGAGAGGCCAAAGTACAGTGGAAGGTGGATAACGCCCTCCAATCGGGTAACTCC
CAGGAGAGTGTCACAGAGCAGGACAGCAAGGACAGCACCTACAGCCTCAGCAGCACCCTGACGCTGAGCAAAGCAGACTA
CGAGAAACACAAAGTCTACGCCTGCGAAGTCACCCATCAGGGCCTGAGCTCGCCCGTCACAAAGAGCTTCAACAGGGGAG
AGTGT Light chain polypeptide
(SEQ ID NO: 202)
DIQMTQSPSSLSASVGDRVTITCRASQSIDNFLNWYQQKPGKAPKLLIYAASSLQSGVPSRFSGSGSGTDFTLTISSLQP
EDFACYYCQHSHSAHPITFGQGTRLEIKRTVAAPSVFIFPPSDEQLKSGTASVVCLLNNFYPREAKVQWKVDNALQSGNS
QESVTEQDSKDSTYSLSSTLTLSKADYEKHKVYACEVTHQGLSSPVTKSFNRGEC H4H14731P
Heavy chain DNA
(SEQ ID NO: 203)
CAGCTGCAGCTGCAGGAGTCGGGCCCAGGACTGGTGAAGCCTTCGGAGACCCTGTCCCTCACCTGCACTGTCTCTGGTGG
CTCCATCAGCAGTAGTAATTACTACTGGGGCTGGATCCGCCAGCCCCCAGGGAAGAGACTGGAGTGGATTGGGAGTATCT
ATTATAGTGGGAGCACCTACTACAACCCGTCCCTCAAGACTCGAGTCACCATATCCGTAGACACGTCCAAGAATCAGTTC
TCCCTGAAGCTGACCTCTGTGACCGCCGCAGACACGGCTGTGTATTACTGTGCGAGAGAGGAAGCAGCAGCTTTGACGCA
CTTTGACTTCTGGGGCCAGGGAACCCTGGTCACCGTCTCCTCAGCCTCCACCAAGGGCCCATCGGTCTTCCCCCTGGCGC
CCTGCTCCAGGAGCACCTCCGAGAGCACAGCCGCCCTGGGCTGCCTGGTCAAGGACTACTTCCCCGAACCGGTGACGGTG
TCGTGGAACTCAGGCGCCCTGACCAGCGGCGTGCACACCTTCCCGGCTGTCCTACAGTCCTCAGGACTCTACTCCCTCAG
CAGCGTGGTGACCGTGCCCTCCAGCAGCTTGGGCACGAAGACCTACACCTGCAACGTAGATCACAAGCCCAGCAACACCA
AGGTGGACAAGAGAGTTGAGTCCAAATATGGTCCCCCATGCCCACCCTGCCCAGCACCTGAGTTCCTGGGGGGACCATCA
GTCTTCCTGTTCCCCCCAAAACCCAAGGACACTCTCATGATCTCCCGGACCCCTGAGGTCACGTGCGTGGTGGTGGACGT
GAGCCAGGAAGACCCCGAGGTCCAGTTCAACTGGTACGTGGATGGCGTGGAGGTGCATAATGCCAAGACAAAGCCGCGGG
AGGAGCAGTTCAACAGCACGTACCGTGTGGTCAGCGTCCTCACCGTCCTGCACCAGGACTGGCTGAACGGCAAGGAGTAC
AAGTGCAAGGTCTCCAACAAAGGCCTCCCGTCCTCCATCGAGAAAACCATCTCCAAAGCCAAAGGGCAGCCCCGAGAGCC
ACAGGTGTACACCCTGCCCCCATCCCAGGAGGAGATGACCAAGAACCAGGTCAGCCTGACCTGCCTGGTCAAAGGCTTCT
ACCCCAGCGACATCGCCGTGGAGTGGGAGAGCAATGGGCAGCCGGAGAACAACTACAAGACCACGCCTCCCGTGCTGGAC -continued

TCCGACGGCTCCTTCTTCCTCTACAGCAGGCTCACCGTGGACAAGAGCAGGTGGCAGGAGGGGAATGTCTTCTCATGCTC

CGTGATGCATGAGGCTCTGCACAACCACTACACAGAAGTCCCTCTCCCTGTCTCTGGGTAAATGA

Heavy chain polypeptide
(SEQ ID NO: 204)
QLQLQESGPGLVKPSETLSLTCTVSGGSISSSNYYWGWIRQPPGKRLEWIGSIYYSGSTYYNPSLKTRVTISVDTSKNQF

SLKLTSVTAADTAVYYCAREEAAALTHFDFWGQGTLVTVSSASTKGPSVFPLAPCSRSTSESTAALGCLVKDYFPEPVTV

SWNSGALTSGVHTFPAVLQSSGLYSLSSVVTVPSSSLGTKTYTCNVDHKPSNTKVDKRVESKYGPPCPPCPAPEFLGGPS

VFLFPPKPKDTLMISRTPEVTCVVVDVSQEDPEVQFNWYVDGVEVHNAKTKPREEQFNSTYRVVSVLTVLHQDWLNGKEY

KCKVSNKGLPSSIEKTISKAKGQPREPQVYTLPPSQEEMTKNQVSLTCLVKGFYPSDIAVEWESNGQPENNYKTTPPVLD

SDGSFFLYSRLTVDKSRWQEGNVFSCSVMHEALHNHYTQKSLSLSLGK

Light chain DNA
(SEQ ID NO: 205)
GACATCCAGATGACCCAGTCTCCATCCTCCCTGTCTGCATCTGTAGGAGACAGAGTCACCATCACTTGCCGGGCAAGTCA

GAGCATTAGCAACTATTTAAATTGGTATCAGCAGAAACCAGGGAAAGCCCCTAAGCTCCTGATCTTTGCTGCATCCAGTT

TACAAAGTGGGGTCCCATCAAGGTTCAGTGGCAGTGGATCTGGGACAGATTTCACTCTCACCATCAGCAGTCTGCAACCT

GAAGATTTTGCAACTTACTACTGTCAACATAGTCACAGTTCCCATCCGATCACCTTCGGCCAAGGGACACGACTGGAGAT

TAAACGAACTGTGGCTGCACCATCTGTCTTCATCTTCCCGCCATCTGATGAGCAGTTGAAATCTGGAACTGCCTCTGTTG

TGTGCCTGCTGAATAACTTCTATCCCAGAGAGGCCAAAGTACAGTGGAAGGTGGATAACGCCCTCCAATCGGGTAACTCC

CAGGAGAGTGTCACAGAGCAGGACAGCAAGGACAGCACCTACAGCCTCAGCAGCACCCTGACGCTGAGCAAAGCAGACTA

CGAGAAACACAAAGTCTACGCCTGCGAAGTCACCCATCAGGGCCTGAGCTCGCCCGTCACAAAGAGCTTCAACAGGGGAG

AGTGT

Light chain polypeptide
(SEQ ID NO: 206)
DIQMTQSPSSLSASVGDRVTITCRASQSISNYLNWYQQKPGKAPKLLIFAASSLQSGVPSRFSGSGSGTDFTLTISSLQP

EDFATYYCQHSHSSHPITFGQGTRLEIKRTVAAPSVFIFPPSDEQLKSGTASVVCLLNNFYPREAKVQWKVDNALQSGNS

QESVTEQDSKDSTYSLSSTLTLSKADYEKHKVYACEVTHQGLSSPVTKSFNRGEC

H4H14732P
Heavy chain DNA
(SEQ ID NO: 207)
GAAGTGCAGCTGGTGGAGTCTGGGGGAGGCTTGGTACAGCCTGGCAGGTCCCTGAGACTCTCCTGTGCAGCCTCTGGATT

CACCTTTGATGATTATGCCATGCACTGGGTCCGGCAAGCTCCAGGGAAGGGCCTGGAGTGGGTCTCAGGTATTAATTGGG

CTGGTTATAACATAGACTATGCGGACTCTGTGAAGGGCCGATTCACCATCTCCAGAGACAACGCCAAGAACTCCCTGTAT

CTGCAAATGAACAGTCTGAGAGCTGAGGACACGGCCTTGTATTACTGTGCAAAAGATATGCGTGGATTCAGTTATGGTTT

CCCCTTTGACTACTGGGGCCAGGGAACCCTGGTCACCGTCTCCTCAGCCTCCACCAAGGGCCCATCGGTCTTCCCCCTGG

CGCCCTGCTCCAGGAGCACCTCCGAGAGCACAGCCGCCCTGGGCTGCCTGGTCAAGGACTACTTCCCCGAACCGGTGACG

GTGTCGTGGAACTCAGGCGCCCTGACCAGCGGCGTGCACACCTTCCCGGCTGTCCTACAGTCCTCAGGACTCTACTCCCT

CAGCAGCGTGGTGACCGTGCCCTCCAGCAGCTTGGGCACGAAGACCTACACCTGCAACGTAGATCACAAGCCCAGCAACA

CCAAGGTGGACAAGAGAGTTGAGTCCAAATATGGTCCCCCATGCCCACCCTGCCCAGCACCTGAGTTCCTGGGGGGACCA

TCAGTCTTCCTGTTCCCCCCAAAACCCAAGGACACTCTCATGATCTCCCGGACCCCTGAGGTCACGTGCGTGGTGGTGGA

CGTGAGCCAGGAAGACCCCGAGGTCCAGTTCAACTGGTACGTGGATGGCGTGGAGGTGCATAATGCCAAGACAAAGCCGC

GGGAGGAGCAGTTCAACAGCACGTACCGTGTGGTCAGCGTCCTCACCGTCCTGCACCAGGACTGGCTGAACGGCAAGGAG

TACAAGTGCAAGGTCTCCAACAAAGGCCTCCCGTCCTCCATCGAGAAAACCATCTCCAAAGCCAAAGGGCAGCCCCGAGA

GCCACAGGTGTACACCCTGCCCCCATCCCAGGAGGAGATGACCAAGAACCAGGTCAGCCTGACCTGCCTGGTCAAAGGCT

-continued

```
TCTACCCCAGCGACATCGCCGTGGAGTGGGAGAGCAATGGGCAGCCGGAGAACAACTACAAGACCACGCCTCCCGTGCTG

GACTCCGACGGCTCCTTCTTCCTCTACAGCAGGCTCACCGTGGACAAGAGCAGGTGGCAGGAGGGGAATGTCTTCTCATG

CTCCGTGATGCATGAGGCTCTGCACAACCACTACACACAGAAGTCCCTCTCCCTGTCTCTGGGTAAATGA
```

Heavy chain polypeptide
(SEQ ID NO: 208)
```
EVQLVESGGGLVQPGRSLRLSCAASGFTFDDYAMHWVRQAPGKGLEWVSGINWAGYNIDYADSVKGRFTISRDNAKNSLY

LQMNSLRAEDTALYYCAKDMRGFSYGFPFDYWGQGTLVTVSSASTKGPSVFPLAPCSRSTSESTAALGCLVKDYFPEPVT

VSWNSGALTSGVHTFPAVLQSSGLYSLSSVVTVPSSSLGTKTYTCNVDHKPSNTKVDKRVESKYGPPCPPCPAPEFLGGP

SVFLFPPKPKDTLMISRTPEVTCVVVDVSQEDPEVQFNWYVDGVEVHNAKTKPREEQFNSTYRVVSVLTVLHQDWLNGKE

YKCKVSNKGLPSSIEKTISKAKGQPREPQVYTLPPSQEEMTKNQVSLTCLVKGFYPSDIAVEWESNGQPENNYKTTPPVL

DSDGSFFLYSRLTVDKSRWQEGNVFSCSVMHEALHNHYTQKSLSLSLGK
```

Light chain DNA
(SEQ ID NO: 209)
```
GACATCCAGATGACCCAGTCTCCATCCTCCCTGTCTGCATCTGTAGGAGACAGAGTCACCATCACTTGCCGGGCAAGTCA

GAGCATTAGCAGCTATTTAAATTGGTATCAGCAGAAACCAGGGAAAGCCCCTAAGCTCCTGATCTATGCTGCATCCAGTT

TGCAAAGTGGGGTCCCGTCAAGGTTCAGTGGCAGTGGATCTGGGACAGATTTCACTCTCACCATCAGCAGTCTGCAACCT

GAAGATTTTGCAACTTACTACTGTCAACAGAGTTACAGTACCCCTCCGATCACCTTCGGCCAAGGGACACGACTGGAGAT

TAAAACTGTGGCTGCACCATCTGTCTTCATCTTCCCGCCATCTGATGAGCAGTTGAAATCTGGAACTGCCTCTGTTGTGT

GCCTGCTGAATAACTTCTATCCCAGAGAGGCCAAAGTACAGTGGAAGGTGGATAACGCCCTCCAATCGGGTAACTCCCAG

GAGAGTGTCACAGAGCAGGACAGCAAGGACAGCACCTACAGCCTCAGCAGCACCCTGACGCTGAGCAAAGCAGACTACGA

GAAACACAAAGTCTACGCCTGCGAAGTCACCCATCAGGGCCTGAGCTCGCCCGTCACAAAGAGCTTCAACAGGGGAGAGT

GTTAG
```

Light chain polypeptide
(SEQ ID NO: 210)
```
DIQMTQSPSSLSASVGDRVTITCRASQSISSYLNWYQQKPGKAPKLLIYAASSLQSGVPSRFSGSGSGTDFTLTISSLQP

EDFATYYCQQSYSTPPITFGQGTRLEIKTVAAPSVFIFPPSDEQLKSGTASVVCLLNNFYPREAKVQWKVDNAKQSGNSQ

ESVTEQDSKDSTYSLSSTLTLSKADYEKHKVYACEVTHQGLSSPVTKSFNRGEC
```

H4H14734P2
Heavy chain DNA
(SEQ ID NO: 211)
```
GAGGTGCAGCTGGTGGAGTCTGGGGGAGGCTTGGTAAAGCCGGGGGGGTCCCTTAGACTCTCCTGTGCAGCCTCTGGATT

TATTTTCAGTAACGCCTGGATGAACTGGGTCCGCCAGGCTCCAGGGAAGGGACTGGCGTGGGTTGGCCGTATTAAAACCG

AAACTGATGGTGGGACAACAGACTACGCTGCACCCGTAAAAGGCAGATTCACCATCTCAAGAGATGACTCAAAAAACACG

CTGTATCTGCAAATGAACAGCGTGAAAACCGAGGACACAGCCGTGTATTACTGTACAGGGGGATACAGCTATGGTGACGA

TAGCAGCAGCTGGAACGAGGGCTACTACTACTACGGTATGGACGTCTGGGGCCAAGGGACCACGGTCACCGTCTCCTCAG

CCTCCACCAAGGGCCCATCGGTCTTCCCCCTGGCGCCCTGCTCCAGGAGCACCTCCGAGAGCACAGCCGCCCTGGGCTGC

CTGGTCAAGGACTACTTCCCCGAACCGGTGACGGTGTCGTGGAACTCAGGCGCCCTGACCAGCGGCGTGCACACCTTCCC

GGCTGTCCTACAGTCCTCAGGACTCTACTCCCTCAGCAGCGTGGTGACCGTGCCCTCCAGCAGCTTGGGCACGAAGACCT

ACACCTGCAACGTAGATCACAAGCCCAGCAACACCAAGGTGGACAAGAGAGTTGAGTCCAAATATGGTCCCCCATGCCCA

CCCTGCCCAGCACCTGAGTTCCTGGGGGGACCATCAGTCTTCCTGTTCCCCCCAAAACCCAAGGACACTCTCATGATCTC

CCGGACCCCTGAGGTCACGTGCGTGGTGGTGGACGTGAGCCAGGAAGACCCCGAGGTCCAGTTCAACTGGTACGTGGATG

GCGTGGAGGTGCATAATGCCAAGACAAAGCCGCGGGAGGAGCAGTTCAACAGCACGTACCGTGTGGTCAGCGTCCTCACC

GTCCTGCACCAGGACTGGCTGAACGGCAAGGAGTACAAGTGCAAGGTCTCCAACAAAGGCCTCCCGTCCTCCATCGAGAA

AACCATCTCCAAAGCCAAAGGGCAGCCCCGAGAGCCACAGGTGTACACCCTGCCCCCATCCCAGGAGGAGATGACCAAGA

ACCAGGTCAGCCTGACCTGCCTGGTCAAAGGCTTCTACCCCAGCGACATCGCCGTGGAGTGGGAGAGCAATGGGCAGCCG
```

-continued

```
GAGAACAACTACAAGACCACGCCTCCCGTGCTGGACTCCGACGGCTCCTTCTTCCTCTACAGCAGGCTCACCGTGGACAA

GAGCAGGTGGCAGGAGGGGAATGTCTTCTCATGCTCCGTGATGCATGAGGCTCTGCACAACCACTACACACAGAAGTCCC

TCTCCCTGTCTCTGGGTAAATGA
```

Heavy chain polypeptide
(SEQ ID NO: 212)
```
EVQLVESGGGLVKPGGSLRLSCAASGFIFSNAWMNWVRQAPGKGLAWVGRIKTETDGGTTDYAAPVKGRFTISRDDSKNT

LYLQMNSVKTEDTAVYYCTGGYSYGDDSSSWNEGYYYYGMDVWGQGTTVTVSSASTKGPSVFPLAPCSRSTSESTAALGC

LVKDYFPEPVTVSWNSGALTSGVHTFPAVLQSSGLYSLSSVVTVPSSSLGTKTYTCNVDHKPSNTKVDKRVESKYGPPCP

PCPAPEFLGGPSVFLFPPKPKDTLMISRTPEVTCVVVDVSQEDPEVQFNWYVDGVEVHNAKTKPREEQFNSTYRVVSVLT

VLHQDWLNGKEYKCKVSNKGLPSSIEKTISKAKGQPREPQVYTLPPSQEEMTKNQVSLTCLVKGFYPSDIAVEWESNGQP

ENNYKTTPPVLDSDGSFFLYSRLTVDKSRWQEGNVFSCSVMHEALHNHYTQKSLSLSLGK
```

Light chain DNA
(SEQ ID NO: 213)
```
GACATCCAGATGACCCAGTCTCCATCCTCCCTGTCTGCATCTGTAGGAGACAGAGTCACCATCACTTGCCGGGCAAGTCA

GAGCATTAGCAGCTATTTAAATTGGTATCAGCAGAAACCAGGGAAAGCCCCTAAGCTCCTGATCTATGCTGCATCCAGTT

TGCAAAGTGGGGTCCCGTCAAGGTTCAGTGGCAGTGGATCTGGGACAGATTTCACTCTCACCATCAGCAGTCTGCAACCT

GAAGATTTTGCAACTTACTACTGTCAACAGAGTTACAGTACCCCTCCGATCACCTTCGGCCAAGGGACACGACTGGAGAT

TAAAACTGTGGCTGCACCATCTGTCTTCATCTTCCCGCCATCTGATGAGCAGTTGAAATCTGGAACTGCCTCTGTTGTGT

GCCTGCTGAATAACTTCTATCCCAGAGAGGCCAAAGTACAGTGGAAGGTGGATAACGCCCTCCAATCGGGTAACTCCCAG

GAGAGTGTCACAGAGCAGGACAGCAAGGACAGCACCTACAGCCTCAGCAGCACCCTGACGCTGAGCAAAGCAGACTACGA

GAAACACAAAGTCTACGCCTGCGAAGTCACCCATCAGGGCCTGAGCTCGCCCGTCACAAAGAGCTTCAACAGGGGAGAGT

GTTAG
```

Light chain polypeptide
(SEQ ID NO: 214)
```
DIQMTQSPSSLSASVGDRVTITCRASQSISSYLNWYQQKPGKAPKLLIYAASSLQSGVPSRFSGSGSGTDFTLTISSLQP

EDFATYYCQQSYSTPPITFGQGTRLEIKTVAAPSVFIFPPSDEQLKSGTASVVCLLNNFYPREAKVQWKVDNALQSGNSQ

ESVTEQDSKDSTYSLSSTLTLSKADYEKHKVYACEVTHQGLSSPVTKSFNRGEC
```

H4H14757P
Heavy chain DNA
(SEQ ID NO: 215)
```
GAAGTGCAGCTGGTGGAGTCTGGGGGAGGCTTGGTACAGCCTGGCAGGTCCCTGAGACTCTCCTGTACAGCCTCTGGATT

CACCTTTGATGATTATGCCATGCACTGGGTCCGGCAAGCTCCAGGGAAGGGCCTGGAGTGGGTCTCAGGTATTCGTTGGA

ATGGTGGTAGTATAGGCTATGTGGACTCTGTGAAGGGCCGATTCACCATCTCCAGAGACAACGCCAAGAAGTCCCTGCAT

CTGCAAATGAACAGTCTAAAAACTGAGGACACGGCCTTGTATTACTGTGCAAAGATATAGGCGATATTTTGACTGGTTT

TTATGGAGAATACGGAATGGACGTCTGGGGCCAAGGGACCACGGTCACCGTCTCCTCAGCCTCCACCAAGGGCCCATCGG

TCTTCCCCCTGGCGCCCTGCTCCAGGAGCACCTCCGAGAGCACAGCCGCCCTGGGCTGCCTGGTCAAGGACTACTTCCCC

GAACCGGTGACGGTGTCGTGGAACTCAGGCGCCCTGACCAGCGGCGTGCACACCTTCCCGGCTGTCCTACAGTCCTCAGG

ACTCTACTCCCTCAGCAGCGTGGTGACCGTGCCCTCCAGCAGCTTGGGCACGAAGACCTACACCTGCAACGTAGATCACA

AGCCCAGCAACACCAAGGTGGACAAGAGAGTTGAGTCCAAATATGGTCCCCCATGCCCACCCTGCCCAGCACCTGAGTTC

CTGGGGGGACCATCAGTCTTCCTGTTCCCCCCAAAACCCAAGGACACTCTCATGATCTCCCGGACCCCTGAGGTCACGTG

CGTGGTGGTGGACGTGAGCCAGGAAGACCCCGAGGTCCAGTTCAACTGGTACGTGGATGGCGTGGAGGTGCATAATGCCA

AGACAAAGCCGCGGGAGGAGCAGTTCAACAGCACGTACCGTGTGGTCAGCGTCCTCACCGTCCTGCACCAGGACTGGCTG

AACGGCAAGGAGTACAAGTGCAAGGTCTCCAACAAAGGCCTCCCGTCCTCCATCGAGAAAACCATCTCCAAAGCCAAAGG

GCAGCCCCGAGAGCCACAGGTGTACACCCTGCCCCCATCCCAGGAGGAGATGACCAAGAACCAGGTCAGCCTGACCTGCC

TGGTCAAAGGCTTCTACCCCAGCGACATCGCCGTGGAGTGGGAGAGCAATGGGCAGCCGGAGAACAACTACAAGACCACG
```

-continued

CCTCCCGTGCTGGACTCCGACGGCTCCTTCTTCCTCTACAGCAGGCTCACCGTGGACAAGAGCAGGTGGCAGGAGGGGAA

TGTCTTCTCATGCTCCGTGATGCATGAGGCTCTGCACAACCACTACACACAGAAGTCCCTCTCCCTGTCTCTGGGTAAAT

GA

Heavy chain polypeptide
(SEQ ID NO: 216)
EVQLVESGGGLVQPGRSLRLSCTASGFTFDDYAMHWVRQAPGKGLEWVSGIRWNGGSIGYVDSVKGRFTISRDNAKKSLH

LQMNSLKTEDTALYYCAKDIGDILTGFYGEYGMDVWGQGTTVTVSSASTKGPSVFPLAPCSRSTSESTAALGCLVKDYFP

EPVTVSWNSGALTSGVHTFPAVLQSSGLYSLSSVVTVPSSSLGTKTYTCNVDHKPSNTKVDKRVESKYGPPCPPCPAPEF

LGGPSVFLFPPKPKDTLMISRTPEVTCVVVDVSQEDPEVQFNWYVDGVEVHNAKTKPREEQFNSTYRVVSVLTVLHQDWL

NGKEYKCKVSNKGLPSSIEKTISKAKGQPREPQVYTLPPSQEEMTKNQVSLTCLVKGFYPSDIAVEWESNGQPENNYKTT

PPVLDSDGSFFLYSRLTVDKSRWQEGNVFSCSVMHEALHNHYTQKSLSLSLGK

Light chain DNA
(SEQ ID NO: 217)
GACATCCAGATGACCCAGTCTCCATCCTCCCTGTCTGCATCTGAAGGAGACAGAGTCACCATCACTTGCCGGGCAAGTCA

GAGCATTAGCAGCTATTTAAATTGGTATCAGCAGAAAGCAGGGAAAGCCCCTAACCTCCTGATCTATGCTGCATCCAGTT

TGCAAAGTGGGGTCCCATCAAGGTTCAGTGGCAGTGGATCTGGGACAGAGTACACTCTCACCATCAGCAGTCTGCAACCT

GAAGATTTTGCAACTTACTACTGTCAACAGAGTTACATTATCCCGTACACTTTTGGCCAGGGGACCAAGCTGGAGATCAA

ACGAACTGTGGCTGCACCATCTGTCTTCATCTTCCCGCCATCTGATGAGCAGTTGAAATCTGGAACTGCCTCTGTTGTGT

GCCTGCTGAATAACTTCTATCCCAGAGAGGCCAAAGTACAGTGGAAGGTGGATAACGCCCTCCAATCGGGTAACTCCCAG

GAGAGTGTCACAGAGCAGGACAGCAAGGACAGCACCTACAGCCTCAGCAGCACCCTGACGCTGAGCAAAGCAGACTACGA

GAAACACAAAGTCTACGCCTGCGAAGTCACCCATCAGGGCCTGAGCTCGCCCGTCACAAAGAGCTTCAACAGGGGAGAGT

GT

Light chain polypeptide
(SEQ ID NO: 218)
DIQMTQSPSSLSASEGDRVTITCRASQSISSYLNWYQQKAGKAPNLLIYAASSLQSGVPSRFSGSGSGTEYTLTISSLQP

EDFATYYCQQSYIIPYTFGQGTKLEIKRTVAAPSVFIFPPSDEQLKSGTASVVCLLNNFYPREAKVQWKVDNALQSGNSQ

ESVTEQDSKDSTYSLSSTLTLSKADYEKHKVYAVEVTHQGLSSPVTKSFNRGEC

H4H14758P
Heavy chain DNA
(SEQ ID NO: 219)
GAAGTGCAGCTGGTGGAGTCTGGGGGAGGGTTGGTACAGCCTGGCAGGTCCCTGAGACTCTCCTGTGCAGCCTCTGGATT

CACCTTTGATGATTATGCCATGCACTGGGTCCGGCAAGCTCCAGGGAAGGGCCTGGAGTGGGTCTCAAGTGTTAGGTGGA

ATGGTGGTATTATAGGCTATGCGGACTCTGTGAAGGGCCGATTCACCATCTCCAGAGACAACGCCAAGAACTCCCTGTAT

CTGCAAATGAACAGTCTGAGACCTGAGGACACGGCCCTCTATTACTGTGCAAAAGATATAGGCGATGTTTTGACTGGTTA

TTATGGAGAATACGGTATGGACGTCTGGGGCCAAGGGACCACGGTCACCGTCTCCTCAGCCTCCACCAAGGGCCCATCGG

TCTTCCCCCTGGCGCCCTGCTCCAGGAGCACCTCCGAGAGCACAGCCGCCCTGGGCTGCCTGGTCAAGGACTACTTCCCC

GAACCGGTGACGGTGTCGTGGAACTCAGGCGCCCTGACCAGCGGCGTGCACACCTTCCCGGCTGTCCTACAGTCCTCAGG

ACTCTACTCCCTCAGCAGCGTGGTGACCGTGCCCTCCAGCAGCTTGGGCACGAAGACCTACACCTGCAACGTAGATCACA

AGCCCAGCAACACCAAGGTGGACAAGAGAGTTGAGTCCAAATATGGTCCCCCATGCCCACCCTGCCCAGCACCTGAGTTC

CTGGGGGGACCATCAGTCTTCCTGTTCCCCCCAAAACCCAAGGACACTCTCATGATCTCCCGGACCCCTGAGGTCACGTG

CGTGGTGGTGGACGTGAGCCAGGAAGACCCCGAGGTCCAGTTCAACTGGTACGTGGATGGCGTGGAGGTGCATAATGCCA

AGACAAAGCCGCGGGAGGAGCAGTTCAACAGCACGTACCGTGTGGTCAGCGTCCTCACCGTCCTGCACCAGGACTGGCTG

AACGGCAAGGAGTACAAGTGCAAGGTCTCCAACAAAGGCCTCCCGTCCTCCATCGAGAAAACCATCTCCAAAGCCAAAGG

GCAGCCCCGAGAGCCACAGGTGTACACCCTGCCCCCATCCCAGGAGGAGATGACCAAGAACCAGGTCAGCCTGACCTGCC

TGGTCAAAGGCTTCTACCCCAGCGACATCGCCGTGGAGTGGGAGAGCAATGGGCAGCCGGAGAACAACTACAAGACCACG

-continued

CCTCCCGTGCTGGACTCCGACGGCTCCTTCTTCCTCTACAGCAGGCTCACCGTGGACAAGAGCAGGTGGCAGGAGGGGAA

TGTCTTCTCATGCTCCGTGATGCATGAGGCTCTGCACAACCACTACACAGAAGTCCCTCTCCCTGTCTCTGGGTAAAT

GA

Heavy chain polypeptide
(SEQ ID NO: 220)
EVQLVESGGGLVQPGRSLRLSCAASGFTFDDYAMHWVRQAPGKGLEWVSSVRWNGGIIGYADSVKGRFTISRDNAKNSLY

LQMNSLRPEDTALYYCAKDIGDVLTGYYGEYGMDVWGQGTTVTVSSASTKGPSVFPLAPCSRSTSESTAALGCLVKDYFP

EPVTVSWNSGALTSGVHTFPAVLQSSGLYSLSSVVTVPSSSLGTKTYTCNVDHKPSNTKVDKRVESGYGPPCPPCPAPEF

LGGPSVFLFPPKPKDTLMISRTPEVTCVVVDVSQEDPEVQFNWYVDGVEVHNAKTKPREEQFNSTYRVVSVLTVLHQDWL

NGKEYKCKVSNKGLPSSIEKTISKAKGQPREPQVYTLPPSQEEMTKNQVSLTCLVKGFYPSDIAVEWESNGQPENNYKTT

PPVLDSDGSFFLYSRLTVDKSRWQEGNVFSCSVMHEALHNHYTQKSLSLSLGK

Light chain DNA
(SEQ ID NO: 221)
GACATCCAGATGACCCAGTCTCCATCCTCCCTGTCTGCATCTGTGGGAGACAGAGTCACCATCGCTTGCCGGGCAAGTCA

GAGCATTACCACCTATTTAAATTGGTATCAGCAGAAACCAGGGAAAGCCCCTAAACTCCTGATCTATGCTGCATCCAGTT

TGCAAAGTGGGGTCCCATCAAGGTTCAGTGGCAGTGGATCTGGGACAGATTTCACTCTCACCATCAGTAGTCTGCAACCT

GAAGATTTTGCAACTTACTACTGTCAACAGAGTTACATTTCCCCGTACACTTTTGGCCAGGGGACCAAGCTGGAGATCAA

ACGAACTGTGGCTGCACCATCTGTCTTCATCTTCCCGCCATCTGATGAGCAGTTGAAATCTGGAACTGCCTCTGTTGTGT

GCCTGCTGAATAACTTCTATCCCAGAGAGGCCAAAGTACAGTGGAAGGTGGATAACGCCCTCCAATCGGGTAACTCCCAG

GAGAGTGTCACAGAGCAGGACAGCAAGGACAGCACCTACAGCCTCAGCAGCACCCTGACGCTGAGCAAAGCAGACTACGA

GAAACACAAAGTCTACGCCTGCGAAGTCACCCATCAGGGCCTGAGCTCGCCCGTCACAAAGAGCTTCAACAGGGGAGAGT

GT

Light chain polypeptide
(SEQ ID NO: 222)
DIQMTQSPSSLSASVGDRVTIACRASQSITTYLNWYQQKPGKAPKLLIYAASSLQSGVPSRFSGSGSGTDFTLTISSLQP

EDFATYYCQQSYISPYTFGQGTKLEIKRTVAAPSVFIFPPSDEQLKSGTASVVCLLNNFYPREAKVQWKVDNALQSGNSQ

ESVTEQDSKDSTYSLSSTLTLSKADYEKHKVYACEVTHQGLSSPVTKSFNRVEC

H4H14760P2
Heavy chain DNA
(SEQ ID NO: 223)
CAGGTGCAGCTGGTGGAGTCTGGGGGAGGCGTGGTCCAGCCTGGGAAGTCCCTGAGACTCTCCTGTGCAGCCTCTGGATT

CACCTTCAGTAATTATGGCATACACTGGGTCCGCCAGGCTCCAGGCAAGGGGCTGGAGTGGGTGGCGATTATATTATATG

ATGGAAGTAATCAACACTATGCAGATTCCGTGAAGGGCCGATTCACCATTTCCAGAGACAATTCCAAAAACACGCTGTAT

CTTCAAATGAACAACCTGAGAGCTGAGGACACGGCCGTTTATTACTGTGCGAGAGATCTTGATCTTTGGAGTGGTTATTA

TACAAACGGGGACGGTATGGACGTCTGGGGCCAAGGGACCACGGTCACCGTCTCCTCAGCCTCCACCAAGGGCCCATCGG

TCTTCCCCCTGGCGCCCTGCTCCAGGAGCACCTCCGAGAGCACAGCCGCCCTGGGCTGCCTGGTCAAGGACTACTTCCCC

GAACCGGTGACGGTGTCGTGGAACTCAGGCGCCCTGACCAGCGGCGTGCACACCTTCCCGGCTGTCCTACAGTCCTCAGG

ACTCTACTCCCTCAGCAGCGTGGTGACCGTGCCCTCCAGCAGCTTGGGCACGAAGACCTACACCTGCAACGTAGATCACA

AGCCCAGCAACACCAAGGTGGACAAGAGAGTTGAGTCCAAATATGGTCCCCCATGCCCACCCTGCCCAGCACCTGAGTTC

CTGGGGGGACCATCAGTCTTCCTGTTCCCCCCAAAACCCAAGGACACTCTCATGATCTCCCGGACCCCTGAGGTCACGTG

CGTGGTGGTGGACGTGAGCCAGGAAGACCCCGAGGTCCAGTTCAACTGGTACGTGGATGGCGTGGAGGTGCATAATGCCA

AGACAAAGCCGCGGGAGGAGCAGTTCAACAGCACGTACCGTGTGGTCAGCGTCCTCACCGTCCTGCACCAGGACTGGCTG

AACGGCAAGGAGTACAAGTGCAAGGTCTCCAACAAAGGCCTCCCGTCCTCCATCGAGAAAACCATCTCCAAAGCCAAAGG

GCAGCCCCGAGAGCCACAGGTGTACACCCTGCCCCCATCCCAGGAGGAGATGACCAAGAACCAGGTCAGCCTGACCTGCC

TGGTCAAAGGCTTCTACCCCAGCGACATCGCCGTGGAGTGGGAGAGCAATGGGCAGCCGGAGAACAACTACAAGACCACG

```
CCTCCCGTGCTGGACTCCGACGGCTCCTTCTTCCTCTACAGCAGGCTCACCGTGGACAAGAGCAGGTGGCAGGAGGGGAA

TGTCTTCTCATGCTCCGTGATGCATGAGGCTCTGCACAACCACTACACACAGAAGTCCCTCTCCCTGTCTCTGGGTAAAT
GA
```

Heavy chain polypeptide
(SEQ ID NO: 224)
```
QVQLVESGGGVVQPGKSLRLSCAASGFTFSNYGIWHVRQAPGKGLEWVAIILYDSSNQHYADSVKGRFTISRDNSKNTLY

LQMNNLRAEDTAVYYCARDLDLWSGYYTNGDGMDVWGQGTTVTVSSASTKGPSVFPLAPCSRSTSESTAALGCLVKDYFP

EPVTVSWNSGALTSGVHTFPAVLQSSGLYSLSSVVTVPSSSLGTKTYTCNVDHKPSNTKVDKRVESKYGPPCPPCPAPEF

LGGPSVFLFPPKPKDTLMISRTPEVTCVVVDVSQEDPEVQFNWYVDGVEVHNAKTKPREEQFNSTYRVVSVLTVLHQDWL

NGKEYKCKVSNKGLPSSIEKTISKAKGQPREPQVYTLPPSQEEMTKNQVSLTCLDKGFYPSDIAVEWESNGQPENNYKTT

PPVLDSDGSFFLYSRLTVDKSRWQEGNVFSCSVMHEALHNHYTQKSLSLSLGK
```

Light chain DNA
(SEQ ID NO: 225)
```
GACATCCAGATGACCCAGTCTCCATCCTCCCTGTCTGCATCTGTAGGAGACAGAGTCACCATCACTTGCCGGGCAAGTCA

GAGCATTAGCAGCTATTTAAATTGGTATCAGCAGAAACCAGGGAAAGCCCCTAAGCTCCTGATCTATGCTGCATCCAGTT

TGCAAAGTGGGGTCCCGTCAAGGTTCAGTGGCAGTGGATCTGGGACAGATTTCACTCTCACCATCAGCAGTCTGCAACCT

GAAGATTTTGCAACTTACTACTGTCAACAGAGTTACAGTACCCCTCCGATCACCTTCGGCCAAGGGACACGACTGGAGAT

TAAAACTGTGGCTGCACCATCTGTCTTCATCTTCCCGCCATCTGATGAGCAGTTGAAATCTGGAACTGCCTCTGTTGTGT

GCCTGCTGAATAACTTCTATCCCAGAGAGGCCAAAGTACAGTGGAAGGTGGATAACGCCCTCCAATCGGGTAACTCCCAG

GAGAGTGTCACAGAGCAGGACAGCAAGGACAGCACCTACAGCCTCAGCAGCACCCTGACGCTGAGCAAAGCAGACTACGA

GAAACACAAAGTCTACGCCTGCGAAGTCACCCATCAGGGCCTGAGCTCGCCCGTCACAAAGAGCTTCAACAGGGGAGAGT

GTTAG
```

Light chain polypeptide
(SEQ ID NO: 226)
```
DIQMTQSPSSLSASVGDRVTITCRASQSISSYLNWYQQKPGKAPKLLIYAASSLQSGVPSRFSGSGSGTDFTLTISSLQP

EDFATYYCQQYSYTPPITFGQGTRLEIKTVAAPSVFIFPPSDEQLKSGTASVVCLLNNFYPREAKVQWKVDNALQSGNSQ

ESVTEQDSKDSTYSLSSTLTLSKADYEKHKVYACEVTHQGLSSPVTKSFNRGEC
```

Example 2: Bioassay with HEK293/D9(NFκB-Luciferase)/hIL-36R HEK293/NFκB-Luciferase/mfIL-36R Cells IL-36 receptor (IL-36R) is a single-pass membrane receptor for a subset of members of the IL-1 family of cytokines, IL-36α, IL-36s, and IL-36γ, and upon binding to these ligands, there is recruitment of its co-receptor, the IL-1R accessory protein (IL-1RAcP), which induces a signaling cascade that involves NFκB and mitogen-activated kinase pathways (Sims et al, 2010). A bioassay was developed to detect the transcriptional activation by NFκB via IL-36R activation using reporter cell lines that stably express either full-length human IL-36R (hIL-36R: amino acids 1 through 575 of accession number NP_003845.2) or Macaca fascicularis IL-36R (MfIL-36R) along with a luciferase reporter [NFκB response element (5x)-luciferase-IRES-GFP] in HEK293 cells. IL-1RAcP is endogenously expressed in the HEK293 cell line. The resulting stable cell lines, referred to as HEK293/NFκB-luc/hIL-36R and HEK293/NFκB-luc/MfIL-36R, was isolated and maintained in DMEM containing 10% FBS, NEAA, penicillin/streptomycin/glutamine, and 500 µg/mL G418.

For the bioassay, cells were seeded into 96-well assay plates at 10,000 cells/well in OPTIMEM supplemented with 0.1% FBS and then incubated at 37° C. in 5% $CO_2$ overnight. The next day, to determine the dose response of ligands, human IL-36α (hIL-36α; R&D Systems, #6995/IL), human IL-36β (hIL-36β; R&D Systems, #6334-IL), or human IL-36γ (hIL-36γ; R&D Systems, #6835-IL) were serially diluted at 1:3 (from 10 nM to 0.0002 nM) and added to cells. A control containing dilution buffer but no IL-36 ligand was also added to one sample of cells. To measure inhibition, antibodies were serially diluted at 1:3 (from 100 nM to 0.002 nM) plus a control sample containing no antibody and pre-incubated with the cells followed by addition of constant concentrations of hIL-36α, hIL-36β, or hIL-36γ. For testing with HEK293/NFκB-luc/hIL-36R cells, 20 pM of hIL-36α, 15 pM of hIL-36β, or 10 pM of hIL-36γ was used as a constant concentration and for testing with HEK293/NFκB-luc/mfIL-36R cells, 500 pM of hIL-36α, 600 pM of hIL-36β, or 300 pM of hIL-36γ was used as a constant concentration. After 5.5 hours of incubation at 37° C. in 5% $CO_2$, OneGlo reagent (Promega, #E6051) was added to the samples and luciferase activity was then measured using a Victor X (Perkin Elmer) plate reader.

The results were analyzed using nonlinear regression (4-parameter logistics) with Prism 6 software (GraphPad) to obtain $EC_{50}$ and $IC_{50}$ values. To determine the maximum inhibition, the range between the maximum and minimum RLU values for each antibody was calculated as a percentage of the RLU range between no IL-36 ligand and the constant amount of IL-36 ligand used per assay.

As shown in Table 2-1, 9 out of 12 anti-IL-36R antibodies of the invention tested completely blocked the stimulation of HEK293/NFκB-luc/hIL-36R cells by 20 pM hIL-36α with $IC_{50}$ values ranging from 100 pM to 970 pM. One of the IL-36R antibodies tested demonstrated partial blockade of hIL-36α stimulation of HEK293/NFκB-luc/hIL-36R cells with a maximum percent blockade of 22%. One of the IL-36R antibodies tested demonstrated weak blockade of hIL-36α stimulation of HEK293/NFκB-luc/hIL-36R cells with a maximum percent blockade of 61%, while another of the anti-IL-36R antibodies tested did not demonstrated any inhibition of hIL-36α stimulation. Six out of 12 anti-IL-36R antibodies of the invention tested completely blocked the stimulation of HEK293/NFκB-luc/hIL-36R cells by 15 pM hIL-36@ with $IC_{50}$ values ranging from 120 pM to 1.3 nM. One of the IL-36R antibodies tested demonstrated weak blockade of hIL-36β stimulation of HEK293/NFκB-luc/hIL-36R cells with a maximum percent blockade of 69% and 5 anti-IL-36R antibodies tested did not demonstrate measurable inhibition of hIL-36β stimulation. Six out of 12 anti-IL-36R antibodies of the invention tested completely blocked the stimulation of HEK293/NFκB-luc/hIL-36R cells by 10 pM hIL-36γ with $IC_{50}$ values ranging from 120 pM to 1.2 nM. Four anti-IL-36R antibodies of the invention tested demonstrated partial blockade of hIL-36γ stimulation with maximum percent blockade ranging from 24 to 87%. One anti-IL-36R antibody of the invention tested showed weak blockade of hIL-36γ stimulation with maximum percent blockade of 69%, and one anti-IL36R antibody of the invention did not demonstrate inhibition of hIL-36γ stimulation. The isotype control antibody tested did not demonstrate inhibition of IL-36 ligand stimulation of the HEK293/NFκB-luc/hIL-36R cells. As shown in Table 2-1, hIL-36α, hIL-36β, and hIL-36γ activated HEK293/NFκB-luc/hIL-36R cells with $EC_{50}$ values of 12 pM, 14 pM, and 8.4 pM respectively.

As shown in Table 2-2, six out of 12 anti-IL-36R antibodies of the invention tested completely or nearly completely blocked the stimulation of HEK293/NFκB-luc/MfIL-36R cells by 500 pM hIL-36α with $IC_{50}$ values ranging from 60 pM to 3.1 nM. Two anti-IL-36R antibodies of the invention tested demonstrated weak blockade of hIL-36α stimulation of HEK293/NFκB-luc/MfIL-36R cells with maximum percent blockade of 29 and 47%, while 4 anti-IL-36R antibodies did not show inhibition of hIL-36α stimulation of this cell line. Six out of 12 anti-IL-36R antibodies of the invention tested completely or nearly completely blocked the stimulation of HEK293/NFκB-luc/MfIL-36R cells by 600 pM hIL-36β with $IC_{50}$ values ranging from 120 pM to 7.1 nM. Three anti-IL-36R antibodies of the invention tested demonstrated weak blockade of hIL-36β stimulation of HEK293/NFκB-luc/MfIL-36R cells with maximum percent blockade ranging from 36 to 48%, while three anti-IL-36R antibodies of the invention did not show inhibition of hIL-36β stimulation of this cell line. Six out of anti-IL-36R antibodies of the invention tested completely or nearly completely blocked the stimulation of HEK293/NFκB-luc/MfIL-36R cells by 300 pM hIL-36γ with $IC_{50}$ values ranging from 85 pM to 5.4 nM. Three anti-IL-36R antibodies of the invention tested showed weak blockade of hIL-36γ stimulation of HEK293/NFκB-luc/MfIL-36R cells with maximum percent blockade ranging from 25 to 43%, while three anti-IL-36R antibodies of the invention did not show inhibition of hIL-36γ stimulation of this cell line. The isotype control antibody tested did not demonstrate inhibition of IL-36 ligand stimulation of the HEK293/NFκB-luc/MfIL-36R cells. As shown in Table 2-1, hIL-36α, hIL-36β, and hIL-36γ activated HEK293/NFκB-luc/MfIL-36R cells with $EC_{50}$ values of 170 pM, 270 pM, and 62 pM respectively.

TABLE 2-1

Anti-IL-36R antibody inhibition of stimulation of HEK293/NFκB-luc/hIL-36R cells by hIL-36 ligands.

| | Ligand | | | | |
|---|---|---|---|---|---|
| | hIL-36α | | hIL-36β | | hIL-36γ |
| | | | $EC_{50}$ | | |
| | 1.2E−11M | | 1.4E−11M | | 8.4E−12M |
| | | | Constant | | |
| | 20pM | | 15pM | | 10pM |
| Antibodies | $IC_{50}$ [M] | Max Inhibition (%) | $IC_{50}$ [M] | Max Inhibition (%) | $IC_{50}$ [M] | Max Inhibition (%) |
| H4H14699P2 | 1.3E−10 | 100 | 1.3E−10 | 100 | 1.4E−10 | 99 |
| H4H14700P2 | 1.9E−10 | 101 | 2.0E−10 | 100 | 12E−10 | 100 |
| H4H14706P2 | 1.0E−10 | 101 | 1.2E−10 | 101 | 1.2E−10 | 99 |
| H4H14708P2 | 1.3E−10 | 101 | 2.0E−10 | 100 | 1.6E−10 | 99 |
| H4H14709P | 1.4E−10 (partial) | 22 | No inhibition | No inhibition | 1.3E−10 (partial) | 24 |
| H4H14728P | 9.7E−10 | 97 | 1.3E−09 | 99 | 1.2E−09 | 99 |
| H4H14731P | 7.8E−10 | 99 | 9.4E−10 | 99 | 7.3E−10 | 99 |
| H4H14732P2 | >1.0E−08 | 61 | >1.0E−08 | 69 | >1.0E−08 | 69 |
| H4H14734P2 | No inhibition | No inhibition | No inhibition | No inhibition | No inhibition | No inhibition |
| H4H14757P | 1.8E−10 | 101 | No inhibition | No inhibition | 1.3E−10 (partial) | 87 |

TABLE 2-1-continued

Anti-IL-36R antibody inhibition of stimulation of HEK293/
NFκB-luc/hIL-36R cells by hIL-36 ligands.

| | Ligand | | | | | |
|---|---|---|---|---|---|---|
| | hIL-36α | | hIL-36β | | hIL-36γ | |
| | | | $EC_{50}$ | | | |
| | 1.2E−11M | | 1.4E−11M | | 8.4E−12M | |
| | | | Constant | | | |
| | 20pM | | 15pM | | 10pM | |
| Antibodies | $IC_{50}$ [M] | Max Inhibition (%) | $IC_{50}$ [M] | Max Inhibition (%) | $IC_{50}$ [M] | Max Inhibition (%) |
| H4H14758P | 1.2E−10 | 100 | No inhibition | No inhibition | 1.6E−10 (partial) | 57 |
| H4H14760P2 | 4.9E−10 | 99 | No inhibition | No inhibition | 7.0E−10 (partial) | 49 |
| Isotype control antibody | No inhibition | No inhibition | No inhibition | No inhibition | No inhibition | No inhibition |

TABLE 2-2

Anti-IL-36R antibody inhibition of stimulation of HEK293/
NFκB-luc/MfIL-36R cells by hIL-36 ligands.

| | Ligand | | | | | |
|---|---|---|---|---|---|---|
| | hIL-36α | | hIL-36β | | hIL-36γ | |
| | | | $EC_{50}$ | | | |
| | 1.7E−10M | | 2.7E−10M | | 6.2E−11M | |
| | | | Constant | | | |
| | 500pM | | 600pM | | 300pM | |
| Antibodies | $IC_{50}$ [M] | Max Inhibition (%) | $IC_{50}$ [M] | Max Inhibition (%) | $IC_{50}$ [M] | Max Inhibition (%) |
| H4H14699P2 | 8.4E−11 | 97 | 1.9E−10 | 98 | 2.0E−10 | 97 |
| H4H14700P2 | 1.2E−10 | 99 | 1.8E−10 | 99 | 1.8E−10 | 99 |
| H4H14706P2 | 6.0E−11 | 100 | 1.2E−10 | 100 | 8.5E−11 | 100 |
| H4H14708P2 | 8.9E−11 | 99 | 1.2E−10 | 100 | 1.2E−10 | 100 |
| H4H14709P | No inhibition | No inhibition | No inhibition | No inhibition | No inhibition | No inhibition |
| H4H14728P | 1.3E−09 | 93 | 1.5E−09 | 95 | 2.0E−09 | 93 |
| H4H14731P | 3.1E−09 | 84 | 7.1E−09 | 78 | 5.4E−09 | 75 |
| H4H14732P2 | >1.0E−07 | 47 | >1.0E−07 | 43 | >1.0E−07 | 36 |
| H4H14734P2 | No inhibition | No inhibition | No inhibition | No inhibition | No inhibition | No inhibition |
| H4H14757P | >1.0E−07 | 29 | >1.0E−07 | 36 | >1.0E−07 | 25 |
| H4H14758P | No inhibition | No inhibition | No inhibition | No inhibition | No inhibition | No inhibition |
| H4H14760P2 | No inhibition | No inhibition | >1.0E−07 | 48 | >1.0E−07 | 43 |
| Isotype control antibody | No inhibition | No inhibition | No inhibition | No inhibition | No inhibition | No inhibition |

Example 3: IL-36R Octet Cross-Competition

Binding competition between a panel of different anti-IL-36R antibodies was determined using a real time, label-free bio-layer interferometry assay on an Octet® HTX biosensor (ForteBio, A Division of Pall Life Sciences). The entire experiment was performed at 25° C. in 0.01 M HEPES pH 7.4, 0.15 M NaCl, 3 mM EDTA, 0.05% v/v Surfactant Tween-20, 0.002% $NaN_3$ and 1 mg/mL BSA (HBS-ET kinetics buffer) with the plate shaking at the speed of 1000 rpm. To assess whether two antibodies are able to compete with one another for binding to their respective epitopes on the recombinant human IL-36R extracellular domain expressed with a C-terminal myc-myc-hexahistidine tag (hIL-36R-MMH: mROR1 signal sequence (M1-A29)-human IL36R(D20-Y337)-mycmycHis$_6$), around 0.3 nM of hIL-36R-MMH was first captured onto anti-His antibody coated Octet biosensors (Fortebio Inc, #18-5079) by submerging the biosensors for 3 minutes into wells containing 30 μg/mL of hIL-36R-MMH.

The antigen-captured biosensors were then saturated with a first anti-IL-36R antibody (subsequently referred to as mAb-1) by submerging into wells containing 50 μg/mL solution of mAb-1 for 4 minutes. The biosensors were then subsequently submerged into wells containing a 50 μg/mL solution of a second anti-IL-36R antibody (subsequently referred to as mAb-2) for 3 minutes. The biosensors were washed in HBS-ET kinetics buffer in between every step of the experiment. The real-time binding response was monitored during the entire course of the experiment and the maximum binding response for all the steps was recorded. The response of mAb-2 binding to hIL-36R-MMH pre-complexed with mAb-1 was compared and competitive/non-competitive behavior of different anti-IL-36R antibodies was determined as shown in Table 3-1.

TABLE 3-1

Cross-competition of anti-IL-36R antibodies for binding to human IL-36R-MMH

| First antibody (mAb-1) binding to captured hIL-36R-MMH | Second antibody (mAb-2) shown to compete with mAb-1 |
| --- | --- |
| H4H14699P2 | H4H14700P2 |
|  | H4H14706P2 |
|  | H4H14708P2 |
|  | H4H14732P2 |
| H4H14700P2 | H4H14699P2 |
|  | H4H14706P2 |
|  | H4H14708P2 |
|  | H4H14732P2 |
| H4H14706P2 | H4H14699P2 |
|  | H4H14700P2 |
|  | H4H14708P2 |
|  | H4H14732P2 |
| H4H14708P2 | H4H14699P2 |
|  | H4H14700P2 |
|  | H4H14706P2 |
|  | H4H14732P2 |
| H4H14732P2 | H4H14699P2 |
|  | H4H14700P2 |
|  | H4H14706P2 |
|  | H4H14708P2 |
| H4H14757P | H4H14758P |
|  | H4H14760P2 |
| H4H14758P | H4H14757P |
|  | H4H14760P2 |
| H4H14760P2 | H4H14757P |
|  | H4H14758P |
| H4H14728P | H4H14731P |
| H4H14731P | H4H14728P |
| H4H14709P | H4H14734P2 |
| H4H14734P2 | H4H14709P |

Example 4: Antibody Binding Kinetics

Equilibrium dissociation constants ($K_D$ values) for IL-36R binding to purified anti-IL-36R antibodies were determined using a real-time surface plasmon resonance biosensor using a Biacore 4000 instrument. The Biacore sensor surface was first derivatized by amine coupling with a monoclonal mouse anti-human Fc antibody (GE, #BR-1008-39) to capture anti-IL-36R monoclonal antibodies. All binding studies were performed in 0.01 M Hepes pH 7.4, 0.15 M NaCl, 3 mM EDTA, and 0.05% v/v Surfactant Tween-20 (HBS-ET running buffer) at 25° C. and 37° C. Different concentrations of IL-36R reagents, human IL-36R extracellular domain expressed with a C-terminal myc-myc-hexahistidine tag (hIL-36R-MMH), *Macaca fascicularis* IL-36R extracellular domain expressed with a C-terminal myc-myc-hexahistidine tag (mfIL-36R-MMH: mROR1 signal sequence (M1-A29). *Macaca fascicularis* IL36R_ecto domain (D20-A336).mycmycHis6), human IL-36R extracellular domain expressed with a C-terminal mouse IgG2a Fc tag (hIL-36R-mFc: mROR1 signal sequence (M1-A29)-human IL36R (D20-Y337)-mouse IgG2aFc (E98-K330)) or an in-line fusion protein of human IL-36R extracellular domain and IL1RAcP extracellular domain expressed with mouse IgG2a Fc tag (hIL-36R-Trap-mFc: mROR1 signal sequence (M1-A29)-human IL36R ecto domain (D20-Y337)-human IL1RacP ecto domain (S21-E359)-mouse IgG2aFc) in HBS-ET running buffer (ranging from 100 nM to 3.7 nM, 3-fold dilutions) were injected over the anti-IL-36R antibody captured surface for 4 minutes at a flow rate of 30 μL/minute and their dissociation in HBS-ET running buffer was monitored for 10 minutes. Kinetic association rate constant ($k_a$) and dissociation rate constant ($k_d$) were determined by fitting the real-time sensorgrams to a 1:1 binding model using Scrubber 2.0c curve fitting software. Binding dissociation equilibrium constants ($K_D$) and dissociative half-lives (t ½) were calculated from the kinetic rate constants as:

$$K_D(M) = \frac{kd}{ka},$$

and $$t^{1/2}(\min) = \frac{\ln(2)}{60 * kd}$$

Binding kinetic parameters for hIL-36R-MMH, mfIL-36R-MMH or hIL-36R.mFc binding to different anti-IL-36R antibodies of the invention at 25° C. and 37° C. are shown in Tables 4-1 through 4-8. At 25° C., hIL-36R-MMH bound to all of the anti-IL-36R antibodies of the invention with $K_D$ values ranging from 2.18 nM to 13.9 nM, as shown in Table 4-1. At 37° C., hIL-36R-MMH bound to all of the anti-IL-36R antibodies of the invention with $K_D$ values ranging from 4.25 nM to 29.5 nM, as shown in Table 4-2. At 25° C., mfIL-36R-MMH bound to 9 of the 12 anti-IL-36R antibodies of the invention with $K_D$ values ranging from 7.87 nM to 34.4 nM, as shown in Table 4-3. At 37° C., mfIL-36R-MMH bound to 9 of the 12 anti-IL-36R antibodies of the invention with $K_D$ values ranging from 14.4 nM to 58.2 nM, as shown in Table 4-4. At 25° C., hIL-36R-mFc bound to 11 of the 12 anti-IL-36R antibodies of the invention with $K_D$ values ranging from 173 pM to 5.79 nM, as shown in Table 4-5. One anti-IL-36R antibody of the invention demonstrated inconclusive binding to hIL-36R-mFc under the experimental conditions at 25° C. At 37° C., hIL-36R-mFc bound to all of the anti-IL-36R antibodies of the invention with $K_D$ values ranging from 205 pM to 28.7 nM, as shown in Table 4-6. At 25° C., hIL-36R-Trap-mFc bound to all of the anti-IL-36R antibodies of the invention with $K_D$ values ranging from 212 pM to 14 nM, as shown in Table 4-7. At 37° C., hIL-36R-Trap-mFc bound to all of the anti-IL-36R antibodies of the invention with $K_D$ values ranging from 264 pM to 40.9 nM, as shown in Table 4-8.

TABLE 4-1

Binding Kinetics parameters of anti-IL-36R antibodies binding to hIL-36R-MMH at 25° C.

| Antibody | mAb Capture Level (RU) | 100 nM hIL-36R-MMH Bound (RU) | $k_a$ (1/Ms) | $k_d$ (1/s) | $K_D$ (M) | $t_{1/2}$ (min) |
|---|---|---|---|---|---|---|
| H4H14699P2 | 198 ± 0.6 | 74 | 1.65E+05 | 1.68E−03 | 1.02E−08 | 7 |
| H4H14700P2 | 159 ± 0.3 | 67 | 1.20E+05 | 5.79E−04 | 4.82E−09 | 20 |
| H4H14706P2 | 199 ± 0.5 | 89 | 1.21E+05 | 4.95E−04 | 4.08E−09 | 23 |
| H4H14708P2 | 209 ± 0.9 | 76 | 9.14E+04 | 6.23E−04 | 6.82E−09 | 19 |
| H4H14709P | 156 ± 0.2 | 64 | 7.23E+04 | 2.96E−04 | 4.09E−09 | 39 |
| H4H14728P | 175 ± 0.6 | 69 | 983E+04 | 7.73E−04 | 7.87E−09 | 15 |
| H4H14731P | 204 ± 0.6 | 54 | 9.22E+04 | 3.43E−04 | 3.72E−09 | 34 |
| H4H14732P2 | 197 ± 0.3 | 26 | 4.10E+04 | 5.69E−04 | 1.39E−08 | 20 |
| H4H14734P2 | 174 ± 0.8 | 22 | 3.32E+04 | 4.04E−04 | 1.22E−08 | 29 |
| H4H14757P | 180 ± 0.9 | 94 | 1.82E+05 | 3.96E−04 | 2.18E−09 | 29 |
| H4H14758P | 177 ± 0.7 | 87 | 1.21E+05 | 9.23E−04 | 7.63E−09 | 13 |
| H4H14760P2 | 180 ± 0.5 | 61 | 6.79E+04 | 4.15E−04 | 6.11E−09 | 28 |

TABLE 4-2

Binding Kinetics parameters of anti-IL-36R antibodies binding to hIL-36R-MMH at 37° C.

| Antibody | mAb Capture Level (RU) | 100 nM hIL-36R-MMH Bound (RU) | $k_a$ (1/Ms) | $k_d$ (1/s) | $K_D$ (M) | $t_{1/2}$ (min) |
|---|---|---|---|---|---|---|
| H4H14699P2 | 257 ± 1.2 | 89 | 1.42E+05 | 4.18E−03 | 2.95E−08 | 2.8 |
| H4H14700P2 | 218 ± 0.7 | 89 | 1.76E+05 | 1.84E−03 | 1.05E−08 | 6 |
| H4H14706P2 | 266 ± 1 | 113 | 1.50E+05 | 1.30E−03 | 8.65E−09 | 9 |
| H4H14708P2 | 280 ± 2.5 | 106 | 1.36E+05 | 1.86E−03 | 1.36E−08 | 6 |
| H4H14709P | 218 ± 0.9 | 106 | 1.31E+05 | 5.54E−04 | 4.25E−09 | 21 |
| H4H14728P | 242 ± 0.7 | 93 | 1.36E+05 | 2.93E−03 | 2.15E−08 | 4 |
| H4H14731P | 262 ± 0.7 | 81 | 1.37E+05 | 9.71E−04 | 7.11E−09 | 12 |
| H4H14732P2 | 272 ± 0.8 | 34 | 4.21E+04 | 1.16E−03 | 2.76E−08 | 10 |
| H4H14734P2 | 248 ± 0.8 | 25 | 5.39E+04 | 7.49E−04 | 1.39E−08 | 15 |
| H4H14757P | 262 ± 1.0 | 129 | 2.10E+05 | 1.09E−03 | 5.18E−09 | 11 |
| H4H14758P | 247 ± 1.2 | 111 | 1.58E+05 | 2.37E−03 | 1.50E−08 | 5 |
| H4H14760P2 | 252 ± 0.8 | 83 | 9.06E+04 | 2.08E−03 | 2.30E−08 | 6 |

TABLE 4-3

Binding Kinetics parameters of anti-IL-36R antibodies binding to mfIL-36R-MMH at 25° C.

| Antibody | mAb Capture Level (RU) | 100 nM hIL-36R-MMH Bound (RU) | $k_a$ (1/Ms) | $k_d$ (1/s) | $K_D$ (M) | $t_{1/2}$ (min) |
|---|---|---|---|---|---|---|
| H4H4699P2 | 198 ± 0.4 | 53 | 6.38E+04 | 1.83E−03 | 2.87E−08 | 6 |
| H4H14700P2 | 158 ± 0.3 | 48 | 6.02E+04 | 6.35E−04 | 1.06E−08 | 18 |
| H4H14706P2 | 199 ± 0.4 | 65 | 6.72E+04 | 5.52E−04 | 8.21E−09 | 21 |
| H4H14708P2 | 209 ± 0.9 | 51 | 4.50E+04 | 5.79E−04 | 1.29E−08 | 20 |
| H4H14709P | 156 ± 0.3 | 34 | 2.80E+04 | 4.01E−04 | 1.43E−08 | 29 |
| H4H14728P | 175 ± 0.6 | 51 | 5.15E+04 | 4.06E−04 | 7.87E−09 | 28 |
| H4H14731P | 203 ± 0.4 | 33 | 5.98E+04 | 9.51E−04 | 1.59E−08 | 12 |
| H4H14732P2 | 197 ± 0.4 | 12 | 1.88E+04 | 6.49E−04 | 3.44E−08 | 18 |
| H4H14734P2 | 175 ± 0.6 | 12 | 2.60E+04 | 2.54E−04 | 9.78E−09 | 46 |
| H4H14757P | 183 ± 0.7 | 1 | NB* | NB* | NB* | NB* |
| H4H14758P | 179 ± 0.6 | −1 | NB* | NB* | NB* | NB* |
| H4H14760P2 | 181 ± 0.4 | 0 | NB* | NB* | NB* | NB* |

*NB indicates that under the experimental conditions, mfIL-36R-MMH reagent did not bind to the captured anti-IL-36R antibody

TABLE 4-4

Binding Kinetics parameters of anti-IL-36R antibodies binding to mfIL-36R-MMH at 37° C.

| Antibody | mAb Capture Level (RU) | 100 nM mfIL-36R-MMH Bound (RU) | $k_a$ (1/Ms) | $k_d$ (1/s) | $K_D$ (M) | $t_{1/2}$ (min) |
|---|---|---|---|---|---|---|
| H4H14699P2 | 257 ± 0.4 | 59 | 7.80E+04 | 4.54E−03 | 5.82E−08 | 2.5 |
| H4H14700P2 | 218 ± 0.7 | 67 | 7.14E+04 | 1.98E−03 | 2.78E−08 | 6 |
| H4H14706P2 | 266 ± 0.4 | 84 | 7.47E+04 | 1.42E−03 | 1.90E−08 | 8 |
| H4H14708P2 | 279 ± 2.8 | 75 | 5.96E+04 | 1.81E−03 | 3.04E−08 | 6 |
| H4H14709P | 220 ± 1.4 | 66 | 4.91E+04 | 8.71E−04 | 1.77E−08 | 13 |
| H4H14728P | 243 ± 0.7 | 77 | 6.48E+04 | 1.34E−03 | 2.07E−08 | 9 |
| H4H14731P | 261 ± 0.3 | 41 | 6.68E+04 | 3.22E−03 | 4.82E−08 | 4 |
| H4H14732P2 | 273 ± 0.8 | 17 | 3.19E+04 | 1.64E−03 | 5.15E−08 | 7 |
| H4H14734P2 | 248 ± 0.6 | 12 | 3.61E+04 | 5.21E−04 | 1.44E−08 | 22 |
| H4H14757P | 264 ± 1.5 | 4 | NB* | NB* | NB* | NB* |
| H4H14758P | 248 ± 0.9 | −1 | NB* | NB* | NB* | NB* |
| H4H14760P2 | 253 ± 0.9 | 2 | NB* | NB* | NB* | NB* |

*NB indicates that under the experimental conditions, mfIL-36R-MMH reagent did not bind to the captured anti-IL-36R antibody

TABLE 4-5

Binding Kinetics parameters of anti-IL-36R antibodies binding to hIL-36R-mFc at 25° C.

| Antibody | mAb Capture Level (RU) | 100 nM hIL-36R-mFc Bound (RU) | $k_a$ (1/Ms) | $k_d$ (1/s) | $K_D$ (M) | $t_{1/2}$ (min) |
|---|---|---|---|---|---|---|
| H4H14699P2 | 197 ± 0.8 | 150 | 5.64E+05 | 2.03E−04 | 3.59E−10 | 57 |
| H4H14700P2 | 158 ± 0.3 | 128 | 5.17E+05 | 1.20E−04 | 2.33E−10 | 96 |
| H4H14706P2 | 197 ± 1.7 | 163 | 5.75E+05 | 1.32E−04 | 2.30E−10 | 87 |
| H4H14708P2 | 207 ± 2.3 | 146 | 4.03E+05 | 1.28E−04 | 3.17E−10 | 90 |
| H4H14709P | 155 ± 0.7 | 142 | 2.57E+05 | 8.62E−05 | 3.35E−10 | 134 |
| H4H14728P | 174 ± 0.5 | 7 | IC* | IC* | IC* | IC* |
| H4H14731P | 204 ± 0.3 | 10 | 5.58E+04 | 3.23E−04 | 5.79E−09 | 36 |
| H4H14732P2 | 197 ± 0.6 | 145 | 5.70E+05 | 7.97E−04 | 1.40E−09 | 14 |
| H4H14734P2 | 174 ± 0.5 | 77 | 6.22E+04 | 1.01E−04 | 1.63E−09 | 114 |
| H4H14757P | 182 ± 1.4 | 167 | 5.75E+05 | 9.97E−05 | 1.73E−10 | 116 |
| H4H14758P | 179 ± 0.8 | 161 | 5.26E+05 | 1.63E−04 | 3.09E−10 | 71 |
| H4H14760P2 | 181 ± 0.8 | 121 | 2.07E+05 | 1.09E−04 | 5.26E−10 | 106 |

*IC indicates that under the experimental conditions, hIL-36R.mFc binding is inconclusive

TABLE 4-6

Binding Kinetics parameters of anti-IL-36R antibodies binding to hIL-36R-mFc at 37° C.

| Antibody | mAb Capture Level (RU) | 100 nM hIL-36R-mFc Bound (RU) | $k_a$ (1/Ms) | $k_d$ (1/s) | $K_D$ (M) | $t_{1/2}$ (min) |
|---|---|---|---|---|---|---|
| H4H14699P2 | 258 ± 0.7 | 186 | 5.94E+05 | 4.56E−04 | 7.67E−10 | 25 |
| H4H14700P2 | 218 ± 0.5 | 174 | 5.35E+05 | 2.09E−04 | 3.90E−10 | 55 |
| H4H14706P2 | 266 ± 0.6 | 207 | 5.93E+05 | 2.66E−04 | 4.49E−10 | 43 |
| H4H14708P2 | 280 ± 2.5 | 203 | 4.60E+05 | 2.00E−04 | 4.35E−10 | 58 |
| H4H14709P | 218 ± 1.2 | 211 | 5.43E+05 | 1.12E−04 | 2.05E−10 | 104 |
| H4H14728P | 243 ± 1.0 | 11 | 1.62E+04 | 4.65E−04 | 2.87E−08 | 25 |
| H4H14731P | 261 ± 0.5 | 12 | 6.99E+04 | 4.50E−04 | 6.43E−09 | 26 |
| H4H14732P2 | 273 ± 1.2 | 195 | 6.35E+05 | 1.27E−03 | 2.00E−09 | 9 |
| H4H14734P2 | 247 ± 1.0 | 96 | 5.27E+04 | 1.22E−04 | 2.31E−09 | 95 |
| H4H14757P | 264 ± 2.0 | 235 | 6.16E+05 | 1.50E−04 | 2.43E−10 | 77 |
| H4H14758P | 248 ± 0.7 | 210 | 5.54E+05 | 2.86E−04 | 5.17E−10 | 40 |
| H4H14760P2 | 254 ± 0.9 | 173 | 2.17E+05 | 2.22E−04 | 1.02E−09 | 52 |

TABLE 4-7

Binding Kinetics parameters of anti-IL-36R antibodies binding to hIL-36R-Trap-mFc at 25° C.

| Antibody | mAb Capture Level (RU) | 100 nM hIL-36R-mFc Bound (RU) | $k_a$ (1/Ms) | $k_d$ (1/s) | $K_D$ (M) | $t_{1/2}$ (min) |
|---|---|---|---|---|---|---|
| H4H14699P2 | 196 ± 0.7 | 188 | 4.98E+05 | 2.28E04 | 4.58E−10 | 51 |
| H4H14700P2 | 156 ± 0.7 | 157 | 4.42E+05 | 1.25E−04 | 2.83E−10 | 92 |
| H4H14706P2 | 195 ± 0.6 | 205 | 4.77E+05 | 1.10E−04 | 2.32E−10 | 105 |
| H4H14708P2 | 205 ± 2.1 | 172 | 3.61E+05 | 1.29E−04 | 3.57E−10 | 90 |
| H4H14709P | 155 ± 0.4 | 173 | 2.00E+05 | 8.07E−05 | 4.04E−10 | 143 |
| H4H14728P | 175 ± 0.5 | 63 | 4.03E+04 | 5.65E−04 | 1.40E−08 | 20 |
| H4H14731P | 203 ± 0.5 | 60 | 4.52E+04 | 2.01E−04 | 4.45E−09 | 57 |
| H4H14732P2 | 197 ± 0.4 | 161 | 4.62E+05 | 1.36E−03 | 2.95E−09 | 8 |
| H4H14734P2 | 174 ± 0.5 | 85 | 4.89E+04 | 1.10E−04 | 2.24E−09 | 105 |
| H4H14757P | 181 ± 0.5 | 202 | 4.85E+05 | 1.03E−04 | 2.12E−10 | 113 |
| H4H14758P | 179 ± 0.6 | 197 | 4.36E+05 | 1.80E−04 | 4.13E−10 | 64 |
| H4H14760P2 | 181 ± 1.0 | 134 | 1.58E+05 | 1.00E−04 | 6.36E−10 | 115 |

TABLE 4-8

Binding Kinetics parameters of anti-IL-36R antibodies binding to hIL-36R-Trap-mFc at 37° C.

| Antibody | mAb Capture Level (RU) | 100 nM hIL-36R-Trap-mFc Bound (RU) | $k_a$ (1/Ms) | $k_d$ (1/s) | $K_D$ (M) | $t_{1/2}$ (min) |
|---|---|---|---|---|---|---|
| H4H14699P2 | 256 ± 0.8 | 229 | 4.84E+05 | 5.13E−04 | 1.06E−09 | 23 |
| H4H14700P2 | 217 ± 0.5 | 216 | 4.55E+05 | 2.53E−04 | 5.55E−10 | 46 |
| H4H14706P2 | 266 ± 0.8 | 264 | 4.91E+05 | 2.71E−04 | 5.51E−10 | 43 |
| H4H14708P2 | 280 ± 1 | 239 | 3.85E+05 | 2.53E−04 | 6.56E−10 | 46 |
| H4H14709P | 218 ± 1.3 | 257 | 4.67E+05 | 1.23E−04 | 2.64E−10 | 94 |
| H4H14728P | 243 ± 0.5 | 89 | 4.85E+04 | 1.98E−03 | 4.09E−08 | 6 |
| H4H14731P | 261 ± 0.4 | 78 | 5.26E+04 | 5.14E−04 | 9.77E−09 | 22 |
| H4H14732P2 | 272 ± 01 | 212 | 5.01E+05 | 1.82E−03 | 3.63E−09 | 6 |
| H4H14734P2 | 248 ± 0.5 | 99 | 4.84E+04 | 1.43E−04 | 2.96E−09 | 81 |
| H4H14757P | 263 ± 1.2 | 281 | 5.23E+05 | 1.96E−04 | 3.74E−10 | 59 |
| H4H14758P | 248 ± 0.6 | 251 | 4.68E+05 | 3.63E−04 | 7.77E−10 | 32 |
| H4H14760P2 | 254 ± 1.1 | 195 | 1.66E+05 | 2.83E−04 | 1.70E−09 | 41 |

Additional binding experiments were performed to determine the effect of pH on the rate of dissociation of IL-36R bound to purified anti-IL-36R antibodies, which was determined using a real-time surface plasmon resonance biosensor using a Biacore T200 instrument. The Biacore sensor surface was first derivatized by amine coupling with a monoclonal mouse anti-human Fc antibody (GE, #BR-1008-39) to capture anti-IL-36R antibodies. These Biacore binding studies were performed using two running buffers PBS-T, pH7.4 (8.1 mM Na$_2$HPO$_4$, 1.9 mM NaH$_2$PO$_4$, 3 mM KCl, 137 mM NaCl, 0.05% v/v Tween-20, adjusted to pH 7.4) and PBS-T, pH 6.0 (6.6 mM Na$_2$HPO$_4$, 3.4 mM NaH$_2$PO$_4$, 3 mM KCl, 137 mM NaCl, 0.05% v/v Tween-20, adjusted to pH6.0). Different concentrations of hIL-36R-MMH and mfIL-36R-MM H prepared in PBS-T, pH7.4 buffer (ranging from 100 nM to 11.11 nM, 3-fold dilutions) were injected over the anti-IL-36R antibody captured surface for 4 minutes at a flow rate of 50 μL/minute and their dissociation in two running buffers, PBS-T, pH7.4 and PBS-T, pH 6.0, was monitored for 10 minutes. All of these binding kinetics experiments were performed at 25° C. and 37° C. Kinetic dissociation constant ($k_d$) were determined by fitting the real-time sensorgrams to a 1:1 binding model using Scrubber 2.0c curve fitting software. Binding dissociative half-lives (t½) were calculated from $k_d$ as:

$$t^{1/2}(\min) = \frac{\ln(2)}{60 * kd}$$

Binding dissociation rate constants for hIL-36R-MMH or mfIL-36R-MMH binding to different anti-IL-36R antibodies at 25° C. and 37° C. in two running buffers PBS-T, pH7.4 and PBS-T, pH 6.0 are shown in Tables 4-9 through 4-12.

TABLE 4-9

Binding dissociation rate constant of anti-IL-36R monoclonal antibodies binding to hIL-36R-MMH in two running buffers performed at 25° C.

| | PBS-T, pH 7.4 Running Buffer | | | | PBS-T, pH 6.0 Running Buffer | | | |
|---|---|---|---|---|---|---|---|---|
| mAb PID | mAb Capture Level (RU) | 100 nM Human IL-36R-MMH Bound (RU) | $k_d$ (1/s) | $t\frac{1}{2}$ (min) | mAb Capture Level (RU) | 100 nM Human IL-36R-MMH Bound (RU) | $k_d$ (1/s) | $t\frac{1}{2}$ (min) |
| H4H14699P2 | 255 ± 2.7 | 84 | 1.93E−03 | 6 | 278 ± 0.6 | 79 | 2.93E−03 | 4 |
| H4H14700P2 | 330 ± 0.9 | 128 | 7.95E−04 | 15 | 350 ± 0.9 | 120 | 1.72E−03 | 7 |
| H4H14706P2 | 298 ± 0.9 | 119 | 6.16E−04 | 19 | 312 ± 2.2 | 109 | 9.27E−04 | 12 |
| H4H14708P2 | 268 ± 2.8 | 87 | 7.96E−04 | 15 | 283 ± 2.5 | 79 | 1.63E−03 | 7 |
| H4H14709P | 283 ± 0.8 | 111 | 4.20E−04 | 28 | 300 ± 1.8 | 99 | 8.42E−04 | 14 |
| H4H14728P | 265 ± 1.7 | 103 | 8.98E−04 | 13 | 269 ± 2 | 96 | 8.87E−04 | 13 |
| H4H14731P | 282 ± 1.9 | 65 | 5.53E−04 | 21 | 281 ± 0.9 | 43 | 6.79E−04 | 17 |
| H4H14732P2 | 244 ± 1.5 | 32 | 8.65E−04 | 13 | 255 ± 1.3 | 28 | 9.18E−04 | 13 |
| H4H14734P2 | 230 ± 1.3 | 20 | 7.38E−04 | 16 | 240 ± 1.8 | 18 | 7.87E−04 | 15 |
| H4H14757P | 226 ± 0.6 | 105 | 5.97E−04 | 19 | 235 ± 1.5 | 98 | 8.87E−04 | 13 |
| H4H14758P | 244 ± 2.5 | 108 | 1.12E−03 | 10 | 255 ± 1.6 | 103 | 1.80E−03 | 6 |
| H4H14760P2 | 257 ± 1.5 | 80 | 5.45E−04 | 21 | 266 ± 1.3 | 69 | 9.72E−04 | 12 |

TABLE 4-10

Binding dissociation rate constant of anti-IL-36R monoclonal antibodies binding to hIL-36R-MMH in two running buffers performed at 37° C.

| | PBS-T, pH 7.4 Running Buffer | | | | PBS-T, pH 6.0 Running Buffer | | | |
|---|---|---|---|---|---|---|---|---|
| mAb PID | mAb Capture Level (RU) | 100 nM hIL-36R-MMH Bound (RU) | $k_d$ (1/s) | $t\frac{1}{2}$ (min) | mAb Capture Level (RU) | 100 nM hIL-36R-MMH Bound (RU) | $k_d$ (1/s) | $t\frac{1}{2}$ (min) |
| H4H14699P2 | 312 ± 2.9 | 96 | 4.15E−03 | 3 | 300 ± 14.2 | 83 | 5.81E−03 | 2 |
| H4H14700P2 | 422 ± 5.7 | 153 | 1.69E−03 | 7 | 435 ± 1.5 | 144 | 3.50E−03 | 3 |
| H4H14706P2 | 367 ± 3.5 | 140 | 1.31E−03 | 9 | 378 ± 2 | 132 | 2.33E−03 | 5 |
| H4H14708P2 | 313 ± 6.8 | 105 | 1.77E−03 | 7 | 318 ± 4.6 | 95 | 3.37E−03 | 3 |
| H4H14709P | 372 ± 3 | 159 | 7.04E−04 | 16 | 380 ± 2.9 | 146 | 1.72E−03 | 7 |
| H4H14728P | 306 ± 1 | 121 | 2.96E−03 | 4 | 302 ± 1.3 | 114 | 3.06E−03 | 4 |
| H4H14731P | 272 ± 3.9 | 91 | 1.08E−03 | 11 | 276 ± 1.6 | 84 | 2.01E−03 | 6 |
| H4H14732P2 | 303 ± 3 | 40 | 1.10E−03 | 10 | 310 ± 2 | 36 | 1.23E−03 | 9 |
| H4H14734P2 | 287 ± 1.4 | 20 | 1.21E−03 | 10 | 289 ± 1.8 | 17 | 1.69E−03 | 7 |
| H4H14757P | 254 ± 0.7 | 113 | 1.29E−03 | 9 | 267 ± 1 | 109 | 2.60E−03 | 4 |
| H4H14758P | 308 ± 1.2 | 126 | 2.26E−03 | 5 | 314 ± 0.5 | 120 | 3.39E−03 | 3 |
| H4H14760P2 | 311 ± 1.4 | 94 | 1.87E−03 | 6 | 317 ± 2.1 | 85 | 3.90E−03 | 3 |

TABLE 4-11

Binding dissociation rate constant of anti-IL-36R monoclonal antibodies binding to mfIL-36R-MMH in two running buffers performed at 25° C.

| | PBS-T, pH 7.4 Running Buffer | | | | PBS-T, pH 6.0 Running Buffer | | | |
|---|---|---|---|---|---|---|---|---|
| mAb PID | mAb Capture Level (RU) | 100 nM Human mfIL-36R-MMH Bound (RU) | $k_d$ (1/s) | $t\frac{1}{2}$ (min) | mAb Capture Level (RU) | 100 nM Human mfIL-36R-MMH Bound (RU) | $k_d$ (1/s) | $t\frac{1}{2}$ (min) |
| H4H14699P2 | 258 ± 1.5 | 55 | 2.04E−03 | 6 | 276 ± 0.7 | 48 | 3.22E−03 | 4 |
| H4H14700P2 | 331 ± 1.8 | 91 | 8.21E−04 | 14 | 350 ± 1.7 | 80 | 1.71E−03 | 7 |
| H4H14706P2 | 295 ± 1.7 | 80 | 6.46E−04 | 18 | 312 ± 1.5 | 71 | 9.65E−04 | 12 |
| H4H14708P2 | 270 ± 2 | 57 | 7.52E−04 | 15 | 281 ± 1.2 | 47 | 1.50E−03 | 8 |
| H4H14709P | 282 ± 1.3 | 57 | 5.19E−04 | 22 | 301 ± 0.7 | 48 | 1.12E−03 | 10 |
| H4H14728P | 264 ± 2 | 74 | 5.44E−04 | 21 | 269 ± 1.2 | 68 | 6.16E−04 | 19 |

TABLE 4-11-continued

Binding dissociation rate constant of anti-IL-36R monoclonal antibodies binding to mfIL-36R-MMH in two running buffers performed at 25° C.

| | PBS-T, pH 7.4 Running Buffer | | | | PBS-T, pH 6.0 Running Buffer | | | |
|---|---|---|---|---|---|---|---|---|
| mAb PID | mAb Capture Level (RU) | 100 nM Human mfIL-36R-MMH Bound (RU) | $k_d$ (1/s) | $t^{1/2}$ (min) | mAb Capture Level (RU) | 100 nM Human mfIL-36R-MMH Bound (RU) | $k_d$ (1/s) | $t^{1/2}$ (min) |
| H4H14731P | 279 ± 2.2 | 36 | 1.37E−03 | 8 | 279 ± 1.9 | 23 | 1.52E−03 | 8 |
| H4H14732P2 | 245 ± 0.9 | 14 | 7.87E−04 | 15 | 253 ± 0.9 | 12 | 1.15E−03 | 10 |
| H4H14734P2 | 229 ± 2.2 | 9 | 5.05E−04 | 23 | 238 ± 1.2 | 8 | 6.31E−04 | 18 |
| H4H14757P | 224 ± 1.8 | 1 | NB* | NB* | 235 ± 0.9 | 1 | NB* | NB* |
| H4H14758P | 243 ± 0.5 | 0 | NB* | NB* | 254 ± 1 | 1 | NB* | NB* |
| H4H14760P2 | 257 ± 1.9 | 1 | NB* | NB* | 266 ± 1.2 | 1 | NB* | NB* |

*NB indicates that under the current experimental conditions, no binding of mfIL-36R-MMH to anti-hFc captured anti-IL-36R mAb was observed.

TABLE 4-12

Binding dissociation rate constant of anti-IL-36R monoclonal antibodies binding to mfIL-36R-MMIA in two running buffers performed at 37° C.

| | PBS-T, pH 7.4 Running Buffer | | | | PBS-T, pH 6.0 Running Buffer | | | |
|---|---|---|---|---|---|---|---|---|
| mAb PID | mAb Capture Level (RU) | 100 nM Human mfIL-36R-MMH Bound (RU) | kd (1/s) | $t^{1/2}$ (min) | mAb Capture Level (RU) | 100 nM Human mfIL-36R-MMH Bound (RU) | kd (1/s) | $t^{1/2}$ (min) |
| H4H14699P2 | 310 ± 4.9 | 58 | 4.59E−03 | 3 | 308 ± 1.9 | 50 | 6.22E−03 | 2 |
| H4H14700P2 | 422 ± 1.1 | 108 | 1.80E−03 | 6 | 434 ± 1.8 | 97 | 3.33E−03 | 3 |
| H4H14706P2 | 366 ± 1.3 | 95 | 1.38E−03 | 8 | 375 ± 1.6 | 85 | 2.64E−03 | 4 |
| H4H14708P2 | 302 ± 3.6 | 66 | 1.69E−03 | 7 | 314 ± 2.2 | 58 | 3.10E−03 | 4 |
| H4H14709P | 370 ± 2.3 | 92 | 9.87E−04 | 12 | 379 ± 1 | 80 | 2.94E−03 | 4 |
| H4H14728P | 305 ± 2.5 | 98 | 1.39E−03 | 8 | 301 ± 1.2 | 91 | 1.91E−03 | 6 |
| H4H14731P | 266 ± 4 | 43 | 3.61E−03 | 3 | 279 ± 1.8 | 40 | 5.38E−03 | 2 |
| H4H14732P2 | 302 ± 1.4 | 18 | 9.37E−04 | 12 | 309 ± 1.7 | 16 | 1.57E−03 | 7 |
| H4H14734P2 | 283 ± 0.8 | 9 | 7.87E−04 | 15 | 287 ± 1.9 | 7 | 1.19E−03 | 10 |
| H4H14757P | 255 ± 0.5 | 0 | NB* | NB* | 267 ± 1.9 | −1 | NB* | NB* |
| H4H14758P | 306 ± 1 | 0 | NB* | NB* | 314 ± 2.5 | 1 | NB* | NB* |
| H4H14760P2 | 309 ± 1.6 | 1 | NB* | NB* | 315 ± 1.3 | 1 | NB* | NB* |

*NB indicates that under the current experimental conditions, no binding of mfIL-36R-MMH to anti-hFc captured anti-IL-36R mAb was observed

Example 5: In Vivo Evaluation of Anti-IL36R in IMQ-Induced Skin Inflammation and Chronic Colitis Mouse Models The anti-human IL-36R monoclonal antibodies of the present invention were tested in vivo in acute and chronic Imiquimod (IMQ)-induced skin inflammation, and chronic dextran sodium sulfate (DSS)-induced colitis in humanized IL-36R/hIL-36α, β, γ mice. Cytokine detection was performed in skin and colon homogenates using a proinflammatory panel 1 (mouse) multiplex immunoassay kit. Detection of Lipocalin 2 (Lcn2) in fecal homogenates was performed using a mouse Duoset Lipocalin-2/NGAL ELISA kit. Measurement of myeloperoxidase (MPO) activity in the colon homogenates was done using a mouse MPO ELISA kit.

The anti-IL36R antibodies, H4H14706P2 and H4H14708P2, were used along with a human, isotype matched control IgG4 antibody.

To examine the role of IL-36R in skin and intestinal inflammation and to test the efficacy of hIL-36R antagonism in vivo, anti-human IL-36R monoclonal antibodies of the present invention were tested in the murine models of Imiquimod (IMQ)-induced skin inflammation and DSS-induced chronic colitis. In both models, Velocigene generated homozygous mice expressing human IL-36R and human IL-36α, β, γ and endogenous mouse IL-36Ra were utilized (resulting mice are referred to as DITRA-like mice, due to decreased affinity of mouse IL-36Ra for human IL-36R which resembles the mutation observed in DITRA (Deficiency of Interleukin Thirty-six Receptor Antagonist) patients (Marrakchi et al., Interleukin-36-receptor antagonist deficiency and generalized pustular psoriasis, N Engl J Med 365:620-628 (2011)).

A mouse humanized strain with the genotype Il1rI2$^{hu/hu}$ Il1f6$^{hu/hu}$ Il1f8$^{hu/hu}$ Il1f9$^{hu/hu}$ was generated. In this mouse strain, human IL1F6, IL1F8, and IL1F9 replaced the endogenous mouse IL1F6, IL1F8, and IL1F9 (also called IL36α, β and γ respectively); and a chimeric IL1RL2 replaced the endogenous mouse IL1RL2. The chimeric IL1RL2 had a human IL1RL2 extracellular domain and a mouse intracellular domain. This resulted in a chimeric receptor that maintained the intracellular signaling specificity of mice, while rendering the extracellular domain human and, thus, able to bind to the human ligands IL1F6, IL1F8, and IL1F9.

Acute and chronic IMQ-induced skin Inflammation Induction and antibody treatment in DITRA-like mice. To induce skin inflammation, 8-10 weeks old humanized DITRA-like female mice had their back hair shaved using mouse hair trimmer (Oster, MiniMax, Cat #78049-100) and skin depilated with 0.5 g Veet hair removal gel three days prior to IMQ cream application. A daily topical dose of 62.5 mg of commercially available IMQ cream (5%) (Aldara, GM Health Care Limited, NDC 99207-206-12) or Vaseline (CVS Pharmacy) was applied on the shaved back skin of the mice for four consecutive days for acute and nine days for chronic disease induction. A daily topical dose of 62.5 mg of Aldara translated into a daily dose of 3.125 mg of an active compound. In acute IMQ-induced skin inflammation, anti-human IL-36R antibodies, H4H14706P2 and H4H14708P2, were administered subcutaneously into back skin at 10 mg/kg and 1 mg/kg on three days before (−3 d) and one day after (d1) starting the IMQ application. Control group received PBS and 10 mg/kg of hIgG4 Isotype control injections. In chronic IMQ-induced skin inflammation, anti-human IL-36R antibodies, H4H14706P2 and H4H14708P2, were administered subcutaneously into back skin at 10 mg/kg therapeutically on d4 and d8. Two or three days after the start of IMQ application, the back skin of the mice started to display signs of erythema, scaling and thickening. The severity of inflammation was measured on a daily basis using an adapted version of the clinical Psoriasis Area and Severity Index. Erythema, scaling and thickening were scored independently on a scale from 0-4: 0, none; 1, slight; 2, moderate; 3, marked; and 4, very marked (van der Fits et al., Imiquimod-induced psoriasis-like skin inflammation in mice is mediated via the IL-23/IL-17 axis. J Immunol 2009, 182:5836-5845). On d4 of acute and d11 of chronic IMQ-induced skin inflammation, skin thickness was measured using a caliper (Kaefer).

Histopathology. Skin tissues of 6 mm diameter from murine back were fixed in 10% buffered formalin, and 4-5 μm paraffin embedded sections were stained with hematoxylin and eosin. Skin sections were evaluated blindly for the presence of parakeratosis, orthokeratosis, Munro's microabscess, acanthosis, epidermal ulceration, inflammation in the dermis and hypodermis, blood vessel congestion in the dermis and hypodermis, follicular hyperkeratosis and epithelial hyperplasia. A 0-4 scoring scale was used: 0-within normal limits, 1-minimal, 2-mild, 3-moderate and 4-severe. A total pathology score was calculated for each mouse by adding the individual histopathological feature scores. Data analysis was performed using GraphPad Prism™ software. Danilenko, Review paper preclinical models of psoriasis, Vet Pathol. 2008 July; 45(4):563-75; Lowes et al., Pathogenesis and therapy of psoriasis, Nature. 2007 Feb. 22; 445(7130):866-73; Mecklenburg et al., Proliferative and non-proliferative lesions of the rat and mouse integument, J Toxicol Pathol. 2013; 26 (3 Suppl):27S-57S; Uribe-Herranz et al., IL-1R1 signaling facilitates Munro's microabscess formation in psoriasiform imiquimod-induced skin inflammation, J Invest Dermatol. 2013 June; 133(6):1541-9; van der Fits et al., Imiquimod-induced psoriasis-like skin inflammation in mice is mediated via the IL-23/IL-17 axis, J Immunol. 2009 May 1; 182(9):5836-45.

Measurement of cytokines in skin homogenates. Full thickness skin tissues of 6 mm diameter from murine back were taken and placed in 15 mL tube containing T-per buffer (Thermo Scientific, Cat #378510), 1× Halt Protease Inhibitor Cocktail (Thermo Scientific, Cat #87786) and 5 M EDTA Solution (Thermo Scientific, Cat 3 78429). Skin tissues were disrupted at 28000 rpm for 1 minute using a Polytron (PT10-35 GT-D, Cat #9158158) and put on ice. Generated skin homogenates were centrifuged at 1500 rpm for 8 minutes at 4° C. and the supernatants were collected into 96-well plates. Skin homogenates were subjected to Bradford protein assay using protein assay dye (BioRad, Cat #500-0006) to quantify the total protein content. Cytokine concentrations in the skin homogenates were measured using a Proinflammatory Panel 1 (mouse) multiplex immunoassay kit (MesoScale Discovery, Cat #K15048D) according to manufacturer's instructions. In brief, 50 μL/well of calibrators and samples (diluted in Diluent 41) were added to the plates pre-coated with capture antibodies and incubated at room temperature while shaking at 700 rpm for 2 hours. The plates were then washed 3 times with 1×PBS containing 0.05% (w/v) Tween-20, followed by the addition of 25 μL of Detection Antibody Solution diluted in Diluent 45. After 2-hours incubation at room temperature while shaking, the plates were washed 3 times, and 150 μL of 2× Read Buffer was added to each well. Electrochemiluminescence was immediately read on a MSD Spector® instrument. Data analysis was performed using GraphPad Prism™ software. Cytokine levels were normalized to total protein content.

Induction of DSS-induced model of chronic colitis and antibody treatment in DITRA-like mice. To induce chronic DSS-mediated colitis, female DITRA-like mice aged 12-20 weeks with an average body weight of more than 23 g were given 3% DSS (Sigma-Aldrich Cat #87786) in drinking water for 7 days followed by distilled water for 10 days. This cycle was repeated two times until d28. Control group received distilled water for the duration of the study. Anti-human IL-36R antibodies, H4H14706P2 and H4H14708P2, were administered intraperitoneally at 10 mg/kg and 5 mg/kg bi-weekly starting on d7. Control group received PBS and 10 mg/kg of hIgG4 Isotype control injections. Mice were weighted and monitored for clinical signs of colitis (e.g., stool consistency and fecal blood) on a daily basis. On d28, mice were euthanized and colon lengths were measured.

Measurement of Lcn-2 in colon homogenates. To monitor intestinal inflammation throughout the study, feces from individual DITRA-like mice were collected into 2 mL deep well plates on a weekly basis and stored at −80° C. Upon the completion of the study, feces collected on different days were subjected to homogenization. In brief, fecal samples were reconstituted with 1 mL PBS containing 0.1% Tween-20, 1× Halt Protease Inhibitor Cocktail (Thermo Scientific, Cat #87786) and 5 M EDTA Solution (Thermo Scientific, Cat3 78429). After adding 2 Tungsten 3 mm Carbide Beads to the wells (Qiagen, Cat #69997), the plates were placed on a shaker at highest speed overnight at 4° C. Homogenous fecal suspensions were centrifuged at 1200 rpm for 10 minutes at 4° C. and the supernatants were collected into 96-well plates. Fecal Lipocalin-2 (Lcn2) levels were measured using mouse Duoset Lipocalin-2/NGAL ELISA kit (R&D Systems, Cat #DY1857) according to manufacturer's instructions. Data analysis was performed using GraphPad Prism™ software.

Measurement of Myeloperoxidase (MPO) activity in colon homogenates. Pieces of the distal part of the colon were taken into 2 mL microcentrifuge tubes containing 2 Tungsten 3 mm Carbide Beads (Qiagen, Cat #69997) containing T-per buffer (Thermo Scientific, Cat #378510), 1× Halt Protease Inhibitor Cocktail (Thermo Scientific, Cat #87786) and 5 M EDTA Solution (Thermo Scientific, Cat #78429). Colon tissues were disrupted using Qiagen Tissue Lyser II at a frequency of 27.5 $s^{-1}$ for 10 minutes. Tubes were centrifuged at 1500 rpm for 8 minutes at 4° C. and the supernatants were collected into 96-well plates. Colon homogenates were subjected to Bradford protein assay using protein assay dye (BioRad, Cat #500-0006) to quantify the total protein content. Myeloperoxidase (MPO) activity in the colon homogenates was measured using mouse MPO ELISA Kit (Hycult Biotech, Cat #HK210-02) according to manufacturer's instructions. Data analysis was performed using GraphPad Prism™ software. MPO levels were normalized to total protein content.

Measurement of cytokines in colon homogenates. Cytokine concentrations in the colon homogenates were measured using a Proinflammatory Panel 1 (mouse) multiplex immunoassay kit (MesoScale Discovery, Cat #K15048D) according to manufacturer's instructions. In brief, 50 L/well of calibrators and samples (diluted in Diluent 41) were added to the plates pre-coated with capture antibodies and incubated at room temperature while shaking at 700 rpm for 2 hours. The plates were then washed 3 times with 1×PBS containing 0.05% (w/v) Tween-20, followed by the addition of 25 μL of Detection Antibody Solution diluted in Diluent 45. After 2-hour incubation at room temperature while shaking, the plates were washed 3 times, and 150 μL of 2× Read Buffer was added to each well. Electrochemiluminescence was immediately read on a MSD Spector® instrument. Data analysis was performed using GraphPad Prism™ software. Cytokine levels were normalized to total protein content.

Statistical analysis. Statistical significance within the groups was determined by one-way Anova with Tukey's multiple comparison post-test ($^{\#}$, *p<0.01; $^{\#\#}$, p<0.001; $^{190\ \#\#}$, *p<0.001; $^{\#\#\#\#}$, ****p<0.0001).

Results Summary and Conclusions

Anti-human IL-36R monoclonal antibodies inhibit acute skin inflammation in DITRA-like mice at prophylactic dosing. To examine the role of IL-36R in skin inflammation, two anti-human IL-36R monoclonal antibodies, H4H14706P2 and H4H14708P2, were tested in IMQ-induced model of psoriasiform dermatitis that closely resembles human psoriasis lesions in terms of the phenotypic and histological characteristics (van der Fits et al., Imiquimod-induced psoriasis-like skin inflammation in mice is mediated via the IL-23/IL-17 axis, J Immunol 2009, 182:5836-5845; Swindell et al., Genome-wide expression profiling of five mouse models identifies similarities and differences with human psoriasis, PLoS One 2011, 6: e18266; Okayasu et al., A novel model in the induction of reliable experimental and chronic ulcerative colitis in mice, Gastroenterology 1990, 98:694-702). IMQ was applied daily to the shaved back skin of DITRA-like mice for four consecutive days. H4H14706P2 and H4H14708P2 antibodies were administered at 10 mg/kg and 1 mg/kg on −3d and d1. Control groups received PBS and hIgG4 Isotype control injections at 10 mg/kg. On d4, skin thickness was measured and tissue harvested for subsequent histopathological evaluation and protein isolation. Both H4H14706P2 and H4H14708P2 antibodies significantly decreased IMQ-induced skin thickness in a dose dependent manner compared to Isotype control (Table 5-1). Histopathological evaluation of the skin lesions revealed a significant reduction in total pathology score including parakeratosis and Munro's microabscess with anti-human IL-36R antibody treatment (Table 5-2).

TABLE 5-1

Anti-human IL-36R antibodies reduced skin thickness in acute IMQ-induced skin inflammation. Thickness is presented in μm. Statistical significance within the groups was determined by one-way Anova with Tukey's multiple comparison post-test and standard error of mean (SEM±) calculated: $^{\#}$significantly different from Vaseline-treated group; *significantly different from PBS- and Isotype-treated groups. N = 9/group.

| Vaseline | | IMQ | | | | |
|---|---|---|---|---|---|---|
| | | H4H14706P2 | | H4H14706132 | | hIgG4 Isotype |
| PBS | PBS | 1 mg/kg | 10 mg/kg | 1 mg/kg | 10 mg/kg | 10 mg/kg |
| 496.7 ± 8.8 | 825 ± 30$^{\#\#\#\#}$ | 674.4 ± 56* | 546.7 ± 30.3 | 624.4 ± 67* | 586.7 ± 53**** | 822 ± 29.6$^{\#\#\#\#}$ | p value:
$^{\#}$, *p < 0.01;
$^{\#\#}$, **p < 0.001;
$^{\#\#\#}$, ***p < 0.001;
$^{\#\#\#\#}$, ****p < 0.0001

TABLE 5-2

Anti-human IL-36R antibodies reduced skin thickness in acute IMQ-induced skin inflammation. Statistical significance within the groups was determined by one-way Anova with Tukey's multiple comparison post-test and standard error of mean (SEM±) calculated: #significantly different from Vaseline-treated group; *significantly different from PBS- and Isotype-treated groups. N = 9/group.

| Vaseline | IMQ | | | | | |
|---|---|---|---|---|---|---|
| | | H4H14706P2 | | H4H14708P2 | | hIgG4 Isotype |
| PBS | PBS | 1 mg/kg | 10 mg/kg | 1 mg/kg | 10 mg/kg | 10 mg/kg |
| 0 | 20.3 ± 3#### | 17.1 ± 2.4 | 7 ± 3.6**** | 14.2 ± 2* | 8.9 ± 2.4**** | 20.6 ± 1.7#### | p value:
, *p < 0.01;
, **p < 0.001;
, ***p < 0.001;
, ****p < 0.0001

TABLE 5-3 hIL-36R antagonism significantly reduced pro-inflammatory cytokines in IMQ-treated skin of DITRA-like mice (acute skin inflammation model). Cytokine levels in PBS/Vaseline control groups were subtracted from all the treatment groups. Statistical significance within the groups was determined by one-way Anova with Tukey's multiple comparison post-test and standard error of mean (SEM±) calculated: *significantly different from PBS- and Isotype-treated groups. N = 9/group.

| Cytokines (pg per mg of total protein) | IMQ | | | | | |
|---|---|---|---|---|---|---|
| | | H4H14706P2 | | H4H14708P2 | | hIgG4 Isotype |
| | PBS | 1 mg/kg | 10 mg/kg | 1 mg/kg | 10 mg/kg | 10 mg/kg |
| KC-GRO | 122.5 ± 31.5 | 41.5 ± 12.4**** | 13.7 ± 4.3**** | 35.2 ± 16.7**** | 32.3 ± 23.5**** | 80.4 ± 12.9 |
| IL-6 | 134.8 ± 13 | 31.9 ± 12.4**** | 18.8 ± 8.4**** | 42.6 ± 17.7**** | 37.8 ± 26.9**** | 143.5 ± 57.5 |
| IL-1β | 84.4 ± 15.2 | 18.5 ± 10.1**** | 4.9 ± 3.7**** | 17.5 ± 13.8**** | 7.4 ± 5.6**** | 68.1 ± 15.1 |
| THF-α | 87.8 ± 6.5 | 23.6 ± 7.4** | 8.2 ± 3.7 | 18.9 ± 8 | 9.5 ± 4.4** | 80.3 ± 15.8 | p value:
, *p < 0.01;
, **p < 0.001;
, ***p < 0.001;
, ****p < 0.0001

Anti-human IL-36R monoclonal antibodies Inhibit chronic skin inflammation at therapeutic dosing. To further examine the therapeutic efficacy of hIL-36R antagonism in vivo, anti-human IL-36R antibodies were tested in chronic IMQ-induced model of skin inflammation. For the duration of two weeks, IMQ was applied to the shaved back skin of DITRA-like mice for nine days separated by two days without the application. H4H14706P2 and H4H14708P2 antibodies were administered subcutaneously at d4 and d8 at 10 mg/kg dose. Control groups received PBS and hIgG4 Isotype control injections at 10 mg/kg. On d11 skin thickness was measured and tissue harvested for subsequent histopathological evaluation and protein isolation. As shown in Tables 5-4 and 5-5, H4H14706P2 and H4H14708P2 antibodies showed significant and comparable efficacy in reducing IMQ-induced skin thickness and pathology lesion scores in DITRA-like mice. Therapeutic administration of H4H14706P2 and H4H14708P2 led to a significant inhibition of IMQ-induced production of pro-inflammatory cytokines in the skin of DITRA-like mice (Table 5-6).

TABLE 5-4

Therapeutic administration of anti-human IL-36R antibodies reduced skin thickness in chronic IMQ-induced skin inflammation. Thickness is presented in μm. Statistical significance within the groups was determined by one-way Anova with Tukey's multiple comparison post-test and standard error of mean (SEM±) calculated: #significantly different from Vaseline-treated group; *significantly different from PBS- and Isotype-treated groups. N = 9/group.

| Vaseline | IMQ | | | |
|---|---|---|---|---|
| PBS | PBS | H4H14706P2 | H4H14708P2 | hIgG4 Isotype |
| 505 ± 70 | 953 ± 74#### | 667 ± 50** | 674 ± 38** | 951 ± 56.7#### | p value: #,*p < 0.01; ##,p < 0.001; ###,*p < 0.001; ####,****p < 0.0001

TABLE 5-5

Therapeutic administration of anti-human IL-36R antibodies reduced total pathology score in chronic IMQ-induced skin inflammation. Statistical significance within the groups was determined by one-way Anova with Tukey's multiple comparison post-test and standard error of mean (SEM±) calculated: #significantly different from Vaseline-treated group; *significantly different from PBS- and Isotype-treated groups. N = 9/group.

| Vaseline | IMQ | | | |
|---|---|---|---|---|
| PBS | PBS | H4H14706P2 | H4H14708P2 | hIgG4 Isotype |
| 0 | 17.2 ± 2.9#### | 12.5 ± 2.2* | 9.6 ± 1.9*** | 18 ± 2.7#### | p value: #,*p < 0.01; ##,p < 0.001; ###,*p < 0.001; ####,****p < 0.0001

TABLE 5-6 hIL-36R antagonism significantly inhibited pro-inflammatory cytokines in chronic IMQ-induced skin inflammation. Cytokine levels in PBS/Vaseline control groups were subtracted from all the treatment groups. Statistical significance within the groups was determined by one-way Anova with Tukey's multiple comparison post-test and standard error of mean (SEM±) calculated: *significantly different from PBS- and Isotype-treated groups. N = 9/group.

| | IMQ | | | |
|---|---|---|---|---|
| | PBS | H4H14706P2 | H4H14708P2 | hIgG4 Isotype |
| KC-GRO | 4.5 ± 1.7 | 0.6 ± 0.3**** | 0.8 ± 0.4**** | 4.4 ± 2.9 |
| IL-6 | 21.1 ± 6.7 | 5.1 ± 1**** | 6.8 ± 1.4**** | 22.9 ± 13.9 |
| IL-1β | 29.4 ± 11.6 | 1.8 ± 0.9**** | 1.9 ± 0.7**** | 23.6 ± 19.4 |
| TNF-α | 12 ± 2.7 | 2.1 ± 0.8** | 1.8 ± 0.4** | 14.4 ± 9.3 | p value: #,*p < 0.01; ##,p < 0.001; ###,*p < 0.001; ####,****p < 0.0001

Altogether, these data demonstrated prophylactic and therapeutic efficacy of anti-human IL-36R antibodies in ameliorating IMQ-induced skin inflammation in vivo. H4H14706P2 and H4H14708P2 antibodies displayed comparable ability to significantly reduce both acute and chronic IMQ-induced skin pathology in DITRA-like mice.

Anti-human IL-36R monoclonal antibodies ameliorate DSS-Induced chronic colitis in DITRA-like mice at therapeutic dosing. To explore the role of IL-36R antagonism in intestinal inflammation, a chemical model of intestinal injury was used. This model utilized oral administration of DSS that damaged the colonic epithelium (Okayasu et al., A novel model in the induction of reliable experimental and chronic ulcerative colitis in mice, Gastroenterology 1990, 98:694-702) and triggered potent inflammatory responses (Rakoff-Nahoum et al., Recognition of commensal microflora by toll-like receptors is required for intestinal homeostasis. Cell 2004, 118: 229-241) exhibiting the main features of IBD—in particular ulcerative colitis. DITRA-like mice were subjected to chronic DSS-induced colitis by administration of 2-3% DSS for 7 days followed by 10 days of water for two cycles. H4H14706P2 and H4H14708P2 antibodies were administered at 10 mg/kg and 5 mg/kg bi-weekly starting on d7. Control groups received PBS and hIgG4 Isotype control intraperitoneal injections at 10 mg/kg. To monitor intestinal inflammation at different stages of the disease, feces from individual mice were collected on a weekly basis to measure fecal Lipocalin-2 (Lcn2) protein, a non-invasive biomarker of inflammation in intestinal injury (Thorsvik et al., Fecal neutrophil gelatinase-associated lipocalin as a biomarker for inflammatory bowel disease. J Gastroenterol Hepatol 2017, 32:128-135). As shown in Table 5-7, PBS- and hIgG4-treated groups displayed significant upregulation of fecal Lcn2 levels on d12, 19 (not shown) and 28 compared to water alone. On the contrary, two therapeutic administrations of H4H14706P2 and H4H14708P2 resulted in a significant reduction in Lcn2 levels in a dose-dependent manner on d12 compared to PBS- and Isotype-treated groups. Sustained reduction of fecal Lcn2 levels was observed in anti-human IL-36 antibody-treated groups at d19 (not shown) and d28 supporting a role for anti-IL-36R antibodies in reducing intestinal inflammation in DITRA-like mice (Table 5-7). H4H14706P2 antibody displayed better ability to reduce Lcn2 levels and, thus, intestinal inflammation, compared to H4H14708P2 (Table 5-7).

TABLE 5-7 hIL-36R antagonism significantly reduced fecal Lcn2 levels in DITRA-like mice in chronic DSS-induced colitis. Statistical significance within the groups was determined by one-way Anova with Tukey's multiple comparison post-test and standard error of mean (SEM±) calculated: #significantly different from water-treated group; *significantly different from PBS and Isotype-treated groups. N = 6-8/group.

| Water | | | DSS | | | | | |
|---|---|---|---|---|---|---|---|---|
| | | | | Day 12 | | | | |
| | | | | H4H14706P2 | | H4H14708P2 | | hIg4 Isotype |
| d0 | d28 | d0 | PBS | 10 mg/kg | 5 mg/kg | 10 mg/kg | 5 mg/kg | 10 mg/kg |
| 0 | 0 | 0 | 1502 ± 525#### | 332 ± 107**** | 544 ± 153**** | 698 ± 272* | 791 ± 5.7 | 1879 ± 138#### |
| | | | | DSS Day 28 | | | | |
| | | | | H4H14706P2 | | H4H14708P2 | | hIg4 Isotype |
| | | | PBS | 10 mg/kg | 5 mg/kg | 10 mg/kg | 5 mg/kg | 10 mg/kg |
| | | | 1379 ± 390#### | 325 ± 134** | 373 ± 217* | 635 ± 141 | 600 ± 23* | 1448 ± 386#### | p value:
, *p < 0.01;
, **p < 0.001;
, ***p < 0.001;
, ****p < 0.0001 hIL-36R blockade with H4H14706P2 and H4H14708P2 antibodies led to a decrease in MPO activity (Table 5-8) and 61-95% reduction in pro-inflammatory cytokines (Table 5-9) in the colon DSS-treated DITRA-like mice.

TABLE 5-8

Therapeutic administration of anti-human IL-36R antibodies decreased MPO activity in the colon of DSS-treated DITRA-like mice. MPO levels are presented as ng per mg of total protein. Statistical significance within the groups was determined by one-way Anova with Tukey's multiple comparison post-test and standard error of mean (SEM±) calculated: #significantly different from water-treated group; *significantly different from PBS- and Isotype-treated groups. N = 6-8/group.

| Water | | DSS | | | | |
|---|---|---|---|---|---|---|
| | | H4H14706P2 | | H4H14708P2 | | hIgG4 Isotype |
| PBS | PBS | 10 mg/kg | 5 mg/kg | 10 mg/kg | 5 mg/kg | 10 mg/kg |
| 0 | 69 ± 91#### | 6.1 ± 2.3* | 20.5 ± 6.1* | 29.6 ± 7.5 | 23.5 ± 12.7 | 64.7 ± 5.6### | p value:
, *p < 0.01;
, **p < 0.001;
, ***p < 0.001;
, ****p < 0.0001

TABLE 5-9

Therapeutic administration of anti-human IL-36R antibodies decreased pro inflammatory cytokines in the colon of DSS-treated DITRA-like mice. MPO levels are presented as no per mg of total protein. Statistical significance within the groups was determined by one-way Anova with Tukey's multiple comparison post-test and standard error of mean (SEM±) calculated: #significantly different from water-treated group: * significantly different from PBS- and Isotype-treated groups. N = 6-8/group.

| Cytokines (pg per mg of total protein) | Water | DSS | | | | | |
|---|---|---|---|---|---|---|---|
| | | | H4H14706P2 | | H4H14708P2 | | hIgG4 Isotype |
| | PBS | PBS | 10 mg/kg | 5 mg/kg | 10 mg/kg | 5 mg/kg | 10 mg/kg |
| KC-GRO | 0.54 ± 0.3 | 98 ± 30#### | 14.7 ± 3*** | 22.9 ± 8** | 38.2 ± 26* | 26.4 ± 0.7* | 110 ± 12### |
| IL-6 | 0.69 ± 0.2 | 345 ± 155#### | 17.1 ± 6**** | 93 ± 75** | 69 ± 11*** | 59 ± 3.4*** | 627 ± 250### |
| IL-1β | 1.2 ± 0.3 | 128 ± 17#### | 13.4 ± 6*** | 27 ± 11** | 42 ± 46* | 34 ± 11* | 125 ± 22### |
| THF-α | 0.98 ± 0.3 | 74 ± 14#### | 9.2 ± 4.7** | 16 ± 8.8 | 7.7 ± 4 | 4.3 ± 2.1** | 28 ± 15### | p value:
, *p < 0.01;
, **p < 0.001;
, ***p < 0.001;
, ****p < 0.0001

Consistent with observations of more reduced Lcn2 levels, H4H14706P2 antibody displayed superior efficacy in reducing MPO activity and pro-inflammatory cytokines in the colon compared to H4H14708P2.

Example 6. Epitope Mapping of H4H14706P2, H4H14708P2, and H4H14731P Binding to IL-36R by Hydrogen Deuterium Exchange Hydrogen Deuterium exchange epitope mapping with mass spectrometry (HDX-MS) was performed to determine the amino acid residues of IL-36R (a recombinant human IL-36R designated as hIL-36R.mmH and having the amino acid sequence as set forth in SEQ ID NO: 227) interacting with H4H14706P2, H4H14708P2, and H4H14731P (anti-hIL-36R monoclonal antibodies). A general description of the H/D exchange method is set forth in e.g., Ehring (1999) Analytical Biochemistry 267(2):252-259; and Engen and Smith (2001) Anal. Chem. 73:256A-265A.

The HDX-MS experiments were performed on an integrated HDX/MS platform, consisting of a Leaptec HDX PAL system for the deuterium labeling and quenching, a Waters Acquity M-Class (Auxiliary solvent manager) for the sample digestion and loading, a Waters Acquity M-Class (μBinary solvent manager) for the analytical gradient, and Thermo Q Exactive HF mass spectrometer for peptide mass measurement.

The labeling solution was prepared as PBS buffer in $D_2O$ at pD 7.0 (10 mM phosphate buffer, 140 mM NaCl, and 3 mM KCl, equivalent to pH 7.4 at 25° C.). For deuterium labeling, 11 μL of IL-36R.mmH (REGN2105, 45.6 μM in H4H14706P2 and H4H14708P2 experiments, or 63.3 μM in H4H14731P experiment) or IL-36R.mmH premixed with H4H14706P2, H4H14708P2, or H4H14731P in 1:0.7 molar ratio (Ag-Ab complex) was incubated at 20° C. with 44 μL $D_2O$ labeling solution for various time-points in duplicate (e.g., Undeuterated control=0 second; deuterium-labeled for 5 minutes and 10 minutes). The deuteration reaction was quenched by adding 55 μL of pre-chilled quench buffer (0.5 M TCEP-HCl, 8 M urea and 1% formic acid) to each sample for a 5-minute incubation at 20° C. The quenched sample was then injected into a Waters HDX Manager for online pepsin/protease XIII digestion. The digested peptides were separated by a C8 column (1.0 mm×50 mm, NovaBioassays) with a 13-minute gradient from 10%-32% B (mobile phase A: 0.5% formic acid in water, mobile phase B: 0.1% formic acid in acetonitrile). The eluted peptides were analyzed by Q Exactive HF mass spectrometry in LC-MS/MS or LC-MS mode.

The LC-MS/MS data of undeuterated IL-36R sample were searched against a database including IL-36R and its randomized sequence using Byonic search engine (Protein Metrics). The search parameters (in ELN) were set as default using non-specific enzymatic digestion and human glycosylation as common variable modification. The list of identified peptides was then imported into the HDX Workbench software (version 3.3) to calculate the deuterium uptake of each peptide detected by LC-MS from all deuterated samples. For a given peptide, the centroid mass (intensity-weighted average mass) at each time point was used to calculate the deuterium uptake (D) and percentage of deuterium uptake (% D).

Deuterium Uptake($D$-uptake) = Average Mass (deuterated) − Average Mass (undeuterated)

Percentage of deuterium uptake(%$D$) = $\dfrac{D\text{-uptake for peptide at each time point} \times 100\%}{\text{Maximum } D\text{-uptake of the peptide(defined in } ELN)}$ A total of 163 peptides from REGN2105 (hIL-36R.mmH) were identified from both hIL-36R.mmH alone and hIL-36R.mmH in complex with H4H14706P2 samples, representing 81.5% sequence coverage of hIL-36R. Any peptide which exhibited a differential percent D-uptake value above 5% was defined as significantly protected. Peptides corresponding to amino acids 113-122 (YKQILHLGKD) (SEQ ID NO: 229) (amino acids 113-122 of SEQ ID NO: 227) on REGN2105 were significantly protected by H4H14706P2.

A total of 148 peptides from REGN2105 (hIL-36R.mmH) were identified from both hIL-36R.mmH alone and hIL-36R.mmH in complex with H4H14708P2 samples, representing 80.1% sequence coverage of hIL-36R. Any peptide which exhibited a differential percent D-uptake value above 5% was defined as significantly protected. Peptides corresponding to amino acids 113-122 (YKQILHLGKD) (SEQ ID NO: 229) (amino acids 113-122 of SEQ ID NO: 227) on REGN21R5 were significantly protected by H4H14708P2.

A total of 237 peptides from REGN2N15 (hIL-36R.mmH) were identified from both hIL-36R.mmH alone and hIL-36R.mmH in complex with H4H14731P samples, representing 88.2% sequence coverage of hIL-36R. Any peptide which exhibited a differential percent 0-uptake value above 5% was defined as significantly protected. Peptides corresponding to amino acids 264-277 (GVETHVSFREHNLY) (SEQ ID NO: 230) (amino acids 264-277 of SEQ ID NO: 227) on REGN2105 were significantly protected by H4H14731P.

TABLE 6-1

IL-36R.mmH peptides with significant protection upon binding to H4H14706P2

| | | 5 min | | | 10 min | | | |
|---|---|---|---|---|---|---|---|---|
| IL-36R Residues | Charge (+) | REGN2105 Centroid MH+ | REGN2105 + H4H14706P2 Centroid MH+ | ΔD | REGN2105 Centroid MH+ | REGN2105 + H4H14706P2 Centroid MH+ | ΔD | Δ% D |
| 113-119 | 2 | 918.84 | 918.60 | −0.24 | 918.97 | 918.71 | −0.26 | −6.2 |
| 113-122 | 1 | 1218.76 | 1218.29 | −0.47 | 1218.91 | 1218.45 | −0.46 | −7.2 |
| 113-122 | 2 | 1219.97 | 1219.52 | −0.45 | 1220.10 | 1219.66 | −0.44 | −6.9 |
| 116-119 | 1 | 497.13 | 497.01 | −0.12 | 497.19 | 497.03 | −0.17 | −8.9 |
| 116-122 | 1 | 798.29 | 797.98 | −0.31 | 798.35 | 797.99 | −0.35 | −8.3 |

TABLE 6-2

IL-36R.mmH peptides with significant protection upon binding to H4H14708P2

| | | 5 min | | | 10 min | | | |
|---|---|---|---|---|---|---|---|---|
| IL-36R Residues | Charge (+) | REGN2105 Centroid MH+ | REGN2105 + H4H14708P2 Centroid MH+ | ΔD | REGN2105 Centroid MH+ | REGN2105 + H4H14708P2 Centroid MH+ | ΔD | Δ% D |
| 113-119 | 2 | 918.84 | 918.59 | −0.25 | 918.97 | 918.69 | −0.28 | −6.6 |
| 113-122 | 1 | 1218.73 | 1218.13 | −0.61 | 1218.90 | 1218.31 | −0.58 | −9.3 |
| 113-122 | 2 | 1219.97 | 1219.51 | −0.46 | 1220.10 | 1219.58 | −0.51 | −7.6 |
| 116-119 | 1 | 497.13 | 497.01 | −0.12 | 497.19 | 497.03 | −0.17 | −9.0 |
| 116-122 | 1 | 798.29 | 797.90 | −0.39 | 798.35 | 797.93 | −0.42 | −10.1 |

TABLE 6-3

IL-36R.mmH peptides with significant protection upon binding to H4H14731P

| IL-36R Residues | Charge (+) | 5 min | | | 10 min | | | |
|---|---|---|---|---|---|---|---|---|
| | | REGN2105 Centroid MH⁺ | REGN2105 + H4H14731P Centroid MH⁺ | ΔD | REGN2105 Centroid MH⁺ | REGN2105 + H4H14731P Centroid MH⁺ | ΔD | Δ% D |
| 264-271 | 2 | 880.18 | 879.93 | −0.24 | 880.24 | 879.91 | −0.32 | −5.9 |
| 267-271 | 1 | 592.76 | 592.58 | −0.18 | 592.78 | 592.56 | −0.23 | −8.5 |
| 268-271 | 1 | 491.44 | 491.23 | −0.21 | 491.47 | 491.22 | −0.25 | −14.4 |
| 268-276 | 3 | 1144.59 | 1144.25 | −0.34 | 1144.60 | 1144.21 | −0.39 | −6.6 |
| 268-277 | 3 | 1307.97 | 1307.56 | −0.41 | 1308.01 | 1307.48 | −0.53 | −7.3 |
| 271-276 | 2 | 818.86 | 818.67 | −0.19 | 818.86 | 818.63 | −0.23 | −6.5 |

Amino acid sequence of recombinant human IL-36R (IL1RL2; interleukin 1 receptor-like 2; REGN2105) (hIL36R.mmH): Monomeric human IL-36R (amino acids D20-Y337, Accession #Q9HB29), with a C-terminal myc-myc-hexahistidine (mmH) tag (underlined):

(SEQ ID NO: 227)
DGCKDIFMKNEILSASQPFAFNCTFPPITSGEVSVTWYKNSSKIPVSKII

QSRIHQDETWILFLPMEWGDSGVYQCVIKGRDSCHRIHVNLTVFEKHWCD

TSIGGLPNLSDEYKQILHLGKDDSLTCHLHFPKSCVLGPIKWYKDCNEIK

GERFTVLETRLLVSNVSAEDRGNYACQAILTHSGKQYEVLNGITVSITER

AGYGGSVPKIIYPKNHSIEVLQLGTTLIVDCNVTDTKDNTNLRCWRVNNT

LVDDYYDESKRIREGVETHVSFREHNLYTVNITFLEVKMEDYGLPFMCHA

GVSTAYIILQLPAPDFRAY<u>EQKLISEEDLGGEQKLISEEDLHHHHHH</u>.

Example 7: In Vivo Evaluation of Anti-IL36R in IMQ-Induced and Oxazolone-Induced Skin Inflammation and Chronic Colitis Mouse Models The anti-human IL-36R monoclonal antibodies of the present invention were tested in primary human cell assays in vitro; and compared with other anti-human IL-36R monoclonal antibodies in in vivo Imiquimod (IMQ)-induced skin inflammation assays in humanized IL-36R/hIL-36α, β, γ mice. Also, the anti-human IL-36R monoclonal antibodies of the present invention were tested in vivo in an oxazolone-induced model of colitis in humanized IL-36R/hIL-36α, β, γ mice.

IL-8 was detected in culture supernatants using DuoSet ELISA kit for Human CXCL8/IL-8 (R&D Systems) and cytokine was detected in skin and colon homogenates using Proinflammatory Panel 1 (mouse and human) Multiplex Immunoassay kit (MSD). Monoclonal antibodies tested were H4H14706P2, H4H14708P2, APE6155 (IgG4) and a human IgG4 isotype control (REGN1002).

The APE6155 heavy chain (comprising an IgG4 constant domain) comprises the amino acid sequence:

(SEQ ID NO: 239)
QVQLVQSGAEVKKPGASVKVSCKASGYTFTNYWMNWVRQAPRQGLEWMGM

FHPTGDVTRLNQKFKDRVTMTRDTSTSTVYMELSSLRSEDTAVYYCARTT

SMIIGGFAYWGQGLTVTVSSASTKGPSVFPLAPCSRSTSESTAALGCLVK

DYFPEPVTVSWNSGALTSGVHTFAPVLQSSGLYSLSSVVTVPSSSLGTKT

YTCNVDHKPSNTKVDKRVESKYGPPCPPCPAPPVAGPSVFLFPPKPKDTL

MISRTPEVTCVVVDVSQEDPEVQFNWYVDGVEVHNAKTKPREEQFNSTYR

VVSVLTVLHQDWLNGKEYKCKVSNKGLPSSIEKTISKAKGQPREPQVYTL

PPSQEEMTKNQVSLTCLVKGFYPSDIAVEWESNGQPENNYKTTPPVLDSD

GSFFLYSRLTVDKSRWQEGNVFSCSVMHEALHNHYTQKSLSLSLGK

The APE6155 light chain (comprising a Kappa constant domain) comprises the amino acid sequence:

(SEQ ID NO: 240)
DIVMTQTPLSLSVTPGQPASISVRSSKSLLHRNAITYFYWYLHKPGQPPQ

LLIYQMSNLASGVPDRFSGSGSGTDFTLKISRVEAEDVGVYYCAQNLELP

LTFGGGTKVEIKRTVAAPSVFIFPPSDEQLKSGTASVVCLLNNFYPREAK

VQWKVDNALQSGNSQESVTEQDSKDSTYSLSSTLTLSKADYEKHKVYACE

VTHQGLSSPVTKSFNRGEC

See WO2016/168542.

Testing anti-human IL-36R antibodies in vitro in primary human cells assays in vitro. Normal Human Epidermal Keratinocytes (NHLF: Lonza, Cat #00192627, lot #254498) and Intestinal MyoFibroblast (InMyoFib; Lonza, Cat #CC-2902, lot #0000254498) were cultured in vitro for 4-5 passages in KGM-Gold™ supplemented with BulletKit™ (Lonza, Cat #CC-00192060, lot #0000484385) and SmGm™-2 supplemented with BulletKit™ (Lonza, Cat #CC-3182, lot #00004736694), respectively. Human CD14+ monocytes were isolated from peripheral blood of 3 different donors using EasySep Human Monocyte Isolation Kit (StemCell, Cat #19359) per manufacturer's instructions. A day before the assay, primary human cells were plated in corresponding Media at 10000 per well in 96-well flat bottom plate and incubated overnight at 37° C. Cells were stimulated in the presence of constant concentration (10 nM) or serially diluted (starting from 1500 nM) rhIL-36α/IL-1F6 [aa6-158] (R&D Systems, Cat #6995-IL-010/CF, lot #DAFZ0313051), rhIL-36β/IL-1F8 [aa5-157] (R&D Systems, Cat #6834-IL-010/CF, lot #DAKU0514062 and rhIL-36γ/IL-1F9 [aa18-169] (R&D Systems, Cat #6835-IL-010/CF, lot #DAPK0215011) alone or in combination. Serial dilutions starting from 2400 nM of anti-human IL-36R antibodies were added to the wells. Plates were incubated for 24 hours at 37° C. and supernatants were collected to measure IL-8 using DuoSet ELISA Development System for Human CXCL8/IL-8 (R&D Systems, Cat #DY208-05, lot #325963). To obtain $EC_{50}$ and $IC_{50}$ values, the results were analyzed using nonlinear regression (4-parameter logistics) in GraphPad Prism™ software.

Testing and comparing anti-human IL-36R antibodies in IMQ-induced skin inflammation. To induce skin inflammation, 8-10 weeks old humanized DITRA-like female mice had their back hair shaved using mouse hair trimmer (Oster, MiniMax, Cat #78049-100) and skin depilated with 0.5 g Veet hair removal gel three days prior to IMQ cream application. A daily topical dose of 62.5 mg of commercially available IMQ cream (5%) (Aldara, GM Health Care Limited, NDC 99207-206-12, lot #QJ044A) or Vaseline (CVS Pharmacy, NDC 59779-902-88) was applied on the shaved back skin of the mice for four consecutive days. A daily topical dose of 62.5 mg of Aldara translated into a daily dose of 3.125 mg of an active compound. Anti-human IL-36R antibodies—H4H14706P2, H4H14708P2 and APE6155 (IgG4), were administered subcutaneously into back skin at 10 mg/kg on −3 d and d1. Control group received PBS and 10 mg/kg of hIgG4 Isotype control (REGN1002) injections. Two or three days after the start of IMQ application, the back skin of the mice started to display signs of erythema, scaling and thickening. The severity of inflammation was measured on a daily basis using an adapted version of the clinical Psoriasis Area and Severity Index. Erythema, scaling and thickening were scored independently on a scale from 0-4: 0, none; 1, slight; 2, moderate; 3, marked; and 4, very marked (van der Fits et al. Imiquimod-induced psoriasis-like skin inflammation in mice is mediated via the IL-23/IL-17 axis. J Immunol 2009, 182:5836-5845). Skin thickness was measured using caliper on d5 (Kaefer).

Histopathology. Skin tissues of 6 mm diameter from murine back were fixed in 10% buffered formalin, and 4-5 μm paraffin embedded sections were stained with hematoxylin and eosin. Skin sections were evaluated blindly for the presence of parakeratosis, orthokeratosis, Munro's microabscess, acanthosis, epidermal ulceration, inflammation in the dermis and hypodermis, blood vessel congestion in the dermis and hypodermis, follicular hyperkeratosis and epithelial hyperplasia. A 0-4 scoring scale was used: 0-within normal limits, 1-minimal, 2-mild, 3-moderate and 4-severe. A total pathology score was calculated for each mouse by adding the individual histopathological feature scores. Data analysis was performed using GraphPad Prism™ software.

Measurement of cytokines in skin homogenates. Full thickness skin tissues of 6 mm diameter from murine back were taken and placed in 15 mL tube containing T-per buffer (Thermo Scientific, Cat #378510, lot #RF236217), 1× Halt Protease Inhibitor Cocktail (Thermo Scientific, Cat #87786, lot #QG221763) and 5 M EDTA Solution (Thermo Scientific, Cat 3 78429). Skin tissues were disrupted at 28000 rpm for 1 minute using a Polytron (PT10-35 GT-D, Cat #9158158) and put on ice. Generated skin homogenates were centrifuged at 1500 rpm for 8 minutes at 4° C. and the supernatants were collected into 96-well plates. Skin homogenates were subjected to Bradford protein assay using protein assay dye (BioRad, Cat #500-0006, lot #210008149) to quantify the total protein content. Cytokine concentrations in the skin homogenates were measured using a Proinflammatory Panel 1 (mouse) multiplex immunoassay kit (MesoScale Discovery, Cat #K15048D) according to manufacturer's instructions. In brief, 50 μL/well of calibrators and samples (diluted in Diluent 41) were added to the plates pre-coated with capture antibodies and incubated at room temperature while shaking at 700 rpm for 2 hours. The plates were then washed 3 times with 1×PBS containing 0.05% (w/v) Tween-20, followed by the addition of 25 μL of Detection Antibody Solution diluted in Diluent 45. After 2-hours incubation at room temperature while shaking, the plates were washed 3 times, and 150 μL of 2× Read Buffer was added to each well. Electrochemiluminescence was immediately read on a MSD Spector® instrument. Data analysis was performed using GraphPad Prism™ software. Cytokine levels were normalized to total protein content.

Testing anti-human IL-36R monoclonal antibodies in oxazolone-induced intestinal inflammation—Induction of oxazolone-induced model of chronic colitis and antibody treatment in DITRA-like mice. Oxazolone colitis was induced as previously described (Heller et al., Oxazolone colitis, a Th2 colitis model resembling ulcerative colitis, is mediated by IL-13-producing NK-T cells. Immunity 2002, 17: 629-638). Briefly, in order to pre-sensitize DITRA-like mice, a 2×2 $cm^2$ field of the abdominal skin was shaved, and 100 μl of a 3% solution oxazolone ((4-ethoxymethylene-2-phenyl-2-oxazoline-5-one; Sigma Aldrich) diluted in 100% ethanol was applied. On days 5 and 7 after pre-sensitization, mice were challenged intrarectally with 50 μl of 1.5% oxazolone diluted in 50% ethanol under general anesthesia. Control mice were pre-sensitized with 100% ethanol and received intrarectal injection of 50% ethanol. Anti-human IL-36R antibodies—H4H14706P2 and H4H14708P2, were administered intraperitoneally at 10 mg/kg on d2, 5 and 7. Control group received PBS and 10 mg/kg of hIgG4 Isotype control (REGN1002) injections. Mice were weighted and monitored for clinical signs of colitis (e.g., stool consistency and fecal blood) on a daily basis. On d8, mice were euthanized and colons were collected.

Measurement of cytokines in colon homogenates. Pieces of distal part of the colon were taken into 2 mL microcentrifuge tubes containing 2 Tungsten 3 mm Carbide Beads (Qiagen) containing T-per buffer (Thermo Scientific), 1× Halt Protease Inhibitor Cocktail (Thermo Scientific) and 5M EDTA Solution (Thermo Scientific). Colon tissues were disrupted using Qiagen Tissue Lyser II at frequency of 27.5 $s^{-1}$ for 10 minutes. Tubes were centrifuged at 1500 rpm for 8 minutes at 4° C. and the supernatants were collected into 96-well plates. All tissue homogenates were subjected to Bradford protein assay using protein assay dye (BioRad) to quantify the total protein content.

Cytokine concentrations in the colon homogenates were measured using a Proinflammatory Panel 1 (mouse) multiplex immunoassay kit (MesoScale Discovery Cat #K15048D) according to manufacturer's instructions. In brief, 50 μL/well of calibrators and samples (diluted in Diluent 41) were added to the plates pre-coated with capture antibodies and incubated at room temperature while shaking at 700 rpm for 2 hours. The plates were then washed 3 times with 1×PBS containing 0.05% (w/v) Tween-20, followed by the addition of 25 μL of Detection Antibody Solution diluted in Diluent 45. After 2-hour incubation at room temperature while shaking, the plates were washed 3 times, and 150 μL of 2× Read Buffer was added to each well. Electrochemiluminescence was immediately read on MSD Spector® instrument. Data analysis was performed using GraphPad Prism™ software. Cytokine levels were normalized to total protein content.

Statistical analysis. Statistical significance within the groups was determined by one-way Anova with Tukey's multiple comparison post-test (*p<0.05, p<0.005, *p<0.0005, ****p<0.00001).

Results summary and conclusions—Anti-human IL-36R monoclonal antibodies potently inhibit human IL-36R signaling in primary human cells in vitro. Human Epidermal Keratinocytes (NHEK), Human Intestinal Myofibroblasts (InMyoFib) and Peripheral Blood (PB)-derived CD14+ Monocytes were stimulated in vitro with 10 nM of IL-36α, β and γ. Serially diluted anti-human IL-36R monoclonal antibodies (H4H14706P2 and H4H14708P2) were added to the cultures, supernatants were collected 24 hours post-incubation and human IL-8 production in response to IL-36 stimulation was measured. The anti-human IL-36R monoclonal antibodies potently inhibit all three IL-36 cytokines in Human Epidermal Keratinocytes, Human Intestinal Myofibroblasts and Peripheral Blood (PB)-derived CD14+ Monocytes in vitro with $IC_{50}$ 1-6 nM (Table 7-1).

bodies displayed greater potency in significantly decreasing IMQ-induced skin thickness compared to APE6155 (Table 7-2). Histopathological evaluation of the skin lesions revealed a greater reduction in total pathology score including parakeratosis and Munro's microabscess with anti-human IL-36R antibodies treatments (Table 7-3).

TABLE 7-2

Anti-human IL-36R antibodies, H4H14706P2 and H4H14708P2, are more potent than APE6155 anti-human IL-36R antibody in reducing skin thickness in IMQ-induced skin inflammation.¯

| Vaseline | IMQ | | | | |
|---|---|---|---|---|---|
| PBS | PBS | H4H14706P2 | H4H14708P2 | APE6155 | hIgG4 Isotype |
| 607 ± 18 | 748 ± 45 | 586 ± 34** | 585 ± 24** | 689 ± 81 | 740 ± 42.5 |

¯Thickness is presented in μm. Statistical significance within the groups was determined by one-way Anova with Tukey's multiple comparison post-test and standard error of mean (SEM±) calculated: *significantly different from PBS- and Isotype-treated groups. n = 9/group.

TABLE 7-1

Anti-human IL-36R antibodies, H4H14706P2 and H4H14708P2, inhibited human IL-36α, β and γ in human primary cells in vitro.

| Cells | Normal Epidermal Keratinocytes (NHEK) | | | Intestinal MyoFibroblasts (InMyoFib) | | | PB-derived CD14+ Monocytes | | |
|---|---|---|---|---|---|---|---|---|---|
| hIL-36 Ligands | α | β | γ | α | β | γ | α | β | γ |
| EC50[M] | 1.43E−09 | 1.18E−09 | 4.00E−09 | 1.41E−09 | 1.18E−09 | 1.46E−09 | 2.75E−09 | 2.63E−09 | 2.75E−09 |
| Constant for Inhibition | 10 nM | 10 nM | 10 nM | 10 nM | 10 nM | 10 nM | 10 nM | 10 nM | 10 nM |
| Protein/hIL-36R ab | IC50 [M] | IC50 [M] | IC50 [M] | IC50 [M] | IC50 [M] | IC50 [M] | IC50 [M] | IC50 [M] | IC50 [M] |
| H4H14706P2 | 4.42E−09 | 3.62E−09 | 2.11E−09 | 4.89E−09 | 3.62E−09 | 4.59E−09 | 1.15E−09 | 1.74E−09 | 1.58E−09 |
| H4H14708P2 | 5.06E−09 | 5.79E−09 | 3.63E−09 | 5.72E−09 | 5.3E−09 | 5.40E−09 | 2.38E−09 | 2.24E−09 | 1.95E−09 |
| hIgG Ctr (REGN1002) | None | None | None | None | None | None | None | None | None |

Anti-human IL-36R monoclonal antibodies H4H14706P2 and H4H14708P2 are more potent than the APE6155 antibody in Inhibiting IMQ-induced skin inflammation in DITRA-like mice. H4H14706P2 and H4H14708P2 and APE6155 anti-human IL-36R monoclonal antibodies were tested head-to-head in IMQ-induced model of psoriasiform dermatitis. IMQ was applied daily to the shaved back skin of DITRA-like mice for four consecutive days. H4H14706P2 and H4H14708P2 and APE6155 antibodies were administered at 10 mg/kg on −3 d and d1. Control groups received PBS and hIgG4 Isotype control injections at 10 mg/kg. On d5, skin thickness was measured and tissue harvested for subsequent histopathological evaluation and protein isolation. Both H4H14706P2 and H4H14708P2 anti-

TABLE 7-3

Anti-human IL-36R antibodies, H4H14706P2 and H4H14708P2, displayed greater potency than APE6155 in reducing the total pathology score in IMQ-induced skin inflammation.$

| Vaseline | IMQ | | | | |
|---|---|---|---|---|---|
| PBS | PBS | H4H14706P2 | H4H14708P2 | APE6155 | hIgG4 Isotype |
| 2 ± 0.6 | 17 ± 2.5 | 11 ± 1.4*** | 11.6 ± 1.9** | 13.4 ± 3 | 16 ± 1.5 |

$Statistical significance within the groups was determined by one-way Anova with Tukey's multiple comparison post-test and standard error of mean (SEM±) calculated: *significantly different from PBS- and Isotype-treated groups. n = 9/group.

Additionally, human IL-36R blockade with H4H14706P2 and H4H14708P2 antibodies resulted in greater reduction in KC-GRO, IL-6, IL-1β and TNFα production in skin homogenates compared to COMP5382 (Table 7-4).

TABLE 7-4

Anti-human IL-36R antibodies, H4H14706P2 and H4H14708P2, displayed greater potency than APE6155 in reducing pro-inflammatory cytokines in the skin.[∞]

| Cytokines (pg per mg of total tissue) | IMQ | | | | |
|---|---|---|---|---|---|
| | PBS | H4H14706P2 | H4H14708P2 | APE6155 | hIgG4 Isotype |
| KC-GRO | 64 ± 10 | 19 ± 5.5** | 23 ± 7** | 40 ± 16 | 65 ± 22 |
| IL-6 | 160 ± 47 | 41 ± 14**** | 51 ± 16**** | 128 ± 59 | 165 ± 87 |
| IL-1β | 128 ± 43 | 8.6 ± 1.9**** | 10 ± 1.3**** | 28 ± 17**** | 117 ± 49 |
| TNF-α | 72 ± 22 | 11 ± 4.2* | 12 ± 2.9* | 20.5 ± 9.8 | 65 ± 22 |

[∞]Values are presented as "pg per mg of total tissue". Statistical significance within the groups was determined by one-way Anova with Tukey's multiple comparison post-test and standard error of mean (SEM±) calculated: *significantly different from PBS- and Isotype-treated groups. n = 9/group.

Anti-human IL-36R monoclonal antibodies ameliorate Oxazolone-Induced colitis in DITRA-like mice. To further explore biological function of IL-36 in the gut, we tested the efficacy of IL-36R blockade in oxazolone-induced colitis, another preclinical model of IBD with the histologic resemblance to human ulcerative colitis (Heller et al.). Prophylactic administration of anti-human IL-36R antibodies, H4H14706P2 and H4H14708P2, significantly reduced oxazolone-induced disease severity in DITRA-like mice compared to PBS and isotype control treated groups as reflected in levels of IL-4, IL-6 and TNF-α in the colon of oxazolone-treated DITRA-like mice (Table 7-5).

TABLE 7-5

Human IL-36R antagonism ameliorates oxazolone-induced colitis in DITRA-like mice in vivo.[♦]

| Cytokines (pg per mg of total tissue) | | Oxazolone | | | |
|---|---|---|---|---|---|
| | Vehicle | PBS | H4H14706P2 | H4H14708P2 | hIgG4 Isotype |
| IL-4 | 2 ± 0.4 | 509 ± 148 | 51.5 ± 28**** | 111 ± 35**** | 296 ± 106 |
| IL-6 | 34 ± 29 | 2128 ± 1255 | 198 ± 131** | 214 ± 116** | 2276 ± 1338 |
| TNF-α | 95 ± 36 | 822 ± 149 | 387 ± 126** | 569 ± 136 | 859 ± 148 |

[♦]DITRA-like mice were pre-sensitized with 3% solution of oxazolone dissolved in 100% Ethanol and intrarectally administered with 1.5% oxazolone and vehicle (50% Ethanol) 5 days later. Mice were intraperitoneally injected with PBS, anti-human IL-36R mAb and hIgG4 Isotype control on days 2, 5 and 7 after pre-sensitization. Levels of pro-inflammatory cytokines in colon homogenates in oxazolone- and vehicle-treated DITRA-like mice injected with PBS, anti-human IL-36R mAb and hIgG4 Isotype control. Values are presented as "pg per mg of total tissue". Statistical significance within the groups was determined by one-way Anova with Tukey's multiple comparison post-test and standard error of mean (SEM±) calculated: *represents significant difference from PBS-treated group. n = 5/group.

Example 8: Bioassay Using Human HEK293/NFκB-Luc/hIL36R Cell Line for Schild Analysis To characterize the inhibitory properties of the anti-IL36R antibodies, H4H14706P2 and H4H14708P2, a Schild analysis was performed. This method assesses the nature of antagonism by inhibitors and measures the affinity of a competitive antagonist when a number of conditions are fulfilled (Colquhoun, Why the Schild method is better than Schild realized, Trends Pharmacol Sci. 2007 December; 28(12):608-14).

For the bioassay, HEK293/NFκB-luc/hIL-36R cells are seeded onto 96-well assay plates at 10,000 cells/well in low serum media, 0.1% FBS and OPTIMEM, and incubated at 37° C. and 5% $CO_2$ overnight. Next day, antibody was added to cells at different, fixed concentrations (9 nM, 3 nM, 1 nM, 0.3 nM or 0.1 nM) and pre-incubated with cells for 15 minutes at room temperature. A condition without antibody was also included. IL-36α, IL-36β, or IL-36γ were then serially diluted from 100 nM to 2 pM or 100 nM to 0.1 pM and were added to cells along with sample without any ligand. Luciferase activity was detected after 5.5 hrs of incubation in 37° C. and 5% $CO_2$ with Victor X5 or EnVision™ Multilabel Plate Reader (Perkin Elmer) and the results were analyzed using Gaddum/Schild $EC_{50}$ shift with Prism 7 (GraphPad).

A Schild analysis of H4H14706P2 and H4H14708P2 showed that increasing amount of antibodies caused parallel rightward shift of the IL36 ligand dose-response curves and that the inhibitory effect of H4H14706P2 and H4H14708P2 was surmountable by increasing amounts of IL36 ligand, suggesting competitive inhibition of H4H14706P2 and H4H14708P2 (FIGS. 3A-3F).

Example 9: Pharmacokinetic (PK) Studies

Female cynomolgus monkeys were assigned to dose groups for PK characterization; animals (3 animals/group) received a single SC injection of 5 or 0.5 mg/kg of H4H14708P2 or APE6155. Blood samples were collected from all animals at pre-dose and at 4, 24, 48, 72, 120, 168, 240, 336, 504, 576, 672, 840, 912, 1008, 1080, 1176, 1248, 1344, 1512 and 1680 hours post dose. Concentrations of total H4H14708P2 or APE6155 in serum were determined using a non-validated enzyme-linked immunosorbent assays (ELISAs). The method was designed to measure total human IgG concentrations in cynomolgus serum. Pharmacokinetic parameters were estimated using non-compartmental analysis. H4H14708P2 was observed to have about 1.3-fold greater exposure than APE6155 at 5 mg/kg dosage and about 1.2-fold greater exposure than APE6155 at 0.5 mg/kg dosage. See FIG. 4.

All references cited herein are incorporated by reference to the same extent as if each individual publication, database entry (e.g., Genbank sequences or GeneID entries), patent application, or patent, was specifically and individually indicated to be incorporated by reference. This statement of incorporation by reference is intended by Applicants, to relate to each and every individual publication, database entry (e.g., Genbank sequences or GeneID entries), patent application, or patent even if such citation is not immediately adjacent to a dedicated statement of incorporation by reference. The inclusion of dedicated statements of incorporation by reference, if any, within the specification does not in any way weaken this general statement of incorporation by reference. Citation of the references herein is not intended as an admission that the reference is pertinent prior art, nor does it constitute any admission as to the contents or date of these publications or documents.

We claim:

1. A method for making an antibody or antigen-binding fragment thereof that specifically binds Interleukin-36 Receptor (IL-36R), wherein the antibody or antigen-binding fragment thereof comprises:
   (i) a heavy chain immunoglobulin or variable region thereof that comprises the CDR-H1, CDR-H2 and CDR-H3 of a heavy chain immunoglobulin variable region comprising the amino acid sequence set forth in SEQ ID NO: 2, and a light chain immunoglobulin or variable region thereof that comprises the CDR-L1, CDR-L2 and CDR-L3 of a light chain immunoglobulin variable region comprising the amino acid sequence set forth in SEQ ID NO: 10;
   (ii) a heavy chain immunoglobulin or variable region thereof that comprises the CDR-H1, CDR-H2 and CDR-H3 of a heavy chain immunoglobulin variable region comprising the amino acid sequence set forth in SEQ ID NO: 18, and a light chain immunoglobulin or variable region thereof that comprises the CDR-L1, CDR-L2 and CDR-L3 of a light chain immunoglobulin variable region comprising the amino acid sequence set forth in SEQ ID NO: 26; or
   (iii) a heavy chain immunoglobulin or variable region thereof that comprises the CDR-H1, CDR-H2 and CDR-H3 of a heavy chain immunoglobulin variable region comprising the amino acid sequence set forth in SEQ ID NO: 34, and a light chain immunoglobulin or variable region thereof that comprises the CDR-L1, CDR-L2 and CDR-L3 of a light chain immunoglobulin variable region comprising the amino acid sequence set forth in SEQ ID NO: 42;
   (iv) a heavy chain immunoglobulin or variable region thereof that comprises the CDR-H1, CDR-H2 and CDR-H3 of a heavy chain immunoglobulin variable region comprising the amino acid sequence set forth in SEQ ID NO: 50, and a light chain immunoglobulin or variable region thereof that comprises the CDR-L1, CDR-L2 and CDR-L3 of a light chain immunoglobulin variable region comprising the amino acid sequence set forth in SEQ ID NO: 58;
   (v) a heavy chain immunoglobulin or variable region thereof that comprises the CDR-H1, CDR-H2 and CDR-H3 of a heavy chain immunoglobulin variable region comprising the amino acid sequence set forth in SEQ ID NO: 66, and a light chain immunoglobulin or variable region thereof that comprises the CDR-L1, CDR-L2 and CDR-L3 of a light chain immunoglobulin variable region comprising the amino acid sequence set forth in SEQ ID NO: 74;
   (vi) a heavy chain immunoglobulin or variable region thereof that comprises the CDR-H1, CDR-H2 and CDR-H3 of a heavy chain immunoglobulin variable region comprising the amino acid sequence set forth in SEQ ID NO: 82, and a light chain immunoglobulin or variable region thereof that comprises the CDR-L1, CDR-L2 and CDR-L3 of a light chain immunoglobulin variable region comprising the amino acid sequence set forth in SEQ ID NO: 90;
   (vii) a heavy chain immunoglobulin or variable region thereof that comprises the CDR-H1, CDR-H2 and CDR-H3 of a heavy chain immunoglobulin variable region comprising the amino acid sequence set forth in SEQ ID NO: 98, and a light chain immunoglobulin or variable region thereof that comprises the CDR-L1, CDR-L2 and CDR-L3 of a light chain immunoglobulin variable region comprising the amino acid sequence set forth in SEQ ID NO: 106;

(viii) a heavy chain immunoglobulin or variable region thereof that comprises the CDR-H1, CDR-H2 and CDR-H3 of a heavy chain immunoglobulin variable region comprising the amino acid sequence set forth in SEQ ID NO: 114, and a light chain immunoglobulin or variable region thereof that comprises the CDR-L1, CDR-L2 and CDR-L3 of a light chain immunoglobulin variable region comprising the amino acid sequence set forth in SEQ ID NO: 122;

(ix) a heavy chain immunoglobulin or variable region thereof that comprises the CDR-H1, CDR-H2 and CDR-H3 of a heavy chain immunoglobulin variable region comprising the amino acid sequence set forth in SEQ ID NO: 130, and a light chain immunoglobulin or variable region thereof that comprises the CDR-L1, CDR-L2 and CDR-L3 of a light chain immunoglobulin variable region comprising the amino acid sequence set forth in SEQ ID NO: 122;

(x) a heavy chain immunoglobulin or variable region thereof that comprises the CDR-H1, CDR-H2 and CDR-H3 of a heavy chain immunoglobulin variable region comprising the amino acid sequence set forth in SEQ ID NO: 138, and a light chain immunoglobulin or variable region thereof that comprises the CDR-L1, CDR-L2 and CDR-L3 of a light chain immunoglobulin variable region comprising the amino acid sequence set forth in SEQ ID NO: 146;

(xi) a heavy chain immunoglobulin or variable region thereof that comprises the CDR-H1, CDR-H2 and CDR-H3 of a heavy chain immunoglobulin variable region comprising the amino acid sequence set forth in SEQ ID NO: 154, and a light chain immunoglobulin or variable region thereof that comprises the CDR-L1, CDR-L2 and CDR-L3 of a light chain immunoglobulin variable region comprising the amino acid sequence set forth in SEQ ID NO: 162; or (xii) a heavy chain immunoglobulin or variable region thereof that comprises the CDR-H1, CDR-H2 and CDR-H3 of a heavy chain immunoglobulin variable region comprising the amino acid sequence set forth in SEQ ID NO: 170, and a light chain immunoglobulin or variable region thereof that comprises the CDR-L1, CDR-L2 and CDR-L3 of a light chain immunoglobulin variable region comprising the amino acid sequence set forth in SEQ ID NO: 122;

said method comprising:
(a) introducing one or more polynucleotides encoding the heavy chain immunoglobulin or variable region thereof and the light chain immunoglobulin or variable region thereof of said antibody or antigen-binding fragment thereof into an isolated host cell;
(b) culturing the host cell in a medium under conditions favorable to expression of the one or more polynucleotides; and
(c) optionally, isolating the antibody or antigen-binding fragment thereof from the host cell and/or medium in which the host cell is grown.

2. The method of claim 1 wherein the host cell is a Chinese hamster ovary cell.

3. The method of claim 1, wherein the antibody or antigen-binding fragment thereof comprises a CDR-H1 comprising the amino acid sequence set forth in SEQ ID NO: 52, a CDR-H2 comprising the amino acid sequence set forth in SEQ ID NO: 54, a CDR-H3 comprising the amino acid sequence set forth in SEQ ID NO: 56, a CDR-L1 comprising the amino acid sequence set forth in SEQ ID NO: 60, a CDR-L2 comprising the amino acid sequence set forth in SEQ ID NO: 62, and a CDR-L3 comprising the amino acid sequence set forth in SEQ ID NO: 64.

4. The method of claim 1, wherein the antibody or antigen-binding fragment thereof comprises:
(a) a heavy chain immunoglobulin variable region that comprises the amino acid sequence set forth in SEQ ID NO: 2, and a light chain immunoglobulin variable region that comprises the amino acid sequence set forth in SEQ ID NO: 10;
(b) a heavy chain immunoglobulin variable region that comprises the amino acid sequence set forth in SEQ ID NO: 18, and a light chain immunoglobulin variable region that comprises the amino acid sequence set forth in SEQ ID NO: 26;
(c) a heavy chain immunoglobulin variable region that comprises the amino acid sequence set forth in SEQ ID NO: 34, and a light chain immunoglobulin variable region that comprises the amino acid sequence set forth in SEQ ID NO: 42;
(d) a heavy chain immunoglobulin variable region that comprises the amino acid sequence set forth in SEQ ID NO: 50, and a light chain immunoglobulin variable region that comprises the amino acid sequence set forth in SEQ ID NO: 58;
(e) a heavy chain immunoglobulin variable region that comprises the amino acid sequence set forth in SEQ ID NO: 66, and a light chain immunoglobulin variable region that comprises the amino acid sequence set forth in SEQ ID NO: 74;
(f) a heavy chain immunoglobulin variable region that comprises the amino acid sequence set forth in SEQ ID NO: 82, and a light chain immunoglobulin variable region that comprises the amino acid sequence set forth in SEQ ID NO: 90;
(g) a heavy chain immunoglobulin variable region that comprises the amino acid sequence set forth in SEQ ID NO: 98, and a light chain immunoglobulin variable region that comprises the amino acid sequence set forth in SEQ ID NO: 106;
(h) a heavy chain immunoglobulin variable region that comprises the amino acid sequence set forth in SEQ ID NO: 114, and a light chain immunoglobulin variable region that comprises the amino acid sequence set forth in SEQ ID NO: 122;
(i) a heavy chain immunoglobulin variable region that comprises the amino acid sequence set forth in SEQ ID NO: 130, and a light chain immunoglobulin variable region that comprises the amino acid sequence set forth in SEQ ID NO: 122;
(j) a heavy chain immunoglobulin variable region that comprises the amino acid sequence set forth in SEQ ID NO: 138, and a light chain immunoglobulin variable region that comprises the amino acid sequence set forth in SEQ ID NO: 146;
(k) a heavy chain immunoglobulin variable region that comprises the amino acid sequence set forth in SEQ ID NO: 154, and a light chain immunoglobulin variable region that comprises the amino acid sequence set forth in SEQ ID NO: 162; or
(l) a heavy chain immunoglobulin variable region that comprises the amino acid sequence set forth in SEQ ID NO: 170, and a light chain immunoglobulin variable region that comprises the amino acid sequence set forth in SEQ ID NO: 122.

5. The method of claim 4, wherein the antibody or antigen-binding fragment thereof comprises a heavy chain immunoglobulin variable region comprising the amino acid sequence set forth in SEQ ID NO: 50, and a light chain immunoglobulin variable region comprising the amino acid sequence set forth in SEQ ID NO: 58.

6. The method of claim 1, wherein the heavy chain immunoglobulin variable region is linked to an IgG heavy chain constant region and the light chain immunoglobulin variable region is linked to a kappa or lambda light chain constant region.

7. The method of claim 6, wherein the antibody or antigen-binding fragment thereof comprises:
   (a) a heavy chain immunoglobulin that comprises the amino acid sequence set forth in SEQ ID NO: 180, and a light chain immunoglobulin that comprises the amino acid sequence set forth in SEQ ID NO: 182;
   (b) a heavy chain immunoglobulin that comprises the amino acid sequence set forth in SEQ ID NO: 184, and a light chain immunoglobulin that comprises the amino acid sequence set forth in SEQ ID NO: 186;
   (c) a heavy chain immunoglobulin that comprises the amino acid sequence set forth in SEQ ID NO: 188, and a light chain immunoglobulin that comprises the amino acid sequence set forth in SEQ ID NO: 190;
   (d) a heavy chain immunoglobulin that comprises the amino acid sequence set forth in SEQ ID NO: 192, and a light chain immunoglobulin that comprises the amino acid sequence set forth in SEQ ID NO: 194;
   (e) a heavy chain immunoglobulin that comprises the amino acid sequence set forth in SEQ ID NO: 196, and a light chain immunoglobulin that comprises the amino acid sequence set forth in SEQ ID NO: 198;
   (f) a heavy chain immunoglobulin that comprises the amino acid sequence set forth in SEQ ID NO: 200, and a light chain immunoglobulin that comprises the amino acid sequence set forth in SEQ ID NO: 202;
   (g) a heavy chain immunoglobulin that comprises the amino acid sequence set forth in SEQ ID NO: 204, and a light chain immunoglobulin that comprises the amino acid sequence set forth in SEQ ID NO: 206;
   (h) a heavy chain immunoglobulin that comprises the amino acid sequence set forth in SEQ ID NO: 208, and a light chain immunoglobulin that comprises the amino acid sequence set forth in SEQ ID NO: 210;
   (i) a heavy chain immunoglobulin that comprises the amino acid sequence set forth in SEQ ID NO: 212, and a light chain immunoglobulin that comprises the amino acid sequence set forth in SEQ ID NO: 214;
   (j) a heavy chain immunoglobulin that comprises the amino acid sequence set forth in SEQ ID NO: 216, and a light chain immunoglobulin that comprises the amino acid sequence set forth in SEQ ID NO: 218;
   (k) a heavy chain immunoglobulin that comprises the amino acid sequence set forth in SEQ ID NO: 220, and a light chain immunoglobulin that comprises the amino acid sequence set forth in SEQ ID NO: 222; or
   (l) a heavy chain immunoglobulin that comprises the amino acid sequence set forth in SEQ ID NO: 224, and a light chain immunoglobulin that comprises the amino acid sequence set forth in SEQ ID NO: 226.

8. The method of claim 6, wherein the IgG is an IgG1 or IgG4.

9. The method of claim 1, wherein the antibody or antigen-binding fragment thereof comprises a heavy chain immunoglobulin comprising the amino acid sequence set forth in SEQ ID NO: 192, and light chain immunoglobulin comprising the amino acid sequence set forth in SEQ ID NO: 194.

10. A polynucleotide comprising a nucleic acid sequence encoding a heavy chain immunoglobulin variable region of an antibody that specifically binds IL-36R, wherein the heavy chain immunoglobulin variable region comprises a CDR-H1 comprising the amino acid sequence set forth in SEQ ID NO: 52, a CDR-H2 comprising the amino acid sequence set forth in SEQ ID NO: 54, and a CDR-H3 comprising the amino acid sequence set forth in SEQ ID NO: 56.

11. The polynucleotide of claim 10, wherein the heavy chain immunoglobulin variable region comprises the amino acid sequence set forth in SEQ ID NO: 50.

12. The polynucleotide of claim 10, wherein the nucleic acid sequence comprises the nucleotide sequence of SEQ ID NO: 49 or a variant having at least 95% sequence identity to SEQ ID NO: 49.

13. A vector comprising the polynucleotide of claim 10.

14. A polynucleotide comprising a nucleic acid sequence encoding a light chain immunoglobulin variable region of an antibody that specifically binds IL-36R, wherein the light chain immunoglobulin variable region comprises a CDR-L1 comprising the amino acid sequence set forth in SEQ ID NO: 60, a CDR-L2 comprising the amino acid sequence set forth in SEQ ID NO: 62, and a CDR-L3 comprising the amino acid sequence set forth in SEQ ID NO: 64.

15. The polynucleotide of claim 14, wherein the light chain immunoglobulin variable region comprises the amino acid sequence set forth in SEQ ID NO: 58.

16. The polynucleotide of claim 14, wherein the nucleic acid sequence comprises the nucleotide sequence of SEQ ID NO: 57 or a variant having at least 95% sequence identity to SEQ ID NO: 57.

17. A vector comprising the polynucleotide of claim 14.

18. A combination of polynucleotides comprising a first polynucleotide and a second polynucleotide, wherein:
   the first polynucleotide comprises a nucleic acid sequence encoding a heavy chain immunoglobulin variable region of an antibody that specifically binds IL-36R, wherein the heavy chain immunoglobulin variable region comprises a CDR-H1 comprising the amino acid sequence set forth in SEQ ID NO: 52, a CDR-H2 comprising the amino acid sequence set forth in SEQ ID NO: 54, and a CDR-H3 comprising the amino acid sequence set forth in SEQ ID NO: 56; and
   the second polynucleotide comprises a nucleic acid sequence encoding a light chain immunoglobulin variable region of an antibody that specifically binds IL-36R, wherein the light chain immunoglobulin variable region comprises a CDR-L1 comprising the amino acid sequence set forth in SEQ ID NO: 60, a CDR-L2 comprising the amino acid sequence set forth in SEQ ID NO: 62, and a CDR-L3 comprising the amino acid sequence set forth in SEQ ID NO: 64.

19. An isolated host cell comprising the combination of polynucleotides of claim 18.

20. The host cell of claim 19, wherein the host cell is a Chinese hamster ovary cell.

21. A polynucleotide encoding an antibody or antigen-binding fragment thereof that specifically binds IL-36R, wherein the antibody or antigen-binding fragment thereof comprises a heavy chain immunoglobulin variable region that comprises a CDR-H1 comprising the amino acid sequence set forth in SEQ ID NO: 52, a CDR-H2 comprising the amino acid sequence set forth in SEQ ID NO: 54, and a CDR-H3 comprising the amino acid sequence set forth in SEQ ID NO: 56, and a light chain immunoglobulin variable region that comprises a CDR-L1 comprising the amino acid sequence set forth in SEQ ID NO: 60, a CDR-L2 comprising the amino acid sequence set forth in SEQ ID NO: 62, and a CDR-L3 comprising the amino acid sequence set forth in SEQ ID NO: 64.

22. The polynucleotide of claim 21, wherein the heavy chain immunoglobulin variable region comprises the amino acid sequence set forth in SEQ ID NO: 50 and the light chain immunoglobulin variable region comprises the amino acid sequence set forth in SEQ ID NO: 58.

23. An isolated host cell comprising the polynucleotide of claim 21.

* * * * *